US011034746B2

(12) United States Patent
Wieczorek et al.

(10) Patent No.: US 11,034,746 B2
(45) Date of Patent: Jun. 15, 2021

(54) DOUBLE-ACYLATED GLP-1 DERIVATIVES

(71) Applicant: Novo Nordisk AS, Bagsvaerd (DK)

(72) Inventors: Birgit Wieczorek, Koebenhavn N (DK); Jane Spetzler, Broenshoej (DK); Thomas Kruse, Herlev (DK); Lars Linderoth, Hilleroed (DK); Jacob Kofoed, Vaerloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/968,950

(22) Filed: May 2, 2018

(65) Prior Publication Data

US 2018/0251512 A1 Sep. 6, 2018

Related U.S. Application Data

(63) Continuation of application No. 15/346,323, filed on Nov. 8, 2016, now Pat. No. 10,005,827, which is a continuation of application No. 14/961,064, filed on Dec. 7, 2015, now Pat. No. 9,527,900, which is a continuation of application No. 14/009,902, filed as application No. PCT/EP2012/056642 on Apr. 12, 2012, now Pat. No. 9,266,940.

(60) Provisional application No. 61/474,913, filed on Apr. 13, 2011.

(30) Foreign Application Priority Data

Apr. 12, 2011 (EP) ..................................... 11162087

(51) Int. Cl.
| | |
|---|---|
| *A61K 38/26* | (2006.01) |
| *A61K 47/54* | (2017.01) |
| *C07K 14/605* | (2006.01) |
| *A61K 47/60* | (2017.01) |
| *A61K 38/00* | (2006.01) |

(52) U.S. Cl.
CPC ............ *C07K 14/605* (2013.01); *A61K 38/26* (2013.01); *A61K 47/542* (2017.08); *A61K 47/543* (2017.08); *A61K 47/60* (2017.08); *A61K 38/00* (2013.01)

(58) Field of Classification Search
CPC .... A61K 38/26; A61K 47/542; A61K 47/543; C07K 14/065; C07K 14/605
See application file for complete search history.

(56) References Cited

U.S. PATENT DOCUMENTS

| | | | |
|---|---|---|---|
| 5,545,618 A | 8/1996 | Buckley et al. | |
| 5,773,647 A | 6/1998 | Leone-Bay et al. | |
| 5,866,536 A | 2/1999 | Leone-Bay et al. | |
| 5,968,899 A | 10/1999 | Sekine et al. | |
| 6,268,343 B1 | 7/2001 | Knudsen et al. | |
| 6,348,447 B1 | 2/2002 | Hellstrom et al. | |
| 6,458,924 B2 | 10/2002 | Knudsen et al. | |
| 7,049,283 B2 | 5/2006 | Ault et al. | |
| 7,235,627 B2 | 6/2007 | Knudson et al. | |
| 7,271,149 B2 | 9/2007 | Glaesner et al. | |
| 7,417,028 B2 | 8/2008 | Ewing et al. | |
| 8,039,018 B2 | 10/2011 | Majuru et al. | |
| 8,053,429 B2 | 11/2011 | Cumming et al. | |

(Continued)

FOREIGN PATENT DOCUMENTS

| | | |
|---|---|---|
| CN | 101010339 A | 8/2007 |
| CN | 101133082 A | 2/2008 |

(Continued)

OTHER PUBLICATIONS

Chae S Y et al., Journal Title: Journal of the Controlled Release,Title: The Fatty Acid Conjugated Exendin-4 Analogs for Type 2 Antidiabetic Therapeutics ,Year: 2010, vol. 144,pp. 10-16.
EP09179390.1 Priority Application Filed on Dec. 16, 2009 by Novo Nordisk.
EP10190515.6 Priority Application Filed on Nov. 9, 2010 by Novo Nordisk.
Dolensky et al., "New Building Blocks for Fluorinated Imidazole," Jorunal of Organic Chemistry, vol. 66(13), pp. 4687-4691 (2001).
Knudsen et al., "Potent Derivatives of Glucagon-Like Peptide-1 With Pharmacokinetic Properties Suitable for Once Daily Administration," Journal of Medicinal Chemistry, 2000, vol. 43(9), pp. 1664-1669.

(Continued)

*Primary Examiner* — Jeffrey E. Russel
(74) *Attorney, Agent, or Firm* — Leon Y. Lum

(57) ABSTRACT

The invention relates to a derivative of a GLP-1 analogue, which analogue comprises a first K residue at a position corresponding to position 27 of GLP-1(7-37) (SEQ ID NO: 1); a second K residue at a position corresponding to position T of GLP-1(7-37), where T is an integer in the range of 7-37 except 18 and 27; and a maximum of ten amino acid changes as compared to GLP-1(7-37); wherein the first K residue is designated $K^{27}$, and the second K residue is designated $K^{T}$; which derivative comprises two albumin binding moieties attached to $K^{27}$ and $K^{T}$, respectively, via a linker, wherein the albumin binding moiety comprises a protracting moiety selected from HOOC—$(CH_2)_2$—CO— and HOOC—$C_6H_4$—O—$(CH_2)_y$—CO—; in which x is an integer in the range of 6-16, and y is an integer in the range of 3-17; wherein the linker comprises an element of the formula —NH—$(CH_2)_2$—O—$(CH_2)_2)_k$—O—$(CH_2)_n$—CO—, wherein k is an integer in the range of 1-5, and n is an integer in the range of 1-5; or a pharmaceutically acceptable salt, amide, or ester thereof. The invention also relates to the pharmaceutical use thereof, for example in the treatment and/or prevention of all forms of diabetes and related diseases, as well as to corresponding novel GLP-1 analogues. The derivatives are suitable for oral administration.

40 Claims, No Drawings
Specification includes a Sequence Listing.

(56) References Cited

U.S. PATENT DOCUMENTS

| | | |
|---|---|---|
| 8,097,698 B2 | 1/2012 | Knudsen et al. |
| 8,536,122 B2 | 9/2013 | Lau et al. |
| 8,648,041 B2 | 2/2014 | Garibay et al. |
| 8,895,694 B2 | 11/2014 | Spetzler et al. |
| 9,067,977 B2 | 6/2015 | Spetzler et al. |
| 9,266,940 B2 | 2/2016 | Wieczorek et al. |
| 9,278,123 B2 | 3/2016 | Sauerberg et al. |
| 9,527,900 B2 | 12/2016 | Linderoth et al. |
| 9,993,430 B2 | 6/2018 | Jensen et al. |
| 10,005,827 B2 * | 6/2018 | Spetzler ............... C07K 14/605 |
| 10,086,047 B2 | 10/2018 | Sauerberg et al. |
| 10,278,923 B2 | 5/2019 | Nielsen et al. |
| 10,335,369 B2 | 7/2019 | Vilhelmsen |
| 2001/0011071 A1 | 8/2001 | Knudsen et al. |
| 2005/0009748 A1 | 1/2005 | Dinh et al. |
| 2005/0148497 A1 | 7/2005 | Khan |
| 2006/0078622 A1 | 4/2006 | Majuru et al. |
| 2006/0078623 A1 | 4/2006 | Dhoot et al. |
| 2006/0286129 A1 | 12/2006 | Sarubbi |
| 2007/0049557 A1 | 3/2007 | Ahmed et al. |
| 2007/0203058 A1 | 8/2007 | Lau et al. |
| 2007/0224262 A1 | 9/2007 | Majuru et al. |
| 2008/0076705 A1 | 3/2008 | Kodra et al. |
| 2008/0153779 A1 | 6/2008 | Liao et al. |
| 2008/0194676 A1 | 8/2008 | Abbas et al. |
| 2008/0207507 A1 | 8/2008 | Lau et al. |
| 2008/0255250 A1 | 10/2008 | Gomez-Orellana et al. |
| 2009/0088369 A1 | 4/2009 | Steiness |
| 2009/0124639 A1 | 5/2009 | Oyewumi et al. |
| 2009/0143330 A1 | 6/2009 | Levchik et al. |
| 2009/0156478 A1 | 6/2009 | Lau et al. |
| 2010/0016229 A1 | 1/2010 | Sarubbi |
| 2010/0069410 A1 | 3/2010 | Majuru et al. |
| 2010/0151009 A1 | 6/2010 | Levchik |
| 2010/0210526 A1 | 8/2010 | Joshi |
| 2010/0239658 A1 | 9/2010 | Majuru et al. |
| 2010/0292133 A1 | 11/2010 | Spetzler et al. |
| 2011/0142800 A1 | 6/2011 | Kidron et al. |
| 2011/0166321 A1 | 7/2011 | Garibay et al. |
| 2011/0218148 A1 | 9/2011 | Azria et al. |
| 2013/0053311 A1 | 2/2013 | Kalthoff et al. |
| 2013/0240587 A1 | 9/2013 | Buchhalter |
| 2013/0345134 A1 | 12/2013 | Sauerberg et al. |
| 2014/0011732 A1 | 1/2014 | Spetzler et al. |
| 2014/0296131 A1 | 10/2014 | Spetzler et al. |
| 2015/0025003 A1 | 1/2015 | Spetzler et al. |
| 2015/0031606 A1 | 1/2015 | Vilhelmsen |
| 2015/0072926 A1 | 3/2015 | Vilhelmsen et al. |
| 2015/0150811 A1 | 6/2015 | Jensen et al. |
| 2016/0067184 A1 | 3/2016 | Nielsen et al. |
| 2016/0151462 A1 | 6/2016 | Sauerberg et al. |
| 2017/0312225 A1 | 11/2017 | Nielsen et al. |
| 2018/0021272 A1 | 1/2018 | Burshtein et al. |
| 2018/0028622 A1 | 2/2018 | Burshtein et al. |
| 2018/0036234 A1 | 2/2018 | Burshtein et al. |
| 2018/0036382 A1 | 2/2018 | Burshtein et al. |
| 2018/0050096 A1 | 2/2018 | Burshtein et al. |
| 2018/0235888 A1 | 8/2018 | Jensen et al. |
| 2018/0360918 A1 | 12/2018 | Sauerberg et al. |
| 2019/0216739 A1 | 7/2019 | Nielsen et al. |
| 2019/0231876 A1 | 8/2019 | Pedersen et al. |
| 2019/0314283 A1 | 10/2019 | Vilhelmsen |
| 2020/0000728 A1 | 1/2020 | Pedersen et al. |
| 2020/0079834 A1 | 3/2020 | Wieczorek et al. |

FOREIGN PATENT DOCUMENTS

| | | |
|---|---|---|
| CN | 101463081 A | 6/2009 |
| EP | 0708179 A2 | 4/1996 |
| EP | 1364967 A2 | 11/2003 |
| EP | 2565202 A1 | 3/2013 |
| EP | 2651398 A1 | 10/2013 |
| JP | 05-506427 | 9/1993 |
| JP | 2001-504105 A | 3/2001 |
| JP | 2004131398 A | 4/2004 |
| JP | 2006-520818 A | 9/2006 |
| JP | 2007-536268 A | 12/2007 |
| JP | 2008-509933 A | 4/2008 |
| JP | 2009542711 A | 12/2009 |
| JP | 2010-530962 A | 9/2010 |
| JP | 4585037 B2 | 11/2010 |
| JP | 2011509077 A | 3/2011 |
| JP | 2012-121923 A | 6/2012 |
| JP | 2013543814 A | 12/2013 |
| JP | 20145034526 A | 2/2014 |
| JP | 2015-515459 A | 5/2015 |
| KR | 20060100428 A | 9/2006 |
| KR | 102072202 | 1/2020 |
| NZ | 219575 A | 4/1990 |
| RU | 2158138 C2 | 10/2000 |
| RU | 2226402 C2 | 4/2004 |
| WO | 9111457 A1 | 8/1991 |
| WO | 96/29342 | 9/1996 |
| WO | 9725064 A1 | 7/1997 |
| WO | 9808871 A1 | 3/1998 |
| WO | 9820895 A1 | 5/1998 |
| WO | 99/43705 A1 | 9/1999 |
| WO | 99/43706 A1 | 9/1999 |
| WO | 99/43707 A1 | 9/1999 |
| WO | 99/43708 A1 | 9/1999 |
| WO | 00/07617 A1 | 2/2000 |
| WO | 00/16797 A2 | 3/2000 |
| WO | 00/34331 | 6/2000 |
| WO | 200048589 A1 | 8/2000 |
| WO | 200050012 A1 | 8/2000 |
| WO | 00/69911 | 11/2000 |
| WO | 0066629 A1 | 11/2000 |
| WO | 01/04156 | 1/2001 |
| WO | 0124777 A1 | 4/2001 |
| WO | 200141737 A2 | 6/2001 |
| WO | 02/46227 A2 | 6/2002 |
| WO | 0248192 A2 | 6/2002 |
| WO | 2003005944 A1 | 1/2003 |
| WO | 03/011892 A2 | 2/2003 |
| WO | 03063838 A1 | 8/2003 |
| WO | 03/072195 A2 | 9/2003 |
| WO | 2004/067548 A2 | 8/2004 |
| WO | 2004093823 A2 | 11/2004 |
| WO | 2005004900 A1 | 1/2005 |
| WO | 2005014049 A2 | 2/2005 |
| WO | 2005/027978 A2 | 3/2005 |
| WO | 2005/058954 A1 | 6/2005 |
| WO | 2005/058958 A2 | 6/2005 |
| WO | 2005049061 A2 | 6/2005 |
| WO | 2005099672 A1 | 10/2005 |
| WO | 2005107462 A2 | 11/2005 |
| WO | 2005107773 A2 | 11/2005 |
| WO | 2005/121090 A1 | 12/2005 |
| WO | 2006/005667 A2 | 1/2006 |
| WO | 2006/037810 | 4/2006 |
| WO | 2006/082204 A1 | 8/2006 |
| WO | 2006084164 A2 | 8/2006 |
| WO | 2006/097535 A2 | 9/2006 |
| WO | 2006/097536 A2 | 9/2006 |
| WO | 2006/097537 A2 | 9/2006 |
| WO | 2006/097538 | 9/2006 |
| WO | 2006/097538 A1 | 9/2006 |
| WO | 2006096515 A2 | 9/2006 |
| WO | 2006097537 A2 | 9/2006 |
| WO | 2006103661 A2 | 10/2006 |
| WO | 2006/127948 A2 | 11/2006 |
| WO | 2006124047 A2 | 11/2006 |
| WO | 2006124047 A3 | 11/2006 |
| WO | 2007024700 A2 | 3/2007 |
| WO | 2007061434 A2 | 5/2007 |
| WO | 2007067964 A2 | 6/2007 |
| WO | 2007093226 A1 | 8/2007 |
| WO | 2007117706 A2 | 10/2007 |
| WO | 2007/128817 A2 | 11/2007 |
| WO | 2007146234 A2 | 12/2007 |
| WO | 2008003050 A2 | 1/2008 |
| WO | 2008020096 A1 | 2/2008 |
| WO | 2008028859 A1 | 3/2008 |
| WO | 2008033888 A2 | 3/2008 |

(56) References Cited

FOREIGN PATENT DOCUMENTS

| | | |
|---|---|---|
| WO | 2008039351 A2 | 4/2008 |
| WO | 2008109385 A2 | 9/2008 |
| WO | 2008/154619 A1 | 12/2008 |
| WO | 2009/030771 A1 | 3/2009 |
| WO | 2009030738 A1 | 3/2009 |
| WO | 2009032749 A2 | 3/2009 |
| WO | 2009/050738 A2 | 4/2009 |
| WO | 2009059188 A1 | 5/2009 |
| WO | 2009/083549 A1 | 7/2009 |
| WO | 2009083549 A1 | 7/2009 |
| WO | 2010020978 A1 | 2/2010 |
| WO | 2010/029159 A1 | 3/2010 |
| WO | 2010/043319 A1 | 4/2010 |
| WO | 2010/092163 A2 | 8/2010 |
| WO | 2011/029551 A2 | 3/2011 |
| WO | 2011084618 A2 | 7/2011 |
| WO | 2011094531 A1 | 8/2011 |
| WO | 2011109787 A1 | 9/2011 |
| WO | 2011116139 A2 | 9/2011 |
| WO | 2011138421 A1 | 11/2011 |
| WO | 2012080471 A1 | 6/2012 |
| WO | 2012140117 A1 | 10/2012 |
| WO | 2013009545 A1 | 1/2013 |
| WO | 2013139694 | 9/2013 |
| WO | 2013139694 A1 | 9/2013 |
| WO | 2013139695 A1 | 9/2013 |
| WO | 2013189988 A1 | 12/2013 |
| WO | 2014005858 A1 | 1/2014 |
| WO | 2014177683 A1 | 11/2014 |
| WO | 2016128970 A1 | 8/2016 |
| WO | 2016128971 A1 | 8/2016 |
| WO | 2016128972 A1 | 8/2016 |
| WO | 2016128973 A1 | 8/2016 |
| WO | 2016128974 A1 | 8/2016 |
| WO | 2017060500 A1 | 4/2017 |

OTHER PUBLICATIONS

Dumelin et al.., "A Portable Albumin Binder From a DNA-Encoded Chemical Library", Angewandte Chemie (International Edition in English), vol. 47(17), pp. 3196-3201 (2008).

Rawlay SS et al. Journal of Organic Chemistry. "Oxidation of Primary, Secondary, and Tertiary Amines With Neutral Permanganate. A Simple Method for Degrading Amines to Aldehydes and Ketones." 1967. vol. 32(10). pp. 3129-3131.

Travis B R et al. Organic Letters. "Facile Oxidation of Aldehydes to Acids and Esters With Oxone." 2003. vol. 5(7). pp. 1031-1034.

Murage E N et al. Bioorganic & Medicinal Chemistry. "Search for ¿-Helical Propensity in the Receptor-Bound Conformation of Glucagon-Like Peptide-1." 2008. vol. 16. pp. 10106-10112.

Melanie Davies et al, "Effect of Oral Semaglutide Compared With Placebo and Subcutaneous Semaglutide on Glycemic Control in Patients With Type 2 Diabetes: A Randomized Clinical Trial," JAMA the Journal of the American Medical Association, 2017, vol. 318, No. 15, p. 1460.

Steinert et al., "Oral Administration of Glucagon-Like Peptide 1 or Peptide YY 3-36 Affects Food Intake in Healthy Male Subjects," Am J Clin Nutr, Oct. 2010, vol. 92, No. 4, pp. 810-817.

He Xiaorong et al., Mechanistic Study of the Effect of Roller Compaction and Lubricant on Tablet Mechanical Strength, Journal: Journal of Pharmaceutical Sciences,Year: 2007, vol. 96, No. 5, pp. 1342-1355.

Mollan Jr. Matthew J. et al., The effects of lubrication on the compaction and post-compaction properties of directly compressible maltodextrins, Journal: International Journal of Pharmaceutics, Year: 1996, vol. 144, Issue 1, pp. 1-9.

Rowe Raymond C et al., Book: Handbook of Pharmaceutical Excipients, Title: Acesulfame Potassium, Edition—5th, Year: 2006, Complete book.

Steinert R E et al., Orally Administered Glucagon-Like Peptide-1 Affects Glucose Homeostasis Following an Oral Glucose Tolerance Test in Healthy Male Subjects, Journal: Clinical Pharmacology and Therapeutics, Year: 2009, vol. 36, No. 6, pp. 644-650.

von Eggelkraut-Gottanka Stephan G. et al., Roller Compaction and Tabletting of St. John's Wort Plant Dry Extract Using a Gap Width and Force Controlled Roller; Compactor. II. Study of Roller Compaction Variables on Granule and Tablet Properties by a 33 Factorial Design, Journal: Pharmaceutical Development and Technology, Year: 2002, vol. 7, No. 4, pp. 447-455.

Beglinger C et al., Clinical Pharmacology and Therapeutics,"Pharmacokinetics and Pharmacodynamic Effects of Oral GLP-1 and PYY3-36: A Proof-of-Concept Study in Healthy Subjects" 2008, vol. 84, No. 4, pp. 468-474.

Steinert RE et al, American Journal of Clinical Nutrition,"Oral Administration of Glucagon-Like Peptide 1 or Peptide YY 3-36 Affects Food Intake in Healthy Male Subjects", 2010, vol. 92, pp. 810-817.

Beglinger C et al., Pharmacokinetics and Pharmacodynamic Effects of Oral GLP-1 and PYY3-36: A Proof-of-concept Study in Healthy Subjects, Journal: Clinical Pharmacology & Therapeutics, Nature Publishing Group, Year: 2008. vol. 84, No. 4, pp. 468-474.

Leonard Thomas W et al., Promoting absorption of drugs in humans using medium-chain fatty acid-based solid dosage forms:GIPET™, Journal: Expert Opinion Drug Delivery, Year 2006, vol. 3(5), pp. 685-692.

Maher Sam et al., Overcoming poor permeability: translating permeation enhancers for oral peptide delivery, Journal: Drug Discovery Today:Technologies, Year 2011, vol. 9, No. 2, pp. e113-e119.

Maher Sam et al., Safety and efficacy of sodium caprate in promoting oral drug absorption: from in vitro to the clinic, Journal: Advanced Drug Delivery Reviews, Year: 2009, vol. 61, pp. 1427-1449.

Michel Marre et al., GLP-1 receptor agonists today, Journal: Diabetes Research; and Clinical Practice, Year: 2011, vol. 93, No. 3, pp. 317-327.

Walsch Edwin G et al., Oral delivery of macromolecules: rationale underpinning Gastrointestinal Permeation Enhancement Technology (GIPET®), Journal: Therapeutic Delivery, Year 2011, vol. 2, No. 12, pp. 1595-1610. Oth.

Makoto Otsuka, Chemoinformetrical evaluation of granule and tablet properties of pharmaceutical preparations by near-infrared spectroscopy, "Chemometrics and Intelligent Laboratory Systems" Year 2006, vol. 82, No. 1-2, pp. 109-114.

Shah R. B et al. Process Analytical Technology: Chemometric Analysis of Raman and Near Infra-red Spectroscopic Data for Predicting Physical Properties of Extended Release Matrix Tablets, "Journal of Pharmaceutical Sciences" Year 2007, vol. 96, No. 5, pp. 1356-1365.

Aenugu H.P.R et al. Near Infra Red Spectroscopy—An Overview, "International Journal of ChemTech Research" Year 2011, vol. 3, No. 2, pp. 825-836.

Donoso M et al. Prediction of Tablet Hardness and Porosity Using Near-Infrared Diffuse Reflectance Spectroscopy as a Nondestructive Method, "Pharmaceutical Development and Technology" Year 2003, vol. 8, No. 4, pp. 357-366.

Jeckel et al. Importance of particle size knowledge for tablet porosity determination by NIRS, "Tablet Tech Seminar, FMC Biopolymer" Year 2007, retrieved from the Internet: URL:http://www.pharmtech.uni-bonn.de/forschung/arbeitskreis-porf-steffens/download-16, the whole document.

Remington, The Science and Practice of Pharmacy, 22nd Edition, 2012.

Felix Kratz "A Clinical Update of Using Albumin as a Drug Vehicle—A Commentary" Journal of Controlled Release 2014 vol. 190 pp. 331-336.

Rivera et al. Oral Delivery of Heparin in Combination with Sodium N-[8-(2-Hydroxybenzoyl)amino]caprylate: Pharmacological Considerations. Pharmaceutical Research 1997 vol. 14 No. 12 pp. 1830-1834.

Su Young Chae et al. "Preparation, Characterization and Application of Biotinylated and Biotin-PEGylated Glucagon-Like Peptide-1 Analogues for Enhanced Oral Delivery." Bioconjugate Chemistry 2008 vol. 19 No. 1 pp. 334-341.

(56) References Cited

OTHER PUBLICATIONS

Emisphere Technologies. "Carriers Enhance Drug Delivery" Manufacturing Chemistry 1999 vol. 70 No. 6 pp. 25-26.
Adam W. G. Alani et al., "Mechanistic Understanding of Oral Drug Absorption Enhancement of Cromolyn Sodium by an Amino Acid Derivative," Pharmaceutical Research, 2008, vol. 25, No. 1, pp. 48-54.
Granulation Handbook, May 30, 1975, 1st Edition First Press, p. 173-197.
Design and evaluation of formulation for oral administration, Feb. 10, 1995, p. 264-279.
Bhansali et al., "Historical Overview of Incretin Based Therapies," Supplement to JAPI, 2010, vol. 58, pp. 10-14.
Valentino et al., "Central and Peripheral Molecular Targets for Antiobesity Pharmacotherapy," Clinical Pharmacology and Therapeutics, 2010, vol. 87, No. 6, pp. 652-662.
Bastin et al., "Salt Selection and Optimisation Procedures for Pharmaceutical New Chemical Entities," Org Proc Res & Devt, 2000, vol. 4, pp. 427-435.
Drug Data Report, 2006, vol. 28, p. 933.
Anonymous, "Eligen@ Technology. Summary and Value Proposition", Emisphere, Feb. 24, 2017, pp. 1-10, URL: https://www.emisphere.com/wp-content/uploads/2017/02/Eligen-Technology-Presentation_2.15-Update.pdf, XP055520567.
Keck et al., Modeme Pharmazeutische Technologie, 2009, pp. 8-14.
Kidron et al., "A Novel Per-Oral Insulin Formulation: Proof of Concept Study in Non-Diabetic Subjects," Diabetic Medicine, 2004, vol. 21, pp. 354-357.
Letter to Sandoz International GmbH regarding English translation of claim of patent JP4585037, dated Aug. 29, 2018.
Mullins, "Statistics for the Quality Control Chemistry Laboratory," 2003, Chapter I, pp. 10-17.
SNAC, Synchem, http://www.synchem.de/product/snac, accessed Aug. 16, 2018.
Valentino et al., "Current Trends in Targeting the Hormonal Regulation of Appetite and Energy Balance to Treat Obesity," Expert Rev Endocrinol Metab, 2010, vol. 5, pp. 765-783.
WHO Drug Information, "International Nonproprietary Names for Pharmaceutical Substances," 2009, vol. 23, No. 2, p. 164.
U.S. Appl. No. 61/425,087, filed Dec. 20, 2010.
EP Application No. 10195285.1, filed Dec. 16, 2010.
Wang et al., "Non-peptidic glucose-like peptide-1 receptor agonists: aftermath of serendipitous discovery," Acta Pharmacol. Sinica, 2010, vol. 31, pp. 1026-1030.
Baynes, Kevin C. R., "The evolving world of GLP-1 agonist therapies for type 2 diabetes" Therapeutic Advances in Endocrinology and Metabolism, 2010, vol. 1, No. 2, pp. 61-67.
Buckley, Stephen T. et al., "Transcellular stomach absorption of a derivatized glucagon-like peptide-1 receptor agonist" Science Translational Medicine, Nov. 14, 2018, vol. 10, pp. 1-14.
Christensen, Mikkel et al., "Once-Weekly GLP-1 Agonists: How Do They Differ from Exenatide and Liraglutide?" Curr Diab Rep, 2010, vol. 10, pp. 124-132.
Davies, Melanie et al., "Effect of Oral Semaglutide Compared with Placebo and Subcutaneous Semaglutide on Glycemic Control in Patients with Type 2 Diabetes" JAMA, 2017, vol. 318, pp. 1460-1470.
Declaration by the Inventor, Flemming S. Nielsen, dated Feb. 11, 2019.
EMEA Assessment Report EMEA/379172/2009 for Victoza (liraglutide), 2009.
Goldberg, Michael et al., "Challenges for the Oral Delivery of Macromolecules" Nature Reviews Drug Discovery, 2003, vol. 2, pp. 289-294.
Granhall, Charlotte et al., "Safety and Pharmacokinetics of Single and Multiple Ascending Doses of the Novel Oral Human GLP-1 Analogue, Oral Semaglutide, in Healthy Subjects and Subjects with Type 2 Diabetes" Clinical Pharmacokinetics, published Dec. 18, 2018.
Hellriegel, Edward T. et al., "Interpatient variability in bioavailability is related to the extent of absorption: Implications or bioavailability and bioequivalence studies" Clinical Pharmacology & Therapeutics, Dec. 1996, vol. 60, No. 6, pp. 601-607.
King, Simon, "ViewPoints: Novo Nordisk R&D chief predicts an oral revolution for biologics" Nov. 14, 2018, Available from: [http://www.firstwordpharma.com/print/1604592?tsid=17].
Lee, Hye J., "Protein Drug Oral Delivery: The Recent Progress" Archives of Pharmacal Research, 2002, vol. 25, No. 5, pp. 572-584.
Madsen, Kjeld et al., "Structure—Activity and Protraction Relationship of Long-Acting Glucagon-like Peptide-1 Derivatives: Importance of Fatty Acid Lenght, Polarity, and Bulkiness" J. Med. Chem., 2007, vol. 50, pp. 6126-6132.
Morishita, Mariko et al., "Is the oral route possible for peptide and protein drug delivery?" Drug Discovery Today, Oct. 2006, vol. 11, No. 19/20, pp. 905-910.
Novo Nordisk Company announcement No. 14/2015, Novo Nordisk announces positive results for phase 2 trial with oral semaglutide in people with type 2 diabetes, www.novonordisk.com CVR No. 24256790, dated Feb. 20, 2015, p. 1-2.
Novo Nordisk Company announcement No. 52/2015, Novo Nordisk to initiate phase 3a development of oral semaglutide, a once-daily oral GLP-1 analogue, www.novonordisk.com CVR No. 24256790, dated Aug. 26, 2015, p. 1-2.
Novo Nordisk Company announcement No. 17/2018, Novo Nordisk successfully completes the first phase 3a trial, Pioneer 1, with oral semaglutide, www.novonordisk.com CVR No. 24256790, dated Feb. 22, 2018, p. 1-3.
Novo Nordisk Company announcement No. 47/2018, Oral semaglutide shows superior improvement in HbA1C vs empagliflozin in the PIONEER 2 trial, www.novonordisk.com CVR No. 24256790, dated May 29, 2018, p. 1-3.
Novo Nordisk Company announcement No. 51/2018, Oral semaglutide shows statiistically significantly greater reductions in HbA1c and weight compared to Victoza® and sitagliptin in the PIONEER 4 and 7 trials, www.novonordisk.com CVR No. 24256790, dated Jun. 20, 2018, p. 1-4.
Novo Nordisk Company announcement No. 53/2018, Oral semaglutide shows superior reductions in HbA1c and weight compared to sitagliptin in the long-term safety and efficacy trial, PIONEER 3, www.novonordisk.com CVR No. 24256790, dated Jun. 28, 2018, p. 1-3.
Novo Nordisk Company announcement No. 66/2018, Oral semaglutide provides superior HbA1c and weight reductions versus placebo in people with type 2 diabetes and renal impairment in the PIONEER 5 trial, www.novonordisk.com CVR No. 24256790, dated Aug. 20, 2018, p. 1-3.
Novo Nordisk Company announcement No. 74/2018, Oral semaglutide demonstrates greater reductions in HbA1c and body weight and comparable number of adverse events vs dulaglutide in Japanese people with type 2 diabetes, www.novonordisk.com CVR No. 24256790, dated Sep. 20, 2018, p. 1-3.
Novo Nordisk Company announcement No. 81/2018, Oral semaglutide demonstrates statistically significant reductions in HbA1c and body weight in people with long duration of type 2 diabetes treated with insulin, www.novonordisk.com CVR No. 24256790, dated Oct. 26, 2018, p. 1-3.
Novo Nordisk Company announcement No. 89/2018, Oral semaglutide demonstrates greater reductions in both HbA1c and body weight compared to Victoza® in Japanese people with type 2 diabetes, www.novonordisk.com CVR No. 24256790, dated Nov. 22, 2018, p. 1-2.
Novo Nordisk Company announcement No. 90/2018, Oral semaglutide demonstrates a favourable cardiovascular safety profile and a significant reduction in cardiovascular death and all-casue mortality in people with type 2 diabetes in the PIONEER 6 trial, www.novonordisk.com CVR No. 24256790, dated Nov. 23, 2018, p. 1-3.
Owens, D.R. et al., "Alternative routes of insulin delivery" Diabetic Medicine, 2003, vol. 20, pp. 886-898.
Thepharmaletter, "'8-10 years ahead' of field in oral delivery, senior execs say Novo is becoming a GLP-1 company" May 16, 2018, [cited Jan. 24, 2019] Available from: [https://www.thepharmaletter.

(56) References Cited

OTHER PUBLICATIONS com/article/8-10-years-ahead-of-field-in-oral-delivery-senior-execs-say-novo-nordisk-is-becoming-a-glp-1-company].
Watson, Estelle et al., "Population Pharmacokinetics of Liraglutide, a Once-Daily Human Glucagon-Like Peptide-1 Analog, in Healthy Volunteers and Subjects With Type 2 Diabetes, and Comparison to Twice-Daily Exenatide" J. Clin Pharmacology, 2010, vol. 50, pp. 886-894.
Antony J Hickey et al., Pharmaceutical Process Engineering (Second edition) (2010) p. 155-168.
Bruce J. Aungst, "Absorption enhancers: applications and advances," The MPS Journal, 2011, vol. 14, No. 1, pp. 10-18.
Diabetes Close Up, Baby Steps, Mar./Apr. 2011, No. 106, pp. 1-50.
Dilip M. Parikh, Handbook of Pharmaceutical Granulation Technology (Second edition) (2005), Process-related variables, pp. 7-19 and 311-331.
EP Application 12160743, filed Mar. 22, 2012.
EP Application 13153459, filed Jan. 31, 2013.
Full European prosecution file of EP 2 827 885 B1. Available at the EPO Register, https://register.epo.org/application?number=EP13709231&lng=en&tab=doclist, accessed May 31, 2019.
Dilip M Parikh, Handbook of Pharmaceutical Granulation Technology, Drugs and pharmaceutical sciences, Second Edition, 2005, vol. 154, Introduction, pp. 1-6.
Post-published details of trial NCT01037582 https://clinicaltrials.gov/ct2/show/NCT01037582, accessed May 31, 2019.
Published details of trial NCT01037582 (Dec. 2009) https://clinicaltrials.gov/ct2/history/NCT01037582?A=1&B=1&C=merged#StudyPageTop, accessed May 31, 2019.
R. F. Witkamp, "Current and Future Drug Targets in Weight Management," Pharm Res, 2011, vol. 28, pp. 1792-1818.
Salem et al., "Approaches to the pharmacological treatment of obesity," Expert Rev Clin Pharmacol, 2010, vol. 3, No. 1, pp. 73-88.
Barrera-Medrano et al., The Handbook of Powder Technology "Granulation", Chp. 25 granule structure, vol. 11, 2007, p. 1189-1212.
U.S. Appl. No. 61/748,840, filed Jan. 4, 2013.
Steinert et al., 2010, Am J Clin Nutr, vol. 92, pp. 810-817.
Nauck et al., 2012, Abstracts of the 48th European Association for the Study of Diabetes Annual Meeting of the EASD, Oct. 1-5, 2012, Berlin, Germany, Diabetologia, 2012, vol. 55, Suppl, S7.
Fonseca et al., "Efficacy and Safety of the Once-Daily GLP-1 Receptor Agonist Lixisenatide in Monotherapy," Diabetes Care, 2012, vol. 35, pp. 1225-1231.
Study NCT02014259, version 1, published Dec. 18, 2013, accessed Jun. 5, 2019.
"Drug Absorption, Distribution and Elimination; Pharmacokinetics" http://www.columbia.edu/itc/gsas/g9600/2004/GrazianoReadings/Drugabs.pdf, available since at least Apr. 24, 2006, accessed on Jun. 3, 2019.
"Standards of Medical Care in Diabetes-2010", Diabetes Care, vol. 33, supplement 1, Jan. 2010, pp. S11-S61.
Andrew D. Morris, MD, "Addressing dosing frequency in diabetes: a simple approach to improving adherence to therapy and clinical outcomes," The Diabetes Educator, 2003, vol. 29, No. 3, pp. 440-453.
B.J. Aungst, "Absorption Enhancers: Applications and Advances," The AAPS Journal, 2012, vol. 14, No. 1, pp. 10-18.
ClinicalTrials.gov archive: History of Changes for Study NCT01686945, trackchange of version of Apr. 15, 2013 (published Apr. 16, 2013) as compared to version of Sep. 13, 2012 (published Sep. 18, 2012).
ClinicalTrials.gov archive: History of Changes for Study NCT01923181 (NN9924-3790) (2019).
Clinicaltrials.gov, NCT01686945, page as viewed in Apr. 2013, https://clinicaltrials.gov/ct2/history/NCT01686945?A=5&B=5&C=merged#StudyPageTop.
Coskun et al., "LY3298176, a novel dual GIP and GLP-1 receptor agonist for the treatment of type 2 diabetes mellitus: From discovery to clinical proof of concept," Molecular Metabolism, 2018, vol. 18, pp. 3-14.
David J. Edmonds et al., "Oral GLP-1 Modulators for the Treatment of Diabetes". Annual Reports in Medicinal Chemistry, 2013, 1st edition, vol. 48, Chapter 9, pp. 119-130.
DJ. Birkett, "Pharmacokinetics made easy 11 Designing dose regimens," Australian Prescriber, 1996, vol. 19, No. 3, pp. 76-88.
E. Mutschler et al., Mutschler Arzneimittelwirkungen, Lehrbuch der Pharmakologie and Toxikologie, 8th edition 2001, pp. 48-51.
Emisphere Annual Report and Proxy 2013, publicly available at the latest on Apr. 17, 2014.
EU Clinical Trials Register Summary EudraCT No. 2012-004994-16 (NN9924-3790), published Jul. 30, 2013, accessed Jun. 7, 2019.
EU Leaflet of Linagliptin, 1st authorization in EU: Aug. 24, 2011 (p. 2, 3 & 13).
Sakr et al., "Oral Solid Dosage Forms," Remington, Essentials of Pharmaceutics, 1st Edition, Chapter 30, pp. 581-610 (2012).
Summary of Product Characteristics for Valtrex 500mg Tablets, 2019.
Teng et al., "Systematical approach of formulation and process development using roller compaction," European Journal of Pharmaceutics and Biopharmaceutics, 2009, vol. 73, pp. 219-229.
The Handbook of Pharmaceutical Granulation Technology, Chapters 2, 8, and 9, 2010.
Uros Markoja, Semaglutide-Experiment report for opposition against EP2827845B1, dated Sep. 24, 2019, pp. 1-6.
Valtrex prescribing information, Oct. 2007.
Venables et al., "Powder Mixing," Drug Development and Industrial Pharmacy, 2001, vol. 27, No. 7, pp. 599-612.
Tyagi et al., "Oral peptide delivery: Translational challenges due to physiological effects," J. Controlled Release, 2018, vol. 287, pp. 167-176.
Dahlgren et al., "Intestinal absorption-modifying excipients: A current update on preclinical in vivo evaluations," European J. of Pharm. and Biopharmaceutics, 2019, vol. 142, pp. 411-420.
Figures presenting plasma concentration, described in EU Patent No. 2991671, dated Aug. 15, 2018.
FDA News Release, "FDA approved first oral GLP-1 treatment for type 2 diabetes," Sep. 20, 2019.
Carly Helfand, "Novo Nordisk wins FDA green light for "holy grail" diabetes drug Rybelsus," Fierce Pharma, Sep. 20, 2019, https://www.fiercepharma.com/pharma/novo-nordisk-wins-fda-green-light-for-holy-grail-oral-semaglulide, accessed Oct. 4, 2019.
Full European prosecution file of EP 2 827 885 B1. Published Jan. 28, 2015, Available at the EPO Register, https://register.epo.org/application?number=EP13709231&lng=en&tab=doclist, accessed May 31, 2019.
Post-published details of trial NCT01037582. First posted Dec. 23, 2009 https://clinicaltrials.gov/ct2/show/NCT01037582, accessed May 31, 2019.
Published details of trial NCT01037582 First Version Dec. 21, 2009 https://clinicaltrials.gov/ct2/history/NCT01037582?A=1&B=1&C=merged#StudyPageTop, accessed May 31, 2019.
Table summarizing the components of the tablet compositions B to F, described in EP Patent No. 2827885, dated Aug. 15, 2018.
Schematic drawing of tablets E and F described in EP Patent. No. 2827885, dated Aug. 15, 2018.
Overview of claim 1 of the main and auxiliary requests, European Application No. EP2651398, filed May 14, 2013.
EU Leaflet of Linagliptin-Metformin, 1st authorization in EU:Jul. 20, 2012 (p. 2, 3 & 21).
EU Leaflet of Metformin, 1st authorization in EU: Jul. 31, 2001 (p. 1, 2 & 11).
EU Leaflet of Saxagliptin, 1st authorization in EU: Oct. 1, 2009 (p. 1 & 18).
EU Leaflet of Sitagliptin, 1st authorization in EU: Mar. 21, 2007 (p. 2, 3 & 16).
EU Leaflet of Sitagliptin-Metformin, 1st authorization in EU: Jul. 16, 2008 (p. 2, 3 & 20).
EU Leaflet of Vildagliptin, 1st authorization in EU: Sep. 26, 2007 (p. 2, 3 & 18).
EU Leaflet of Vildagliptin-Metformin, 1st authorization in EU: Nov. 14, 2007 (p. 2, 3 & 21),
European Patent Application 13166205, filed May 2, 2013.

(56) References Cited

OTHER PUBLICATIONS

Geiser et al., "Clinical Pharmacokinetics of Dulaglutide in Patients with Type 2 Diabetes: Analyses of Data from Clinical Trials". Clinical Pharmacokinetics, 2016, vol. 55, pp. 625-634.
Granhall et al, Safety and Pharmacokinetics of Single and Multiple Ascending Doses of the Novel Oral Human GLP-1 Analogue, Oral Semaglutide, in Healthy Subjects and Subjects with Type 2 Diabetes, Clinical Pharmacokinetics, Dec. 2018.
Leon Shargel, Applied Biopharmaceutics and Pharmacokinetics, 6th edition, 2012, Chapter 8, Multiple-Dosage regimens, pp. 153-175.
Linda Felton, Remington, Essentials of Pharmaceutics, 2012, Chapter 37, pp. 708-709 and 712-713.
M. Gonzalez Brao, "48th Annual Meeting of the European Association for the Study of Diabetes (EASD)," Drugs of the Future, 2012, vol. 37, No. 12, pp. 871-878.
Malcolm Rowland et al., "Clinical Pharmacokinetics and Pharmacodynamics: Concepts and Applications," Chapter 11—Multiple-Dose Regimens (pp. 293-329); 4th ed.; Philadelphia: Wolters Kluwer Health/Lippincott William & Wilkins, 2011.
Product details regarding David J. Edmonds et al., "Oral GLP-1 Modulators for the Treatment of Diabetes". Annual Reports in Medicinal Chemistry (2013), 1st edition, vol. 48, chapter 9, pp. 119-130, from amazon.com, accessed on May 3, 2019.
Prosecution file of EP2991671B1, available at the EPO Register, the pdf is not attached. https://register.epo.org/application?number=EP14721834&lng=en&tab=doclist, accessed Jun. 14, 2019.
Quianzon et al., "Lixisenatide—Once daily glucagon-like peptide-1 receptor agonist in the management of type 2 diabetes," 2011, US Endocrinology, Diabetes Management, vol. 7, No. 2, pp. 104-109.
Rosenstock et al., "Potential of albiglutide, a long-acting GLP-1 receptor agonist, in type 2 diabetes: a randomized controlled trial exploring weekly, biweekly, and monthly dosing". Diabetes Care, 2009, vol. 32, No. 10, pp. 1880-1886.
S. Dhillon et al., "Basic Pharmacokinetics," Clinical Pharmacokinetics, 2006, Pharmaceutical Press, London; Chapter 1, pp. 1-44.
Sarfaraz K. Niazi, Handbook of Bioequivalence Testing, 2007, p. 13-15.
Schematic overview of sequences and plasma half-life in humans of "GLP-1 peptides" (2019).
Sisson, "Liraglutide: clinical pharmacology and considerations for therapy," Pharmacotherapy, 2011, vol. 31, pp. 896-911.
Study NCT01686945, version 1, published Sep. 18, 2012, accessed Jun. 6, 2019.
Study NCT01866748, version 1, published May 31, 2013, accessed Jun. 6, 2019.
Study NCT01923181, version 1, published Aug. 15, 2013, accessed Jun. 5, 2019.
Submission of Novo Nordisk dated Feb. 15, 2019 in response to oppositions against EP2651398B1.
Runge et al, "Crystal Structure of the Ligand-Bound Glucagon-Like Peptide-1 Receptor Extracellular Domain," J Biol Chem 2008, vol. 283, No. 17, p. 11340-11347.
Adelhorst, K et al Journal of Biological Chemistry Structure Activity Studies of GLP-1 1994 269 9 6275-6278.
Knudsen, L.B. Journal of Medicinal Chemistry Glucagon-Like Peptide-1: The Basis of a New Glass of Treatment for Type 2 Diabetes 2004 47 17 4128-4134.
Leger et al., "Identification of CJC-1131-Albumin Bioconjugate as a Stable and Bioactive GLP-1 (7-36) Analog," Bioorganic and Medicinal Chemistry Letters, vol. 14, pp. 4395-4398 (2004).
Pan, 2006 Journal of Biological Chemistry vol. 281 pp. 12506-12515.
The Medical Dictionary Online. http://cancerweb.ncl.ac.uk/omd/about.html. 2005.
Nauck, M.A. Regulatory Peptides. "Glucagon-Like Peptide 1 and its Derivatives in the Treatment of Diabetes." 2005. vol. 128(2). pp. 135-148.
David M. Irwin, Trout and chicken Proglucagon: Alternative Splicing Generates mRNA Transcripts Encoding Glucagon-Like Peptide 2, Molecular Endocrinology, 1995, vol. 9 No. 3, 267-277.
"Formulation and Analytical Development for Low-Dose Oral Drug Products," Wiley, 2009, p. 194.
"International Nonproprietary Names for Pharmaceutical Substances (INN)," Who Drug Information, 2009, vol. 23, No. 2, p. 129.
"Sodium Lauryl Sulfate," Handbook of Pharmaceutical Excipients, 2009, 6th Edition, pp. 651-653.
Ajaz S. Hussain, "A Collaborative Search for Efficient Methods of Ensuring Unchanged Product Quality and Performance During Scale-Up of Immediate-Release Solid Oral Dosage Forms," Pharmaceutical Process Scale-Up, 2002, 1st Edition, Chapter 11, pp. 325-352.
Bai et al., Excipient Development for Pharmaceutical, Biotechnology, and Drug Delivery Systems, 2006, Chapter 12, pp. 181-185
C. M. Keck et al., "Moderne Pharmazeutische Technologie— Lehbuch fur Studierende," 1. Auflage (2009), Kapitel 1.2 H. J. Ji.inginger, "Delivery Systeme fur die perorale Applikation van Peptiden," pp. 1-14.
European Application No. 12172739.0, filed Jun. 20, 2012.
File History of European Patent 2827845, filed Mar. 15, 2013.
File History of U.S. Appl. No. 61/662,456, filed Jun. 21, 2012.
Handbook of Pharmaceutical Excipients, 6th Edition, 2009, pp. 404-407 and 651-653.
History of changes for clinical trial NCT01037582, from Mar. 17, 2011, https://clinicaltrials.gov/ct2/history/NCT01037582?A=5&C=merged#StudyPageTop.
Kikuta et al., "Effect of Mixing Time on the Lubricating Properties of Magnesium Stearate and the Final Characteristics of the Compressed Tablets," Drug Development and Industrial Pharmacy, 1994, vol. 20, No. 3, pp. 343-355.
Kusher IV et al., "Scale-up model describing the impact of lubrication on tablet tensile strength," International Journal of Pharmaceutics, vol. 399, Nos. 1-2, pp. 19-30 (2010).
Lieberman et al., Pharmaceutical Dosage Forms: Tablets, 2nd Edition, 1989, Chapter 5, pp. 247-284.
Parikh, Handbook of Pharmaceutical Granulation Technology, 3rd Edition, 2010, Informa Healthcare, pp. 2-3.
Remington, The Science and Practice of Pharmacy, 21st Edition, 2005, Lippincott, Williams & Wilkins, pp. 677, 892-893, 896, and 1040.
Banakar et al, Critical Considerations in Pharmaceutical Bioequivalence Testing, Journal of Pharmacy of University of Marmara, 1995, vol. 11 Nos. 1-2, pp. 55-80.
Emisphere Technologies, Inc., Form 10-K, 2013 Annual Report, Published Mar. 31, 2014.
American Veterinary Medical Association, "The Veterinarian-Client-Patient Relationship (VCPR)," https://www.avma.org/policies/veterinarian-client-patient-relationship, accessed Mar. 11, 2020.
GenScript, "Peptide YY (PYY) (3-36), human," https://www.genscript.com/peptide/RP10354-Peptide_YY_PYY_3_36_human.html, accessed Jan. 27, 2020.
National Institute of Diabetes and Digestive and Kidney Diseases,"Prescription Medications to Treat Overweight and Obesity," Jul. 2016, 10 pages, retrieved on Apr. 13, 2020, URL: https://www.niddk.nih.gov/health-information/weight-management/prescription-medications-treat-overweight-obesity.
W.K. Sietsema, "The absolute oral bioavailability of selected drugs." Mar. 1989, International Journal of Clinical Pharmacology, Therapy and Toxicology, vol. 27, No. 4, pp. 179-211.
Declaration of Doctor Peter Rue, for EP2827885 dated Jul. 29, 2020.
Declaration of Professor Leon Aarons for EP2827885 dated Jul. 29 2020.
Shajahan et al., A flexible technology for modified-release drugs: Multiple-unit pellet system (MUPS) May 2009, Journal of Controlled Release, vol. 147, No. 1, pp. 2-16.
Physicians' Desk Reference, 54th Edition, 2000, p. 1291.
Physicians' Desk Reference, 63rd Edition, 2009, p. 1638.
Arbit et al. "Oral heparin: status review". Thrombosis J, May 2006, vol. 4, No. 6, pp. 1-7.

(56) References Cited

OTHER PUBLICATIONS

Emisphere Announces License Agreement With Novo Nordisk to Develop Oral Formulation of GLP-1 Receptor Agonists for Diabetes, Jun. 23, 2008 retrieved from https://www.biospace.com/article/releases/emisphere-technologies-inc-announces-license-agreement-with-novo-nordisk-inc-to-develop-oral-formulation-of-glp-1-receptor-agonists-for-diabetes-/, 5 pages, retrieved on Dec. 16, 2020.
European Medicines Agency, Rybelsus EPAR Public Assessment Report, Jan. 30, 2020, pp. 1-152, p. 72.
Notice of Opposition by Galenicum, filed Dec. 9, 2020 in European Patent 3326620.
Notice of Opposition by Hexal Ag, filed Dec. 8, 2020 in European Patent 3326620.
Novo Nordisk starts phase 1 trial with long-acting oral GLP-1 analogue, Jan. 13, 2010, 2 pages retrieved from https://pipelinereview.com/index.php/2010011332046/Small-Molecules/Novo-Nordisk-starts-phase-1-trial-with-long-acting-oral-GLP-1-analogue.html, retrieved on Dec. 16, 2020.
Novo Nordisk, "Novo Nordisk to acquire Emisphere Technologies and obtain ownership of the Eligen® SNAC oral Delivery technology", Nov. 6, 2020 retrieved from <https://www.novonordisk.com/content/nncorp/global/en/news-and-mediai/ews-and-ir-materials/news-details.htm?id=33374>, 3 pages retrieved on Dec. 16, 2020.
Notice of Opposition by Teva filed Dec. 4, 2020 in European Patent 3326620.

* cited by examiner

SEQUENCE LISTING

```
<160> NUMBER OF SEQ ID NOS: 36

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 28
<212> TYPE: PRT
<213> ORGANISM: Artificial Sequence
<220> FEATURE:
<223> OTHER INFORMATION: Synthetic

<400> SEQUENCE: 2

His Ala Glu Gly Thr Phe Thr Ser Asp Val Ser Ser Tyr Leu Glu Lys
1               5                   10                  15

Gln Ala Ala Arg Lys Phe Ile Glu Trp Leu Val Gly
            20                  25

<210> SEQ ID NO 3
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = L-histidine, imidazopropionyl,
      alpha-hydroxy-histidine, D-histidine, desamino-histidine,
      2-amino-histidine, beta-hydroxy-histidine, homohistidine,
      Nalpha-acetyl-histidine, Nalpha-formyl-histidine,
      alpha-fluoromethyl-histidine
<220> FEATURE:
<221> NAME/KEY: MISC_FEATURE
<222> LOCATION: (1)..(1)
<223> OTHER INFORMATION: Xaa = alpha-methyl-histidine, 3-pyridylalanine,
      2-pyridylalanine, or 4-pyridylalanine
```

```
<220> FEATURE:
<221> NAME/KEY: MISC_FEATURE
<222> LOCATION: (2)..(2)
<223> OTHER INFORMATION: Xaa = Ala, Gly, Val, Leu, Ile, Thr, Ser, Lys,
      Aib, (1-aminocyclopropyl) carboxylic acid, (1-aminocyclobutyl)
      carboxylic acid, (1-aminocyclopentyl) carboxylic acid,
      (1-aminocyclohexyl) carboxylic acid, (1-aminocycloheptyl)
<220> FEATURE:
<221> NAME/KEY: MISC_FEATURE
<222> LOCATION: (6)..(6)
<223> OTHER INFORMATION: Xaa = Lys or Phe
<220> FEATURE:
<221> NAME/KEY: MISC_FEATURE
<222> LOCATION: (10)..(10)
<223> OTHER INFORMATION: Xaa = Val or Leu
<220> FEATURE:
<221> NAME/KEY: MISC_FEATURE
<222> LOCATION: (12)..(12)
<223> OTHER INFORMATION: Xaa = Ser, Arg, Asn, Gln, or Glu
<220> FEATURE:
<221> NAME/KEY: MISC_FEATURE
<222> LOCATION: (13)..(13)
<223> OTHER INFORMATION: Xaa = Tyr or Gln
<220> FEATURE:
<221> NAME/KEY: MISC_FEATURE
<222> LOCATION: (14)..(14)
<223> OTHER INFORMATION: Xaa = Leu, Lys, or Met
<220> FEATURE:
<221> NAME/KEY: MISC_FEATURE
<222> LOCATION: (16)..(16)
<223> OTHER INFORMATION: Xaa = Gly, Glu, Lys, or Aib
<220> FEATURE:
<221> NAME/KEY: MISC_FEATURE
<222> LOCATION: (17)..(17)
<223> OTHER INFORMATION: Xaa = Gln, Glu, or Arg
<220> FEATURE:
<221> NAME/KEY: MISC_FEATURE
<222> LOCATION: (18)..(18)
<223> OTHER INFORMATION: Xaa = Ala or Lys
<220> FEATURE:
<221> NAME/KEY: MISC_FEATURE
<222> LOCATION: (19)..(19)
<223> OTHER INFORMATION: Xaa = Ala or Val
<220> FEATURE:
<221> NAME/KEY: MISC_FEATURE
<222> LOCATION: (20)..(20)
<223> OTHER INFORMATION: Xaa = Val, His, or Arg
<220> FEATURE:
<221> NAME/KEY: MISC_FEATURE
<222> LOCATION: (24)..(24)
<223> OTHER INFORMATION: Xaa = Ala, Glu, or Arg
<220> FEATURE:
<221> NAME/KEY: MISC_FEATURE
<222> LOCATION: (25)..(25)
<223> OTHER INFORMATION: Xaa = Trp or His
<220> FEATURE:
<221> NAME/KEY: MISC_FEATURE
<222> LOCATION: (28)..(28)
<223> OTHER INFORMATION: Xaa = Glu, Asn, Gly, Gln, or Arg
<220> FEATURE:
<221> NAME/KEY: MISC_FEATURE
<222> LOCATION: (29)..(29)
<223> OTHER INFORMATION: Xaa = Gly, Aib, or absent
<220> FEATURE:
<221> NAME/KEY: MISC_FEATURE
<222> LOCATION: (30)..(30)
<223> OTHER INFORMATION: Xaa = Arg, Gly, Lys, or absent
<220> FEATURE:
<221> NAME/KEY: MISC_FEATURE
<222> LOCATION: (31)..(31)
<223> OTHER INFORMATION: Xaa = Gly, Ala, Glu, Pro, Lys, Arg, or absent
<220> FEATURE:
<221> NAME/KEY: MISC_FEATURE
<222> LOCATION: (32)..(32)
<223> OTHER INFORMATION: Xaa = Ser, Gly, Ala, Glu, Gln, Pro, Arg, or
      absent
<220> FEATURE:
<221> NAME/KEY: MISC_FEATURE
<222> LOCATION: (33)..(33)
```

<223> OTHER INFORMATION: Xaa = Gly or absent

<400> SEQUENCE: 3

Xaa Xaa Glu Gly Thr Xaa Thr Ser Asp Xaa Ser Xaa Xaa Xaa Glu Xaa
1               5                   10                  15

Xaa Xaa Xaa Xaa Lys Phe Ile Xaa Xaa Leu Val Xaa Xaa Xaa Xaa
            20                  25                  30

Xaa

<210> SEQ ID NO 4
<211> LENGTH: 31
<212> TYPE: PRT
<213> ORGANISM: Artificial Sequence
<220> FEATURE:
<223> OTHER INFORMATION: Synthetic

<400> SEQUENCE: 4

His Ala Glu Gly Thr Phe Thr Ser Asp Val Ser Ser Tyr Leu Glu Glu
1               5                   10                  15

Gln Ala Ala Arg Lys Phe Ile Ala Trp Leu Val Arg Gly Arg Lys
            20                  25                  30

<210> SEQ ID NO 5
<211> LENGTH: 33
<212> TYPE: PRT
<213> ORGANISM: Artificial Sequence
<220> FEATURE:
<223> OTHER INFORMATION: Synthetic

<400> SEQUENCE: 5

His Ala Glu Gly Thr Phe Thr Ser Asp Val Ser Ser Tyr Leu Glu Glu
1               5                   10                  15

Gln Ala Ala Arg Lys Phe Ile Glu Trp Leu Val Arg Gly Lys Gly Glu
            20                  25                  30

Gly

<210> SEQ ID NO 6
<211> LENGTH: 30
<212> TYPE: PRT
<213> ORGANISM: Artificial Sequence
<220> FEATURE:
<223> OTHER INFORMATION: Synthetic

<400> SEQUENCE: 6

His Ala Glu Gly Thr Phe Thr Ser Asp Val Ser Ser Tyr Leu Glu Glu
1               5                   10                  15

Gln Ala Ala Arg Lys Phe Ile Ala Trp Leu Val Arg Gly Lys
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Synthetic

<400> SEQUENCE: 7

His Ala Glu Gly Thr Phe Thr Ser Asp Val Ser Ser Tyr Leu Glu Glu
1               5                   10                  15

Gln Ala Val Arg Lys Phe Ile Ala Trp Leu Val Arg Gly Arg Lys
            20                  25                  30

```
<210> SEQ ID NO 8
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib

<400> SEQUENCE: 8

His Xaa Glu Gly Thr Phe Thr Ser Asp Val Ser Ser Tyr Lys Glu Glu
1               5                   10                  15

Gln Ala Ala Arg Lys Phe Ile Glu Trp Leu Val Gly
            20                  25

<210> SEQ ID NO 9
<211> LENGTH: 32
<212> TYPE: PRT
<213> ORGANISM: Artificial Sequence
<220> FEATURE:
<223> OTHER INFORMATION: Synthetic

<400> SEQUENCE: 9

His Ala Glu Gly Thr Phe Thr Ser Asp Val Ser Ser Tyr Leu Glu Gly
1               5                   10                  15

Gln Ala Ala Arg Lys Phe Ile Glu Trp Leu Val Arg Gly Lys Gly Glu
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib

<400> SEQUENCE: 10

His Xaa Glu Gly Thr Phe Thr Ser Asp Val Ser Ser Tyr Leu Glu Lys
1               5                   10                  15

Gln Ala Val Arg Lys Phe Ile Ala His Leu Val Arg Gly Arg Gly
            20                  25                  30

<210> SEQ ID NO 11
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib

<400> SEQUENCE: 11

His Xaa Glu Gly Thr Phe Thr Ser Asp Val Ser Ser Tyr Leu Glu Lys
1               5                   10                  15

Gln Ala Val Arg Lys Phe Ile Ala Trp Leu Val Arg
            20                  25

<210> SEQ ID NO 12
<211> LENGTH: 29
<212> TYPE: PRT
```

<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib

<400> SEQUENCE: 12

His Xaa Glu Gly Thr Phe Thr Ser Asp Val Ser Ser Tyr Leu Glu Lys
1               5                   10                  15

Gln Ala Val Arg Lys Phe Ile Ala Trp Leu Val Arg Gly
            20                  25

<210> SEQ ID NO 13
<211> LENGTH: 32
<212> TYPE: PRT
<213> ORGANISM: Artificial Sequence
<220> FEATURE:
<223> OTHER INFORMATION: Synthetic

<400> SEQUENCE: 13

His Ala Glu Gly Thr Phe Thr Ser Asp Val Ser Ser Tyr Leu Glu Gly
1               5                   10                  15

Gln Ala Ala His Lys Phe Ile Glu Trp Leu Val Arg Gly Lys Gly Glu
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Synthetic

<400> SEQUENCE: 14

His Ala Glu Gly Thr Phe Thr Ser Asp Val Ser Ser Tyr Leu Glu Lys
1               5                   10                  15

Gln Ala Val Arg Lys Phe Ile Glu Trp Leu Val Gln Gly Arg Gly
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Synthetic

<400> SEQUENCE: 15

His Ala Glu Gly Thr Phe Thr Ser Asp Val Ser Ser Tyr Leu Glu Gly
1               5                   10                  15

Gln Ala Val Arg Lys Phe Ile Glu Trp Leu Val Arg Gly Lys Gly Gln
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: Synthetic

<400> SEQUENCE: 16

His Ala Glu Gly Thr Phe Thr Ser Asp Val Ser Ser Tyr Leu Glu Gly
1               5                   10                  15

Gln Ala Val Arg Lys Phe Ile Glu Trp Leu Val Gln Gly Lys Gly Glu
            20                  25                  30

<210> SEQ ID NO 17
<211> LENGTH: 28
<212> TYPE: PRT
<213> ORGANISM: Artificial Sequence
<220> FEATURE:
<223> OTHER INFORMATION: Synthetic

<400> SEQUENCE: 17

His Ala Glu Gly Thr Phe Thr Ser Asp Val Ser Ser Tyr Leu Glu Lys
1               5                   10                  15

Gln Ala Ala Arg Lys Phe Ile Ala His Leu Val Gly
            20                  25

<210> SEQ ID NO 18
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib

<400> SEQUENCE: 18

His Xaa Glu Gly Thr Phe Thr Ser Asp Val Ser Ser Tyr Leu Glu Gly
1               5                   10                  15

Gln Ala Val Arg Lys Phe Ile Ala His Leu Val Gln Gly Arg Lys
            20                  25                  30

<210> SEQ ID NO 19
<211> LENGTH: 31
<212> TYPE: PRT
<213> ORGANISM: Artificial Sequence
<220> FEATURE:
<223> OTHER INFORMATION: Synthetic

<400> SEQUENCE: 19

His Ala Glu Gly Thr Phe Thr Ser Asp Val Ser Ser Tyr Leu Glu Gly
1               5                   10                  15

Gln Ala Val Arg Lys Phe Ile Ala His Leu Val Gln Gly Arg Lys
            20                  25                  30

<210> SEQ ID NO 20
<211> LENGTH: 31
<212> TYPE: PRT
<213> ORGANISM: Artificial Sequence
<220> FEATURE:
<223> OTHER INFORMATION: Synthetic

<400> SEQUENCE: 20

His Ala Glu Gly Thr Phe Thr Ser Asp Val Ser Ser Tyr Leu Glu Glu
1               5                   10                  15

Glu Ala Val Arg Lys Phe Ile Ala His Leu Val Gln Gly Arg Lys
            20                  25                  30

<210> SEQ ID NO 21
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)

<223> OTHER INFORMATION: Xaa = Aib

<400> SEQUENCE: 21

His Xaa Glu Gly Thr Lys Thr Ser Asp Val Ser Ser Tyr Leu Glu Glu
1               5                   10                  15

Gln Ala Ala Arg Lys Phe Ile Ala His Leu Val Gln Gly Arg Gly
            20                  25                  30

<210> SEQ ID NO 22
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib

<400> SEQUENCE: 22

His Xaa Glu Gly Thr Phe Thr Ser Asp Val Ser Ser Tyr Leu Glu Lys
1               5                   10                  15

Gln Ala Ala Arg Lys Phe Ile Ala His Leu Val Gly
            20                  25

<210> SEQ ID NO 23
<211> LENGTH: 31
<212> TYPE: PRT
<213> ORGANISM: Artificial Sequence
<220> FEATURE:
<223> OTHER INFORMATION: Synthetic

<400> SEQUENCE: 23

His Ala Glu Gly Thr Phe Thr Ser Asp Val Ser Ser Tyr Leu Glu Lys
1               5                   10                  15

Gln Ala Val Arg Lys Phe Ile Glu Trp Leu Val Gln Gly Arg Gly
            20                  25                  30

<210> SEQ ID NO 24
<211> LENGTH: 32
<212> TYPE: PRT
<213> ORGANISM: Artificial Sequence
<220> FEATURE:
<223> OTHER INFORMATION: Synthetic

<400> SEQUENCE: 24

His Ala Glu Gly Thr Phe Thr Ser Asp Val Ser Ser Tyr Leu Glu Glu
1               5                   10                  15

Gln Ala Ala His Lys Phe Ile Glu Trp Leu Val Arg Gly Lys Gly Glu
            20                  25                  30

<210> SEQ ID NO 25
<211> LENGTH: 28
<212> TYPE: PRT
<213> ORGANISM: Artificial Sequence
<220> FEATURE:
<223> OTHER INFORMATION: Synthetic

<400> SEQUENCE: 25

His Ala Glu Gly Thr Phe Thr Ser Asp Val Ser Ser Tyr Leu Glu Glu
1               5                   10                  15

Gln Lys Ala Arg Lys Phe Ile Ala His Leu Val Gly
            20                  25

```
<210> SEQ ID NO 26
<211> LENGTH: 31
<212> TYPE: PRT
<213> ORGANISM: Artificial Sequence
<220> FEATURE:
<223> OTHER INFORMATION: Synthetic

<400> SEQUENCE: 26

His Ala Glu Gly Thr Phe Thr Ser Asp Val Ser Ser Tyr Leu Glu Gly
1               5                   10                  15
Gln Ala Val Arg Lys Phe Ile Ala Trp Leu Val Gln Gly Lys Gly
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Synthetic

<400> SEQUENCE: 27

His Ala Glu Gly Thr Phe Thr Ser Asp Val Ser Ser Tyr Leu Glu Glu
1               5                   10                  15
Gln Lys Val Arg Lys Phe Ile Ala His Leu Val Arg Gly Arg Gly
            20                  25                  30

<210> SEQ ID NO 28
<211> LENGTH: 28
<212> TYPE: PRT
<213> ORGANISM: Artificial Sequence
<220> FEATURE:
<223> OTHER INFORMATION: Synthetic

<400> SEQUENCE: 28

His Ala Glu Gly Thr Phe Thr Ser Asp Val Ser Ser Tyr Leu Glu Glu
1               5                   10                  15
Gln Lys Ala Arg Lys Phe Ile Ala His Leu Val Gly
            20                  25

<210> SEQ ID NO 29
<211> LENGTH: 31
<212> TYPE: PRT
<213> ORGANISM: Artificial Sequence
<220> FEATURE:
<223> OTHER INFORMATION: Synthetic

<400> SEQUENCE: 29

His Ala Glu Gly Thr Phe Thr Ser Asp Val Ser Ser Tyr Leu Glu Gly
1               5                   10                  15
Gln Ala Val Arg Lys Phe Ile Ala Trp Leu Val Gln Gly Lys Gly
            20                  25                  30

<210> SEQ ID NO 30
<211> LENGTH: 28
<212> TYPE: PRT
<213> ORGANISM: Artificial Sequence
<220> FEATURE:
<223> OTHER INFORMATION: Snythetic

<400> SEQUENCE: 30

His Ala Glu Gly Thr Phe Thr Ser Asp Val Ser Ser Tyr Leu Glu Glu
1               5                   10                  15
Gln Lys Val Arg Lys Phe Ile Ala Trp Leu Val Gly
            20                  25
```

<210> SEQ ID NO 31
<211> LENGTH: 31
<212> TYPE: PRT
<213> ORGANISM: Artificial Sequence
<220> FEATURE:
<223> OTHER INFORMATION: Syntetic

<400> SEQUENCE: 31

His Ala Glu Gly Thr Phe Thr Ser Asp Val Ser Ser Tyr Leu Glu Glu
1               5                   10                  15

Gln Lys Val Arg Lys Phe Ile Ala Trp Leu Val Arg Gly Arg Gly
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib

<400> SEQUENCE: 32

His Xaa Glu Gly Thr Phe Thr Ser Asp Val Ser Ser Tyr Leu Glu Glu
1               5                   10                  15

Gln Lys Val Arg Lys Phe Ile Ala Trp Leu Val Arg Gly Arg Gly
            20                  25                  30

<210> SEQ ID NO 33
<211> LENGTH: 28
<212> TYPE: PRT
<213> ORGANISM: Artificial Sequence
<220> FEATURE:
<223> OTHER INFORMATION: Synthetic

<400> SEQUENCE: 33

His Ala Glu Gly Thr Phe Thr Ser Asp Val Ser Ser Tyr Leu Glu Glu
1               5                   10                  15

Gln Lys Val Arg Lys Phe Ile Ala Trp Leu Val Gly
            20                  25

<210> SEQ ID NO 34
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib

<400> SEQUENCE: 34

His Xaa Glu Gly Thr Phe Thr Ser Asp Val Ser Ser Tyr Leu Glu Glu
1               5                   10                  15

Gln Ala Ala Arg Lys Phe Ile Glu Trp Leu Val Arg Gly Lys Gly Glu
            20                  25                  30

Gly

<210> SEQ ID NO 35
<211> LENGTH: 33
<212> TYPE: PRT
<213> ORGANISM: Artificial Sequence

```
<220> FEATURE:
<223> OTHER INFORMATION: Synthetic

<400> SEQUENCE: 35

His Ala Glu Gly Thr Phe Thr Ser Asp Val Ser Ser Tyr Leu Glu Glu
1               5                   10                  15

Gln Ala Ala Arg Lys Phe Ile Glu Trp Leu Val Arg Gly Lys Gly Glu
            20                  25                  30

Gly

<210> SEQ ID NO 36
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib

<400> SEQUENCE: 36

His Xaa Glu Gly Thr Phe Thr Ser Asp Val Ser Ser Tyr Leu Glu Glu
1               5                   10                  15

Gln Lys Val Arg Lys Phe Ile Ala His Leu Val Gln Gly Arg Gly
            20                  25                  30
```

DOUBLE-ACYLATED GLP-1 DERIVATIVES

REFERENCE TO RELATED APPLICATIONS

This application is a continuation of U.S. application Ser. No. 15/346,323, filed Nov. 8, 2016, which is a continuation of U.S. application Ser. No. 14/961,064, filed Dec. 7, 2015 (now U.S. Pat. No. 9,527,900, issued Dec. 27, 2016), which is a continuation of U.S. application Ser. No. 14/009,902, filed Dec. 4, 2013 (now U.S. Pat. No. 9,266,940, issued Feb. 23, 2016), which is a 35 U.S.C. § 371 National Stage application of International Application PCT/EP2012/056642 (WO 2012/140117), filed Apr. 12, 2012, which claimed priority of European Patent Application 11162087.8, filed Apr. 12, 2011; and under 35 U.S.C. § 119 of U.S. Provisional Application 61/474,913, filed Apr. 13, 2011; the contents of all above-named applications are incorporated herein by reference.

INCORPORATION-BY-REFERENCE OF THE SEQUENCE LISTING

The instant application contains a Sequence Listing which has been submitted in ASCII format via EFS-Web and is hereby incorporated by reference in its entirety. Said ASCII copy, created on Mar. 28, 2018 and named 8326US04_SeqList.txt, and modified on Jul. 29, 2019 and renamed 8326US04_Seq_List_ST25, is 17 kilobytes in size.

FIELD OF THE INVENTION

The present invention relates to derivatives of analogues of Glucagon-Like Peptide 1 (GLP-1), more in particular to double-acylated GLP-1 derivatives acylated at $K^{27}$ and at another K residue of the peptide, and their pharmaceutical use.

BACKGROUND

Journal of Medicinal Chemistry (2000), vol. 43, no. 9, p. 1664-1669 discloses derivatives of GLP-1(7-37) including some that are double-acylated.

WO 98/08871 A1 discloses a number of GLP-1 derivatives including some that are double-acylated. Liraglutide, a mono-acylated GLP-1 derivative for once daily administration which is marketed as of 2009 by Novo Nordisk A/S, is also disclosed in WO 98/08871 A1 (Example 37).

WO 99/43706 A1 discloses a number of mono- and double-acylated GLP-1 derivatives including some $K^{27,26}$ and $K^{27,34}$ derivatives.

WO 06/097537 A2 discloses a number of GLP-1 derivatives including semaglutide (Example 4), a mono-acylated GLP-1 derivative for once weekly administration which is under development by Novo Nordisk A/S.

Angewandte Chemie International Edition 2008, vol. 47, p. 3196-3201 reports the discovery and characterisation of a class of 4-(p-iodophenyl)butyric acid derivatives which purportedly display a stable noncovalent binding interaction with both mouse serum albumin (MSA) and human serum albumin (HSA).

SUMMARY

The invention relates to derivatives of GLP-1 peptides.

The derivatives are acylated at a lysine substituted for the native glutamic acid at position 27, as well as at another lysine residue. The side chains are albumin binding moieties. They comprise a protracting moiety, preferably selected from fatty diacids, and fatty acids with a distal phenoxy group, all optionally substituted. A carboxy group of the fatty acid or fatty diacid is acylated, optionally via a linker, to a lysine residue of the GLP-1 peptide, preferably at the epsilon-amino group thereof.

The GLP-1 peptide may be an analogue of GLP-1(7-37) (SEQ ID NO: 1) having a total of up to ten amino acid differences as compared to GLP-1(7-37), for example one or more additions, one or more deletions, and/or one or more substitutions.

More in particular, the invention relates to a derivative of a GLP-1 analogue, which analogue comprises a first K residue at a position corresponding to position 27 of GLP-1(7-37) (SEQ ID NO: 1); a second K residue at a position corresponding to position T of GLP-1(7-37), where T is an integer in the range of 7-37 except 18 and 27; and a maximum of ten amino acid changes as compared to GLP-1(7-37); wherein the first K residue is designated $K^{27}$, and the second K residue is designated $K^T$; which derivative comprises two albumin binding moieties attached to $K^{27}$ and $K^T$, respectively, via a linker, wherein each albumin binding moiety comprises a protracting moiety selected from HOOC—$(CH_2)_x$—CO—* and HOOC—$C_6H_4$—O—$(CH_2)_y$—CO—*, in which x is an integer in the range of 6-16, and y is an integer in the range of 3-17, and wherein the linker comprises a linker element of formula Chem. 5:

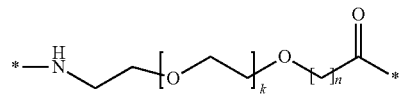

wherein k is an integer in the range of 1-5, and n is an integer in the range of 1-5; or a pharmaceutically acceptable salt, amide, or ester thereof.

The invention also relates to such derivative for use as a medicament, in particular for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

The invention furthermore relates to intermediate products in the form of novel GLP-1 analogues, which are relevant for the preparation of certain derivatives of the invention.

The derivatives of the invention are biologically active. Also, or alternatively, they have a protracted pharmacokinetic profile. Also, or alternatively, they are stable against degradation by gastro intestinal enzymes. Also, or alternatively, they have a high oral bioavailability. These properties are of importance in the development of next generation GLP-1 compounds for subcutaneous, intravenous, and/or in particular oral administration.

DESCRIPTION

In what follows, Greek letters may be represented by their symbol or the corresponding written name, for example: α=alpha; β=beta; ε=epsilon; γ=gamma; ω=omega; etc. Also, the Greek letter of t may be represented by "u", e.g. in μl=ul, or in μM=uM.

An asterisk (*) in a chemical formula designates i) a point of attachment, ii) a radical, and/or iii) an unshared electron.

In a first aspect, the invention relates to a derivative of a GLP-1 analogue, which analogue comprises a first K residue at a position corresponding to position 27 of GLP-1(7-37) (SEQ ID NO: 1); a second K residue at a position corresponding to position T of GLP-1(7-37), where T is an integer in the range of 7-37 except 18 and 27; and a maximum of ten amino acid changes as compared to GLP-1(7-37); wherein the first K residue is designated $K^{27}$, and the second K residue is designated $K^T$; which derivative comprises two albumin binding moieties attached to $K^{27}$ and $K^T$, respectively, via a linker, wherein the albumin binding moiety comprises a protracting moiety selected from Chem. 1 and Chem. 2:

                            Chem. 1:

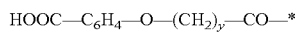
                            Chem. 2:

in which x is an integer in the range of 6-16, and y is an integer in the range of 3-17, and the linker comprises Chem. 5:

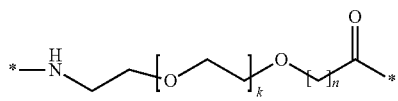
                            Chem. 5 wherein k is an integer in the range of 1-5, and n is an integer in the range of 1-5; or a pharmaceutically acceptable salt, amide, or ester thereof.

GLP-1 Analogues

The term "GLP-1 analogue" or "analogue of GLP-1" as used herein refers to a peptide, or a compound, which is a variant of the human Glucagon-Like Peptide-1 (GLP-1(7-37)), the sequence of which is included in the sequence listing as SEQ ID NO: 1. The peptide having the sequence of SEQ ID NO: 1 may also be designated "native" GLP-1.

In the sequence listing, the first amino acid residue of SEQ ID NO: 1 (histidine) is assigned no. 1. However, in what follows—according to established practice in the art—this histidine residue is referred to as no. 7, and subsequent amino acid residues are numbered accordingly, ending with glycine no. 37. Therefore, generally, any reference herein to an amino acid residue number or a position number of the GLP-1(7-37) sequence is to the sequence starting with His at position 7 and ending with Gly at position 37.

GLP-1 analogues of the derivatives of the invention may be described by reference to i) the number of the amino acid residue in native GLP-1(7-37) which corresponds to the amino acid residue which is changed (i.e., the corresponding position in native GLP-1), and to ii) the actual change. The following are non-limiting examples of suitable analogue nomenclature.

A non-limiting example of a GLP-1 analogue of the derivative of the invention is an analogue that is changed so as to comprise a first lysine residue at a position corresponding to position 27 of GLP-1(7-37), and a second lysine residue at position 12. The amino acid sequence of this analogue is otherwise identical to that of native GLP-1, and this analogue may be designated $K^{12},K^{27}$-GLP-1(7-37). This designation represents the amino acid sequence of native GLP-1 where phenylalanine at position 12 has been substituted with lysine, and glutamic acid at position 27 has been substituted with lysine.

The GLP-1 analogue forming part of the derivative of the invention comprises a maximum of ten amino acid changes when compared with native GLP-1(7-37) (SEQ ID NO: 1). In other words, it is a GLP-1(7-37) peptide in which a number of amino acid residues have been changed when compared to native GLP-1(7-37) (SEQ ID NO: 1). These changes may represent, independently, one or more amino acid substitutions, additions, and/or deletions.

The following are non-limiting examples of appropriate analogue nomenclature.

For example, the analogue [Aib8,Lys22,Val25,Arg26, Lys27,His31,Arg34]-GLP-1-(7-37) designates a GLP-1(7-37) peptide which, when compared to native GLP-1, has the following substitutions: Substitution of alanine at position 8 with Aib (α-aminoisobutyric acid), of glycine at position 22 with lysine, of alanine at position 25 with valine, of lysine at position 26 with arginine, of glutamic acid at position 27 with lysine, of tryptophan at position 31 with histidine, and of lysine at position 34 with arginine. This analogue may also be briefly designated (8Aib, 22K, 25V, 26R, 27K, 31H, 34R).

As another example, the analogue [Aib8,Lys20,Glu22, Arg26,Lys27,Glu30,Gly34]-GLP-1-(7-34) designates a GLP-1(7-37) peptide, which, when compared to native GLP-1, is changed by substitution of alanine at position 8 with Aib, substitution of leucine at position 20 with lysine, substitution of glycine at position 22 with glutamic acid, substitution of lysine at position 26 with arginine, substitution of glutamic acid at position 27 with lysine, substitution of alanine at position 30 with glutamic acid, substitution of lysine at position 34 with glycine, and by deletion of the C-terminus of glycine-arginine-glycine at position 35-36-37. This analogue may also be briefly designated (8Aib, 20K, 22E, 26R, 27K, 30E, 34G, des35-37), where reference to GLP-1(7-37) is implied, and "des" represents a deletion.

As a still further example, an analogue comprising $Glu^{38}$ and $Gly^{39}$ refers to a GLP-1(7-37) peptide, which, when compared to native GLP-1, comprises an addition of the dipeptide of (glutamic acid—glycine) to the C-terminus of GLP-1(7-37). This analogue may also briefly be said to comprise (38E, 39G), where the reference to GLP-1(7-37) is implied.

Analogues "comprising" certain specified changes may comprise further changes, when compared to SEQ ID NO: 1. One example, non-limiting, of an analogue comprising (38E, 39G) is the peptide part of Chem. 51.

As is apparent from the above examples, amino acid residues may be identified by their full name, their one-letter code, and/or their three-letter code. These three ways are fully equivalent.

The expressions "a position equivalent to" or "corresponding position" may be used to characterise the site of change in a variant GLP-1(7-37) sequence by reference to native GLP-1(7-37) (SEQ ID NO: 1). Equivalent or corresponding positions, as well as the number of changes, are easily deduced, e.g. by simple handwriting and eyeballing; and/or a standard protein or peptide alignment program may be used, such as "align" which is a Needleman-Wunsch alignment. The algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM50 and the default identity matrix may be used, and the penalty for the first residue in a gap may be set at −12, or preferably at −10, and the penalties for additional residues in a gap at −2, or preferably at −0.5.

An example of such alignment is inserted hereinbelow, in which sequence no. 1 (SEQ_ID_NO_1) is SEQ ID NO: 1, and sequence no. 2 (SEQ ID NO: 2) (ANALOGUE) is the analogue (22K, 26R, 27K, 30E, 34G, des35-37) thereof:

```
# Aligned_          2
  sequences:
# 1:                SEQ_ID_NO_1
# 2:                ANALOGUE
# Matrix:           EBLOSUM62
# Gap_penalty:      10.0
# Extend_           0.5
  penalty:

# Length:           31
# Identity:         23/31 (74.2%)
# Similarity:       25/31 (80.6%)
# Gaps:              3/31 (9.7%)
# Score:            117.0

SEQ_ID_NO_1    1 HAEGTFTSDVSSYLEGQAAKEFIAWLVKGRG 31
                 |||||||||||||||.|||::||.|||.
ANALOGUE       1 HAEGIFTSDVSSYLEKQAARKFIEWLVG--- 28
(SEQ ID NO: 2)
```

In case of non-natural amino acids such as Aib being included in the sequence, these may, for alignment purposes, be replaced with X. If desired, X can later be manually corrected.

The term "peptide", as e.g. used in the context of the GLP-1 analogues of the derivatives of the invention, refers to a compound which comprises a series of amino acids intereconnected by amide (or peptide) bonds.

The peptides of the invention comprise at least five constituent amino acids connected by peptide bonds. In particular embodiments the peptide comprises at least 10, preferably at least 15, more preferably at least 20, even more preferably at least 25, or most preferably at least 28 amino acids.

In particular embodiments, the peptide is composed of at least five constituent amino acids, preferably composed of at least 10, at least 15, at least 20, at least 25, or most preferably composed of at least 28 amino acids.

In additional particular embodiments, the peptide is a) composed of, or b) consists of, i) 28, ii) 29, iii) 30, iv) 31, v) 32, or vi) 33 amino acids.

In a still further particular embodiment the peptide consists of amino acids interconnected by peptide bonds.

Amino acids are molecules containing an amine group and a carboxylic acid group, and, optionally, one or more additional groups, often referred to as a side chain.

The term "amino acid" includes proteogenic amino acids (encoded by the genetic code, including natural amino acids, and standard amino acids), as well as non-proteogenic (not found in proteins, and/or not coded for in the standard genetic code), and synthetic amino acids. Thus, the amino acids may be selected from the group of proteinogenic amino acids, non-proteinogenic amino acids, and/or synthetic amino acids.

Non-limiting examples of amino acids which are not encoded by the genetic code are gamma-carboxyglutamate, ornithine, and phosphoserine. Non-limiting examples of synthetic amino acids are the D-isomers of the amino acids such as D-alanine and D-leucine, Aib (α-aminoisobutyric acid), β-alanine, and des-amino-histidine (desH, alternative name imidazopropionic acid, abbreviated Imp).

In what follows, all amino acids for which the optical isomer is not stated is to be understood to mean the L-isomer (unless otherwise specified).

The GLP-1 derivatives and analogues of the invention have GLP-1 activity. This term refers to the ability to bind to the GLP-1 receptor and initiate a signal transduction pathway resulting in insulinotropic action or other physiological effects as is known in the art. For example, the analogues and derivatives of the invention can be tested for GLP-1 activity using the assay described in Example 33 herein. The GLP-1 receptor binding assay described in Example 34 herein may also be used for determining GLP-1 activity (the low HSA experiment).

GLP-1 Derivatives

The term "derivative" as used herein in the context of a GLP-1 peptide or analogue means a chemically modified GLP-1 peptide or analogue, in which one or more substituents have been covalently attached to the peptide. The substituent may also be referred to as a side chain.

In a particular embodiment, the side chain is capable of forming non-covalent aggregates with albumin, thereby promoting the circulation of the derivative with the blood stream, and also having the effect of protracting the time of action of the derivative, due to the fact that the aggregate of the GLP-1-derivative and albumin is only slowly disintegrated to release the active pharmaceutical ingredient. Thus, the substituent, or side chain, as a whole is preferably referred to as an albumin binding moiety.

In another particular embodiment the albumin binding moiety comprises a portion which is particularly relevant for the albumin binding and thereby the protraction, which portion may be referred to as a protracting moiety. The protracting moiety may be at, or near, the opposite end of the albumin binding moiety, relative to its point of attachment to the peptide.

In a still further particular embodiment the albumin binding moiety comprises a portion inbetween the protracting moiety and the point of attachment to the peptide, which portion may be referred to as a linker, linker moiety, spacer, or the like. The linker may be optional, and hence in that case the albumin binding moiety may be identical to the protracting moiety.

In particular embodiments, the albumin binding moiety and/or the protracting moiety is lipophilic, and/or negatively charged at physiological pH (7.4).

The albumin binding moiety, the protracting moiety, or the linker may be covalently attached to a lysine residue of the GLP-1 peptide by acylation.

In a preferred embodiment, an active ester of the albumin binding moiety, preferably comprising a protracting moiety and a linker, is covalently linked to an amino group of a lysine residue, preferably the epsilon amino group thereof, under formation of an amide bond (this process being referred to as acylation).

Unless otherwise stated, when reference is made to an acylation of a lysine residue, it is understood to be to the epsilon-amino group thereof.

A derivative comprising two protracting moieties attached to a first and a second K residue (e.g., to $K^{27}$ and $K^T$) via a linker may be referred to as a derivative which has been acylated twice, double-acylated, or dual acylated at the epsilon-amino groups of the first and second lysine residues, e.g. at position 27 and T, respectively, of the GLP-1 peptide.

For the present purposes, the terms "albumin binding moiety", "protracting moiety", and "linker" may include the unreacted as well as the reacted forms of these molecules. Whether or not one or the other form is meant is clear from the context in which the term is used.

In one aspect, each protracting moiety comprises, or consists of, a protracting moiety independently selected from Chem. 1 and Chem. 2:

HOOC—(CH$_2$)$_x$—CO—*      Chem. 1:

HOOC—C$_6$H$_4$—O—(CH$_2$)$_y$—CO—*      Chem. 2:

in which x is an integer in the range of 6-16, and y is an integer in the range of 3-17.

In one embodiment, *—(CH$_2$)$_x$—* refers to straight or branched, preferably straight, alkylene in which x is an integer in the range of 6-16.

In another embodiment, *—(CH$_2$)$_y$—* refers to straight or branched, preferably straight, alkylene in which y is an integer in the range of 3-17.

The term "fatty acid" refers to aliphatic monocarboxylic acids having from 4 to 28 carbon atoms, it is preferably unbranched, and/or even numbered, and it may be saturated or unsaturated.

The term "fatty diacid" refers to fatty acids as defined above but with an additional carboxylic acid group in the omega position. Thus, fatty diacids are dicarboxylic acids.

The nomenclature is as is usual in the art, for example in the above formulas *—COOH as well as HOOC—* refers to carboxy; *—C$_6$H$_4$—* to phenylene; *—CO—*, as well as *—OC—*, to carbonyl (O=C<**); C$_6$H$_5$—O—* to phenoxy. In particular embodiments, the aromatics, such as the phenoxy, and the phenylene radicals, may be, independently, ortho, meta, or para.

As explained above, the GLP-1 derivatives of the present invention are double-acylated, i.e. two albumin binding moieties are covalently attached to the GLP-1 peptide.

In a particular embodiment, the two albumin binding moieites (i.e. the entire side chains) are similar, preferably substantially identical, or, most preferably, identical.

In another particular embodiment, the two protracting moieties are similar, preferably substantially identical, or, most preferably, identical.

In a still further particular embodiment, the two linkers are similar, preferably substantially identical, or, most preferably identical.

The term "substantially identical" includes differences from identity which are due to formation of one or more salts, esters, and/or amides; preferably formation of one or more salts, methyl esters, and simple amides; more preferably formation of no more than two salts, methyl esters, and/or simple amides; even more preferably formation of no more than one salt, methyl ester, and/or simple amide; or most preferably formation of no more than one salt.

In the context of chemical compounds such as the albumin binding moieities, protracting moieties, and linkers, similarity and/or identity may be determined using any suitable computer program and/or algorithm known in the art.

For example, the similarity of two protracting moieties, two linkers, and/or two entire side chains may suitably be determined using molecular fingerprints. Fingerprints is a mathematical method of representing a chemical structure (see e.g. Chemoinformatics: A textbook, Johann Gasteiger and Thomas Engel (Eds), Wiley-VCH Verlag, 2003).

Examples of suitable fingerprints include, without limitation, UNITY fingerprints, MDL fingerprints, and/or ECFP fingerprints, such as ECFP_6 fingerprints (ECFP stands for extended-connectivity fingerprints).

In particular embodiments, the two protracting moieties, the two linkers, and/or the two entire side chains are represented as a) ECFP_6 fingerprints; b) UNITY fingerprints; and/or c) MDL fingerprints.

The Tanimoto coefficient is preferably used for calculating the similarity of the two fingerprints, whether a), b), or c) is used.

In particular embodiments, whether a), b), or c) is used, the two protracting moieties, the two linkers, and/or the two entire side chains, respectively, have a similarity of at least 0.5 (50%); preferably at least 0.6 (60%); more preferably at least 0.7 (70%), or at least 0.8 (80%); even more preferably at least 0.9 (90%); or most preferably at least 0.99 (99%), such as a similarity of 1.0 (100%).

UNITY fingerprints may be calculated using the programme SYBYL (available from Tripos, 1699 South Hanley Road, St. Louis, Mo. 63144-2319 USA). ECFP_6 and MDL fingerprints may be calculated using the programme Pipeline Pilot (available from Accelrys Inc., 10188 Telesis Court, Suite 100, San Diego, Calif. 92121, USA).

For more details, see for example J. Chem. Inf. Model. 2008, 48, 542-549; J. Chem. Inf. Comput. Sci. 2004, 44, 170-178; J. Med. Chem. 2004, 47, 2743-2749; J. Chem. Inf. Model. 2010, 50, 742-754; as well as SciTegic Pipeline Pilot Chemistry Collection: Basic Chemistry User Guide, March 2008, SciTegic Pipeline Pilot Data Modeling Collection, 2008—both from Accelrys Software Inc., San Diego, US.

An example of a similarity calculation is inserted hereinbelow, in which the entire side chain of Chem. 66 was compared with a methyl ester thereof, viz. the mono methyl ester of the glutamine linker moiety (Chem 66a):

Chem. 66a

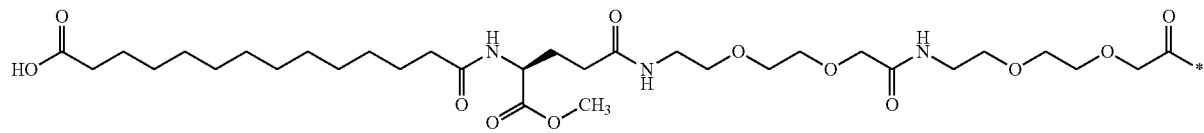

Using a) ECFP_6 fingerprints the similarity is 0.798, using b) UNITY fingerprints the similarity is 0.957; and using MDL fingerprints the similarity is 0.905.

In case of two identical side chains (albumin binding moieties) the derivative may be designated symmetrical.

In particular embodiments, the similarity coefficient is at least 0.80, preferably at least 0.85, more preferably at least 0.90, even more preferably at least 0.95, or most preferably at least 0.99.

Each of the two linkers of the derivative of the invention may comprise the following first linker element:

Chem. 5

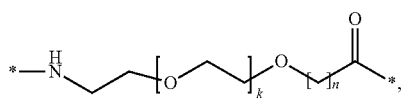

wherein k is an integer in the range of 1-5, and n is an integer in the range of 1-5.

In a particular embodiment, when k=1 and n=1, this linker element may be designated OEG, or a di-radical of 8-amino-3,6-dioxaoctanic acid, and/or it may be represented by the following formula:

*—NH—(CH$_2$)$_2$—O—(CH$_2$)$_2$—O—CH$_2$—CO—*.  Chem. 5a:

In another particular embodiment, each linker of the derivative of the invention may comprise, independently, a second linker element, preferably a Glu di-radical, such as Chem. 6 and/or Chem. 7:

Chem. 6

Chem. 7

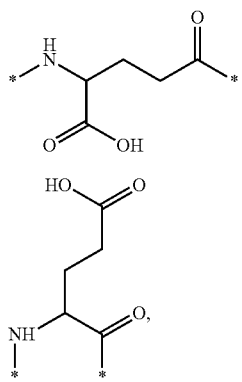

wherein the Glu di-radical may be included p times, where p is an integer in the range of 1-2.

Chem. 6 may also be referred to as gamma-Glu, or briefly gGlu, due to the fact that it is the gamma carboxy group of the amino acid glutamic acid which may here be used for connection to another linker element, or to the epsilon-amino group of lysine. As explained above, the other linker element may, for example, be another Glu residue, or an OEG molecule. The amino group of Glu may in turn form an amide bond with the carboxy group of the protracting moiety, or with the carboxy group of, e.g., an OEG molecule, if present, or with the gamma-carboxy group of, e.g., another Glu, if present.

Chem. 7 may also be referred to as alpha-Glu, or briefly aGlu, or simply Glu, due to the fact that it is the alpha carboxy group of the amino acid glutamic acid which may here be used for connection to another linker element, or to the epsilon-amino group of lysine.

The above structures of Chem. 6 and Chem. 7 cover the L-form, as well as the D-form of Glu.

The derivatives of the invention may exist in different stereoisomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivative.

The concentration in plasma of the GLP-1 derivatives of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoasssay). General protocols for suitable RIA and ELISA assays are found in, e.g., WO09/030738 on p. 116-118. A preferred assay is the LOCI assay described in Example 35, 39, and 40 herein.

Pharmaceutically Acceptable Salt, Amide, or Ester

The derivatives and analogues of the invention may be in the form of a pharmaceutically acceptable salt, amide, or ester.

Salts are e.g. formed by a chemical reaction between a base and an acid, e.g.: 2 NH$_3$+H$_2$SO$_4$→(NH$_4$)$_2$SO$_4$.

The salt may be a basic salt, an acid salt, or it may be neither nor (i.e. a neutral salt). Basic salts produce hydroxide ions and acid salts hydronium ions in water.

The salts of the derivatives of the invention may be formed with added cations or anions that react with anionic or cationic groups, respectively. These groups may be situated in the peptide moiety, and/or in the side chain of the derivatives of the invention.

Non-limiting examples of anionic groups of the derivatives of the invention include free carboxylic groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The ester of the derivatives of the invention may, e.g., be formed by the reaction of a free carboxylic acid group with an alcohol or a phenol, which leads to replacement of at least one hydroxyl group by an alkoxy or aryloxy group The ester formation may involve the free carboxylic group at the C-terminus of the peptide, and/or any free carboxylic group in the side chain.

The amide of the derivatives of the invention may, e.g., be formed by the reaction of a free carboxylic acid group with an amine or a substituted amine, or by reaction of a free or substituted amino group with a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In a particular embodiment, the peptide or derivative is in the form of a pharmaceutically acceptable salt. In another particular embodiment, the derivative is in the form of a pharmaceutically acceptable amide, preferably with an amide group at the C-terminus of the peptide. In a still further particular embodiment, the peptide or derivative is in the form a pharmaceutically acceptable ester.

Intermediate Products

In a second aspect, the invention relates to intermediate products.

One type of intermediate product of the invention takes the form of a GLP-1 analogue which comprises the following changes as compared to GLP-1(7-37) (SEQ ID NO: 1): (i) 38Q; and/or (ii) 39G; or a pharmaceutically acceptable, salt, amide, or ester thereof.

Another intermediate product of the invention in the form of a GLP-1 analogue is an analogue comprising, preferably having, the following amino acid changes, as compared to GLP-1(7-37) (SEQ ID NO: 1): (i) 22E, 26R, 27K, 34R, 37K; (ii) 22E, 26R, 27K, 30E, 34R, 36K, 38E, 39G; (iii) 22E, 26R, 27K, 34R, 36K, des37; (iv) 22E, 25V, 26R, 27K, 34R, 37K; (v) 8Aib, 20K, 22E, 26R, 27K, 30E, 34G, des35-37; (vi) 26R, 27K, 30E, 34R, 36K, 38E; (vii) 8Aib, 22K, 25V, 26R, 27K, 31H, 34R; (iix) 8Aib, 22K, 25V, 26R, 27K, 34R, des35-37; (ix) 8Aib, 22K, 25V, 26R, 27K, 34R, des36-37; (x) 26H, 27K, 30E, 34R, 36K, 38E; (xi) 22K, 25V, 26R, 27K, 30E, 34Q; (xii) 25V, 26R, 27K, 30E, 34R, 36K, 38Q; (xiii) 25V, 26R, 27K, 30E, 34Q, 36K, 38E; (xiv) 22K, 26R, 27K, 31H, 34G, des35-37; (xv) 8Aib, 25V, 26R, 27K, 31H, 34Q, 37K; (xvi) 25V, 26R, 27K, 31H, 34Q, 37K; (xvii) 22E, 23E, 25V, 26R, 27K, 31H, 34Q, 37K; (iixx) 8Aib, 12K, 22E, 26R, 27K, 31H, 34Q; (ixx) 8Aib, 22K, 26R, 27K, 31H, 34G, des35-37; (xx) 22E, 26H, 27K, 30E, 34R, 36K, 38E; (xxi) 22E, 24K, 26R, 27K, 31H, 34G, des35-37; (xxii) 25V, 26R, 27K, 34Q, 36K; (xxiii) 22E, 24K, 25V, 26R, 27K, 31H, 34R; (xxiv) 22E, 24K, 25V, 26R, 27K, 34G, des35-37; (xxv) 22E, 24K, 25V, 26R, 27K, 34R; (xxvi) 8Aib, 22E, 24K, 25V, 26R, 27K, 31H, 34Q; or (xxvii) 8Aib, 22E, 26R, 27K, 30E, 34R, 36K, 38E, 39G; or a pharmaceutically acceptable salt, amide, or ester thereof.

Functional Properties

In a first functional aspect, the derivatives of the invention have a good potency. Also, or alternatively, in a second functional aspect, they have a protracted pharmacokinetic profile. Also, or alternatively, in a third functional aspect, they have a high oral bioavailability. Also, or alternatively, in a fourth functional aspect, their biophysical properties are improved.

Biological Activity (Potency)

According to the first functional aspect, the derivatives of the invention, as well as the constituent GLP-1 peptides as such, are biologically active, or potent.

In a particular embodiment, potency and/or activity refers to in vitro potency, i.e. performance in a functional GLP-1 receptor assay, more in particular to the capability of stimulating cAMP formation in a cell line expressing the cloned human GLP-1 receptor.

The stimulation of the formation of cAMP in a medium containing the human GLP-1 receptor may preferably be determined using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, most preferably the one described in Example 33.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the derivatives of the invention may be determined as described above, and the $EC_{50}$ of the derivative in question determined. The lower the $EC_{50}$, the better the potency.

A suitable medium has the following composition (final in-assay concentrations): 50 mM TRIS-HCl; 5 mM HEPES; 10 mM $MgCl_2$, $6H_2O$; 150 mM NaCl; 0.01% Tween; 0.1% BSA; 0.5 mM IBMX; 1 mM ATP; 1 uM GTP; pH 7.4.

The $EC_{50}$ of the derivatives of the invention is at or below 3500 pM, preferably at or below 3200. The $EC_{50}$ may even be below 1200 pM, preferably below 1000 pM, even more preferably below 500 pM, or most preferably below 200 pM.

In another particular embodiment of the first functional aspect, potency and/or activity refers to the capability of binding to the GLP-1 receptor at a low concentration of albumin. The binding to the GLP-1 receptor at low albumin concentration should be as good as possible, corresponding to a low $IC_{50}$ value. This may be determined as described in Example 35. The $IC_{50}$ (low albumin) of the derivatives of the invention is at or below 500 nM, many are below 100 nM, or even below 10 nM.

In another particular embodiment the derivatives of the invention are potent in vivo, which may be determined as is known in the art in any suitable animal model, as well as in clinical trials.

The diabetic db/db mouse is one example of a suitable animal model, and the blood glucose lowering effect may be determined in such mice in vivo, e.g. as described in Example 36, or as described in Example 43 of WO09/030738.

Also, or alternatively, the effect on food intake in vivo may be determined in pharmacodynamic studies in pigs, e.g. as described in Example 38.

Protraction—Receptor Binding/Low and High Albumin

According to the second functional aspect, the derivatives of the invention are protracted.

GLP-1 Receptor Binding

In a particular embodiment protraction refers to the ability of the derivatives of the invention to bind to the GLP-1 receptor in the presence of a low and a high concentration of albumin, respectively, which may be determined as described in Example 34.

Generally, the binding to the GLP-1 receptor at low albumin concentration should be as good as possible, corresponding to a low $IC_{50}$ value. In one embodiment low albumin refers to 0.005% HSA. In another embodiment low albumin refers to 0.001% HSA.

The $IC_{50}$ value at high albumin concentration is a measure of the influence of albumin on the binding of the derivative to the GLP-1 receptor. As is known, the GLP-1 derivatives also bind to albumin. This is a generally desirable effect, which extends their lifetime in plasma. Therefore, the $IC_{50}$ value at high albumin will generally be higher than the $IC_{50}$ value at low albumin, corresponding to a reduced binding to the GLP-1 receptor, caused by albumin binding competing with the binding to the GLP-1 receptor.

A high ratio ($IC_{50}$ value (high albumin)/$IC_{50}$ value (low albumin)) may therefore be taken as an indication that the derivative in question binds well to albumin (may have a long half-life), and also per se binds well to the GLP-1 receptor (the $IC_{50}$ value (high albumin) is high, and the $IC_{50}$ value (low albumin) is low). On the other hand, albumin binding may not always be desirable, or the binding to albumin may become too strong. Therefore, the desirable ranges for $IC_{50}$ (low albumin), $IC_{50}$ (high albumin)/, and the ratio high/low may vary from compound to compound, depending on the intended use and the circumstances surrounding such use, and on other compound properties of potential interest.

A suitable assay for determining receptor binding at high and low albumin concentration is disclosed in Example 34 herein. The compounds of the invention have a very good receptor binding affinity ($IC_{50}$) in the presence of low albumin. On average the $IC_{50}$ (low albumin) of the compounds tested in Example 34 is 14 nM.

Protraction—Half Life In Vivo in Rats

According to the second functional aspect, the derivatives of the invention are protracted. In a particular embodiment, protraction may suitably be determined as half-life ($T_{1/2}$) in vivo in rats after i.v. administration. The half-life in rat is at least 4 hours, and it may be as high as 10 hours or more.

A suitable assay for determining half-life in vivo in rats after i.v. administration is disclosed in Example 39 herein.

Protraction—Half Life In Vivo in Minipigs

According to the second functional aspect, the derivatives of the invention are protracted. In a particular embodiment protraction may, also or alternatively, be determined as half-life ($T_{1/2}$) in vivo in minipigs after i.v. administration. The half-life is at least 12 hours, it may be at least 24 hours, at least 36 hours, at least 48 hours, or at least 60 hours, or even higher.

A suitable assay for determining half-life in vivo in minipigs after i.v. administration is disclosed in Example 37 herein.

Oral Bioavailability

According to the third functional aspect, the derivatives of the invention have a high oral bioavailability.

The oral bioavailability of commercial GLP-1 derivatives is very low. The oral bioavailability of GLP-1 derivatives under development for i.v. or s.c. administration is also low.

Accordingly, there is a need in the art for GLP-1 derivatives of an improved oral bioavailability. Such derivatives could be suitable candidates for oral administration, as long as their potency is generally satisfactory, and/or as long as their half-life is also generally satisfactory.

The present inventors identified a novel class of GLP-1 derivatives, which have a surprisingly high oral bioavailability, and at the same time a satisfactory potency, and/or half-life.

Also, or alternatively, these derivatives have a surprisingly improved oral bioavailability, and at the same time a high binding affinity (i.e. a low $IC_{50}$ value) to the GLP-1 receptor at a low concentration of albumin.

These features are of importance with a view to obtaining a low daily oral dose of the active pharmaceutical ingredient, which is desirable for various reasons, including, e.g., economy of production, likelihood of potential safety issues, as well as administration comfort issues, and environmental concerns.

Generally, the term bioavailability refers to the fraction of an administered dose of the active pharmaceutical ingredient (API), such as a derivative of the invention that reaches the systemic circulation unchanged. By definition, when an API is administered intravenously, its bioavailability is 100%. However, when it is administered via other routes (such as orally), its bioavailability decreases (due to degradation and/or incomplete absorption and first-pass metabolism). Knowledge about bioavailability is essential when calculating dosages for non-intravenous routes of administration.

Absolute oral bioavailability compares the bioavailability (estimated as the area under the curve, or AUC) of the API in systemic circulation following oral administration, with the bioavailability of the same API following intravenous administration. It is the fraction of the API absorbed through non-intravenous administration compared with the corresponding intravenous administration of the same API. The comparison must be dose normalised if different doses are used; consequently, each AUC is corrected by dividing the corresponding dose administered.

A plasma API concentration vs time plot is made after both oral and intravenous administration. The absolute bioavailability (F) is the dose-corrected AUC-oral divided by AUC-intravenous.

The derivatives of the invention have an absolute oral bioavailability which is higher than that of a) liraglutide, and/or b) semaglutide; preferably at least 10% higher, more preferably at least 20% higher, even more preferably at least 30% higher, or most preferably at least 40% higher. Before testing oral bioavailability the derivatives of the invention may suitably be formulated as is known in the art of oral formulations of insulinotropic compounds, e.g. using any one or more of the formulations described in WO 2008/145728.

Suitable tests predictive of oral bioavailability are described in Examples 35 and 40. According to these tests, after direct injection of the GLP-1 derivative into the intestinal lumen of rats and/or after oral gavage of rats, the concentration (exposure) thereof in plasma is determined, and the subsequent exposure in plasma of the GLP-1 derivative is measured, Biophysical Properties According to the fourth functional aspect, the derivatives of the invention have improved biophysical properties. These properties include but are not limited to physical stability and solubility. Improved biophysical properties may be a result of changed oligomeric properties. The biophysical properties may be measured using standard biophysical methods of protein chemistry. The biophysical properties of the derivatives of the invention may suitably be compared to those of native GLP-1.

Additional particular embodiments of the invention are described in the section headed "particular embodiments".

Production Processes

The production of peptides like GLP-1(7-37) and GLP-1 analogues is well known in the art.

The GLP-1 moiety of the derivatives of the invention (or fragments thereof), such as $K^{12},K^{27}$-GLP-1(7-37) or an analogue or fragment thereof, may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dörwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

Those derivatives of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Specific examples of methods of preparing a number of the derivatives of the invention are included in the experimental part.

Pharmaceutical Compositions

Pharmaceutical compositions comprising a derivative of the invention or a pharmaceutically acceptable salt, amide, or ester thereof, and a pharmaceutically acceptable excipient may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. $19^{th}$ edition (1995), and any later editions).

Non-limiting examples of excipients are: Solvents, diluents, buffers, preservatives, tonicity regulating agents, chelating agents, and stabilisers.

Examples of formulations include liquid formulations, i.e. aqueous formulations comprising water. A liquid formulation may be a solution, or a suspension. An aqueous formulation typically comprises at least 50% w/w water, or at least 60%, 70%, 80%, or even at least 90% w/w of water.

Alternatively, a pharmaceutical composition may be a solid formulation, e.g. a freeze-dried or spray-dried composition, which may be used as is, or whereto the physician or the patient adds solvents, and/or diluents prior to use.

The pH in an aqueous formulation may be anything between pH 3 and pH 10, for example from about 7.0 to about 9.5; or from about 3.0 to about 7.0.

A pharmaceutical composition may comprise a buffer. The buffer may e.g. be selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid, and mixtures thereof.

A pharmaceutical composition may comprise a preservative. The preservative may e.g. be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol), and mixtures thereof. The preservative may be present in a concentration from 0.1 mg/ml to 20 mg/ml.

A pharmaceutical composition may comprise an isotonic agent. The isotonic agent may e.g. be selected from the group consisting of a salt (e.g. sodium chloride), a sugar or sugar alcohol, an amino acid (e.g. glycine, histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), and mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol.

A pharmaceutical composition may comprise a chelating agent. The chelating agent may e.g. be selected from salts of ethylenediaminetetraacetic acid (EDTA), citric acid, and aspartic acid, and mixtures thereof. A pharmaceutical composition may comprise a stabiliser. The stabiliser may e.g. be one or more oxidation inhibitors, aggregation inhibitors, surfactants, and/or one or more protease inhibitors. Non-limiting examples of these various kinds of stabilisers are disclosed in the following.

The term "aggregate formation" refers to a physical interaction between the polypeptide molecules resulting in formation of oligomers, which may remain soluble, or large visible aggregates that precipitate from the solution. Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

A pharmaceutical composition may comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present.

Methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. Any stereoisomer of methionine (L or D) or combinations thereof can be used.

A pharmaceutical composition may comprise a stabiliser selected from the group of high molecular weight polymers or low molecular compounds. The stabiliser may e.g. be selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). A pharmaceutical composition may comprise additional stabilising agents such as, but not limited to, methionine and EDTA, which protect the polypeptide against methionine oxidation, and a nonionic surfactant, which protects the polypeptide against aggregation associated with freeze-thawing or mechanical shearing.

A pharmaceutical composition may comprise one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant may e.g. be selected from the group consisting of anionic surfactants, cationic surfactants, nonionic surfactants, and/or zwitterionic surfactants.

A pharmaceutical composition may comprise one or more protease inhibitors, such as, e.g., EDTA (ethylenediamine tetraacetic acid), and/or benzamidineHCl.

Additional, optional, ingredients of a pharmaceutical composition include, e.g., wetting agents, emulsifiers, antioxidants, bulking agents, metal ions, oily vehicles, proteins (e.g., human serum albumin, gelatine), and/or a zwitterion (e.g., an amino acid such as betaine, taurine, arginine, glycine, lysine and histidine).

Still further, a pharmaceutical composition may be formulated as is known in the art of oral formulations of insulinotropic compounds, e.g. using any one or more of the formulations described in WO 2008/145728.

An administered dose may contain from 0.01 mg-100 mg of the derivative, or from 0.01-50 mg, or from 0.01-20 mg, or from 0.01-10 mg of the derivative.

The derivative may be administered in the form of a pharmaceutical composition. It may be administered to a patient in need thereof at several sites, for example, at topical sites such as skin or mucosal sites; at sites which bypass absorption such as in an artery, in a vein, or in the heart; and at sites which involve absorption, such as in the skin, under the skin, in a muscle, or in the abdomen.

The route of administration may be, for example, lingual; sublingual; buccal; in the mouth; oral; in the stomach; in the intestine; nasal; pulmonary, such as through the bronchioles, the alveoli, or a combination thereof; parenteral; epidermal; dermal; transdermal; conjunctival; uretal; vaginal; rectal; and/or ocular. A composition may be an oral composition, and the route of administration is per oral.

A composition may be administered in several dosage forms, for example as a solution; a suspension; an emulsion; a microemulsion; multiple emulsions; a foam; a salve; a paste; a plaster; an ointment; a tablet; a coated tablet; a chewing gum; a rinse; a capsule such as hard or soft gelatine capsules; a suppositorium; a rectal capsule; drops; a gel; a spray; a powder; an aerosol; an inhalant; eye drops; an ophthalmic ointment; an ophthalmic rinse; a vaginal pessary; a vaginal ring; a vaginal ointment; an injection solution; an in situ transforming solution such as in situ gelling, setting, precipitating, and in situ crystallisation; an infusion solution; or as an implant. A composition may be a tablet, optionally coated, a capsule, or a chewing gum.

A composition may further be compounded in a drug carrier or drug delivery system, e.g. in order to improve stability, bioavailability, and/or solubility. In a particular embodiment a composition may be attached to such system through covalent, hydrophobic, and/or electrostatic interactions. The purpose of such compounding may be, e.g., to decrease adverse effects, achieve chronotherapy, and/or increase patient compliance.

A composition may also be used in the formulation of controlled, sustained, protracting, retarded, and/or slow release drug delivery systems.

Parenteral administration may be performed by subcutaneous, intramuscular, intraperitoneal, or intravenous injection by means of a syringe, optionally a pen-like syringe, or by means of an infusion pump.

A composition may be administered nasally in the form of a solution, a suspension, or a powder; or it may be administered pulmonally in the form of a liquid or powder spray.

Transdermal administration is a still further option, e.g. by needle-free injection, from a patch such as an iontophoretic patch, or via a transmucosal route, e.g. buccally.

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

The treatment with a derivative according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the p-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonits, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3)

modulators, leptin agonists, DA agonists (bromocriptin, doprexin), lipase/amylase inhibitors, RxR (retinoidxreceptor) modulators, TR β agonists; histamine H3 antagonists, Gastric Inhibitory Polypeptide agonists or antagonists (GIP analogs), gastrin and gastrin analogs.

The treatment with a derivative according to this invention may also be combined with a surgery that influences the glucose levels, and/or lipid homeostasis such as gastric banding or gastric bypass.

Pharmaceutical Indications

In a third aspect, the present invention also relates to a derivative of the invention, for use as a medicament.

In particular embodiments, the derivative of the invention may be used for the following medical treatments, all preferably relating one way or the other to diabetes:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells; (iv) prevention and/or treatment of cognitive disorders;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying;

(vi) prevention and/or treatment of diabetic complications, such as neuropathy, including peripheral neuropathy; nephropathy; or retinopathy;

(vii) improving lipid parameters, such as prevention and/or treatment of dyslipidemia, lowering total serum lipids; lowering HDL; lowering small, dense LDL; lowering VLDL: lowering triglycerides; lowering cholesterol; increasing HDL; lowering plasma levels of lipoprotein a (Lp(a)) in a human; inhibiting generation of apolipoprotein a (apo(a)) in vitro and/or in vivo;

(iix) prevention and/or treatment of cardiovascular diseases, such as syndrome X; atherosclerosis; myocardial infarction; coronary heart disease; stroke, cerebral ischemia; an early cardiac or early cardiovascular disease, such as left ventricular hypertrophy; coronary artery disease; essential hypertension; acute hypertensive emergency; cardiomyopathy; heart insufficiency; exercise tolerance; chronic heart failure; arrhythmia; cardiac dysrhythmia; syncopy; atheroschlerosis; mild chronic heart failure; angina pectoris; cardiac bypass reocclusion; intermittent claudication (atheroschlerosis oblitterens); diastolic dysfunction; and/or systolic dysfunction;

(ix) prevention and/or treatment of gastrointestinal diseases, such as inflammatory bowel syndrome; small bowel syndrome, or Crohn's disease; dyspepsia; and/or gastric ulcers;

(x) prevention and/or treatment of critical illness, such as treatment of a critically ill patient, a critical illness polynephropathy (CIPNP) patient, and/or a potential CIPNP patient; prevention of critical illness or development of CIPNP; prevention, treatment and/or cure of systemic inflammatory response syndrome (SIRS) in a patient; and/or for the prevention or reduction of the likelihood of a patient suffering from bacteraemia, septicaemia, and/or septic shock during hospitalisation; and/or (xi) prevention and/or treatment of polycystic ovary syndrome (PCOS).

In a particular embodiment, the indication is selected from the group consisting of (i)-(iii) and (v)-(iix), such as indications (i), (ii), and/or (iii); or indication (v), indication (vi), indication (vii), and/or indication (iix).

In another particular embodiment, the indication is (i). In a further particular embodiment the indication is (v). In a still further particular embodiment the indication is (iix).

The following indications are particularly preferred: Type 2 diabetes, and/or obesity.

Particular Embodiments

The following are particular embodiments of the invention.

1. A derivative of a GLP-1 analogue,
wherein the GLP-1 analogue comprises a first K residue at a position corresponding to position 27 of GLP-1(7-37) (SEQ ID NO: 1); a second K residue at a position corresponding to position T of GLP-1(7-37), where T is an integer in the range of 7-37 except 18 and 27; and a maximum of ten amino acid changes as compared to GLP-1(7-37); wherein the first K residue is designated $K^{27}$, and the second K residue is designated $K^T$;

which derivative comprises a first and a second protracting moiety attached to $K^{27}$ and $K^T$, respectively, via a first and a second linker, respectively, wherein the first and the second protracting moiety is selected from Chem. 1 and Chem. 2:

   Chem. 1:

   Chem. 2:

in which x is an integer in the range of 6-16, y is an integer in the range of 3-17; and the first and second linker comprises Chem. 5:

Chem. 5

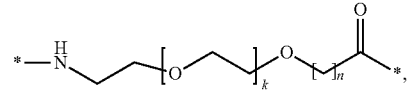

wherein k is an integer in the range of 1-5, and n is an integer in the range of 1-5;

or a pharmaceutically acceptable salt, amide, or ester thereof.

2. The derivative of embodiment 1, wherein T is an integer selected from the range of 7-37 except 18 and 27.

3. The derivative of any of embodiments 1-2, wherein T is selected from any of the ranges of 7-17, 19-26, and 28-37.

4. The derivative of any of embodiments 1-3, wherein T is selected from the range of 7-17.

5. The derivative of any of embodiments 1-4, wherein T is 12.

6. The derivative of any of embodiments 1-3, wherein T is selected from the range of 19-26.

7. The derivative of any of embodiments 1-3, and 6, wherein T is selected from the group consisting of 20, 22, and 24.

8. The derivative of any of embodiments 1-3, and 6-7, wherein T is 20.

9. The derivative of any of embodiments 1-3, and 6-7, wherein T is 22 or 24.
10. The derivative of any of embodiments 1-3, 6-7, and 9, wherein T is 22.
11. The derivative of any of embodiments 1-3, 6-7, and 9, wherein T is 24.
12. The derivative of any of embodiments 1-3, wherein T is selected from the range of 28-37.
13. The derivative of any of embodiments 1-3, and 12, wherein T is selected from the group consisting of 36 and 37.
14. The derivative of any of embodiments 1-3, and 12-13, wherein T is 36.
15. The derivative of any of embodiments 1-3, and 12, wherein T is 37.
16. The derivative of any of embodiments 1-16, wherein the position corresponding to position 27 of GLP-1(7-37) (SEQ ID NO: 1) is identified by handwriting and eyeballing.
17. The derivative of any of embodiments 1-16, wherein the position corresponding to position T of GLP-1(7-37) (SEQ ID NO: 1) is identified by handwriting and eyeballing.
18. The derivative of any of embodiments 1-17, wherein the position corresponding to position 27 of GLP-1(7-37) (SEQ ID NO: 1) is identified by use of a standard protein or peptide alignment program.
19. The derivative of any of embodiments 1-18, wherein the position corresponding to position T of GLP-1(7-37) (SEQ ID NO: 1) is identified by use of a standard protein or peptide alignment program.
20. The derivative of embodiment 19, wherein the alignment program is a Needleman-Wunsch alignment.
21. The derivative of any of embodiments 19-20, wherein the default scoring matrix and the default identity matrix is used.
22. The derivative of any of embodiments 19-21, wherein the scoring matrix is BLOSUM62.
23. The derivative of any of embodiments 19-22, wherein the penalty for the first residue in a gap is −10 (minus ten).
24. The derivative of any of embodiments 19-23, wherein the penalties for additional residues in a gap is −0.5 (minus point five).
25. The derivative of any of embodiments 1-24, wherein the analogue comprises no K residues other than the first and the second K residue.
26. The derivative of any of embodiments 1-25, wherein the protracting moiety is Chem. 1.
27. The derivative of any of embodiments 1-26, wherein x is an even number.
28. The derivative of any of embodiments 1-27, wherein x is 12.
29. The derivative of any of embodiments 1-28, wherein Chem. 1 is represented by Chem. 1a:

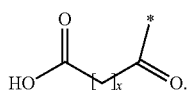

Chem. 1a

30. The derivative of any of embodiments 1-25, wherein the protracting moiety is Chem. 2.
31. The derivative of any of embodiments 1-25, and 30, wherein Chem. 2 is represented by Chem. 2a:

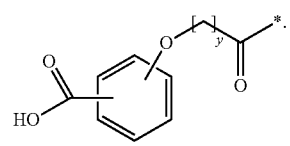

Chem. 2a

32. The derivative of any of embodiments 1-25, and 30-31, wherein y is an odd number.
33. The derivative of any of embodiments 1-25, and 30-32, wherein y is an integer in the range of 9-11.
34. The derivative of any of embodiments 1-25, and 30-33, wherein y is 9.
35. The derivative of any of embodiments 1-25, and 30-33, wherein y is 11.
36. The derivative of any of embodiments 1-25, and 30-35, wherein Chem. 2 is represented by Chem. 2b, or Chem. 2c:

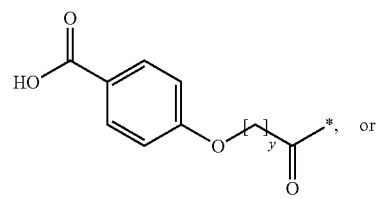

Chem. 2b

, or

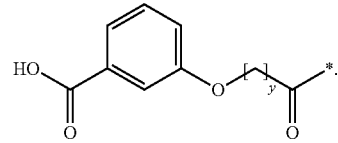

Chem. 2c

37. The derivative of any of embodiments 1-25, and 30-35, wherein Chem. 2 is represented by Chem. 2b.
38. The derivative of any of embodiments 31-35, wherein Chem. 2a is represented by Chem. 2b, or Chem. 2c:

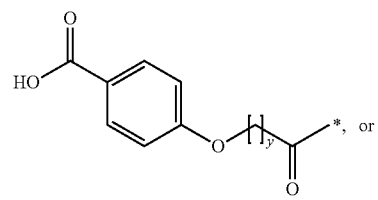

Chem. 2b

, or

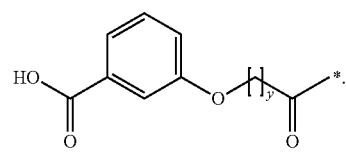

Chem. 2c

39. The derivative of any of embodiments 31-35, and 38, wherein Chem. 2a is represented by Chem. 2b.
40. The derivative of any of embodiments 1-39, wherein Chem. 5 is a first linker element.
41. The derivative of any of embodiments 1-40, wherein k is 1.
42. The derivative of any of embodiments 1-41, wherein n is 1.

43. The derivative of any of embodiments 1-42, wherein Chem. 5 is included m times, wherein m is an integer in the range of 1-10.
44. The derivative of embodiment 43, wherein m is 2.
45. The derivative of any of embodiments 43-44, wherein, when m is not 1, the Chem. 5 elements are interconnected via amide bond(s).
46. The derivative of any of embodiments 1-45, wherein the linker further comprises a second linker element.
47. The derivative of embodiment 46, wherein the second linker element is a Glu di-radical.
48. The derivative of any of embodiments 46-47, wherein the second linker element is selected from Chem. 6, and/or Chem. 7:

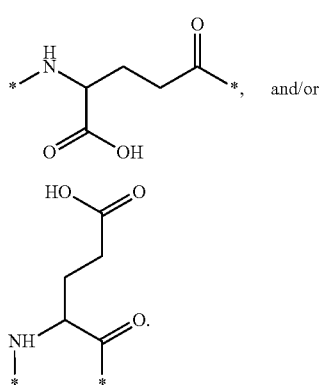

49. The derivative of embodiment 48, wherein the second linker element is Chem. 6.
50. The derivative of any of embodiments 46-49, wherein the Glu di-radical is included p times, wherein p is an integer in the range of 1-2.
51. The derivative of embodiment 50, wherein p is 1.
52. The derivative of embodiment 50, wherein p is 2.
53. The derivative of any of embodiments 46-52, wherein the Glu di-radical is a radical of L-Glu.
54. The derivative of any of embodiments 46-53, wherein one or more Glu di-radicals and one or more Chem. 5 elements are interconnected via amide bond(s).
55. The derivative of any of embodiments 46-54, wherein the linker consists of m times Chem. 5 and p times the Glu di-radical.
56. The derivative of embodiment 55, wherein (m,p) is (2,2) or (2,1).
57. The derivative of embodiment 56, wherein (m,p) is (2,1).
58. The derivative of any of embodiments 55-57, wherein the m Chem. 5 elements and the p Glu di-radicals are interconnected via amide bonds.
59. The derivative of any of embodiments 1-58, wherein the linker and the protracting moiety are interconnected via an amide bond.
60. The derivative of any of embodiments 1-59, wherein the linker and the GLP-1 analogue are interconnected via an amide bond.
61. The derivative of any of embodiments 1-60, wherein the linker is attached to the epsilon-amino group of the first or the second K residue.
62. The derivative of any of embodiments 1-61, wherein the linker has from 5 to 41 C-atoms.
63. The derivative of any of embodiments 1-62, wherein the linker has 17 or 22 C-atoms.
64. The derivative of any of embodiments 1-63, wherein the linker has 17 C-atoms.
65. The derivative of any of embodiments 1-63, wherein the linker has 22 C-atoms.
66. The derivative of embodiments 1-65, wherein the linker has from 4 to 28 hetero atoms.
67. The derivative of any of embodiments 1-66, wherein the linker has 12 or 16 hetero atoms.
68. The derivative of any of embodiments 1-67, wherein the linker has 12 hetero atoms.
69. The derivative of any of embodiments 1-67, wherein the linker has 16 hetero atoms.
70. The derivative of any of embodiments 66-70, wherein the hetero atoms are N—, and/or O-atoms.
71. The derivative of any of embodiments 1-70, wherein the linker has from 1 to 7 N-atoms.
72. The derivative of any of embodiments 1-71, wherein the linker has 3 or 4 N-atoms.
73. The derivative of any of embodiments 1-72, wherein the linker has 3 N-atoms.
74. The derivative of any of embodiments 1-72, wherein the linker has 4 N-atoms.
75. The derivative of any of embodiments 1-74, wherein the linker has from 3 to 21 O-atoms.
76. The derivative of any of embodiments 1-75, wherein the linker has 9 or 12 O-atoms.
77. The derivative of any of embodiments 1-76, wherein the linker has 9 O-atoms.
78. The derivative of any of embodiments 1-76, wherein the linker has 12 O-atoms.
79. The derivative of any of embodiments 1-78, wherein the linker consists of two times Chem. 6 and two times Chem. 5, interconnected via amide bonds and in the sequence indicated, the linker being connected at its *—NH end to the *—CO end of the protracting moiety, and at its *—CO end to the epsilon amino group of $K^{27}$ or $K^T$ of the GLP-1 analogue.
80. The derivative of any of embodiments 1-78, wherein the linker consists of two times Chem. 5 and one time Chem. 6, interconnected via amide bonds and in the sequence indicated, the linker being connected at its *—NH end to the *—CO end of the protracting moiety, and at its free *—CO end to the epsilon amino group of $K^{27}$ or $K^T$ of the GLP-1 analogue.
81. The derivative of any of embodiments 1-78, wherein the linker consists of one time Chem. 6 and two times Chem. 5, interconnected via amide bonds and in the sequence indicated, the linker being connected at its *—NH end to the *—CO end of the protracting moiety, and at its *—CO end to the epsilon amino group of $K^{27}$ or $K^T$ of the GLP-1 analogue.
82. The derivative of any of embodiments 1-78, wherein the linker consists of one time Chem. 6, two times Chem. 5, and one time Chem. 6, interconnected via amide bonds and in the sequence indicated, the linker being connected at its *—NH end to the *—CO end of the protracting moiety, and at its *—CO end to the epsilon amino group of $K^{27}$ or $K^T$ of the GLP-1 analogue.
83. The derivative of any of embodiments 1-82, wherein the two protracting moieties are substantially identical.
84. The derivative of any of embodiments 1-83, wherein the two protracting moieties are a) at least 80%, b) at least 85%, c) at least 90%, d) at least 95%, or e) at least 99% identical.
85. The derivative of any of embodiments 1-83, wherein two protracting moieties have a similarity of a) at least 0.5; b) at least 0.6; c) at least 0.7, d) at least 0.8; e) at least 0.9; or f) at least 0.99.

86. The derivative of any of embodiments 1-85, wherein the two protracting moieties have a similarity of 1.0.
87. The derivative of any of embodiments 1-86, wherein the two linkers are substantially identical.
88. The derivative of any of embodiments 1-87, wherein the two linkers have a similarity of at least 0.5.
89. The derivative of any of embodiments 1-88, wherein the two linkers have a similarity of a) at least 0.6; b) at least 0.7, c) at least 0.8; d) at least 0.9; or e) at least 0.99.
90. The derivative of any of embodiments 1-89, wherein the two linkers have a similarity of 1.0.
91. The derivative of any of embodiments 1-90, wherein the two albumin binders, such as the two side chains consisting of protracting moiety and linker, are substantially identical.
92. The derivative of any of embodiments 1-91, wherein the two albumin binders, such as the two side chains consisting of protracting moiety and linker, are a) at least 80%, b) at least 85%, c) at least 90%, d) at least 95%, or e) at least 99% identical.
93. The derivative of any of embodiments 1-92, wherein the two albumin binders, such as the two side chains consisting of protracting moiety and linker, have a similarity of a) at least 0.5; b) at least 0.6; c) at least 0.7, d) at least 0.8; e) at least 0.9; or f) at least 0.99.
94. The derivative of any of embodiments 1-92, wherein the two albumin binders, such as the two side chains consisting of protracting moiety and linker, have a similarity of 1.0.
95. The derivative of any of embodiments 83-94, wherein the two chemical structures to be compared are represented as fingerprints.
96. The derivative of embodiment 95, wherein the fingerprints are a) ECFP_6 fingerprints; b) UNITY fingerprints; and/or c) MDL fingerprints.
97. The derivative of any of embodiments 95-96, wherein the Tanimoto coefficient is preferably used for calculating the similarity, or identity, of the two fingerprints.
98. The derivative of any of embodiments 1-97, wherein the number of amino acid changes as compared to GLP-1(7-37) (SEQ ID NO: 1) are identified by handwriting and eyeballing.
99. The derivative of any of embodiments 1-98, wherein the number of amino acid changes as compared to GLP-1(7-37) (SEQ ID NO: 1) are identified by use of a standard protein or peptide alignment program.
100. The derivative of embodiment 99, wherein the alignment program is a Needleman-Wunsch alignment.
101. The derivative of any of embodiments 99-100, wherein the default scoring matrix and the default identity matrix is used.
102. The derivative of any of embodiments 99-101, wherein the scoring matrix is BLOSUM62.
103. The derivative of any of embodiments 99-102, wherein the penalty for the first residue in a gap is −10 (minus ten).
104. The derivative of any of embodiments 99-103, wherein the penalties for additional residues in a gap is −0.5 (minus point five).
105. The derivative of any of embodiments 1-104, wherein the amino acid change(s) is (are) at one or more positions corresponding to the following positions in GLP-1(7-37) (SEQ ID NO: 1): 8, 12, 20, 22, 23, 24, 25, 26, 27, 30, 31, 34, 35, 36, 37, 38, and 39.
106. The derivative of any of embodiments 1-105, wherein the analogue comprises at least one of the following changes: $Aib^8$, $K^{12}$, $K^{20}$, $E^{22}$ or $K^{22}$, $E^{23}$, $K^{24}$, $V^{25}$, $R^{26}$ or $H^{26}$, $K^{27}$, $E^{30}$, $H^{31}$, $G^{34}$ or $R^{34}$ or $Q^{34}$, $Des^{35}$, $K^{36}$ or $Des^{36}$, $K^{37}$ or $Des^{37}$, $E^{38}$ or $Q^{38}$, and/or $G^{39}$.
107. The derivative of any of embodiments 1-106, wherein the second K residue is $K^{12}$, and wherein the analogue, in addition to the change $K^{27}$, further comprises i) a change selected from $G^{34}$, $R^{34}$, and $Q^{34}$, and ii) a change selected from $R^{26}$ and $H^{26}$.
108. The derivative of any of embodiments 1-106, wherein the second K residue is $K^{20}$, and wherein the analogue, in addition to the change $K^{27}$, further comprises i) a change selected from $G^{34}$, $R^{34}$, and $Q^{34}$, and ii) a change selected from $R^{26}$ and $H^{26}$.
109. The derivative of any of embodiments 1-106, wherein the second K residue is $K^{22}$, and wherein the analogue, in addition to the change $K^{27}$, further comprises i) a change selected from $G^{34}$, $R^{34}$, and $Q^{34}$, and ii) a change selected from $R^{26}$ and $H^{26}$.
110. The derivative of any of embodiments 1-106, wherein the second K residue is $K^{24}$, and wherein the analogue, in addition to the change $K^{27}$, further comprises i) a change selected from $G^{34}$, $R^{34}$, and $Q^{34}$, and ii) a change selected from $R^{26}$ and $H^{26}$.
111. The derivative of any of embodiments 1-106, wherein the second K residue is $K^{36}$, and wherein the analogue, in addition to the change $K^{27}$, further comprises i) a change selected from $G^{34}$, $R^{34}$, and $Q^{34}$, and ii) a change selected from $R^{26}$ and $H^{26}$.
112. The derivative of any of embodiments 1-106, wherein the second K residue is $K^{37}$, and wherein the analogue, in addition to the change $K^{27}$, further comprises i) a change selected from $G^{34}$, $R^{34}$, and $Q^{34}$, and ii) a change selected from $R^{26}$ and $H^{26}$.
113. The derivative of any of embodiments 1-112, wherein the analogue comprises at least one of the following changes: $Aib^8$, $E^{22}$, $E^{23}$, $V^{25}$, $E^{30}$, $H^{31}$, $Des^{35}$, $Des^{36}$, $Des^{37}$, $E^{38}$ or $Q^{38}$, and/or $G^{39}$.
114. The derivative of any of embodiments 1-113, wherein the analogue comprises $Aib^8$.
115. The derivative of any of embodiments 1-114, wherein the analogue comprises $E^{22}$.
116. The derivative of any of embodiments 1-115, wherein the analogue comprises $E^{23}$.
117. The derivative of any of embodiments 1-116, wherein the analogue comprises $V^{25}$.
118. The derivative of any of embodiments 1-117, wherein the analogue comprises $E^{30}$.
119. The derivative of any of embodiments 1-118, wherein the analogue comprises $H^{31}$.
120. The derivative of any of embodiments 1-119, wherein the analogue comprises $Des^{37}$.
121. The derivative of embodiment 120, wherein the analogue comprises $Des^{36}$.
122. The derivative of any of embodiment 121, wherein the analogue comprises $Des^{35}$.
123. The derivative of any of embodiments 1-119, wherein the analogue comprises $E^{38}$ or $Q^{38}$.
124. The derivative of embodiment 123, wherein the analogue comprises $Q^{38}$.
125. The derivative of embodiment 123, wherein the analogue comprises $E^{38}$.
126. The derivative of any of embodiments 123-125, wherein the analogue comprises $G^{39}$.
127. The derivative of embodiment 122, which is a derivative of GLP-1(7-34) (amino acids 1-28 of SEQ ID NO: 1).
128. The derivative of embodiment 121, which is a derivative of GLP-1(7-35) (amino acids 1-29 of SEQ ID NO: 1).
129. The derivative of embodiment 120, which is a derivative of GLP-1(7-36) (amino acids 1-30 of SEQ ID NO: 1).

130. The derivative of any of embodiments 1-119, which is a derivative of GLP-1(7-37) (amino acids 1-31 of SEQ ID NO: 1).
131. The derivative of any of embodiments 123-125, which is a derivative of GLP-1(7-38) (amino acids 1-31 of SEQ ID NO: 1, plus one C-terminally added amino acid residue).
132 The derivative of any of embodiments 126, which is a derivative of GLP-1(7-39) (amino acids 1-31 of SEQ ID NO: 1, plus two C-terminally added amino acid residues).
133. The derivative of any of embodiments 1-132, wherein the analogue has a maximum of nine amino acid changes.
134. The derivative of any of embodiments 1-132, wherein the analogue has a maximum of eight amino acid changes.
135. The derivative of any of embodiments 1-132, wherein the analogue has a maximum of seven amino acid changes.
136. The derivative of any of embodiments 1-132, wherein the analogue has a maximum of six amino acid changes.
137. The derivative of any of embodiments 1-132, wherein the analogue has a maximum of five amino acid changes.
138. The derivative of any of embodiments 1-132, wherein the analogue has a maximum of four amino acid changes.
139. The derivative of any of embodiments 1-132, wherein the analogue has a maximum of three amino acid changes.
140. The derivative of any of embodiments 1-132, wherein the analogue has a maximum of two amino acid changes.
141. The derivative of any of embodiments 1-132, wherein the analogue has a maximum of one amino acid change.
142. The derivative of any of embodiments 1-140, wherein the analogue has a minimum of one amino acid change.
143. The derivative of any of embodiments 1-139, wherein the analogue has a minimum of two amino acid changes.
144. The derivative of any of embodiments 1-138, wherein the analogue has a minimum of three amino acid changes.
145. The derivative of any of embodiments 1-137, wherein the analogue has a minimum of four amino acid changes.
146. The derivative of any of embodiments 1-136, wherein the analogue has a minimum of five amino acid changes.
147. The derivative of any of embodiments 1-135, wherein the analogue has a minimum of six amino acid changes.
148. The derivative of any of embodiments 1-134, wherein the analogue has a minimum of seven amino acid changes.
149. The derivative of any of embodiments 1-133, wherein the analogue has a minimum of eight amino acid changes.
150. The derivative of any of embodiments 1-132, wherein the analogue has a minimum of nine amino acid changes.
151. The derivative of any of embodiments 1-132, wherein the analogue has one amino acid change.
152. The derivative of any of embodiments 1-132, wherein the analogue has two amino acid changes.
153. The derivative of any of embodiments 1-132, wherein the analogue has three amino acid changes.
154. The derivative of any of embodiments 1-132, wherein the analogue has four amino acid changes.
155. The derivative of any of embodiments 1-132, wherein the analogue has five amino acid changes.
156. The derivative of any of embodiments 1-132, wherein the analogue has six amino acid changes.
157. The derivative of any of embodiments 1-132, wherein the analogue has seven amino acid changes.
158. The derivative of any of embodiments 1-132, wherein the analogue has eight amino acid changes.
159. The derivative of any of embodiments 1-132, wherein the analogue has nine amino acid changes.
160. The derivative of any of embodiments 1-132, wherein the analogue has ten amino acid changes.
161. The derivative of any of embodiments 1-160, wherein the change(s) is (are), independently, substitutions, additions, and/or deletions.
162. The derivative of any of embodiments 1-161, wherein the analogue comprises a GLP-1 analogue of Formula I (SEQ ID NO: 3):

Formula I:
$Xaa_7$-$Xaa_8$-Glu-Gly-Thr-$Xaa_{12}$-Thr-Ser-Asp-$Xaa_{16}$-Ser-$Xaa_{18}$-$Xaa_{19}$-$Xaa_{20}$-Glu-$Xaa_{22}$-$Xaa_{23}$-$Xaa_{24}$-$Xaa_{25}$-$Xaa_{26}$-Lys-Phe-Ile-$Xaa_{30}$-$Xaa_{31}$-Leu-Val-$Xaa_{34}$-$Xaa_{35}$-$Xaa_{36}$-$Xaa_{37}$-$Xaa_{38}$-$Xaa_{39}$, wherein $Xaa_7$ is L-histidine, imidazopropionyl, α-hydroxy-histidine, D-histidine, desamino-histidine, 2-amino-histidine, β-hydroxy-histidine, homohistidine, $N^α$-acetyl-histidine, $N^α$-formyl-histidine, α-fluoromethyl-histidine, α-methyl-histidine, 3-pyridylalanine, 2-pyridylalanine, or 4-pyridylalanine;

$Xaa_8$ is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$Xaa_{12}$ is Lys or Phe;
$Xaa_{16}$ is Val or Leu;
$Xaa_{18}$ is Ser, Arg, Asn, Gln, or Glu;
$Xaa_{19}$ is Tyr or Gln;
$Xaa_{20}$ is Leu, Lys, or Met;
$Xaa_{22}$ is Gly, Glu, Lys, or Aib;
$Xaa_{23}$ is Gln, Glu, or Arg;
$Xaa_{24}$ is Ala or Lys;
$Xaa_{25}$ is Ala or Val;
$Xaa_{26}$ is Val, His, or Arg;
$Xaa_{30}$ is Ala, Glu, or Arg;
$Xaa_{31}$ is Trp or His;
$Xaa_{34}$ is Glu, Asn, Gly, Gln, or Arg;
$Xaa_{35}$ is Gly, Aib, or absent;
$Xaa_{36}$ is Arg, Gly, Lys, or absent;
$Xaa_{37}$ is Gly, Ala, Glu, Pro, Lys, Arg, or absent;
$Xaa_{38}$ is Ser, Gly, Ala, Glu, Gln, Pro, Arg, or absent; and
$Xaa_{39}$ is Gly or absent.

163. The derivative of embodiment 162, wherein the analogue is a GLP-1 analogue of Formula I (SEQ ID NO: 3).
164. The derivative of any of embodiments 162-163, wherein the peptide of Formula I (SEQ ID NO: 3) is an analogue of GLP-1(7-37) (SEQ ID NO: 1).
165. The derivative of any of embodiments 162-164, wherein if $Xaa_{38}$ is absent, then $Xaa_{39}$ is also absent.
166. The derivative of any of embodiments 162-165, wherein if $Xaa_{37}$ is absent, then $Xaa_{38}$ and $Xaa_{39}$ are also absent.
167. The derivative of any of embodiments 162-166, wherein if $Xaa_{36}$ is absent, then $Xaa_{37}$, $Xaa_{38}$, and $Xaa_{39}$ are also absent.
168. The derivative of any of embodiments 162-167, wherein if $Xaa_{35}$ is absent, then $Xaa_{36}$, $Xaa_{37}$, $Xaa_{38}$, and $Xaa_{39}$ are also absent.
169. The derivative of any of embodiments 162-168, wherein $Xaa_7$ is His; $Xaa_8$ is Ala or Aib; $Xaa_{12}$ is Lys or Phe; $Xaa_{16}$ is Val; $Xaa_{18}$ is Ser; $Xaa_{19}$ is Tyr; $Xaa_{20}$ is Leu or Lys; $Xaa_{22}$ is Glu, Gly or Lys; $Xaa_{23}$ is Gln or Glu; $Xaa_{24}$ is Ala or Lys; $Xaa_{25}$ is Ala or Val; $Xaa_{26}$ is His or Arg; $Xaa_{30}$ is Ala or Glu; $Xaa_{31}$ is Trp or His; $Xaa_{34}$ is Gly, Gln, or Arg; $Xaa_{35}$ is Gly or absent; $Xaa_{36}$ is Arg, Lys, or absent; $Xaa_{37}$ is Gly, Lys, or absent; $Xaa_{38}$ is Glu or Gln; and $Xaa_{39}$ is Gly or absent.
170. The derivative of any of embodiments 162-169, wherein $Xaa_7$ is His.

171. The derivative of any of embodiments 162-170, wherein Xaa$_8$ is Ala.
172. The derivative of any of embodiments 162-170, wherein Xaa$_8$ is Aib.
173. The derivative of any of embodiments 162-172, wherein Xaa$_{12}$ is Lys.
174. The derivative of any of embodiments 162-172, wherein Xaa$_{12}$ is Phe.
175. The derivative of any of embodiments 162-174, wherein Xaa$_{16}$ is Val.
176. The derivative of any of embodiments 162-175, wherein Xaa$_{18}$ is Ser.
177. The derivative of any of embodiments 162-176, wherein Xaa$_{19}$ is Tyr.
178. The derivative of any of embodiments 162-177, wherein Xaa$_{20}$ is Leu.
179. The derivative of any of embodiments 162-177, wherein Xaa$_{20}$ is Lys.
180. The derivative of any of embodiments 162-179, wherein Xaa$_{22}$ is Glu.
181. The derivative of any of embodiments 162-179, wherein Xaa$_{22}$ is Gly.
182. The derivative of any of embodiments 162-179, wherein Xaa$_{22}$ is Lys.
183. The derivative of any of embodiments 162-182, wherein Xaa$_{23}$ is Gln.
184. The derivative of any of embodiments 162-182, wherein Xaa$_{23}$ is Glu.
185. The derivative of any of embodiments 162-184, wherein Xaa$_{24}$ is Ala.
186. The derivative of any of embodiments 162-184, wherein Xaa$_{24}$ is Lys.
187. The derivative of any of embodiments 162-186, wherein Xaa$_{25}$ is Ala.
188. The derivative of any of embodiments 162-186, wherein Xaa$_{25}$ is Val.
189. The derivative of any of embodiments 162-188, wherein Xaa$_{26}$ is His.
190. The derivative of any of embodiments 162-188, wherein Xaa$_{26}$ is Arg.
191. The derivative of any of embodiments 162-190, wherein Xaa$_{30}$ is Ala.
192. The derivative of any of embodiments 162-190, wherein Xaa$_{30}$ is Glu.
193. The derivative of any of embodiments 162-192, wherein Xaa$_{31}$ is Trp.
194. The derivative of any of embodiments 162-192, wherein Xaa$_{31}$ is His.
195. The derivative of any of embodiments 162-194, wherein Xaa$_{34}$ is Gly.
196. The derivative of any of embodiments 162-194, wherein Xaa$_{34}$ is Gln.
197. The derivative of any of embodiments 162-194, wherein Xaa$_{34}$ is Arg.
198. The derivative of any of embodiments 162-197, wherein Xaa$_{35}$ is Gly.
199. The derivative of any of embodiments 162-198, wherein Xaa$_{35}$ is absent.
200. The derivative of any of embodiments 162-199, wherein Xaa$_{36}$ is Arg.
201. The derivative of any of embodiments 162-199, wherein Xaa$_{36}$ is Lys.
202. The derivative of any of embodiments 162-199, wherein Xaa$_{36}$ is absent.
203. The derivative of any of embodiments 162-202, wherein Xaa$_{37}$ is Gly.
204. The derivative of any of embodiments 162-202, wherein Xaa$_{37}$ is Lys.
205. The derivative of any of embodiments 162-202, wherein Xaa$_{37}$ is absent.
206. The derivative of any of embodiments 162-205, wherein Xaa$_{38}$ is Glu.
207. The derivative of any of embodiments 162-205, wherein Xaa$_{38}$ is Gln.
208. The derivative of any of embodiments 162-205, wherein Xaa$_{38}$ is absent.
209. The derivative of any of embodiments 162-208, wherein Xaa$_{39}$ is Gly.
210. The derivative of any of embodiments 162-208, wherein Xaa$_{39}$ is absent.
211. The derivative of any of embodiments 1-210, wherein the analogue comprises the following amino acid changes, as compared to GLP-1(7-37) (SEQ ID NO: 1): (i) 22E, 26R, 27K, 34R, 37K; (ii) 22E, 26R, 27K, 30E, 34R, 36K, 38E, 39G; (iii) 22E, 26R, 27K, 34R, 36K, des37; (iv) 22E, 25V, 26R, 27K, 34R, 37K; (v) 8Aib, 20K, 22E, 26R, 27K, 30E, 34G, des35-37; (vi) 26R, 27K, 30E, 34R, 36K, 38E; (vii) 8Aib, 22K, 25V, 26R, 27K, 31H, 34R; (iix) 8Aib, 22K, 25V, 26R, 27K, 34R, des35-37; (ix) 8Aib, 22K, 25V, 26R, 27K, 34R, des36-37; (x) 26H, 27K, 30E, 34R, 36K, 38E; (xi) 22K, 25V, 26R, 27K, 30E, 34Q; (xii) 25V, 26R, 27K, 30E, 34R, 36K, 38Q; (xiii) 25V, 26R, 27K, 30E, 34Q, 36K, 38E; (xiv) 22K, 26R, 27K, 31H, 34G, des35-37; (xv) 8Aib, 25V, 26R, 27K, 31H, 34Q, 37K; (xvi) 25V, 26R, 27K, 31H, 34Q, 37K; (xvii) 22E, 23E, 25V, 26R, 27K, 31H, 34Q, 37K; (iixx) 8Aib, 12K, 22E, 26R, 27K, 31H, 34Q; (ixx) 8Aib, 22K, 26R, 27K, 31H, 34G, des35-37; (xx) 22E, 26H, 27K, 30E, 34R, 36K, 38E; (xxi) 22E, 24K, 26R, 27K, 31H, 34G, des35-37; (xxii) 25V, 26R, 27K, 34Q, 36K; (xxiii) 22E, 24K, 25V, 26R, 27K, 31H, 34R; (xxiv) 22E, 24K, 25V, 26R, 27K, 34G, des35-37; (xxv) 22E, 24K, 25V, 26R, 27K, 34R; (xxvi) 8Aib, 22E, 24K, 25V, 26R, 27K, 31H, 34Q; or (xxvii) 8Aib, 22E, 26R, 27K, 30E, 34R, 36K, 38E, 39G.
212. The derivative of embodiment 211, wherein the analogue has a set of amino acid changes as defined in any of (i)-(xxvii).
213. A compound selected from the following: Chem. 50, Chem. 51, Chem. 52, Chem. 53, Chem. 54, Chem. 55, Chem. 56, Chem. 57, Chem. 58, Chem. 59, Chem. 60, Chem. 61, Chem. 62, Chem. 63, Chem. 64, Chem. 65, Chem. 66, Chem. 67, Chem. 68, Chem. 69, Chem. 70, Chem. 71, Chem. 72, Chem. 73, Chem. 74, Chem. 75, Chem. 76, Chem. 77, Chem. 78, Chem. 79, Chem. 80, and Chem. 81; or a pharmaceutically acceptable salt, amide, or ester thereof.
214. The compound of embodiment 213 which is a compound according to any of embodiments 1-212.
215. A compound characterised by its name, and selected from a listing of each of the names of the compounds of Examples 1-32 herein, or a pharmaceutically acceptable salt, amide, or ester thereof.
216. The compound of embodiment 215 which is a compound according to any of embodiments 1-214.
217. The derivative of any of embodiments 1-216, which has GLP-1 activity.
218. The derivative of embodiment 217, wherein GLP-1 activity refers to the capability of activating the human GLP-1 receptor.
219. The derivative of embodiment 217, wherein activation of the human GLP-1 receptor is measured in an in vitro assay.

220. The derivative of any of embodiments 217-219, wherein activation of the human GLP-1 receptor is measured as the potency of cAMP production.

221. The derivative of any of embodiments 217-220, which has a potency corresponding to an $EC_{50}$
a) below 10000 pM, more preferably below 5000 pM, even more preferably below 4000 pM, or most preferably below 3000 pM;
b) below 2000 pM, preferably below 1500 pM, more preferably below 1200 pM, even more preferably below 1000 pM, or most preferably below 500 pM;
c) below 400 pM, preferably below 300 pM, more preferably below 200 pM, even more preferably below 150 pM, or most preferably below 100 pM; or
d) below 80 pM, preferably below 60 pM, more preferably below 40 pM, even more preferably below 30 pM, or most preferably below 20 pM.

222. The derivative of any of embodiments 217-221, wherein the potency is determined as $EC_{50}$ for the dose-response curve showing dose-dependent formation of cAMP in a medium containing the human GLP-1 receptor.

223. The derivative of any of embodiments 219-222, wherein a stable transfected cell-line such as BHK467-12A (tk-ts3).

224. The derivative of any of embodiments 219-223, wherein for the determination of cAMP a functional receptor assay.

225. The derivative of any of embodiments 219-224, wherein the assay is based on competition between endogenously formed cAMP and exogenously added biotin-labelled cAMP.

226. The derivative of any of embodiments 219-225, in which assay cAMP is captured using a specific antibody.

227. The derivative of any of embodiments 219-226, wherein the assay is the AlphaScreen cAMP Assay.

228. The derivative of any of embodiments 219-227, wherein the assay is described in Example 33.

229. The derivative of any of embodiments 217-228, wherein activation of the human GLP-1 receptor is measured as the capability of binding to the receptor in the presence of a low albumin concentration, wherein the low albumin concentration is 0.005% HSA, or, preferably, 0.001% HSA.

230. The derivative of any embodiment 217-229, for which the ratio [GLP-1 receptor binding affinity ($IC_{50}$) in the presence of 2.0% HSA (high albumin), divided by GLP-1 receptor binding affinity ($IC_{50}$) in the presence of 0.001% HSA (low albumin)] is:
a) at least 1.0, more preferably at least 10, even more preferably at least 25, or most preferably at least 50;
b) at least 60, preferably at least 70, more preferably at least 80, even more preferably at least 90, or most preferably at least 100;
c) at least 125, preferably at least 150, more preferably at least 200, still more preferably at least 250, even more preferably at least 400, or most preferably at least 500; or
d) at least 600, preferably at least 800, even more preferably at least 900, or most preferably at least 1000.

231. The derivative of any of embodiments 217-230, for which the GLP-1 receptor binding affinity ($IC_{50}$) in the presence of 0.001% HSA (low albumin) is
a) below 1000 nM, preferably below 750 nM, more preferably below 500 nM, or most preferably below 400 nM; or
b) below 300 nM, preferably below 250 nM, more preferably below 200 nM, or most preferably below 100 nM; or
c) below 50.0 nM, preferably below 15.0 nM, more preferably below 10.0 nM, even more preferably below 5.0 nM, or most preferably below 1.0 nM
d) below 0.80 nM, preferably below 0.60 nM, more preferably below 0.40 nM, even more preferably below 0.30 nM, or most preferably below 0.20 nM.

232. The derivative of embodiments 217-231, for which the GLP-1 receptor binding affinity ($IC_{50}$) in the presence of 2.0% HSA (high albumin) is
a) below 1000 nM, more preferably below 900 nM, or most preferably below 800 nM; or
b) below 500 nM, preferably below 400 nM, more preferably below 300 nM, even more preferably below 150 nM, or most preferably below 50.0 nM.

166. The derivative of any of embodiments 217-232, wherein the binding affinity to the GLP-1 receptor is measured by way of displacement of $^{125}$I-GLP-1 from the receptor.

233. The derivative of any of embodiments 217-232, wherein a SPA binding assay is used.

234. The derivative of any of embodiments 217-233, wherein the GLP-1 receptor is prepared using a stable, transfected cell line.

235. The derivative of any of embodiments 217-234, wherein a hamster cell line is used, preferably a baby hamster kidney cell line, such as BHK tk-ts13.

236. The derivative of any of embodiments 229-235, wherein the $IC_{50}$ value is determined as the concentration which displaces 50% of $^{125}$I-GLP-1 from the receptor.

237. The derivative of any of embodiments 1-236, which has an oral bioavailability, preferably an absolute oral bioavailability, which is higher than that of semaglutide.

238. The derivative of embodiment 237, wherein oral bioavailability is measured in vivo in rats.

239. The derivative of any of embodiments 237-239, wherein oral bioavailability is measured as exposure in plasma after direct injection into the intestinal lumen.

240. The derivative of any of embodiments 237-239, for which the plasma concentration (pM) of the derivative, determined 30 minutes after injection of a solution of the derivative in the jejunum of rat, divided by the concentration (µM) of the injected solution (dose-corrected exposure at 30 min) is a) at least 39, b) at least 40; c) at least 60; d) at least 80; e) at least 100; f) at least 125; or g) at least 150.

241. The derivative of any of embodiments 237-240, for which the plasma concentration (pM) of the derivative, determined 30 minutes after injection of a solution of the derivative in the jejunum of rat, divided by the concentration (µM) of the injected solution (dose-corrected exposure at 30 min) is a) at least 160, b) at least 180, c) at least 200, or d) at least 250.

242. The derivative of any of embodiments 237-241, wherein the GLP-1 derivative is tested in a concentration of 1000 uM in admixture with 55 mg/ml sodium caprate.

243. The derivative of any of embodiments 237-242, wherein male Sprague Dawley rats are used.

244. The derivative of any of embodiments 237-243, wherein the rats have a body weight upon arrival of approximately 240 g.

245. The derivative of any of embodiments 237-244, wherein the rats are fasted for approximately 18 hours before the experiment.

246. The derivative of any of embodiments 237-245, wherein the rats are taken into general anaesthesia after having fasted and before the injection of the derivative in the jejunum.

247. The derivative of any of embodiments 237-246, wherein the derivative is administered in the proximal part of the jejunum (10 cm distal for the duodenum), or in the mid-intestine (50 cm proximal for the cecum).

248. The derivative of any of embodiments 237-247, wherein 100 μl of the derivative is injected into the jejunal lumen through a catheter with a syringe, and subsequently 200 μl of air is pushed into the jejunal lumen with another syringe, which is then left connected to the catheter to prevent flow back into the catheter.

249. The derivative of any of embodiments 237-248, wherein blood samples (200 ul) are collected into EDTA tubes from the tail vein at desired intervals, such as at times 0, 10, 30, 60, 120 and 240 min, and centrifuged 5 minutes, 10000G, at 4° C. within 20 minutes.

250. The derivative of any of embodiments 237-249, wherein plasma (e.g. 75 ul) is separated, immediately frozen, and kept at −20° C. until analyzed for plasma concentration of the derivative.

251. The derivative of any of embodiments 237-250, wherein LOCI (Luminescent Oxygen Channeling Immunoassay) is used for analyzing the plasma concentration of the derivative.

252. The derivative of any of embodiments 1-251, wherein the derivative is effective at lowering blood glucose in vivo in db/db mice.

253. The derivative of any of embodiments 1-252, wherein the derivative is effective at lowering body weight in vivo in db/db mice.

254. The derivative of any of embodiments 252-253, wherein db/db mice are treated, s.c., with a suitable range of doses of the GLP-1 derivative, and blood glucose and/or bodyweight is/are determined at appropriate intervals.

255. The derivative of any of embodiments 252-254, wherein the dose of the GLP-1 derivative is 0.3 nmol/kg, 1.0 nmol/kg, 3.0 nmol/kg, 10 nmol/kg, 30 nmol/kg, and 100 nmol/kg, wherein kg refers to the body weight of the mouse.

256. The derivative of any of embodiments 252-255, wherein a control group is treated with vehicle, s.c., preferably the medium in which the GLP-1 derivative is dissolved, e.g. with the following composition: 50 mM sodium phosphate, 145 mM sodium chloride, 0.05% tween 80, pH 7.4.

257. The derivative of any of embodiments 252-256, wherein blood glucose is determined, and/or the mice are weighed, at time −½ h (half an hour prior to dosing (t=0)), and at times 1, 2, 4, and 8 h.

258. The derivative of any of embodiments 252-257, wherein the glucose concentration is measured using the glucose oxidase method.

259. The derivative of any of embodiments 252-258, wherein
  (i) $ED_{50}$ (body weight (BW)) is calculated as the dose giving rise to half-maximum effect on delta (e.g., decrease) BW 8 hours following the subcutaneous administration of the derivative; and/or
  (ii) $ED_{50}$ (blood glucose (BG)) is calculated as the dose giving rise to half-maximum effect on AUC (Area Under the Curve) delta (e.g., decrease) BG 8 hours and/or 24 hours following the subcutaneous administration of the derivative.

260. The derivative of any of embodiments 252-259, wherein a sigmoidal dose-response relationship exists, preferably with a clear definition of the maximum response.

261. The derivative of any of embodiments 1-260, which has a more protracted profile of action than liraglutide.

262. The derivative of embodiment 261, wherein protraction means half-life in vivo in a relevant animal species.

263. The derivative of any of embodiments 261-262, wherein the animal is a) db/db mice, b) rat, c) pig, and/or, d) minipig.

264. The derivative of embodiment 263, wherein the animal is minipig.

265. The derivative of any of embodiments 261-264, wherein the derivative is administered i) s.c., and/or, ii) i.v.

266. The derivative of any of embodiments 1-265, wherein the derivative is administered i.v.

267. The derivative of any of embodiments 1-266, wherein the terminal half-life ($T_{1/2}$) after i.v. administration in minipigs is
  a) at least 12 hours, preferably at least 24 hours, more preferably at least 36 hours, even more preferably at least 48 hours, or most preferably at least 60 hours;
  b) at least 7 hours, preferably at least 16 hours, more preferably at least 24 hours, even more preferably at least 30 hours, or most preferably at least 40 hours;
  c) at least 50 hours, preferably at least 60 hours, more preferably at least 70 hours, even more preferably at least 80 hours, or most preferably at least 90 hours.

268. The derivative of any of embodiments 264-267, wherein the minipigs are male Göttingen minipigs.

269. The derivative of any of embodiments 267-268, wherein the minipigs are 7-14 months of age.

270. The derivative of any of embodiments 267-269, wherein the weight of the minipigs is 16-35 kg.

271. The derivative of any of embodiments 267-270, wherein the minipigs are housed individually, and fed once or twice daily, preferably with SDS minipig diet.

272. The derivative of any of embodiments 267-271, wherein the derivative is dosed, i.v., after at least 2 weeks of acclimatisation.

273. The derivative of any of embodiments 267-272, wherein the animals are fasted for approximately 18 h before dosing and for at least 4 h after dosing, and have ad libitum access to water during the whole period.

274. The derivative of any of embodiments 267-273, wherein the GLP-1 derivative is dissolved in 50 mM sodium phosphate, 145 mM sodium chloride, 0.05% tween 80, pH 7.4 to a suitable concentration, preferably from 20-60 nmol/ml.

275. The derivative of any of embodiments 267-275, wherein intravenous injections of the derivative are given in a volume corresponding to 1-2 nmol/kg.

276. The derivative of any of embodiments 1-275, which causes a reduced food intake in pigs.

277. The derivative of embodiment 276, wherein the intake is reduced relative to a control, that is preferably vehicle-treated, or untreated.

278. The derivative of any of embodiments 276-277, wherein the food intake (0-24 h) is
a) 90% or lower relative to the vehicle-treated control, b) preferably 80% or lower, c) more preferably 70% or lower, d) even more preferably 60% or lower, or e) most preferably 50% or lower.

279. The derivative of any of embodiments 276-278, wherein food intake (0-24 h) refers to the first 24 hours after administration of the derivative or vehicle.

280. The derivative of any of embodiments 276-279, wherein the pigs are female Landrace Yorkshire Duroc (LYD) pigs.

281. The derivative of any of embodiments 276-280, wherein the pigs are 3 months of age.

282. The derivative if any of embodiments 276-281, wherein the pigs have a weight of 30-35 kg.
283. The derivative of any of embodiments 276-282, wherein the animals are housed in a group for 1-2 weeks for acclimatisation.
284. The derivative of any of embodiments 276-283, wherein during the experimental period the animals are placed in individual pens from Monday morning to Friday afternoon for measurement of individual food intake.
285. The derivative of any of embodiments 276-284, wherein the animals are fed ad libitum with pig fodder (such as Svinefoder, Antonio).
286. The derivative of any of embodiments 276-285, wherein food intake is monitored on line by logging the weight of fodder every 15 minutes, preferably using the Mpigwin system.
287. The derivative of any of embodiments 276-286, which is dosed 0.3, 1.0, 3.0, 10, or 30 nmol/kg.
288. The derivative of any of embodiments 276-287, which is dissolved in a phosphate buffer (50 mM phosphate, 145 mM sodium chloride, 0.05% tween 80, pH 8), preferably at concentrations of 12, 40, 120, 400, or 1200 nmol/ml.
289. The derivative of any of embodiments 276-288, wherein the phosphate buffer serves as vehicle.
290. The derivative of any of embodiments 276-289, wherein the animals are dosed with a single subcutaneous dose of the derivative, or vehicle (preferably with a dose volume of 0.025 ml/kg), on the morning of day 1, and food intake is measured for 4 days after dosing.
291. The derivative of any of embodiments 1-290, which has a half-life ($T_{1/2}$) in vivo in rats after i.v. administration of a) at least 4 hours, b) at least 6 hours, c) at least 8 hours, or d) at least 10 hours.
292. The derivative of any of embodiments 1-291, which has a half-life ($T_{1/2}$) in vivo in rats after i.v. administration of a) at least 12 hours, b) at least 15 hours, c) at least 18 hours, or d) at least 20 hours.
293. The derivative of any of embodiments 1-292, which has a half-life ($T_{1/2}$) in vivo in rats after i.v. administration of a) at least 24 hours, b) at least 26 hours, or c) at least 30 hours.
294. The derivative of any of embodiments 291-294, in which the rats are male Sprague Dawley rats with a body weight of approximately 400 g.
294. The derivative of any of embodiments 238-294, for which the AUC of the dose-corrected (i.e., divided by the dose in pmol of injected derivative) plasma exposure curve (i.e., concentration in plasma in pM vs time) from time 30 to 180 min is determined (i.e., the result is indicated in (min×pM/pmol) or simply in min/L).
295. The derivative of embodiment 294, wherein the AUC of the dose-corrected plasma exposure curve is
a) at least 50, preferably at least 100, or more preferably at least 150 min/L;
b) at least 200, preferably at least 250, more preferably at least 300, or most preferably at least 320 min/L; or
c) at least 1.5 times, preferably at least 2 times, more preferably at least 3 times, or most preferably at least 4 times the corresponding AUC value for semaglutide.
296. The derivative of any of embodiments 1-295, wherein oral bioavailability is measured in vivo in rats, as exposure in plasma after oral gavage.
297. The derivative of embodiment 296, for which the AUC of the dose-corrected (i.e., divided by the dose in pmol of administered derivative) plasma exposure curve (i.e., concentration in plasma in pM vs time) from time 30 to 180 min is determined (i.e., the result may be indicated in (min×pM/pmol) or simply in min/L).
298. The derivative of embodiment 297, wherein the AUC of the dose-corrected plasma exposure curve is
a) at least 10, preferably at least 20, or more preferably at least 30 min/L;
b) at least 40, preferably at least 50, more preferably at least 60, or most preferably at least 70 min/L; or
c) at least 1.5 times, preferably at least 2 times, more preferably at least 3 times, or most preferably at least 4 times the corresponding AUC value for semaglutide.
299. The derivative of any of embodiments 294-298, wherein the GLP-1 derivative is tested in a concentration of about 1000 uM in a solution of 250 mg/ml of sodium N-[8-(2-hydroxybenzoyl)amino]caprylate (SNAC).
300. The derivative of any of embodiments 294-299, wherein male Sprague Dawley rats are used, preferably with a body weight upon arrival of approximately 240 g.
301. The derivative of any of embodiments 294-300, wherein the rats are fasted for approximately 18 hours before the experiment.
302. The derivative of any of embodiments 294-301, wherein the rats are and taken into general anaesthesia after having fasted and before the injection of the derivative in the jejunum, or the oral gavage, respectively.
303. The derivative of any of embodiments 294-302, wherein for injection in the intestinal lumen the derivative is administered in the proximal part of the jejunum (10 cm distal for the duodenum) or in the mid-intestine (50 cm proximal for the cecum), preferably in the proximal part of the jejunum.
304. The derivative of any of embodiments 294-303, wherein 100 µl of the derivative is injected into the jejunal lumen through a catheter with a 1 ml syringe, and subsequently 200 µl of air is pushed into the jejunal lumen with another syringe, which is then left connected to the catheter to prevent flow back into the catheter.
305. The derivative of any of embodiments 294-304, wherein blood samples (200 ul) are collected into EDTA tubes from the tail vein at desired intervals, such as at times 0, 10, 30, 60, 120 and 240 min, and centrifuged 5 minutes, 10000G, at 4° C. within 20 minutes.
306. The derivative of any of embodiments 294-305, wherein plasma (e.g. 75 ul) is separated, immediately frozen, and kept at −20° C. until analyzed for plasma concentration of the derivative.
307. The derivative of any of embodiments 294-306, wherein LOCI (Luminescent Oxygen Channeling Immunoassay) is used for analyzing the plasma concentration of the derivative.
308. An intermediate product in the form of a GLP-1 analogue which comprises the following change as compared to GLP-1(7-37) (SEQ ID NO: 1): (i) 38Q; and/or (ii) 39G; or a pharmaceutically acceptable salt, amide, or ester thereof.
309. The GLP-1 analogue of embodiment 308 which comprises (38E, 39G).
310. An intermediate product in the form of a GLP-1 analogue which comprises, the following amino acid changes, as compared to GLP-1(7-37) (SEQ ID NO: 1): (i) 22E, 26R, 27K, 34R, 37K; (ii) 22E, 26R, 27K, 30E, 34R, 36K, 38E, 39G; (iii) 22E, 26R, 27K, 34R, 36K, des37; (iv) 22E, 25V, 26R, 27K, 34R, 37K; (v) 8Aib, 20K, 22E, 26R, 27K, 30E, 34G, des35-37; (vi) 26R, 27K, 30E, 34R, 36K, 38E; (vii) 8Aib, 22K, 25V, 26R, 27K, 31H, 34R; (iix) 8Aib, 22K, 25V, 26R, 27K, 34R, des35-37; (ix) 8Aib, 22K, 25V, 26R, 27K, 34R, des36-37; (x) 26H, 27K, 30E, 34R, 36K, 38E; (xi) 22K, 25V, 26R, 27K, 30E, 34Q; (xii) 25V, 26R, 27K, 30E, 34R, 36K, 38Q; (xiii) 25V, 26R, 27K, 30E, 34Q, 36K, 38E; (xiv) 22K, 26R, 27K, 31H, 34G, des35-37; (xv) 8Aib, 25V, 26R, 27K, 31H, 34Q, 37K; (xvi) 25V, 26R, 27K, 31H, 34Q, 37K; (xvii) 22E, 23E, 25V, 26R, 27K, 31H, 34Q, 37K; (iixx) 8Aib, 12K, 22E, 26R, 27K, 31H, 34Q; (ixx) 8Aib, 22K, 26R, 27K, 31H, 34G, des35-37; (xx) 22E, 26H, 27K, 30E, 34R, 36K, 38E; (xxi) 22E, 24K, 26R, 27K, 31H, 34G, des35-37; (xxii) 25V, 26R, 27K, 34Q, 36K; (xxiii) 22E, 24K, 25V, 26R, 27K, 31H, 34R; (xxiv) 22E, 24K, 25V, 26R, 27K, 34G, des35-37; (xxv) 22E, 24K, 25V, 26R, 27K, 34R; (xxvi) 8Aib, 22E, 24K, 25V, 26R, 27K, 31H, 34Q; or (xxvii) 8Aib, 22E, 26R, 27K, 30E, 34R, 36K, 38E, 39G; or a pharmaceutically acceptable salt, amide, or ester thereof.

311. The GLP-analogue of embodiment 310 which has a set of amino acid changes as defined in any of (i)-(xxvii).

312. A derivative according to any of embodiments 1-307, for use as a medicament.

313. A derivative according to any of embodiments 1-307, for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

314. A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression—by administering a pharmaceutically active amount of a derivative according to any of embodiments 1-307.

The following are additional particular embodiments of the invention:

1. A derivative of a GLP-1 analogue,
   which analogue comprises a first K residue at a position corresponding to position 27 of GLP-1(7-37) (SEQ ID NO: 1); a second K residue at a position corresponding to position T of GLP-1(7-37), where T is an integer in the range of 7-37 except 18 and 27; and a maximum of ten amino acid changes as compared to GLP-1(7-37); wherein the first K residue is designated $K^{27}$, and the second K residue is designated $K^T$;
   which derivative comprises two albumin binding moieties attached to $K^{27}$ and $K^T$, respectively, wherein the albumin binding moiety comprises a protracting moiety selected from Chem. 1 and Chem. 2:

HOOC—(CH$_2$)$_x$—CO—*   Chem. 1:

HOOC—C$_6$H$_4$—O—(CH$_2$)$_y$—CO—*   Chem. 2:

in which x is an integer in the range of 6-18, and y is an integer in the range of 3-17;
   with the proviso that when the protracting moiety is Chem. 1, the albumin binding moiety further comprises a linker of formula Chem. 5:

Chem. 5

*—NH—\[CH$_2$CH$_2$—O\]$_k$—CH$_2$—C(=O)—*  (structural formula)

wherein k is an integer in the range of 1-5, and n is an integer in the range of 1-5; or a pharmaceutically acceptable salt, amide, or ester thereof.

2. The derivative of embodiment 1,
   wherein the GLP-1 analogue comprises a first K residue at a position corresponding to position 27 of GLP-1(7-37) (SEQ ID NO: 1); a second K residue at a position corresponding to position T of GLP-1(7-37), where T is an integer in the range of 7-37 except 18 and 27; and a maximum of ten amino acid changes as compared to GLP-1(7-37); wherein the first K residue is designated $K^{27}$, and the second K residue is designated $K^T$;
   which derivative comprises two albumin binding moieties attached to $K^{27}$ and $K^T$, respectively, wherein the albumin binding moiety comprises a protracting moiety of Chem. 2:

HOOC—C$_6$H$_4$—O—(CH$_2$)$_y$—CO—*   Chem. 2:

in which y is an integer in the range of 3-17;
   or a pharmaceutically acceptable salt, amide, or ester thereof.

3. The derivative of any of the previous embodiments, wherein the albumin binding moiety further comprises a linker.

4. The derivative of any of the previous embodiments, wherein the linker comprises i) a Glu di-radical; and/or ii) a linker of formula Chem. 5:

Chem. 5 wherein k is an integer in the range of 1-5, and n is an integer in the range of 1-5.

5. The derivative of any of the previous embodiments, wherein the Glu di-radical is selected from Chem. 6, and/or Chem. 7:

Chem. 6

Chem. 7 preferably Chem. 6.

6. The derivative of any of the previous embodiments,
   wherein the GLP-1 analogue comprises a first K residue at a position corresponding to position 27 of GLP-1(7-37) (SEQ ID NO: 1); a second K residue at a position corresponding to position T of GLP-1(7-37), where T is an integer in the range of 7-37 except 18 and 27; and a maximum of ten amino acid changes as compared to GLP-1(7-37); wherein the first K residue is designated $K^{27}$, and the second K residue is designated $K^T$;

which derivative comprises two albumin binding moieties attached to $K^{27}$ and $K^T$, respectively, wherein the albumin binding moiety comprises
i) a protracting moiety of formula Chem. 1:

Chem. 1:

in which x is an integer in the range of 6-18; and
ii) a linker of formula Chem. 5:

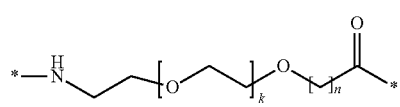

Chem. 5 wherein k is an integer in the range of 1-5, and n is an integer in the range of 1-5; or a pharmaceutically acceptable salt, amide, or ester thereof.

7. The derivative of any of the previous embodiments,
wherein the GLP-1 analogue comprises a first K residue at a position corresponding to position 27 of GLP-1(7-37) (SEQ ID NO: 1); a second K residue at a position corresponding to position T of GLP-1(7-37), where T is an integer in the range of 7-37 except 18 and 27; and a maximum of ten amino acid changes as compared to GLP-1(7-37); wherein the first K residue is designated $K^{27}$, and the second K residue is designated $K^T$;

which derivative comprises two protracting moieties attached to $K^{27}$ and $K^T$, respectively, via a linker, wherein
the protracting moiety is selected from Chem. 1 and Chem. 2:

Chem. 1:

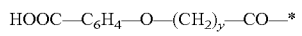

Chem. 2:

in which x is an integer in the range of 6-18, y is an integer in the range of 3-17; and
the linker comprises Chem. 5:

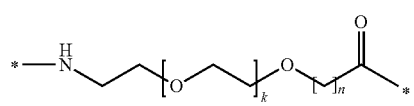

Chem. 5 wherein k is an integer in the range of 1-5, and n is an integer in the range of 1-5;

or a pharmaceutically acceptable salt, amide, or ester thereof.

8. The derivative of any of the previous embodiments, wherein T is an integer selected from the range of 7-37 except 18 and 27.

9. The derivative of any of the previous embodiments, wherein T is selected from any of the ranges of 7-17, 19-26, and 28-37.

10. The derivative of any of the previous embodiments, wherein T is selected from the range of 7-17.

11. The derivative of any of the previous embodiments, wherein T is 12.

12. The derivative of any of the previous embodiments, wherein T is selected from the range of 19-26.

13. The derivative of any of the previous embodiments, wherein T is selected from the group consisting of 20, 22, and 24.

14. The derivative of any of the previous embodiments, wherein T is 20.

15. The derivative of any of the previous embodiments, wherein T is 22 or 24.

16. The derivative of any of the previous embodiments, wherein T is 22.

17. The derivative of any of the previous embodiments, wherein T is 24.

18. The derivative of any of the previous embodiments, wherein T is selected from the range of 28-37.

19. The derivative of any of the previous embodiments, wherein T is selected from the group consisting of 36 and 37.

20. The derivative of any of the previous embodiments, wherein T is 36.

21. The derivative of any of the previous embodiments, wherein T is 37.

22. The derivative of any of the previous embodiments, wherein the position corresponding to position 27 of GLP-1(7-37) (SEQ ID NO: 1) is identified by handwriting and eyeballing.

23. The derivative of any of the previous embodiments, wherein the position corresponding to position T of GLP-1 (7-37) (SEQ ID NO: 1) is identified by handwriting and eyeballing.

24. The derivative of any of the previous embodiments, wherein the position corresponding to position 27 of GLP-1(7-37) (SEQ ID NO: 1) is identified by use of a standard protein or peptide alignment program.

25. The derivative of any of the previous embodiments, wherein the position corresponding to position T of GLP-1 (7-37) (SEQ ID NO: 1) is identified by use of a standard protein or peptide alignment program.

26. The derivative of any of the previous embodiments, wherein the alignment program is a Needleman-Wunsch alignment.

27. The derivative of any of the previous embodiments, wherein the default scoring matrix and the default identity matrix is used.

28. The derivative of any of the previous embodiments, wherein the scoring matrix is BLOSUM62.

29. The derivative of any of the previous embodiments, wherein the penalty for the first residue in a gap is −10 (minus ten).

30. The derivative of any of the previous embodiments, wherein the penalties for additional residues in a gap is −0.5 (minus point five).

31. The derivative of any of the previous embodiments, wherein the analogue comprises no K residues other than the first and the second K residue.

32. The derivative of any of the previous embodiments, wherein the protracting moiety is Chem. 1.

33. The derivative of any of the previous embodiments, wherein x is an even number.

34. The derivative of any of the previous embodiments, wherein x is 12.

35. The derivative of any of the previous embodiments, wherein Chem. 1 is represented by Chem. 1a:

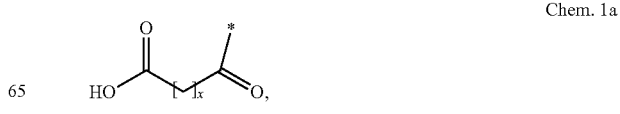

Chem. 1a where x is as defined in any of the previous embodiments.
36. The derivative of any of the previous embodiments, wherein the protracting moiety is Chem. 2, preferably Chem. 2a:

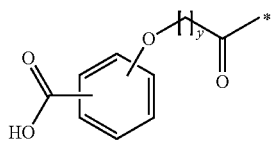

Chem. 2a wherein y is as defined in any of the previous embodiments.
37. The derivative of any of the previous embodiments, wherein y is an odd number.
38. The derivative of any of the previous embodiments, wherein y is 9.
39. The derivative of any of the previous embodiments, wherein Chem. 2 is represented by Chem. 2b, or Chem. 2c:

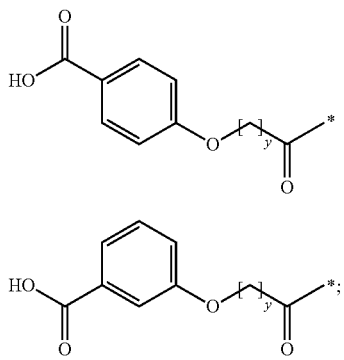

Chem. 2b

Chem. 2c preferably by Chem. 2b;
wherein y is as defined in any of the previous embodiments.
39a. The derivative of any of the previous embodiments, wherein Chem. 2a is represented by Chem. 2b, or Chem. 2c:

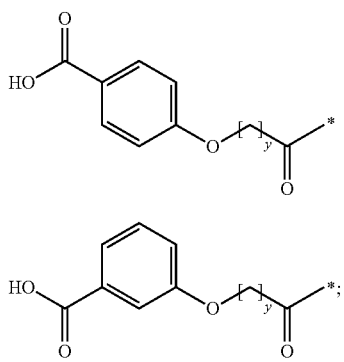

Chem. 2b

Chem. 2c preferably by Chem. 2b;
wherein y is as defined in any of the previous embodiments.
40. The derivative of any of the previous embodiments, which comprises Chem. 5.
41. The derivative of any of the previous embodiments, wherein Chem. 5 is a first linker element.
42. The derivative of any of the previous embodiments, wherein k is 1.
43. The derivative of any of the previous embodiments, wherein n is 1.
44. The derivative of any of the previous embodiments, wherein Chem. 5 is included m times, wherein m is an integer in the range of 1-10.
45. The derivative of any of the previous embodiments, wherein m is 2.
46. The derivative of any of the previous embodiments, wherein, when m is not 1, the Chem. 5 elements are interconnected via amide bond(s).
47. The derivative of any of the previous embodiments, wherein the linker further comprises a second linker element; preferably a Glu di-radical; more preferably selected from Chem. 6, and/or Chem. 7:

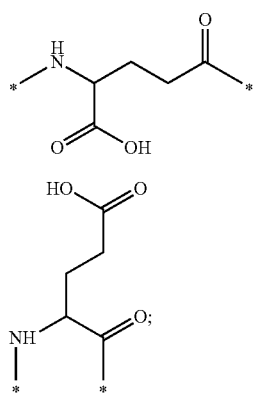

Chem. 6

Chem. 7 most preferably Chem. 6.
48. The derivative of any of the previous embodiments, wherein the Glu di-radical is included p times, wherein p is an integer in the range of 1-2.
49. The derivative of any of the previous embodiments, wherein p is 1.
50. The derivative of any of the previous embodiments, wherein p is 2.
51. The derivative of any of the previous embodiments, wherein the Glu di-radical is a radical of L-Glu.
52. The derivative of any of the previous embodiments, wherein the one or more Glu di-radicals and the one or more Chem. 5 elements are interconnected via amide bond(s).
53. The derivative of any of the previous embodiments, wherein the linker consists of m times Chem. 5 and p times the Glu di-radical.
54. The derivative of any of the previous embodiments, wherein (m,p) is (2,2) or (2,1), preferably (2,1).
55. The derivative of the previous embodiments, wherein the m Chem. 5 elements and the p Glu di-radicals are interconnected via amide bonds.
56. The derivative of any of the previous embodiments, wherein the linker and the protracting moiety are interconnected via an amide bond.
57. The derivative of any of the previous embodiments, wherein the linker and the GLP-1 analogue are interconnected via an amide bond.
58. The derivative of any of the previous embodiments, wherein the linker is attached to the epsilon-amino group of the first or the second K residue.
59. The derivative of any of the previous embodiments, wherein the linker has from 5 to 41 C-atoms; preferably 17 or 22 C-atoms.

60. The derivative of any of the previous embodiments, wherein the linker has 17 C-atoms.
61. The derivative of any of the previous embodiments, wherein the linker has 22 C-atoms.
62. The derivative of the previous embodiments, wherein the linker has from 4 to 28 hetero atoms; preferably 12 or 16 hetero atoms.
63. The derivative of any of the previous embodiments, wherein the linker has 12 hetero atoms.
64. The derivative of any of the previous embodiments, wherein the linker has 16 hetero atoms.
65. The derivative of any of the previous embodiments, wherein the hetero atoms are N—, and/or O-atoms.
66. The derivative of any of the previous embodiments, wherein the linker has from 1 to 7 N-atoms; preferably 3 or 4 N-atoms.
67. The derivative of any of the previous embodiments, wherein the linker has 3 N-atoms.
68. The derivative of any of the previous embodiments, wherein the linker has 4 N-atoms.
69. The derivative of any of the previous embodiments, wherein the linker has from 3 to 21 O-atoms; preferably 9 or 12 O-atoms.
70. The derivative of any of the previous embodiments, wherein the linker has 9 O-atoms.
71. The derivative of any of the previous embodiments, wherein the linker has 12 O-atoms.
72. The derivative of any of the previous embodiments, wherein the linker consists of two times Chem. 6 and two times Chem. 5, interconnected via amide bonds and in the sequence indicated, the linker being connected at its *—NH end to the *—CO end of the protracting moiety, and at its *—CO end to the epsilon amino group of $K^{27}$ or $K^T$ of the GLP-1 analogue.
73. The derivative of any of the previous embodiments, wherein the linker consists of two times Chem. 5 and one time Chem. 6, interconnected via amide bonds and in the sequence indicated, the linker being connected at its *—NH end to the *—CO end of the protracting moiety, and at its free *—CO end to the epsilon amino group of $K^{27}$ or $K^T$ of the GLP-1 analogue.
74. The derivative of any of the previous embodiments, wherein the linker consists of one time Chem. 6 and two times Chem. 5, interconnected via amide bonds and in the sequence indicated, the linker being connected at its *—NH end to the *—CO end of the protracting moiety, and at its *—CO end to the epsilon amino group of $K^{27}$ or $K^T$ of the GLP-1 analogue.
75. The derivative of any of the previous embodiments, wherein the linker consists of one time Chem. 6, two times Chem. 5, and one time Chem. 6, interconnected via amide bonds and in the sequence indicated, the linker being connected at its *—NH end to the *—CO end of the protracting moiety, and at its *—CO end to the epsilon amino group of $K^{27}$ or $K^T$ of the GLP-1 analogue.
76. The derivative of any of the previous embodiments, wherein the two protracting moieites are substantially identical; such as at least 80%, at least 85%, at least 90%, at least 95%, or at least 99% identical.
77. The derivative of any of the previous embodiments, wherein the two protracting moieties have a similarity of at least 0.5; preferably at least 0.6; more preferably at least 0.7, or at least 0.8; even more preferably at least 0.9; or most preferably at least 0.99, such as a similarity of 1.0.
78. The derivative of any of the previous embodiments, wherein the two linkers have a similarity of at least 0.5; preferably at least 0.6; more preferably at least 0.7, or at least 0.8; even more preferably at least 0.9; or most preferably at least 0.99, such as a similarity of 1.0.
79. The derivative of any of the previous embodiments, wherein the two albumin binders, such as the two side chains consisting of protracting moiety and linker, are substantially identical; such as at least 80%, at least 85%, at least 90%, at least 95%, or at least 99% identical.
80. The derivative of any of the previous embodiments, wherein the two albumin binders, such as the two side chains consisting of protracting moiety and linker, have a similarity of at least 0.5; preferably at least 0.6; more preferably at least 0.7, or at least 0.8; even more preferably at least 0.9; or most preferably at least 0.99, such as a similarity of 1.0.
81. The derivative of any of the previous embodiments, wherein the two chemical structures to be compared are represented as fingerprints, such as a) ECFP_6 fingerprints; b) UNITY fingerprints; and/or c) MDL fingerprints; and wherein for each of a), b) and c) the Tanimoto coefficient is preferably used for calculating the similarity, or identity, of the two fingerprints.
82. The derivative of any of the previous embodiments, wherein the number of amino acid changes as compared to GLP-1(7-37) (SEQ ID NO: 1) are identified by handwriting and eyeballing.
83. The derivative of any of the previous embodiments, wherein the number of amino acid changes as compared to GLP-1(7-37) (SEQ ID NO: 1) are identified by use of a standard protein or peptide alignment program.
84. The derivative of any of the previous embodiments, wherein the alignment program is a Needleman-Wunsch alignment.
85. The derivative of any of the previous embodiments, wherein the default scoring matrix and the default identity matrix is used.
86. The derivative of any of the previous embodiments, wherein the scoring matrix is BLOSUM62.
87. The derivative of any of the previous embodiments, wherein the penalty for the first residue in a gap is −10 (minus ten).
88. The derivative of any of the previous embodiments, wherein the penalties for additional residues in a gap is −0.5 (minus point five).
89. The derivative of any of the previous embodiments, wherein the amino acid change(s) is (are) at one or more positions corresponding to the following positions in GLP-1(7-37) (SEQ ID NO: 1): 8, 12, 20, 22, 23, 24, 25, 26, 27, 30, 31, 34, 35, 36, 37, 38, and 39.
90. The derivative of any of the previous embodiments, wherein the analogue comprises at least one of the following changes: $Aib^8$, $K^{12}$, $K^{20}$, $E^{22}$ or $K^{22}$, $E^{23}$, $K^{24}$, $V^{25}$, $R^{26}$ or $H^{26}$, $K^{27}$, $E^{30}$, $H^{31}$, $G^{34}$ or $R^{34}$ or $Q^{34}$, $Des^{35}$, $K^{36}$ or $Des^{36}$, $K^{37}$ or $Des^{37}$, $E^{38}$ or $Q^{38}$, and/or $G^{39}$.
91. The derivative of any of the previous embodiments, wherein the second K residue is $K^{12}$, and wherein the analogue, in addition to the change $K^{27}$, further comprises i) a change selected from $G^{34}$ and $Q^{34}$, and ii) a change selected from $R^{26}$ and $H^{26}$.
92. The derivative of any of the previous embodiments, wherein the second K residue is $K^{20}$, and wherein the analogue, in addition to the change $K^{27}$, further comprises i) a change selected from $G^{34}$ and $Q^{34}$, and ii) a change selected from $R^{26}$ and $H^{26}$.
93. The derivative of any of the previous embodiments, wherein the second K residue is $K^{22}$, and wherein the analogue, in addition to the change $K^{27}$, further comprises i) a change selected from $G^{34}$ and $Q^{34}$, and ii) a change selected from $R^{26}$ and $H^{26}$.

94. The derivative of any of the previous embodiments, wherein the second K residue is $K^{24}$, and wherein the analogue, in addition to the change $K^{27}$, further comprises i) a change selected from $G^{34}$ and $Q^{34}$, and ii) a change selected from $R^{26}$ and $H^{26}$.
95. The derivative of any of the previous embodiments, wherein the second K residue is $K^{36}$, and wherein the analogue, in addition to the change $K^{27}$, further comprises i) a change selected from $G^{34}$ and $Q^{34}$, and ii) a change selected from $R^{26}$ and $H^{26}$.
96. The derivative of any of the previous embodiments, wherein the second K residue is $K^{37}$, and wherein the analogue, in addition to the change $K^{27}$, further comprises i) a change selected from $G^{34}$ and $Q^{34}$, and ii) a change selected from $R^{26}$ and $H^{26}$.
97. The derivative of any of the previous embodiments, wherein the analogue comprises at least one of the following changes: $Aib^8$, $E^{22}$, $E^{23}$, $V^{25}$, $E^{30}$, $H^{31}$, $Des^{35}$, $Des^{36}$, $Des^{37}$, $E^{38}$ or $Q^{38}$, and/or $G^{39}$.
98. The derivative of any of the previous embodiments, wherein the analogue comprises $Aib^8$.
99. The derivative of any of the previous embodiments, wherein the analogue comprises $E^{22}$.
100. The derivative of any of the previous embodiments, wherein the analogue comprises $E^{23}$.
101. The derivative of any of the previous embodiments, wherein the analogue comprises $V^{25}$.
102. The derivative of any of the previous embodiments, wherein the analogue comprises $E^{30}$.
103. The derivative of any of the previous embodiments, wherein the analogue comprises $H^{31}$.
104. The derivative of any of the previous embodiments, wherein the analogue comprises $Des^{35}$.
105. The derivative of any of the previous embodiments, wherein the analogue comprises $Des^{36}$.
106. The derivative of any of the previous embodiments, wherein the analogue comprises $Des^{37}$.
107. The derivative of any of the previous embodiments, wherein the analogue comprises $E^{38}$ or $Q^{38}$, preferably $Q^{38}$, or more preferably $E^{38}$.
108. The derivative of any of the previous embodiments, wherein the analogue comprises $G^{39}$.
109. The derivative of any of the previous embodiments, wherein the analogue comprises $Des^{35}$, $Des^{36}$, and $Des^{37}$.
110. The derivative of any of the previous embodiments, wherein the analogue comprises $Des^{36}$ and $Des^{37}$.
111. The derivative of any of the previous embodiments, which is a derivative of GLP-1(7-34) (amino acids 1-28 of SEQ ID NO: 1).
112. The derivative of any of the previous embodiments, which is a derivative of GLP-1(7-35) (amino acids 1-29 of SEQ ID NO: 1).
113. The derivative of any of the previous embodiments, which is a derivative of GLP-1(7-36) (amino acids 1-30 of SEQ ID NO: 1).
114. The derivative of any of the previous embodiments, which is a derivative of GLP-1(7-37) (amino acids 1-31 of SEQ ID NO: 1).
115. The derivative of any of the previous embodiments, which is a derivative of GLP-1(7-38) (amino acids 1-31 of SEQ ID NO: 1, plus one C-terminally added amino acid residue).
116. The derivative of any of the previous embodiments, which is a derivative of GLP-1(7-39) (amino acids 1-31 of SEQ ID NO: 1, plus two C-terminally added amino acid residues).
117. The derivative of any of the previous embodiments, wherein the analogue has a maximum of ten amino acid changes.
118. The derivative of any of the previous embodiments, wherein the analogue has a maximum of nine amino acid changes.
119. The derivative of any of the previous embodiments, wherein the analogue has a maximum of eight amino acid changes.
120. The derivative of any of the previous embodiments, wherein the analogue has a maximum of seven amino acid changes.
121. The derivative of any of the previous embodiments, wherein the analogue has a maximum of six amino acid changes.
122. The derivative of any of the previous embodiments, wherein the analogue has a maximum of five amino acid changes.
123. The derivative of any of the previous embodiments, wherein the analogue has a maximum of four amino acid changes.
124. The derivative of any of the previous embodiments, wherein the analogue has a maximum of three amino acid changes.
125. The derivative of any of the previous embodiments, wherein the analogue has a maximum of two amino acid changes.
126. The derivative of any of the previous embodiments, wherein the analogue has a maximum of one amino acid changes.
127. The derivative of any of the previous embodiments, wherein the analogue has a minimum of one amino acid changes.
128. The derivative of any of the previous embodiments, wherein the analogue has a minimum of two amino acid changes.
129. The derivative of any of the previous embodiments, wherein the analogue has a minimum of three amino acid changes.
130. The derivative of any of the previous embodiments, wherein the analogue has a minimum of four amino acid changes.
131. The derivative of any of the previous embodiments, wherein the analogue has a minimum of five amino acid changes.
132. The derivative of any of the previous embodiments, wherein the analogue has a minimum of six amino acid changes.
133. The derivative of any of the previous embodiments, wherein the analogue has a minimum of seven amino acid changes.
134. The derivative of any of the previous embodiments, wherein the analogue has a minimum of eight amino acid changes.
135. The derivative of any of the previous embodiments, wherein the analogue has a minimum of nine amino acid changes.
136. The derivative of any of the previous embodiments, wherein the analogue has a minimum of ten amino acid changes.
137. The derivative of any of the previous embodiments, wherein the analogue has one amino acid change.
138. The derivative of any of the previous embodiments, wherein the analogue has two amino acid changes.
139. The derivative of any of the previous embodiments, wherein the analogue has three amino acid changes.

140. The derivative of any of the previous embodiments, wherein the analogue has four amino acid changes.
141. The derivative of any of the previous embodiments, wherein the analogue has five amino acid changes.
142. The derivative of any of the previous embodiments, wherein the analogue has six amino acid changes.
143. The derivative of any of the previous embodiments, wherein the analogue has seven amino acid changes.
144. The derivative of any of the previous embodiments, wherein the analogue has eight amino acid changes.
145. The derivative of any of the previous embodiments, wherein the analogue has nine amino acid changes.
146. The derivative of any of the previous embodiments, wherein the analogue has ten amino acid changes.
147. The derivative of any of the previous embodiments, wherein the change(s) is (are), independently, substitutions, additions, and/or deletions.
148. The derivative of any of the previous embodiments, wherein the analogue a) comprises a GLP-1 analogue of Formula I (SEQ ID NO: 3); and/or b) is a GLP-1 analogue of Formula I (SEQ ID NO: 3):

Formula I: $Xaa_7$-$Xaa_8$-Glu-Gly-Thr-$Xaa_{12}$-Thr-Ser-Asp-$Xaa_{16}$-Ser-$Xaa_{18}$-$Xaa_{19}$-$Xaa_{20}$-Glu-$Xaa_{22}$-$Xaa_{23}$-$Xaa_{24}$-$Xaa_{25}$-$Xaa_{26}$-Lys-Phe-Ile-$Xaa_{30}$-$Xaa_{31}$-Leu-Val-$Xaa_{34}$-$Xaa_{35}$-$Xaa_{36}$-$Xaa_{37}$-$Xaa_{38}$-$Xaa_{39}$, wherein $Xaa_7$ is L-histidine, imidazopropionyl, α-hydroxy-histidine, D-histidine, desamino-histidine, 2-amino-histidine, β-hydroxy-histidine, homohistidine, $N^\alpha$-acetyl-histidine, $N^\alpha$-formyl-histidine, α-fluoromethyl-histidine, α-methyl-histidine, 3-pyridylalanine, 2-pyridylalanine, or 4-pyridylalanine;

$Xaa_8$ is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$Xaa_{12}$ is Lys or Phe;
$Xaa_{16}$ is Val or Leu;
$Xaa_{18}$ is Ser, Arg, Asn, Gln, or Glu;
$Xaa_{19}$ is Tyr or Gln;
$Xaa_{20}$ is Leu, Lys, or Met;
$Xaa_{22}$ is Gly, Glu, Lys, or Aib;
$Xaa_{23}$ is Gln, Glu, or Arg;
$Xaa_{24}$ is Ala or Lys;
$Xaa_{25}$ is Ala or Val;
$Xaa_{26}$ is Val, His, or Arg;
$Xaa_{30}$ is Ala, Glu, or Arg;
$Xaa_{31}$ is Trp or His;
$Xaa_{34}$ is Glu, Asn, Gly, Gln, or Arg;
$Xaa_{35}$ is Gly, Aib, or absent;
$Xaa_{36}$ is Arg, Gly, Lys, or absent;
$Xaa_{37}$ is Gly, Ala, Glu, Pro, Lys, Arg, or absent;
$Xaa_{38}$ is Ser, Gly, Ala, Glu, Gln, Pro, Arg, or absent; and
$Xaa_{39}$ is Gly or absent.

149. The derivative of any of the previous embodiments wherein the peptide of Formula I (SEQ ID NO: 3) is an analogue of GLP-1(7-37) (SEQ ID NO: 1).
150. The derivative of any of the previous embodiments, wherein if $Xaa_{38}$ is absent, then $Xaa_{39}$ is also absent.
151. The derivative of any of the previous embodiments, wherein if $Xaa_{37}$ is absent, then $Xaa_{38}$ and $Xaa_{39}$ are also absent.
152. The derivative of any of the previous embodiments, wherein if $Xaa_{36}$ is absent, then $Xaa_{37}$, $Xaa_{38}$, and $Xaa_{39}$ are also absent.
153. The derivative of any of the previous embodiments, wherein if $Xaa_{35}$ is absent, then $Xaa_{36}$, $Xaa_{37}$, $Xaa_{38}$, and $Xaa_{39}$ are also absent.
154. The derivative of any of the previous embodiments, wherein $Xaa_7$ is His; $Xaa_8$ is Ala or Aib; $Xaa_{12}$ is Lys or Phe; $Xaa_{16}$ is Val; $Xaa_{18}$ is Ser; $Xaa_{19}$ is Tyr; $Xaa_{20}$ is Leu or Lys; $Xaa_{22}$ is Glu, Gly or Lys; $Xaa_{23}$ is Gln or Glu; $Xaa_{24}$ is Ala or Lys; $Xaa_{25}$ is Ala or Val; $Xaa_{26}$ is His or Arg; $Xaa_{30}$ is Ala or Glu; $Xaa_{31}$ is Trp or His; $Xaa_{34}$ is Gly, Gln, or Arg; $Xaa_{35}$ is Gly or absent; $Xaa_{36}$ is Arg, Lys, or absent; $Xaa_{37}$ is Gly, Lys, or absent; $Xaa_{38}$ is Glu or Gln; and $Xaa_{39}$ is Gly or absent.
154a. The derivative of any of the previous embodiments, wherein $Xaa_7$ is His. 154b. The derivative of any of the previous embodiments, wherein $Xaa_8$ is Ala.
154b1. The derivative of any of the previous embodiments, wherein $Xaa_8$ is Aib.
154c. The derivative of any of the previous embodiments, wherein $Xaa_{12}$ is Lys.
154d. The derivative of any of the previous embodiments, wherein $Xaa_{12}$ is Phe.
154e. The derivative of any of the previous embodiments, wherein $Xaa_{16}$ is Val.
154f. The derivative of any of the previous embodiments, wherein $Xaa_{18}$ is Ser.
154g. The derivative of any of the previous embodiments, wherein $Xaa_{19}$ is Tyr.
154h. The derivative of any of the previous embodiments, wherein $Xaa_{20}$ is Leu.
154i. The derivative of any of the previous embodiments, wherein $Xaa_{20}$ is Lys.
154j. The derivative of any of the previous embodiments, wherein $Xaa_{22}$ is Glu.
154k. The derivative of any of the previous embodiments, wherein $Xaa_{22}$ is Gly.
154l. The derivative of any of the previous embodiments, wherein $Xaa_{22}$ is Lys.
154m. The derivative of any of the previous embodiments, wherein $Xaa_{23}$ is Gln.
154n. The derivative of any of the previous embodiments, wherein $Xaa_{23}$ is Glu.
154o. The derivative of any of the previous embodiments, wherein $Xaa_{24}$ is Ala.
154p. The derivative of any of the previous embodiments, wherein $Xaa_{24}$ is Lys.
154q. The derivative of any of the previous embodiments, wherein $Xaa_{25}$ is Ala.
154r. The derivative of any of the previous embodiments, wherein $Xaa_{25}$ is Val.
154s. The derivative of any of the previous embodiments, wherein $Xaa_{26}$ is His.
154t. The derivative of any of the previous embodiments, wherein $Xaa_{26}$ is Arg.
154u. The derivative of any of the previous embodiments, wherein $Xaa_{30}$ is Ala.
154v. The derivative of any of the previous embodiments, wherein $Xaa_{30}$ is Glu.
154x. The derivative of any of the previous embodiments, wherein $Xaa_{31}$ is Trp.
154y. The derivative of any of the previous embodiments, wherein $Xaa_{31}$ is His.
154z. The derivative of any of the previous embodiments, wherein $Xaa_{34}$ is Gly.
154aa. The derivative of any of the previous embodiments, wherein $Xaa_{34}$ is Gln.
154ab. The derivative of any of the previous embodiments, wherein $Xaa_{34}$ is Arg.

154ac. The derivative of any of the previous embodiments, wherein Xaa$_{35}$ is Gly.
154ad. The derivative of any of the previous embodiments, wherein Xaa$_{35}$ is absent.
154ae. The derivative of any of the previous embodiments, wherein Xaa$_{36}$ is Arg.
154af. The derivative of any of the previous embodiments, wherein Xaa$_{36}$ is Lys.
154ag. The derivative of any of the previous embodiments, wherein Xaa$_{36}$ is absent.
154ah. The derivative of any of the previous embodiments, wherein Xaa$_{37}$ is Gly.
154ai. The derivative of any of the previous embodiments, wherein Xaa$_{37}$ is Lys.
154aj. The derivative of any of the previous embodiments, wherein Xaa$_{37}$ is absent.
154ak. The derivative of any of the previous embodiments, wherein Xaa$_{38}$ is Glu.
154al. The derivative of any of the previous embodiments, wherein Xaa$_{38}$ is Gln.
154am. The derivative of any of the previous embodiments, wherein Xaa$_{38}$ is absent.
154an. The derivative of any of the previous embodiments, wherein Xaa$_{39}$ is Gly.
154ao. The derivative of any of the previous embodiments, wherein Xaa$_{39}$ is absent.
155. The derivative of any of the previous embodiments, wherein the analogue comprises, preferably has, the following amino acid changes, as compared to GLP-1(7-37) (SEQ ID NO: 1): (i) 22E, 26R, 27K, 34R, 37K; (ii) 22E, 26R, 27K, 30E, 34R, 36K, 38E, 39G; (iii) 22E, 26R, 27K, 34R, 36K, des37; (iv) 22E, 25V, 26R, 27K, 34R, 37K; (v) 8Aib, 20K, 22E, 26R, 27K, 30E, 34G, des35-37; (vi) 26R, 27K, 30E, 34R, 36K, 38E; (vii) 8Aib, 22K, 25V, 26R, 27K, 31H, 34R; (iix) 8Aib, 22K, 25V, 26R, 27K, 34R, des35-37; (ix) 8Aib, 22K, 25V, 26R, 27K, 34R, des36-37; (x) 26H, 27K, 30E, 34R, 36K, 38E; (xi) 22K, 25V, 26R, 27K, 30E, 34Q; (xii) 25V, 26R, 27K, 30E, 34R, 36K, 38Q; (xiii) 25V, 26R, 27K, 30E, 34Q, 36K, 38E; (xiv) 22K, 26R, 27K, 31H, 34G, des35-37; (xv) 8Aib, 25V, 26R, 27K, 31H, 34Q, 37K; (xvi) 25V, 26R, 27K, 31H, 34Q, 37K; (xvii) 22E, 23E, 25V, 26R, 27K, 31H, 34Q, 37K; (iixx) 8Aib, 12K, 22E, 26R, 27K, 31H, 34Q; (ixx) 8Aib, 22K, 26R, 27K, 31H, 34G, des35-37; (xx) 22E, 26H, 27K, 30E, 34R, 36K, 38E; (xxi) 22E, 24K, 26R, 27K, 31H, 34G, des35-37; (xxii) 25V, 26R, 27K, 34Q, 36K; (xxiii) 22E, 24K, 25V, 26R, 27K, 31H, 34R; (xxiv) 22E, 24K, 25V, 26R, 27K, 34G, des35-37; (xxv) 22E, 24K, 25V, 26R, 27K, 34R; or (xxvi) 8Aib, 22E, 24K, 25V, 26R, 27K, 31H, 34Q.
156. A compound, preferably according to any of the previous embodiments, selected from the following: Chem. 50, Chem. 51, Chem. 52, Chem. 53, Chem. 54, Chem. 55, Chem. 56, Chem. 57, Chem. 58, Chem. 59, Chem. 60, Chem. 61, Chem. 62, Chem. 63, Chem. 64, Chem. 65, Chem. 66, Chem. 67, Chem. 68, Chem. 69, Chem. 70, Chem. 71, Chem. 72, Chem. 73, Chem. 74, Chem. 75, Chem. 76, Chem. 77, Chem. 78, and Chem. 79; or a pharmaceutically acceptable salt, amide, or ester thereof.
157. A compound, preferably according to any of the previous embodiments, characterised by its name, and selected from a listing of each of the names of the compounds of Examples 1-30 herein, or a pharmaceutically acceptable salt, amide, or ester thereof.
158. The derivative of any of the previous embodiments, which has GLP-1 activity.
159. The derivative of any of the previous embodiments, wherein GLP-1 activity refers to the capability of activating the human GLP-1 receptor.
160. The derivative of any of the previous embodiments, wherein activation of the human GLP-1 receptor is measured in an in vitro assay, as the potency of cAMP production.
161. The derivative of any of the previous embodiments, which has a potency corresponding to an EC$_{50}$
a) below 10000 pM, more preferably below 5000 pM, even more preferably below 4000 pM, or most preferably below 3000 pM;
b) below 2000 pM, preferably below 1500 pM, more preferably below 1200 pM, even more preferably below 1000 pM, or most preferably below 500 pM;
c) below 400 pM, preferably below 300 pM, more preferably below 200 pM, even more preferably below 150 pM, or most preferably below 100 pM; or
d) below 80 pM, preferably below 60 pM, more preferably below 40 pM, even more preferably below 30 pM, or most preferably below 20 pM.
162. The derivative of any of the previous embodiments, wherein the potency is determined as EC$_{50}$ for the dose-response curve showing dose-dependent formation of cAMP in a medium containing the human GLP-1 receptor, preferably using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, most preferably the one described in Example 31.
163. The derivative of any of the previous embodiments, for which the ratio [GLP-1 receptor binding affinity (IC$_{50}$) in the presence of 2.0% HSA (high albumin), divided by GLP-1 receptor binding affinity (IC$_{50}$) in the presence of 0.005% HSA (low albumin)] is:
a) at least 1.0, more preferably at least 10, even more preferably at least 25, or most preferably at least 50;
b) at least 60, preferably at least 70, more preferably at least 80, even more preferably at least 90, or most preferably at least 100;
c) at least 125, preferably at least 150, more preferably at least 200, still more preferably at least 250, even more preferably at least 400, or most preferably at least 500; or
d) at least 600, preferably at least 800, even more preferably at least 900, or most preferably at least 1000.
164. The derivative of any of the previous embodiments, for which the GLP-1 receptor binding affinity (IC$_{50}$) in the presence of 0.005% HSA (low albumin) is
a) below 1000 nM, preferably below 750 nM, more preferably below 500 nM, or most preferably below 100 nM; or
b) below 50.0 nM, preferably below 15.0 nM, more preferably below 10.0 nM, even more preferably below 5.0 nM, or most preferably below 1.0 nM.
165. The derivative of any of the previous embodiments, for which the GLP-1 receptor binding affinity (IC$_{50}$) in the presence of 2.0% HSA (high albumin) is
a) below 1100 nM, preferably below 1000 nM, more preferably below 900 nM, or most preferably below 600 nM; or
b) below 500 nM, preferably below 350 nM, more preferably below 200 nM, even more preferably below 100 nM, or most preferably below 50.0 nM.
166. The derivative of any of the previous embodiments, wherein the binding affinity to the GLP-1 receptor is measured by way of displacement of $^{125}$I-GLP-1 from the receptor, preferably using a SPA binding assay.

167. The derivative of any of the previous embodiments, wherein the GLP-1 receptor is prepared using a stable, transfected cell line, preferably a hamster cell line, more preferably a baby hamster kidney cell line, such as BHK tk-ts13.

168. The derivative of any of the previous embodiments, wherein the $IC_{50}$ value is determined as the concentration which displaces 50% of $^{125}$I-GLP-1 from the receptor.

169. The derivative of any of the previous embodiments, which has an oral bioavailability, preferably an absolute oral bioavailability, which is higher than that of semaglutide.

170. The derivative of any of the previous embodiments, wherein oral bioavailability is measured in vivo in rats, as exposure in plasma after direct injection into the intestinal lumen.

171. The derivative of any of the previous embodiments, for which the plasma concentration (pM) of the derivative, determined 30 minutes after injection of a solution of the derivative in the jejunum of rat, divided by the concentration (μM) of the injected solution (dose-corrected exposure at 30 min) is at least 39, or at least 40; preferably at least 60; more preferably at least 80; still more preferably at least 100; even more preferably at least 125; or most preferably at least 150.

172. The derivative of any of the previous embodiments, for which the plasma concentration (pM) of the derivative, determined 30 minutes after injection of a solution of the derivative in the jejunum of rat, divided by the concentration (μM) of the injected solution (dose-corrected exposure at 30 min) is at least 160, preferably at least 180, more preferably at least 200, or most preferably at least 250.

173. The derivative of any of the previous embodiments, wherein the GLP-1 derivative is tested in a concentration of 1000 uM in admixture with 55 mg/ml sodium caprate.

174. The derivative of any of the previous embodiments, wherein male Sprague Dawley rats are used, preferably with a body weight upon arrival of approximately 240 g.

175. The derivative of any of the previous embodiments, wherein the rats are fasted for approximately 18 hours before the experiment.

176. The derivative of any of the previous embodiments, wherein the rats are taken into general anaesthesia after having fasted and before the injection of the derivative in the jejunum.

177. The derivative of any of the previous embodiments, wherein the derivative is administered in the proximal part of the jejunum (10 cm distal for the duodenum), or in the mid-intestine (50 cm proximal for the cecum).

178. The derivative of any of the previous embodiments, wherein 100 μl of the derivative is injected into the jejunal lumen through a catheter with a syringe, and subsequently 200 μl of air is pushed into the jejunal lumen with another syringe, which is then left connected to the catheter to prevent flow back into the catheter.

179. The derivative of any of the previous embodiments, wherein blood samples (200 ul) are collected into EDTA tubes from the tail vein at desired intervals, such as at times 0, 10, 30, 60, 120 and 240 min, and centrifuged 5 minutes, 10000G, at 4° C. within 20 minutes.

180. The derivative of any of the previous embodiments, wherein plasma (e.g. 75 ul) is separated, immediately frozen, and kept at −20° C. until analyzed for plasma concentration of the derivative.

181. The derivative of any of the previous embodiments, wherein LOCI (Luminescent Oxygen Channeling Immunoassay) is used for analyzing the plasma concentration of the derivative.

182. The derivative of any of the previous embodiments, wherein the derivative is effective at lowering blood glucose in vivo in db/db mice.

183. The derivative of any of the previous embodiments, wherein the derivative is effective at lowering body weight in vivo in db/db mice.

184. The derivative of any of the previous embodiments, wherein db/db mice are treated, s.c., with a suitable range of doses of the GLP-1 derivative, and blood glucose and/or bodyweight is/are determined at appropriate intervals.

185. The derivative of any of the previous embodiments, wherein the dose of the GLP-1 derivative is 0.3 nmol/kg, 1.0 nmol/kg, 3.0 nmol/kg, 10 nmol/kg, 30 nmol/kg, and 100 nmol/kg, wherein kg refers to the body weight of the mouse.

186. The derivative of any of the previous embodiments, wherein a control group is treated with vehicle, s.c., preferably the medium in which the GLP-1 derivative is dissolved, e.g. with the following composition: 50 mM sodium phosphate, 145 mM sodium chloride, 0.05% tween 80, pH 7.4.

187. The derivative of any of the previous embodiments, wherein blood glucose is determined, and/or the mice are weighed, at time −½ h (half an hour prior to dosing (t=0)), and at times 1, 2, 4, and 8 h.

188. The derivative of any of the previous embodiments, wherein the glucose concentration is measured using the glucose oxidase method.

189. The derivative of any of the previous embodiments, wherein
(i) $ED_{50}$ (body weight (BW)) is calculated as the dose giving rise to half-maximum effect on delta (e.g., decrease) BW 8 hours following the subcutaneous administration of the derivative; and/or
(ii) $ED_{50}$ (blood glucose (BG)) is calculated as the dose giving rise to half-maximum effect on AUC (Area Under the Curve) delta (e.g., decrease) BG 8 hours and/or 24 hours following the subcutaneous administration of the derivative.

190. The derivative of any of the previous embodiments, wherein a sigmoidal dose-response relationship exists, preferably with a clear definition of the maximum response.

191. The derivative of any of the previous embodiments, which has a more protracted profile of action than liraglutide.

192. The derivative of any of the previous embodiments, wherein protraction means half-life in vivo in a relevant animal species, such as db/db mice, rat, pig, and/or, preferably, minipig; wherein the derivative is administered i) s.c., and/or, ii) i.v.; preferably ii) i.v.

193. The derivative of any of the previous embodiments, wherein the terminal half-life ($T_{1/2}$) after i.v. administration in minipigs is
a) at least 12 hours, preferably at least 24 hours, more preferably at least 36 hours, even more preferably at least 48 hours, or most preferably at least 60 hours;
b) at least 7 hours, preferably at least 16 hours, more preferably at least 24 hours, even more preferably at least 30 hours, or most preferably at least 40 hours;
c) at least 50 hours, preferably at least 60 hours, more preferably at least 70 hours, even more preferably at least 80 hours, or most preferably at least 90 hours.

194. The derivative of any of the previous embodiments, wherein the minipigs are male Göttingen minipigs.

195. The derivative of any of the previous embodiments, wherein the minipigs are 7-14 months of age, and preferably weighing from 16-35 kg.

196. The derivative of any of the previous embodiments, wherein the minipigs are housed individually, and fed once or twice daily, preferably with SDS minipig diet.

197. The derivative of any of the previous embodiments, wherein the derivative is dosed, i.v., after at least 2 weeks of acclimatisation.

198. The derivative of any of the previous embodiments, wherein the animals are fasted for approximately 18 h before dosing and for at least 4 h after dosing, and have ad libitum access to water during the whole period.

199. The derivative of any of the previous embodiments, wherein the GLP-1 derivative is dissolved in 50 mM sodium phosphate, 145 mM sodium chloride, 0.05% tween 80, pH 7.4 to a suitable concentration, preferably from 20-60 nmol/ml.

200. The derivative of any of the previous embodiments, wherein intravenous injections of the derivative are given in a volume corresponding to 1-2 nmol/kg.

201. The derivative of any of the previous embodiments, which increases the glucose stimulated insulin secretion in minipigs.

202. The derivative of any of the previous embodiments, wherein the minipigs are male Göttingen minipigs.

203. The derivative of any of the previous embodiments, wherein the minipigs are 7-14 months of age.

204. The derivative of any of the previous embodiments, wherein the minipigs are housed in single pens, and fed once or twice daily, preferably with SDS minipig fodder.

205. The derivative of any of the previous embodiments, wherein a single dose, optionally after a period with dose escalation, is given i.v., or s.c., in the thin skin behind the ear.

206. The derivative of any of the previous embodiments, wherein the animals are fasted for approximately 18 h before dosing.

207. The derivative of any of the previous embodiments, wherein a baseline group and a number of derivative dose groups corresponding to 2-6 different plasma concentration levels are tested, wherein the baseline group is a) vehicle treated, or b) untreated.

208. The derivative of any of the previous embodiments, wherein the plasma concentration level is 3000-80000 pM.

209. The derivative of any of the previous embodiments, wherein a 1 or 2 hour intravenous glucose tolerance test (IVGTT) is performed.

210. The derivative of any of the previous embodiments, wherein 0.3 g/kg glucose is given i.v. over a period of 30 seconds, and blood samples taken at suitable time points, such as the following time points (t=0 corresponds to the glucose bolus): −10, −5, 0, 2, 5, 10, 15, 20, 25, 30, 40, 50, 60, 70, 80, 90, 100, 110, 120 minutes.

211. The derivative of any of the previous embodiments, wherein the concentration in plasma of the derivative, glucose, and insulin is determined.

212. The derivative of any of the previous embodiments, wherein the derivative concentration is measured at t=0 min, and, optionally, at the end of the test (t=60 min, or t=120 min).

213. The derivative of any of the previous embodiments, wherein glucose is analyzed using the glucose oxidase method.

214. The derivative of any of the previous embodiments, wherein the area under the insulin curve (AUCinsulin) is calculated and used as a measure of insulin secretion.

215. The derivative of any of the previous embodiments, wherein for at least one concentration thereof, the AUCinsulin is higher than the baseline AUCinsulin, preferably at least 110% thereof, more preferably at least 120% thereof, even more preferably at least 130% thereof or most preferably at least 140% thereof.

216. The derivative of any of the previous embodiments, which causes a reduced food intake in pigs relative to a control (preferably vehicle-treated, or untreated);
optionally the food intake (0-24 h) may be 90% or lower relative to the vehicle-treated control, preferably 80% or lower, more preferably 70% or lower, even more preferably 60% or lower, or most preferably 50% or lower;
wherein food intake (0-24 h) refers to the first 24 hours after administration of the derivative or vehicle.

217. The derivative of any of the previous embodiments, wherein the pigs are female Landrace Yorkshire Duroc (LYD) pigs.

218. The derivative of any of the previous embodiments, wherein the pigs are 3 months of age, and preferably have a weight of 30-35 kg.

219. The derivative of any of the previous embodiments, wherein the animals are housed in a group for 1-2 weeks for acclimatisation.

220. The derivative of any of the previous embodiments, wherein during the experimental period the animals are placed in individual pens from Monday morning to Friday afternoon for measurement of individual food intake.

221. The derivative of any of the previous embodiments, wherein the animals are fed ad libitum with pig fodder (such as Svinefoder, Antonio).

222. The derivative of any of the previous embodiments, wherein food intake is monitored on line by logging the weight of fodder every 15 minutes, preferably using the Mpigwin system.

223. The derivative of any of the previous embodiments, which is dosed 0.3, 1.0, 3.0, 10, or 30 nmol/kg, preferably dissolved in a phosphate buffer (50 mM phosphate, 145 mM sodium chloride, 0.05% tween 80, pH 8), more preferably at concentrations of 12, 40, 120, 400, or 1200 nmol/ml.

224. The derivative of any of the previous embodiments, wherein the phosphate buffer serves as vehicle.

225. The derivative of any of the previous embodiments, wherein the animals are dosed with a single subcutaneous dose of the derivative, or vehicle (preferably with a dose volume of 0.025 ml/kg), on the morning of day 1, and food intake is measured for 4 days after dosing.

226. The derivative of any of the previous embodiments, which has a half-life ($T_{1/2}$) in vivo in rats after i.v. administration of at least 4 hours, preferably at least 6 hours, even more preferably at least 8 hours, or most preferably at least 10 hours.

227. The derivative of any of the previous embodiments, which has a half-life ($T_{1/2}$) in vivo in rats after i.v. administration of at least 12 hours, preferably at least 15 hours, even more preferably at least 18 hours, or most preferably at least 20 hours.

228. The derivative of any of the previous embodiments, which has a half-life ($T_{1/2}$) in vivo in rats after i.v. administration of at least 24 hours, preferably at least 26 hours, or most preferably at least 30 hours.

229. The derivative of any of the previous embodiments, in which the rats are male Sprague Dawley rats with a body weight of approximately 400 g.

230. An intermediate product in the form of a GLP-1 analogue which comprises the following change as compared to GLP-1(7-37) (SEQ ID NO: 1): (i) 38Q; and/or (ii) 39G; or a pharmaceutically acceptable salt, amide, or ester thereof.

231. The GLP-1 analogue of embodiment 230 which comprises (38E, 39G).

232. An intermediate product in the form of a GLP-1 analogue which comprises, preferably has, the following amino acid changes, as compared to GLP-1(7-37) (SEQ ID NO: 1): (i) 22E, 26R, 27K, 34R, 37K; (ii) 22E, 26R, 27K, 30E, 34R, 36K, 38E, 39G; (iii) 22E, 26R, 27K, 34R, 36K, des37; (iv) 22E, 25V, 26R, 27K, 34R, 37K; (v) 8Aib, 20K, 22E, 26R, 27K, 30E, 34G, des35-37; (vi) 26R, 27K, 30E, 34R, 36K, 38E; (vii) 8Aib, 22K, 25V, 26R, 27K, 31H, 34R; (iix) 8Aib, 22K, 25V, 26R, 27K, 34R, des35-37; (ix) 8Aib, 22K, 25V, 26R, 27K, 34R, des36-37; (x) 26H, 27K, 30E, 34R, 36K, 38E; (xi) 22K, 25V, 26R, 27K, 30E, 34Q; (xii) 25V, 26R, 27K, 30E, 34R, 36K, 38Q; (xiii) 25V, 26R, 27K, 30E, 34Q, 36K, 38E; (xiv) 22K, 26R, 27K, 31H, 34G, des35-37; (xv) 8Aib, 25V, 26R, 27K, 31H, 34Q, 37K; (xvi) 25V, 26R, 27K, 31H, 34Q, 37K; (xvii) 22E, 23E, 25V, 26R, 27K, 31H, 34Q, 37K; (iixx) 8Aib, 12K, 22E, 26R, 27K, 31H, 34Q; (ixx) 8Aib, 22K, 26R, 27K, 31H, 34G, des35-37; (xx) 22E, 26H, 27K, 30E, 34R, 36K, 38E; (xxi) 22E, 24K, 26R, 27K, 31H, 34G, des35-37; (xxii) 25V, 26R, 27K, 34Q, 36K; (xxiii) 22E, 24K, 25V, 26R, 27K, 31H, 34R; (xxiv) 22E, 24K, 25V, 26R, 27K, 34G, des35-37; (xxv) 22E, 24K, 25V, 26R, 27K, 34R; or (xxvi) 8Aib, 22E, 24K, 25V, 26R, 27K, 31H, 34Q; or a pharmaceutically acceptable salt, amide, or ester thereof.

233. A derivative according to any of the previous embodiments, for use as a medicament.

234. A derivative according to any of the previous embodiments, for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

235. A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression—by administering a pharmaceutically active amount of a derivative according to any of the previous embodiments.

The following are still further particular embodiments of the invention:

1. A derivative of a GLP-1 analogue,
   which analogue comprises a first K residue at a position corresponding to position 27 of GLP-1(7-37) (SEQ ID NO: 1); a second K residue at a position corresponding to position T of GLP-1(7-37), where T is an integer in the range of 7-37 except 18 and 27; and a maximum of ten amino acid changes as compared to GLP-1(7-37); wherein the first K residue is designated $K^{27}$, and the second K residue is designated $K^T$;
   which derivative comprises two protracting moieties attached to $K^{27}$ and $K^T$, respectively, via a linker, wherein the protracting moiety is selected from Chem. 1 and Chem. 2:

  Chem. 1:

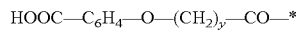  Chem. 2:

in which x is an integer in the range of 6-18, and y is an integer in the range of 3-17; and the linker comprises Chem. 5:

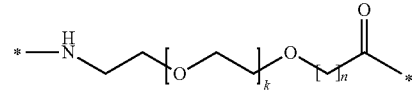  Chem. 5 wherein k is an integer in the range of 1-5, and n is an integer in the range of 1-5;

or a pharmaceutically acceptable salt, amide, or ester thereof.

2. The derivative of embodiment 1, wherein the linker further comprises a Glu di-radical selected from Chem. 6, and/or Chem. 7:

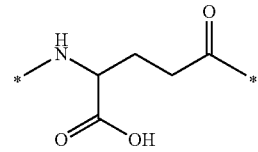  Chem. 6

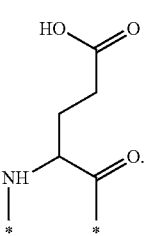  Chem. 7

3. The derivative of any of the previous embodiments, wherein the linker is attached to the epsilon-amino group of the first or the second K residue.

4. The derivative of any of the previous embodiments, wherein T is 12, 20, 22, 24, 36, or 37.

5. The derivative of any of the previous embodiments, wherein the analogue comprises no K residues other than the first and the second K residue.

6. The derivative of any of the previous embodiments, wherein x is 12.

7. The derivative of any of the previous embodiments, wherein y is 9.

8. The derivative of any of the previous embodiments, wherein k is 1.

9. The derivative of any of the previous embodiments, wherein n is 1.

10. The derivative of any of the previous embodiments, wherein the analogue comprises a GLP-1 analogue of Formula I (SEQ ID NO: 3):

$Xaa_7$-$Xaa_8$-Glu-Gly-Thr-$Xaa_{12}$-Thr-Ser-Asp-$Xaa_{16}$-Ser-$Xaa_{18}$-$Xaa_{19}$-$Xaa_{20}$-Glu-$Xaa_{22}$-$Xaa_{23}$-$Xaa_{24}$-$Xaa_{25}$-$Xaa_{26}$-Lys-Phe-Ile-$Xaa_{30}$-$Xaa_{31}$-Leu-Val-$Xaa_{34}$-$Xaa_{35}$-$Xaa_{36}$-$Xaa_{37}$-$Xaa_{38}$-$Xaa_{39}$,   Formula I:

wherein $Xaa_7$ is L-histidine, imidazopropionyl, α-hydroxy-histidine, D-histidine, desamino-histidine, 2-amino-histidine, β-hydroxy-histidine, homohistidine, $N^α$-acetyl-histidine, $N^α$-formyl-histidine, α-fluoromethyl-histidine, α-methyl-histidine, 3-pyridylalanine, 2-pyridylalanine or 4-pyridylalanine;

Xaa$_8$ is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

Xaa$_{12}$ is Lys or Phe;
Xaa$_{16}$ is Val or Leu;
Xaa$_{18}$ is Ser, Arg, Asn, Gln, or Glu;
Xaa$_{19}$ is Tyr or Gln;
Xaa$_{20}$ is Leu, Lys, or Met;
Xaa$_{22}$ is Gly, Glu, Lys, or Aib;
Xaa$_{23}$ is Gln, Glu, or Arg;
Xaa$_{24}$ is Ala or Lys;
Xaa$_{25}$ is Ala or Val;
Xaa$_{26}$ is Val, His, or Arg;
Xaa$_{30}$ is Ala, Glu, or Arg;
Xaa$_{31}$ is Trp or His;
Xaa$_{34}$ is Glu, Asn, Gly, Gln, or Arg;
Xaa$_{35}$ is Gly, Aib, or absent;
Xaa$_{36}$ is Arg, Gly, Lys, or absent;
Xaa$_{37}$ is Gly, Ala, Glu, Pro, Lys, Arg, or absent;
Xaa$_{38}$ is Ser, Gly, Ala, Glu, Gln, Pro, Arg, or absent; and
Xaa$_{39}$ is Gly or absent.

11. A compound according to any of the previous embodiments, selected from the following: Chem. 50, Chem. 51, Chem. 52, Chem. 53, Chem. 54, Chem. 55, Chem. 56, Chem. 57, Chem. 58, Chem. 59, Chem. 60, Chem. 61, Chem. 62, Chem. 63, Chem. 64, Chem. 65, Chem. 66, Chem. 67, Chem. 68, Chem. 69, Chem. 70, Chem. 71, Chem. 72, Chem. 73, Chem. 74, Chem. 75, Chem. 76, Chem. 77, Chem. 78, and Chem. 79; or a pharmaceutically acceptable salt, amide, or ester thereof.

12. An intermediate product in the form of a GLP-1 analogue which comprises the following change as compared to GLP-1(7-37) (SEQ ID NO: 1): (i) 38Q; and/or (ii) 39G; or a pharmaceutically acceptable salt, amide, or ester thereof.

13. A derivative according to any of embodiments 1-11, for use as a medicament.

14. A derivative according to any of embodiments 1-11, for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

15. A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression—by administering a pharmaceutically active amount of a derivative according to any of embodiments 1-11.

EXAMPLES

This experimental part starts with a list of abbreviations, and is followed by a section including general methods for synthesising and characterising analogues and derivatives of the invention. Then follows a number of examples which relate to the preparation of specific GLP-1 derivatives, and at the end a number of examples have been included relating to the activity and properties of these analogues and derivatives (section headed pharmacological methods).

The examples serve to illustrate the invention.

Abbreviations

The following abbreviations are used in the following, in alphabetical order:
Aib: aminoisobutyric acid (α-aminoisobutyric acid)
API: Active Pharmaceutical Ingredient
AUC: Area Under the Curve
BG: Blood Glucose
BHK Baby Hamster Kidney
BW: Body Weight
Boc: t-butyloxycarbonyl
BSA: Bovine serum albumin
collidine: 2,4,6-trimethylpyridine
DCM: dichloromethane
Dde: 1-(4,4-dimethyl-2,6-dioxocyclohexylidene)ethyl
DIC: diisopropylcarbodiimide
DIPEA: diisopropylethylamine
DMAP: 4-dimethylaminopyridine
DMEM: Dulbecco's Modified Eagle's Medium (DMEM)
EDTA: ethylenediaminetetraacetic acid
EGTA: ethylene glycol tetraacetic acid
FCS: Fetal Calf Serum
Fmoc: 9-fluorenylmethyloxycarbonyl
HATU: (O-(7-azabenzotriazol-1-yl)-1,1,3,3-tetramethyluronium hexafluorophosphate)
HBTU: (2-(1H-benzotriazol-1-yl-)-1,1,3,3 tetramethyluronium hexafluorophosphate)
HEPES: 4-(2-hydroxyethyl)-1-piperazineethanesulfonic acid
HFIP 1,1,1,3,3,3-hexafluoro-2-propanol or hexafluoroisopropanol
HOAt: 1-hydroxy-7-azabenzotriazole
HOBt: 1-hydroxybenzotriazole
HPLC: High Performance Liquid Chromatography
HSA: Human Serum Albumin
IBMX: 3-isobutyl-1-methylxanthine
Imp: Imidazopropionic acid (also referred to as des-amino histidine, DesH)
i.v. intravenously
ivDde: 1-(4,4-dimethyl-2,6-dioxocyclohexylidene)-3-methylbutyl
IVGTT: Intravenous Glucose Tolerance Test
LCMS: Liquid Chromatography Mass Spectroscopy
LYD: Landrace Yorkshire Duroc
MALDI-MS: See MALDI-TOF MS
MALDI-TOF MS: Matrix-Assisted Laser Desorption/Ionisation Time of Flight Mass Spectroscopy
MeOH: methanol
Mmt: 4-methoxytrityl
Mtt: 4-methyltrityl
NMP: N-methyl pyrrolidone
OBz: benzoyl ester
OEG: 8-amino-3,6-dioxaoctanic acid
OtBu: tert-butyl ester
PBS: Phosphate Buffered Saline
PD: Pharmacodynamic
Pen/Strep: Pencillin/Streptomycin
PK: Pharmacokinetic
RP: Reverse Phase
RP-HPLC: Reverse Phase High Performance Liquid Chromatography
RT: Room Temperature
Rt: Retention time
s.c.: Subcutaneously
SD: Standard Deviation SEC-HPLC: Size Exclusion High Performance Liquid Chromatography
SEM: Standard Error of Mean
SPA: Scintillation Proximity Assay
SPPS: Solid Phase Peptide Synthesis
tBu: tert-butyl
TFA: trifluoroacetic acid
TIS: triisopropylsilane
Tris: tris(hydroxymethyl)aminomethane or 2-amino-2-hydroxymethyl-propane-1,3-diol
Trt: triphenylmethyl or trityl
Trx: tranexamic acid
UPLC: Ultra Performance Liquid Chromatography Methods of Preparation A. General Methods This section relates to methods for solid phase peptide synthesis (SPPS methods, including methods for de-protection of amino acids, methods for cleaving the peptide from the resin, and for its purification), as well as methods for detecting and characterising the resulting peptide (LCMS, MALDI, and UPLC methods). The solid phase synthesis of peptides may in some cases be improved by the use of di-peptides protected on the di-peptide amide bond with a group that can be cleaved under acidic conditions such as, but not limited to, 2-Fmoc-oxy-4-methoxybenzyl, or 2,4,6-trimethoxybenzyl. In cases where a serine or a threonine is present in the peptide, pseudoproline di-peptides may be used (available from, e.g., Novabiochem, see also W. R. Sampson (1999), J. Pep. Sci., 5, 403). The protected amino acid derivatives used were standard Fmoc-amino acids (supplied from e.g. Anaspec, IRIS, or Novabiochem). The N-terminal amino acid was Boc protected at the alpha amino group (e.g. Boc-His(Boc)-OH, or Boc-His(Trt)-OH for peptides with His at the N-terminus). The epsilon amino group of lysines in the sequence were either protected with Mtt, Mmt, Dde, ivDde, or Boc, depending on the route for attachment of the albumin binding moiety and spacer. The albumin binding moiety and/or linker can be attached to the peptide either by acylation of the resin bound peptide or by acylation in solution of the unprotected peptide. In case of attachment of the albumin binding moiety and/or linker to the protected peptidyl resin, the attachment can be modular using SPPS and suitably protected building blocks such as but not limited to Fmoc-Oeg-OH (Fmoc-8-amino-3,6-dioxaoctanoic acid), Fmoc-Trx-OH (Fmoc-tranexamic acid), Fmoc-Glu-OtBu, octadecanedioic acid mono-tert-butyl ester, nonadecanedioic acid mono-tert-butyl ester, or 4-(9-carboxynonyloxy) benzoic acid tert-butyl ester.

1. Synthesis of Resin Bound Peptide
SPPS Method B

SPPS method B refers to the synthesis of a protected peptidyl resin using Fmoc chemistry on a microwave-based Liberty peptide synthesiser (CEM Corp., North Carolina). A suitable resin is a pre-loaded, low-load Wang resin available from Novabiochem (e.g. low load Fmoc-Lys(Mtt)-Wang resin, 0.35 mmol/g). Fmoc-deprotection was with 5% piperidine in NMP at up to 70 or 75° C. The coupling chemistry was DIC/HOAt in NMP. Amino acid/HOAt solutions (0.3 M in NMP at a molar excess of 3-10 fold) were added to the resin followed by the same molar equivalent of DIC (0.75M in NMP). For example, the following amounts of 0.3 M amino acid/HOAt solution were used per coupling for the following scale reactions: Scale/ml, 0.10 mmol/2.5 ml, 0.25 mmol/5 ml, 1 mmol/15 ml. Coupling times and temperatures were generally 5 minutes at up to 70 or 75° C. Longer coupling times were used for larger scale reactions, for example 10 min. Histidine amino acids were double coupled at 50° C., or quadruple coupled if the previous amino acid was sterically hindered (e.g. Aib). Arginine amino acids were coupled at RT for 25 min then heated to 70 or 75° C. for 5 min. Some amino acids such as but not limited to Aib, were "double coupled", meaning that after the first coupling (e.g. 5 min at 75° C.), the resin is drained and more reagents are added (amino acid, HOAt and DIC), and the mixture is heated again (e.g. 5 min at 75° C.). When a chemical modification of a lysine side chain was desired, the lysine was incorporated as Lys(Mtt). The Mtt group was removed by washing the resin with DCM and suspending the resin in neat (undiluted) hexafluoroisopropanol for 20 minutes followed by washing with DCM and NMP. The chemical modification of the lysine was performed either by manual synthesis (see SPPS method D) or by one or more automated steps on the Liberty peptide synthesiser as described above, using suitably protected building blocks (see General methods), optionally including a manual coupling.

SPPS Method D

SPPS method D refers to synthesis of the protected peptidyl resin using manual Fmoc chemistry. This was typically used for the attachment of the linkers and side chains to the peptide backbone. The following conditions were employed at 0.25 mmol synthesis scale. The coupling chemistry was DIC/HOAt/collidine in NMP at a 4-10 fold molar excess. Coupling conditions were 1-6 h at room temperature. Fmoc-deprotection was performed with 20-25% piperidine in NMP (3×20 ml, each 10 min) followed by NMP washings (4×20 ml). Dde- or ivDde-deprotection was performed with 2% hydrazine in NMP (2×20 ml, each 10 min) followed by NMP washings (4×20 ml). Mtt- or Mmt-deprotection was performed with 2% TFA and 2-3% TIS in DCM (5×20 ml, each 10 min) followed by DCM (2×20 ml), 10% MeOH and 5% DIPEA in DCM (2×20 ml) and NMP (4×20 ml) washings, or by treatment with neat hexafluroisopropanol (5×20 ml, each 10 min) followed by washings as above. The albumin binding moiety and/or linker can be attached to the peptide either by acylation of the resin bound peptide or acylation in solution of the unprotected peptide (see the routes described below). In case of attachment of the albumin binding moiety and/or linker to the protected peptidyl resin the attachment can be modular using SPPS and suitably protected building blocks (see General methods).

Attachment to Resin Bound Peptide—Route I:

Activated (active ester or symmetric anhydride) albumin binding moiety or linker such as octadecanedioic acid mono-(2,5-dioxo-pyrrolidin-1-yl) ester (Ebashi et al. EP511600, 4 molar equivalents relative to resin bound peptide) was dissolved in NMP (25 ml), added to the resin and shaken overnight at room temperature. The reaction mixture was filtered and the resin was washed extensively with NMP, DCM, 2-propanol, methanol and diethyl ether.

Attachment to Resin Bound Peptide—Route II:

The albumin binding moiety was dissolved in NMP/DCM (1:1, 10 ml). The activating reagent such as HOBt (4 molar equivalents relative to resin) and DIC (4 molar equivalents relative to resin) was added and the solution was stirred for 15 min. The solution was added to the resin and DIPEA (4 molar equivalents relative to resin) was added. The resin was shaken 2 to 24 hours at room temperature. The resin was washed with NMP (2×20 ml), NMP/DCM (1:1, 2×20 ml) and DCM (2×20 ml).

Attachment to Peptide in Solution—Route III:

Activated (active ester or symmetric anhydride) albumin binding moiety or linker such as octadecanedioic acid mono-(2,5-dioxo-pyrrolidin-1-yl) ester (Ebashi et al. EP511600) 1-1.5 molar equivalents relative to the peptide was dissolved in an organic solvent such as acetonitrile, THF, DMF, DMSO or in a mixture of water/organic solvent (1-2 ml) and added to a solution of the peptide in water (10-20 ml) together with 10 molar equivalents of DIPEA. In case of protecting groups on the albumin binding residue such as tert-butyl, the reaction mixture was lyophilised overnight and the isolated crude peptide deprotected afterwards. In case of tert-butyl protection groups the deprotection was performed by dissolving the peptide in a mixture of trifluoroacetic acid, water and triisopropylsilane (90:5:5). After 30 min the mixture was evaporated in vacuo and the crude peptide purified by preparative HPLC as described later.

SPPS Method E

SPPS method E refers to peptide synthesis by Fmoc chemistry on a Prelude Solid Phase Peptide Synthesiser from Protein Technologies (Tucson, Ariz. 85714 U.S.A.). A suitable resin is a pre-loaded, low-load Wang resin available from Novabiochem (e.g. low load fmoc-Lys(Mtt)-Wang resin, 0.35 mmol/g). Fmoc-deprotection was with 25% piperidine in NMP for 2×10 min. The coupling chemistry was DIC/HOAt/collidine in NMP. Amino acid/HOAt solutions (0.3 M in NMP at a molar excess of 3-10 fold) were added to the resin followed by the same molar equivalent of DIC (3 M in NMP) and collidine (3 M in NMP). For example, the following amounts of 0.3 M amino acid/HOAt solution were used per coupling for the following scale reactions: Scale/ml, 0.10 mmol/2.5 ml, 0.25 mmol/5 ml. Coupling times were generally 60 minutes. Some amino acids including, but not limited to arginine, Aib or histidine were "double coupled", meaning that after the first coupling (e.g. 60 min), the resin is drained and more reagents are added (amino acid, HOAt, DIC, and collidine), and the mixture allowed to react gain (e.g. 60 min). Some amino acids and fatty acid derivatives including but not limited to Fmoc-OEG-OH, Fmoc-Trx-OH, Fmoc-Glu-OtBu, octadecanedioic acid mono-tert-butyl ester, nonadecanedioic acid mono-tert-butyl ester, or 4-(9-carboxynonyloxy) benzoic acid tert-butyl ester were coupled for prolonged time, for example 6 hours. When a chemical modification of a lysine side chain was desired, the lysine was incorporated as Lys(Mtt). The Mtt group was removed by washing the resin with DCM and suspending the resin in hexafluoroisopropanol/DCM (75:25) for 3×10 minutes followed by washings with DCM, 20% piperidine and NMP. The chemical modification of the lysine was performed either by manual synthesis (see SPPS method D) or by one or more automated steps on the Prelude peptide synthesiser as described above using suitably protected building blocks (see General methods).

2. Cleavage of Peptide from the Resin and Purification

After synthesis the resin was washed with DCM, and the peptide was cleaved from the resin by a 2-3 hour treatment with TFA/TIS/water (95/2.5/2.5 or 92.5/5/2.5) followed by precipitation with diethylether. The peptide was dissolved in a suitable solvent (such as, e.g., 30% acetic acid) and purified by standard RP-HPLC on a C18, 5 μM column, using acetonitrile/water/TFA. The fractions were analysed by a combination of UPLC, MALDI and LCMS methods, and the appropriate fractions were pooled and lyophilised.

3. Methods for Detection and Characterisation

LCMS Methods

LCMS Method 1 (LCMS1)

An Agilent Technologies LC/MSD TOF (G1969A) mass spectrometer was used to identify the mass of the sample after elution from an Agilent 1200 series HPLC system. The de-convolution of the protein spectra was calculated with Agilent's protein confirmation software.

Eluents:
A: 0.1% Trifluoro acetic acid in water
B: 0.1% Trifluoro acetic acid in acetonitrile
Column: Zorbax 5u, 300SB-C3, 4.8×50 mm
Gradient: 25%-95% acetonitrile over 15 min LCMS Method 2 (LCMS2)

A Perkin Elmer Sciex API 3000 mass spectrometer was used to identify the mass of the sample after elution from a Perkin Elmer Series 200 HPLC system.

Eluents:
A: 0.05% Trifluoro acetic acid in water
B: 0.05% Trifluoro acetic acid in acetonitrile
Column: Waters Xterra MS C-18×3 mm id 5 μm
Gradient: 5%-90% acetonitrile over 7.5 min at 1.5 ml/min LCMS Method 3 (LCMS3)

A Waters Micromass ZQ mass spectrometer was used to identify the mass of the sample after elution from a Waters Alliance HT HPLC system.

Eluents:
A: 0.1% Trifluoro acetic acid in water
B: 0.1% Trifluoro acetic acid in acetonitrile
Column: Phenomenex, Jupiter C4 50×4.60 mm id 5 μm
Gradient: 10%-90% B over 7.5 min at 1.0 ml/min LCMS Method 4 (LCMS4)

LCMS4 was performed on a setup consisting of Waters Acquity UPLC system and LCT Premier XE mass spectrometer from Micromass. The UPLC pump was connected to two eluent reservoirs containing:
A: 0.1% Formic acid in water
B: 0.1% Formic acid in acetonitrile The analysis was performed at RT by injecting an appropriate volume of the sample (preferably 2-10 μl) onto the column which was eluted with a gradient of A and B. The UPLC conditions, detector settings and mass spectrometer settings were:

Column: Waters Acquity UPLC BEH, C-18, 1.7 μm, 2.1 mm×50 mm
Gradient: Linear 5%-95% acetonitrile during 4.0 min (alternatively 8.0 min) at 0.4 ml/min
Detection: 214 nm (analogue output from TUV (Tunable UV detector))
MS ionisation mode: API-ES
Scan: 100-2000 amu (alternatively 500-2000 amu), step 0.1 amu UPLC and HPLC Methods Method 05_B5_1

UPLC (method 05_B5_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 0.2 M $Na_2SO_4$, 0.04 M $H_3PO_4$, 10% $CH_3CN$ (pH 3.5)
B: 70% $CH_3CN$, 30% $H_2O$
The following linear gradient was used: 60% A, 40% B to 30% A, 70% B over 8 minutes at a flow-rate of 0.40 ml/min.

Method 05_B7_1

UPLC (method 05_B7_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 0.2 M $Na_2SO_4$, 0.04 M $H_3PO_4$, 10% $CH_3CN$ (pH 3.5)
B: 70% $CH_3CN$, 30% $H_2O$
The following linear gradient was used: 80% A, 20% B to 40% A, 60% B over 8 minutes at a flow-rate of 0.40 ml/min.
Method 04_A2_1

UPLC (method 04_A2_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 90% $H_2O$, 10% $CH_3CN$, 0.25 M ammonium bicarbonate
B: 70% $CH_3CN$, 30% $H_2O$
The following linear gradient was used: 90% A, 10% B to 60% A, 40% B over 16 minutes at a flow-rate of 0.40 ml/min.
Method 04_A3_1

UPLC (method 04_A3_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 90% $H_2O$, 10% $CH_3CN$, 0.25 M ammonium bicarbonate
B: 70% $CH_3CN$, 30% $H_2O$
The following linear gradient was used: 75% A, 25% B to 45% A, 55% B over 16 minutes at a flow-rate of 0.40 ml/min.
Method 04_A4_1

UPLC (method 04_A4_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 90% $H_2O$, 10% $CH_3CN$, 0.25 M ammonium bicarbonate
B: 70% $CH_3CN$, 30% $H_2O$
The following linear gradient was used: 65% A, 35% B to 25% A, 65% B over 16 minutes at a flow-rate of 0.40 ml/min.
Method 08_B2_1

UPLC (method 08_B2_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 99.95% $H_2O$, 0.05% TFA
B: 99.95% $CH_3CN$, 0.05% TFA
The following linear gradient was used: 95% A, 5% B to 40% A, 60% B over 16 minutes at a flow-rate of 0.40 ml/min.

Method 08_B4_1

UPLC (method 08_B4_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 99.95% $H_2O$, 0.05% TFA
B: 99.95% $CH_3CN$, 0.05% TFA
The following linear gradient was used: 95% A, 5% B to 95% A, 5% B over 16 minutes at a flow-rate of 0.40 ml/min.
Method 05_B10_1

UPLC (Method 05_B10_1): The RP-analyses was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing:
A: 0.2 M $Na_2SO_4$, 0.04 M $H_3PO_4$, 10% $CH_3CN$ (pH 3.5)
B: 70% $CH_3CN$, 30% $H_2O$
The following linear gradient was used: 40% A, 60% B to 20% A, 80% B over 8 minutes at a flow-rate of 0.40 ml/min.
Method 01_A4_2

UPLC (Method 01_A4_2): The RP-analysis was performed using a Waters 600S system fitted with a waters 996 diode array detector. UV detections at 214 nm and 254 nm were collected using a Symmetry300 C18, 5 um, 3.9 mm×150 mm column, 42° C. The HPLC system was connected to three eluent reservoirs containing: A: 100% $H_2O$, B: 100% $CH_3CN$, C: 1% trifluoroacetic acid in $H_2O$. The following linear gradient was used: 90% A, 5% B, 5% C to 0% A, 95% B, 5% C over 15 minutes at a flow-rate of 1.0 ml/min.
Method 09_B2_1

UPLC (Method 09_B2_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 40% A, 60% B over 16 minutes at a flow-rate of 0.40 ml/min.
Method 09_B4_1

UPLC (Method 09_B4_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 5% A, 95% B over 16 minutes at a flow-rate of 0.40 ml/min.
Method 05_B8_1

UPLC (Method 05_B8_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 0.2 M $Na_2SO_4$, 0.04 M $H_3PO_4$, 10% $CH_3CN$ (pH 3.5); B: 70% $CH_3CN$, 30% $H_2O$. The following linear gradient was used: 50% A, 50% B to 20% A, 80% B over 8 minutes at a flow-rate of 0.40 ml/min.

Method 10_B14_1

UPLC (Method 10_B14_1): The RP-analysis was performed using a Waters UPLC system fitted with a dual band detector. UV detections at 214 nm and 254 nm were collected using an ACQUITY UPLC BEH ShieldRP18, 1.7 um, 2.1 mm×150 mm column, 50° C. The UPLC system was connected to two eluent reservoirs containing: A: 99.95% $H_2O$, 0.05% TFA; B: 99.95% $CH_3CN$, 0.05% TFA. The following linear gradient was used: 70% A, 30% B to 40% A, 60% B over 12 minutes at a flow-rate of 0.40 ml/min.

Method 04_A6_1

UPLC (Method 04_A6_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 10 mM TRIS, 15 mM ammonium sulphate, 80% $H_2O$, 20%, pH 7.3; B: 80% $CH_3CN$, 20% $H_2O$. The following linear gradient was used: 95% A, 5% B to 10% A, 90% B over 16 minutes at a flow-rate of 0.35 ml/min.

Method 01_B4_1

HPLC (Method 01_B4_1): The RP-analysis was performed using a Waters 600S system fitted with a Waters 996 diode array detector. UV detections were collected using a Waters 3 mm×150 mm 3.5 um C-18 Symmetry column. The column was heated to 42° C. and eluted with a linear gradient of 5-95% acetonitrile, 90-0% water, and 5% trifluoroacetic acid (1.0%) in water over 15 minutes at a flow-rate of 1 ml/min.

Method 04_A7_1

UPLC (Method 04_A7_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 10 mM TRIS, 15 mM ammonium sulphate, 80% $H_2O$, 20%, pH 7.3; B: 80% $CH_3CN$, 20% $H_2O$. The following linear gradient was used: 95% A, 5% B to 40% A, 60% B over 16 minutes at a flow-rate of 0.40 ml/min.

Method 05_B9_1

UPLC (Method 05_B9_1): The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 0.2 M $Na_2SO_4$, 0.04 M $H_3PO_4$, 10% $CH_3CN$ (pH 3.5); B: 70% $CH_3CN$, 30% $H_2O$. The following linear gradient was used: 70% A, 30% B to 20% A, 80% B over 8 minutes at a flow-rate of 0.40 ml/min.

Method 10_B12_1

UPLC (Method 10_B12_1): The RP-analysis was performed using a Waters UPLC system fitted with a dual band detector. UV detections at 214 nm and 254 nm were collected using an ACQUITY UPLC BEH ShieldRP18, 1.7 um, 2.1 mm×150 mm column, 50° C. The UPLC system was connected to two eluent reservoirs containing: A: 99.95% $H_2O$, 0.05% TFA; B: 99.95% $CH_3CN$, 0.05% TFA. The following linear gradient was used: 50% A, 50% B to 0% A, 100% B over 16 minutes at a flow-rate of 0.40 ml/min.

Method 04_A9_1

UPLC (Method 04_A9_1): The RP-analysis was performed using a Waters UPLC system fitted with a dual band detector. UV detections at 214 nm and 254 nm were collected using an ACQUITY UPLC BEH Shield RP18, C18, 1.7 um, 2.1 mm×150 mm column, 60° C. The UPLC system was connected to two eluent reservoirs containing: A: 200 mM $Na_2SO_4$+20 mM $Na_2HPO_4$+20 mM $NaH_2PO_4$ in 90% $H_2O$/10% $CH_3CN$, pH 7.2; B: 70% $CH_3CN$, 30% $H_2O$. The following step gradient was used: 90% A, 10% B to 80% A, 20% B over 3 minutes, 80% A, 20% B to 50% A, 50% B over 17 minutes at a flow-rate of 0.40 ml/min.

MALDI-MS Method

Molecular weights were determined using matrix-assisted laser desorption and ionisation time-of-flight mass spectroscopy, recorded on a Microflex or Autoflex (Bruker). A matrix of alpha-cyano-4-hydroxy cinnamic acid was used.

NMR Method

Proton NMR spectra were recorded using a Brucker Avance DPX 300 (300 MHz) with tetramethylsilane as an internal standard. Chemical shifts (δ) are given in ppm and splitting patterns are designated as follows: s, singlet; d, doublet; dd, double doublet; dt, double triplet t, triplet, tt, triplet of triplets; q, quartet; quint, quintet; sext, sextet; m, multiplet, and br=broad.

B. Synthesis of Intermediates

1. Synthesis of Mono Esters of Fatty Diacids

Overnight reflux of the C12, C14, C16 and C18 diacids with Boc-anhydride, DMAP, and t-butanol in toluene gives predominately the t-butyl mono ester. Obtained is after work-up a mixture of mono acid, diacid and diester. Purification is carried out by washing, short plug silica filtration and crystallisation.

B. Synthesis of Compounds of the Invention

Example 1

N$^{\epsilon 27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], N$^{\epsilon 37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Glu$^{22}$,Arg$^{26}$, Lys$^{27}$,Arg$^{34}$, Lys$^{37}$]-GLP-1-(7-37)-peptide (SEQ ID NO: 4)

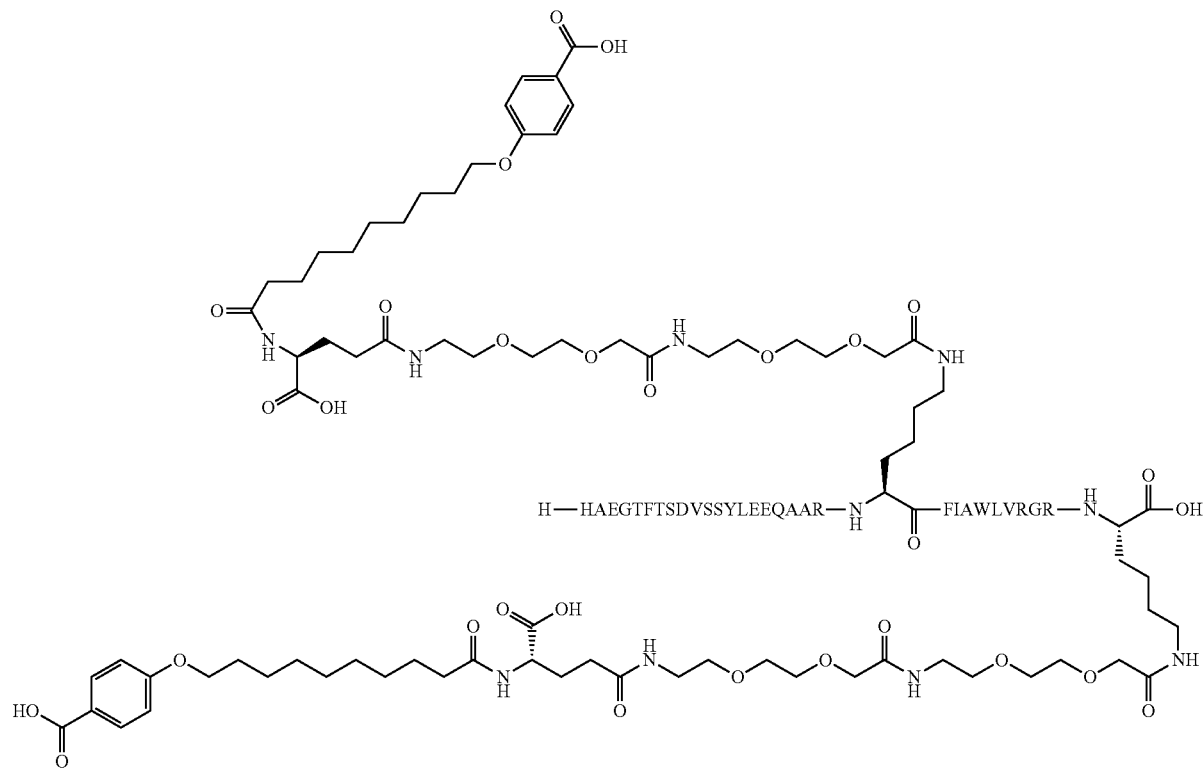

Chem. 50

Preparation method: SPPS method B
UPLC (Method 09_B2_1): Rt=12.4 min
UPLC (Method: 04_A3_1): Rt=8.3 min
LCMS4: Rt=2.0 min, m/z=1659 (m/3), 1244 (m/4), 996 (m/5)

Example 2

$N^{\varepsilon 27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\varepsilon 36}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Glu$^{22}$,Arg$^{26}$,Lys$^{27}$,Glu$^{30}$,Arg$^{34}$,Lys$^{36}$]-GLP-1-(7-37)-peptidyl-Glu-Gly (SEQ ID NO: 5)

Chem. 51

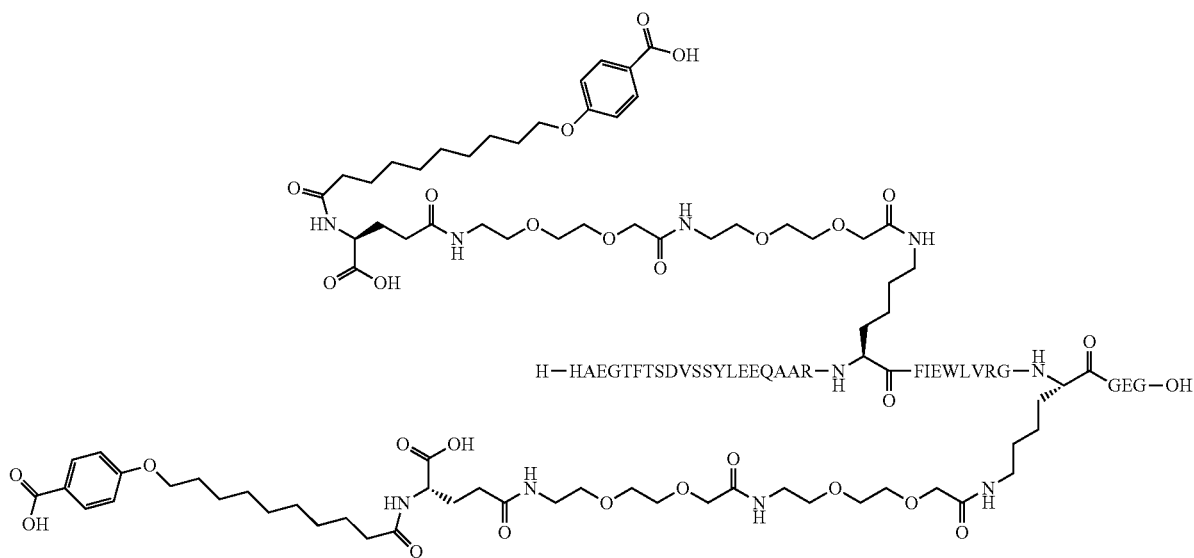

Preparation method: SPPS method B
UPLC (Method 09_B2_1): Rt=13.1 min
UPLC (Method 04_A7_1): Rt=6.3 min
LCMS4: Rt=2.1 min, m/z=1707 (m/3), 1280 (m/4), 1025 (m/5)

Example 3

N$^{\epsilon 27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], N$^{\epsilon 36}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Glu$^{22}$,Arg$^{26}$,Lys$^{27}$,Arg$^{34}$,Lys$^{36}$],des-Gly37-GLP-1-(7-36)-peptide (SEQ ID NO: 6)

Chem. 52

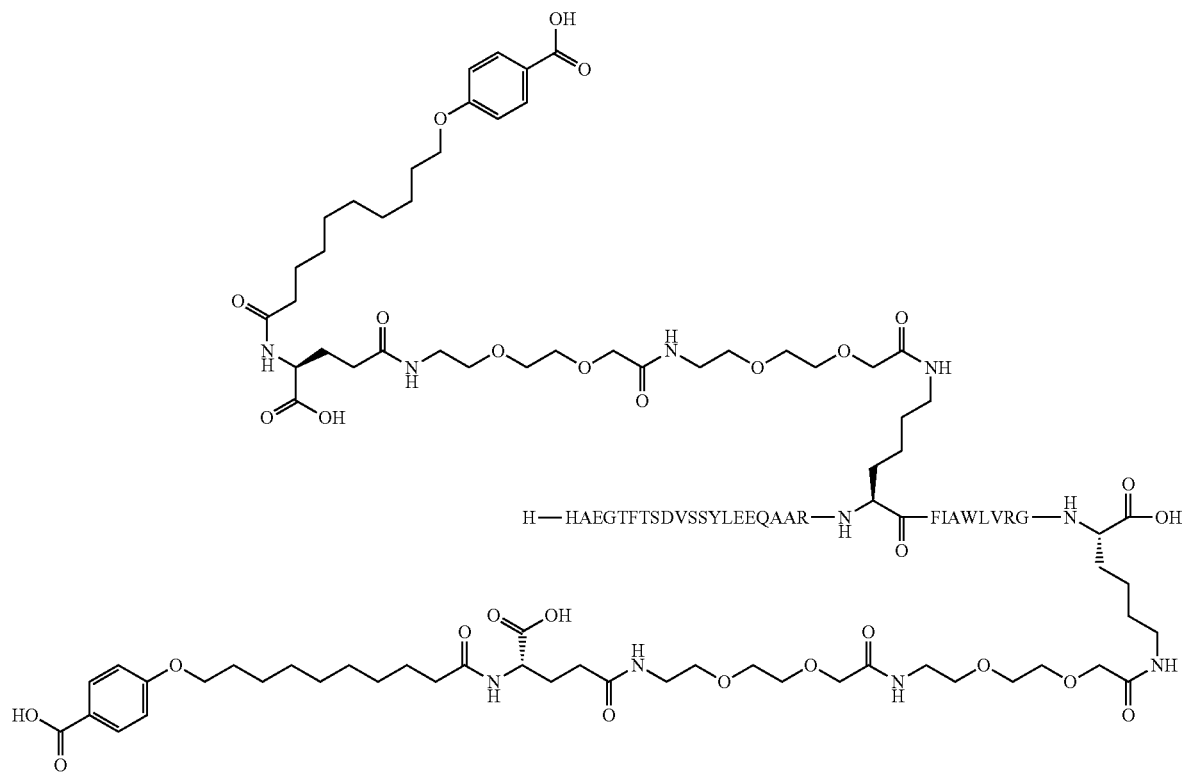

Preparation method: SPPS method B
UPLC (Method 09_B2_1): Rt=13.3 min
UPLC (Method 05_B5_1): Rt=6.5 min
LCMS4: Rt=2.3 min, m/z=1607 (m/3), 1205 (m/4), 964 (m/5)

Example 4

$N^{\epsilon 27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Glu$^{22}$,Val$^{25}$,Arg$^{26}$, Lys$^{27}$,Arg$^{34}$, Lys$^{37}$]-GLP-1-(7-37)-peptide (SEQ ID NO: 7)

Chem. 53

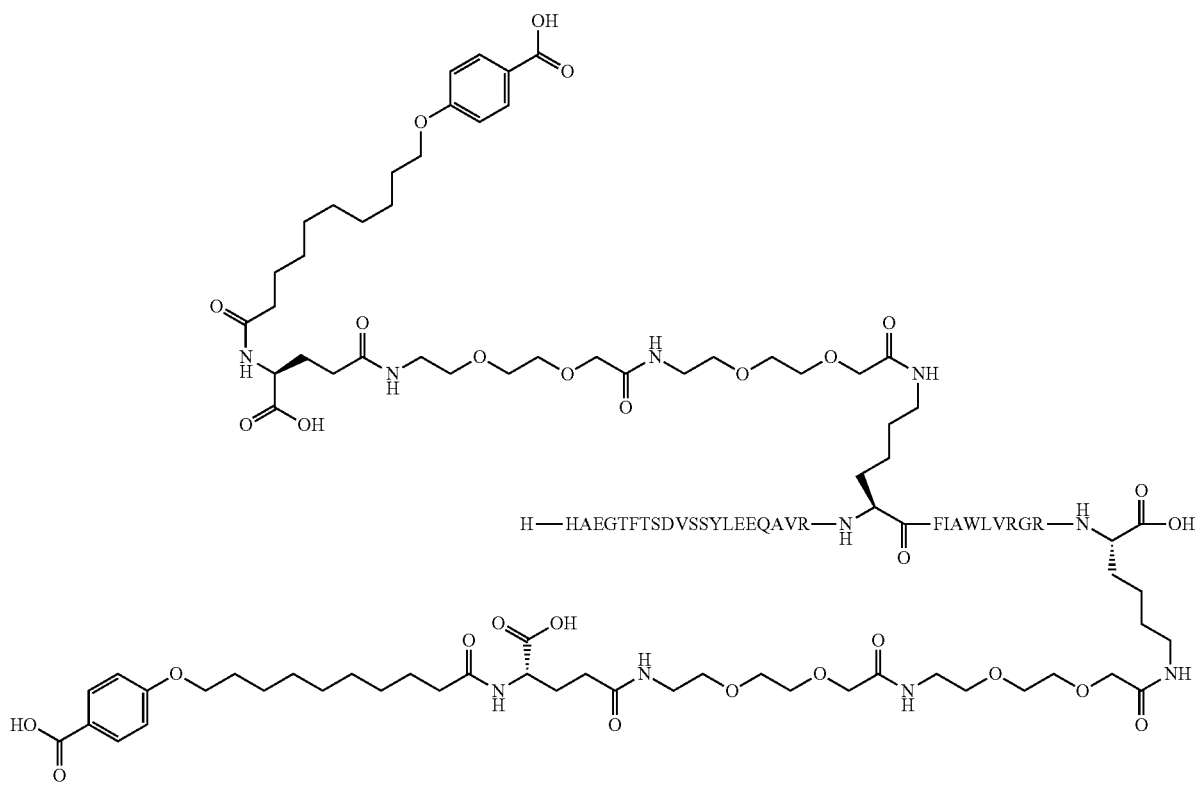

Preparation method: SPPS method B
UPLC (Method 09_B2_1): Rt=13.0 min
UPLC (Method 04_A7_1): Rt=6.9 min
LCMS4: Rt=2.0 min, m/z=1668 (m/3), 1251 (m/4), 1001 (m/5)

Example 5

$N^{\varepsilon 20}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\varepsilon 27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib$^8$, Lys$^{20}$,Glu$^{22}$,Arg$^{26}$,Lys$^{27}$,Glu$^{30}$,Gly$^{34}$]-GLP-1-(7-34)-peptide (SEQ ID NO: 8)

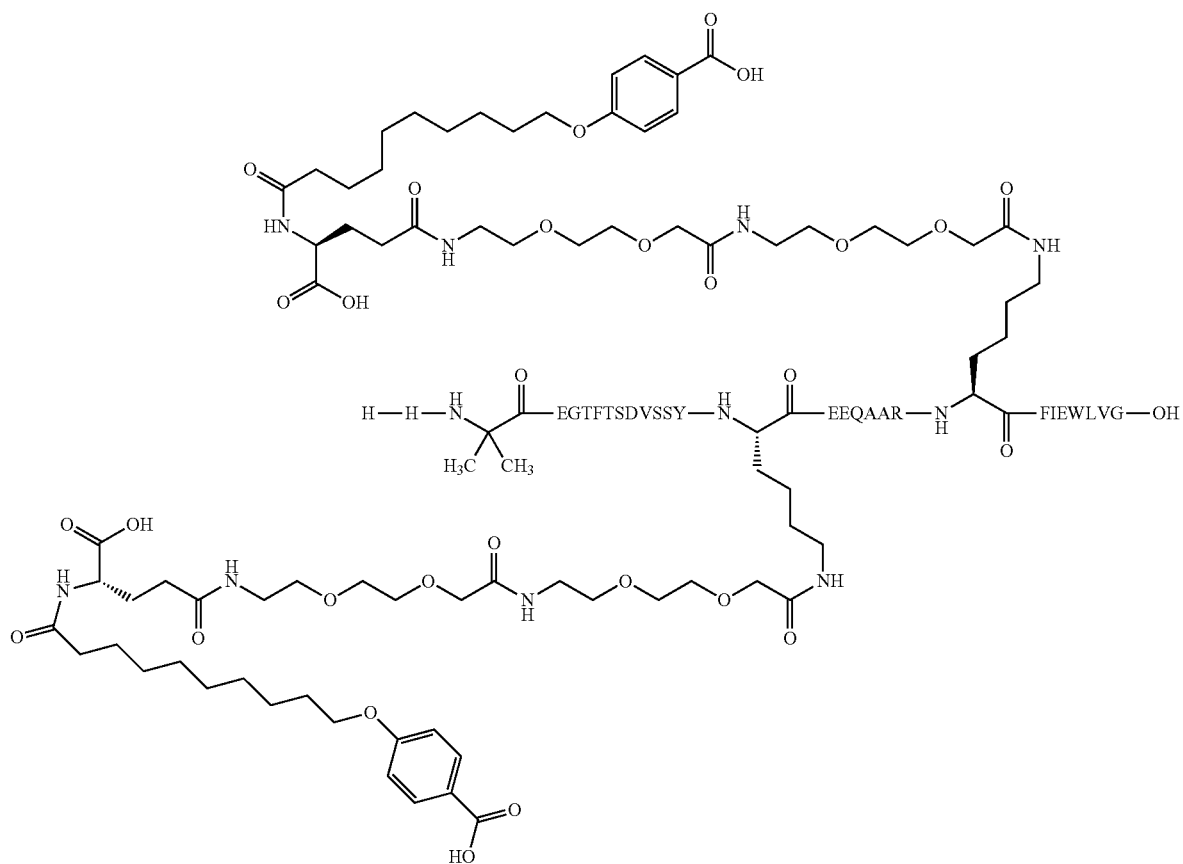

Chem. 54

Preparation method: SPPS method B
UPLC (Method 08_B4_1): Rt=9.02 min
UPLC (Method 04_A6_1): Rt=4.61 min
LCMS4: Rt=2.17 min, m/z=1540 (m/3), 1155 (m/4)

Example 6

N$^{\varepsilon 27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], N$^{\varepsilon 36}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Arg$^{26}$,Lys$^{27}$,Glu30,Arg$^{34}$,Lys$^{36}$]-GLP-1-(7-37)-peptidyl-Glu (SEQ ID NO: 9)

Chem. 55

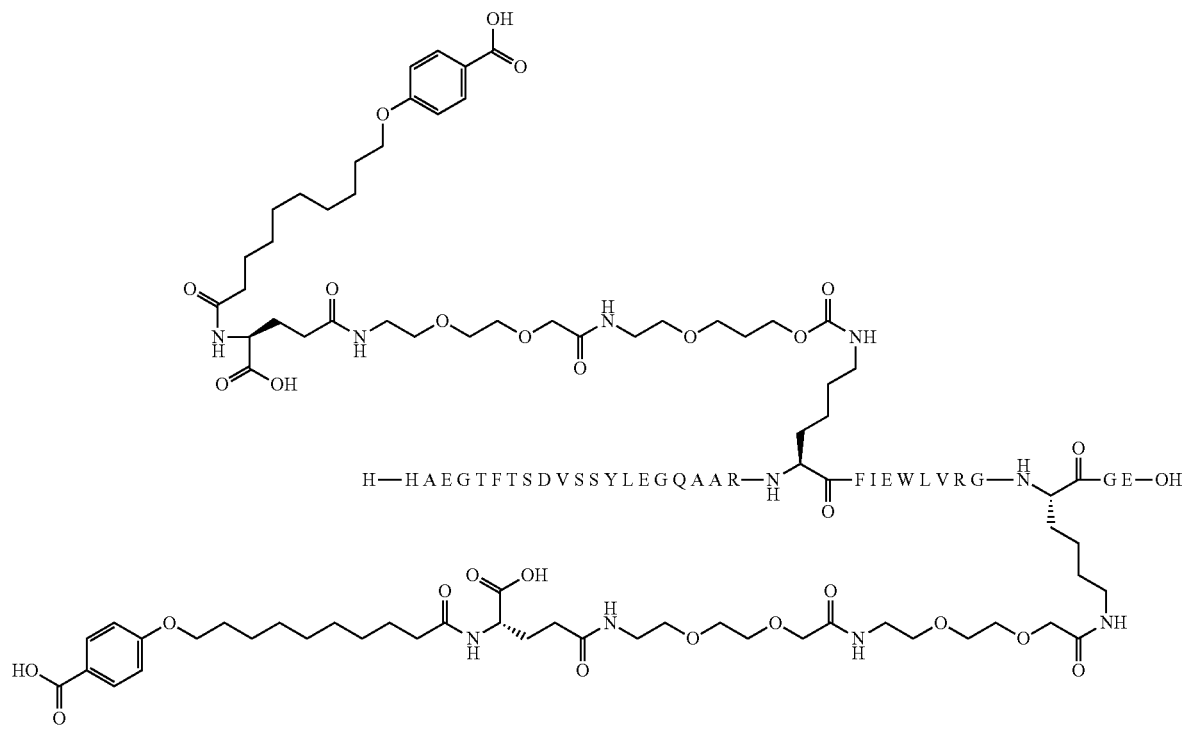

Preparation method: SPPS method B
UPLC (Method 09_B2_1): Rt=13.0 min
UPLC (Method 05_B5_1): Rt=5.6 min
LCMS4: Rt=2.2 min, m/z=1664 (m/3), 1248 (m/4), 999 (m/5)

Example 7

N$^{\varepsilon 22}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], N$^{\varepsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$, Lys$^{22}$,Val$^{25}$,Arg$^{26}$, Lys$^{27}$, His$^{31}$,Arg$^{34}$]-GLP-1-(7-37)-peptide (SEQ ID NO: 10)

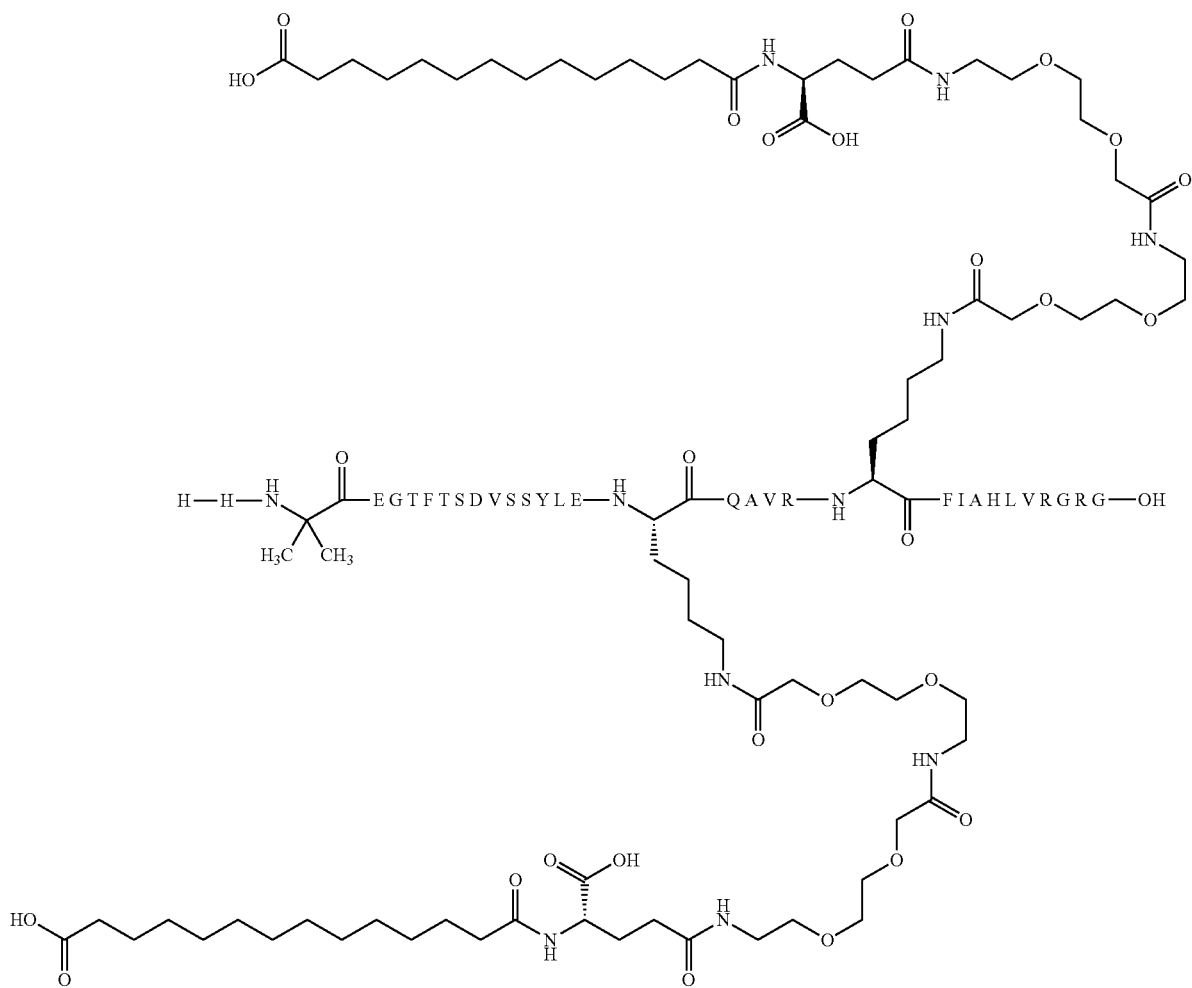

Chem. 56

Preparation method: SPPS method B
LCMS2: Rt=4.00 min, m/z=1599 (m/3), 1199 (m/4)
UPLC (Method 08_B4_1): Rt=7.83 min
UPLC (Method 05_B9_1): Rt=7.45 min

Example 8

N$^{\varepsilon22}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], N$^{\varepsilon27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$,Lys$^{22}$,Val$^{25}$,Arg$^{26}$,Lys$^{27}$,Arg$^{34}$]-GLP-1-(7-34)-peptide (SEQ ID NO: 11)

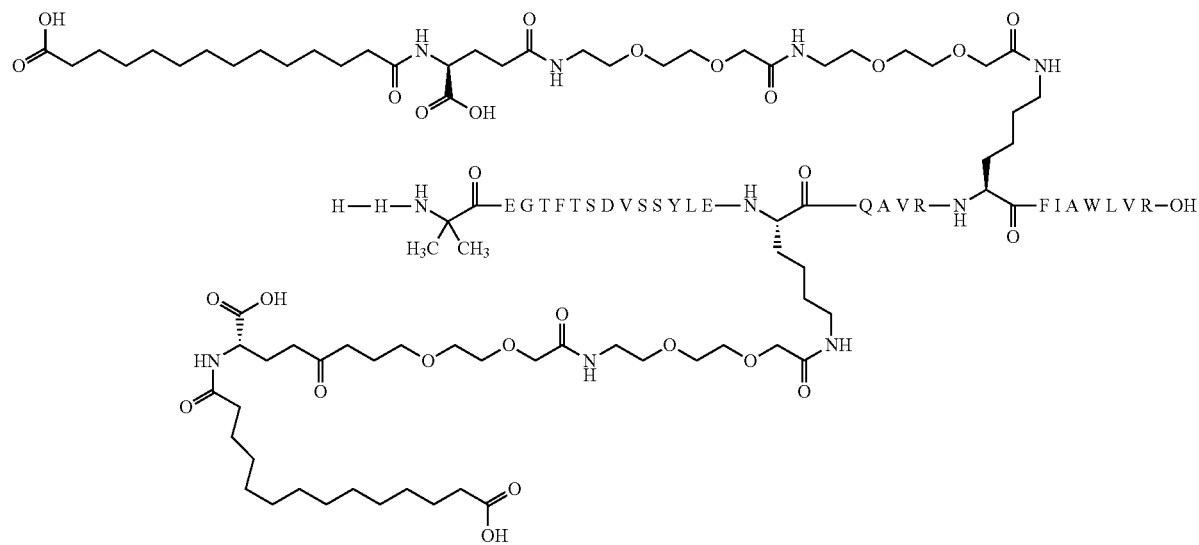

Chem. 57

Preparation method: SPPS method B
UPLC (Method 10_B12_): Rt=8.92 min
LCMS4: Rt=2.58 min, m/z=1525 (m/3), 1144 (m/4), 915 (m/5)

Example 9

$N^{\epsilon 22}$-[2-[2-[2-[[2-[2-[2-[[(4S)-4-carboxy-4-(13-carboxytridecanoylamino)butanyl]amino]ethoxy]ethoxy]acetyl]amino]ethoxy]ethoxy]acetyl], $N^{\epsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$, Lys$^{22}$,Val$^{25}$,Arg$^{26}$,Lys$^{27}$,Arg34]-GLP-1-(7-35)-peptide (SEQ ID NO: 12)

Chem. 58

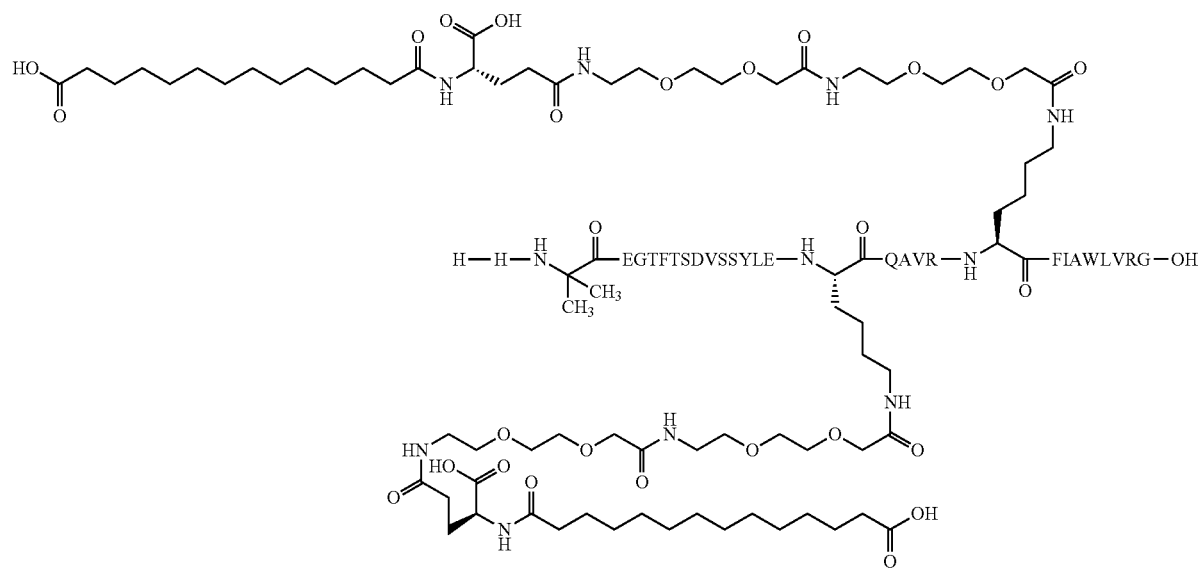

Preparation method: SPPS method E
The theoretical molecular mass of 4628 Da was confirmed by MALDI-MS
UPLC (method 09_B4_1): Rt=9.29 min
UPLC (method 04_A6_1): Rt=6.49 min

Example 10

$N^{\epsilon27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon36}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[His$^{26}$,Lys$^{27}$,Glu$^{30}$,Arg$^{34}$,Lys$^{36}$]-GLP-1-(7-37)-peptidyl-Glu (SEQ ID NO: 13)

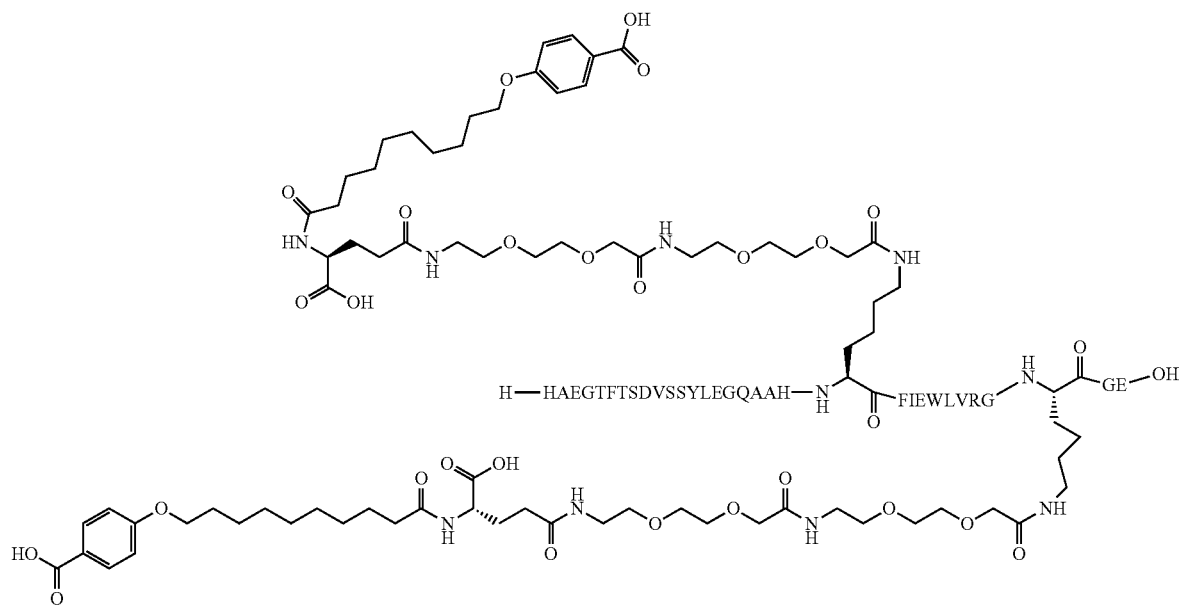

Chem. 59

Preparation method: SPPS method B
UPLC (Method 08_B2_1): Rt=12.9 min
UPLC (Method 05_B5_1): Rt=5.5 min
LCMS4: Rt=2.2 min, m/z=1657 (m/3), 1243 (m/4), 995 (m/5)

Example 11

N$^{\varepsilon 22}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], N$^{\varepsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Lys$^{22}$, Val$^{25}$,Arg$^{26}$, Lys$^{27}$,Glu$^{30}$,Gln$^{34}$]-GLP-1-(7-37)-peptide (SEQ ID NO: 14)

Chem. 60

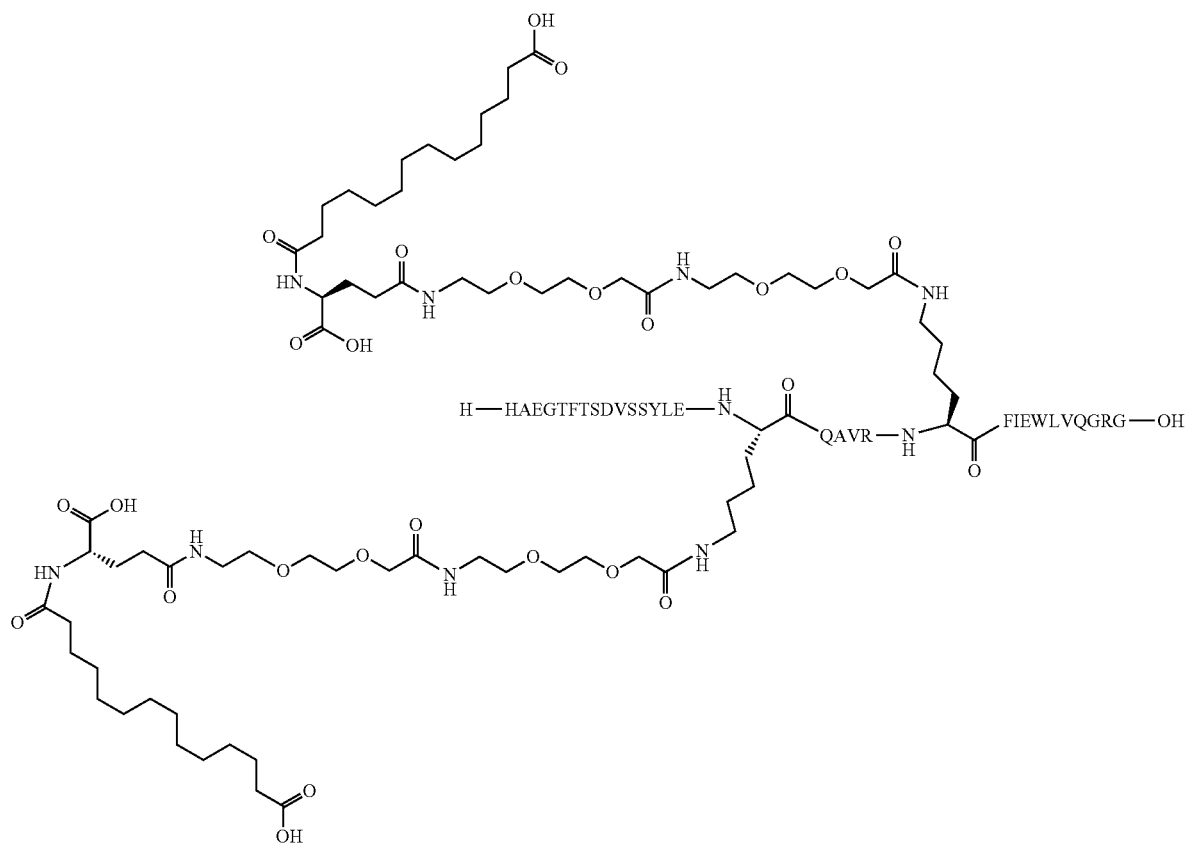

Preparation method: SPPS method B
UPL (Method 08_B2_1): Rt=13.5 min
LCMS4: Rt=2.2 min, m/z=1621 (m/3), 1216 (m/4), 973 (m/5)

Example 12

$N^{\alpha}(N^{\epsilon 27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 36}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Val$^{25}$,Arg$^{26}$,Lys$^{27}$,Glu$^{30}$,Arg$^{34}$,Lys$^{36}$]-GLP-1-(7-37)-peptidyl)-Gln (SEQ ID NO: 15)

Chem. 61

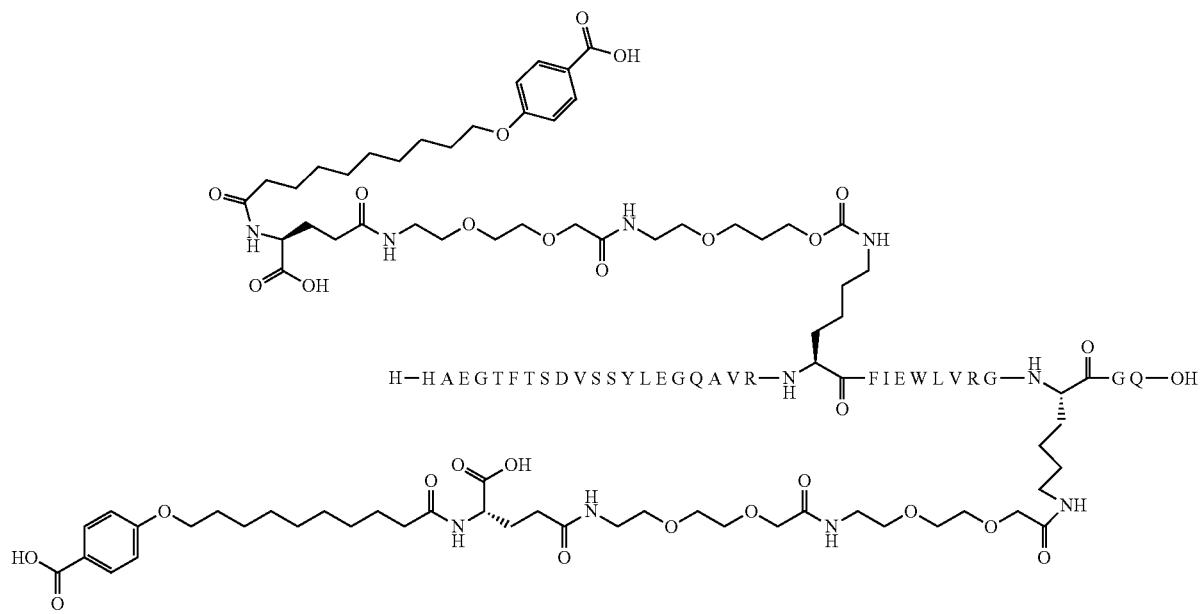

Preparation method: SPPS method B
UPLC (Method 09_B4_1): Rt=8.9 min
UPLC (Method 05_B7_1): Rt=8.8 min
LCMS4: Rt=2.2 min, m/z=1673 (m/3), 1255 (m/4), 1004 (m/5)

Example 13

$N^{\epsilon27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon36}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Val$^{25}$,Arg$^{26}$,Lys$^{27}$,Glu$^{30}$,Gln$^{34}$,Lys$^{36}$]-GLP-1-(7-37)-peptidyl-Glu (SEQ ID NO: 16)

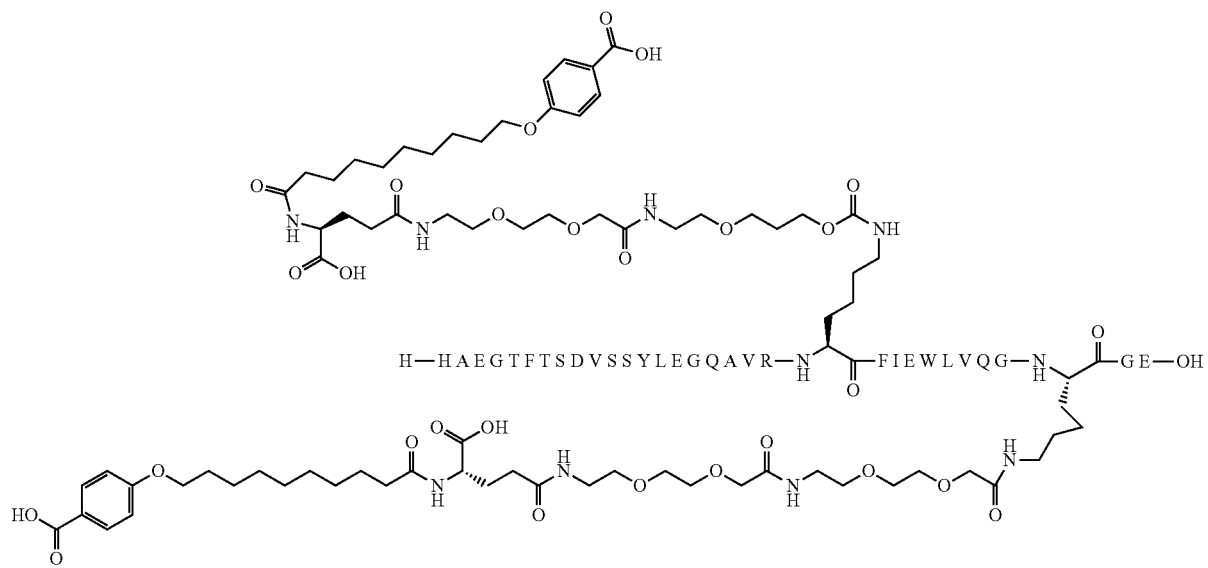

Chem. 62

Preparation method: SPPS method B
UPLC (Method 05_B9_1): Rt=7.9 min
UPLC (Method 05_B7_1): Rt=8.8 min
LCMS4: Rt=2.3 min, m/z=1663 (m/3), 1248 (m/4), 999 (m/5)

Example 14

N$^{\varepsilon 22}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl], N$^{\varepsilon 27}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl]-[Lys$^{22}$,Arg$^{26}$,Lys$^{27}$,His$^{31}$,Gly$^{34}$]-GLP-1-(7-34)-peptide (SEQ ID NO: 17)

Chem. 63

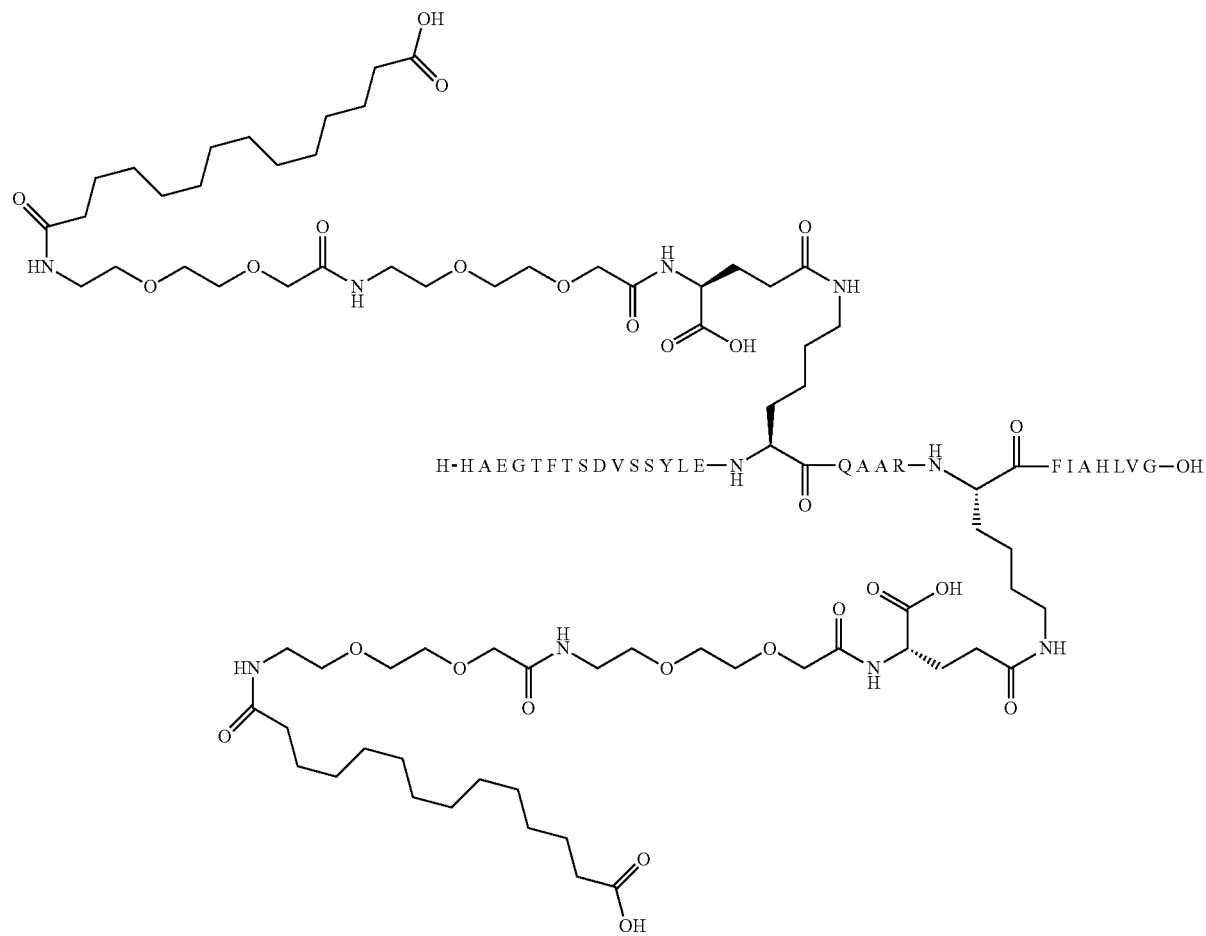

Preparation method: SPPS method B
UPLC (Method 08_B4_1): Rt=8.5 min
UPLC (Method 05_B7_1): Rt=8.8 min
LCMS4: Rt=2.1 min, m/z=1462 (m/3), 1097 (m/4), 878 (m/5)

Example 15

N$^{\epsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], N$^{\epsilon 37}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$, Val$^{25}$,Arg$^{26}$, Lys$^{27}$,His$^{31}$,Gln$^{34}$,Lys$^{37}$]-GLP-1-(7-37)-peptide (SEQ ID NO: 18)

Chem. 64

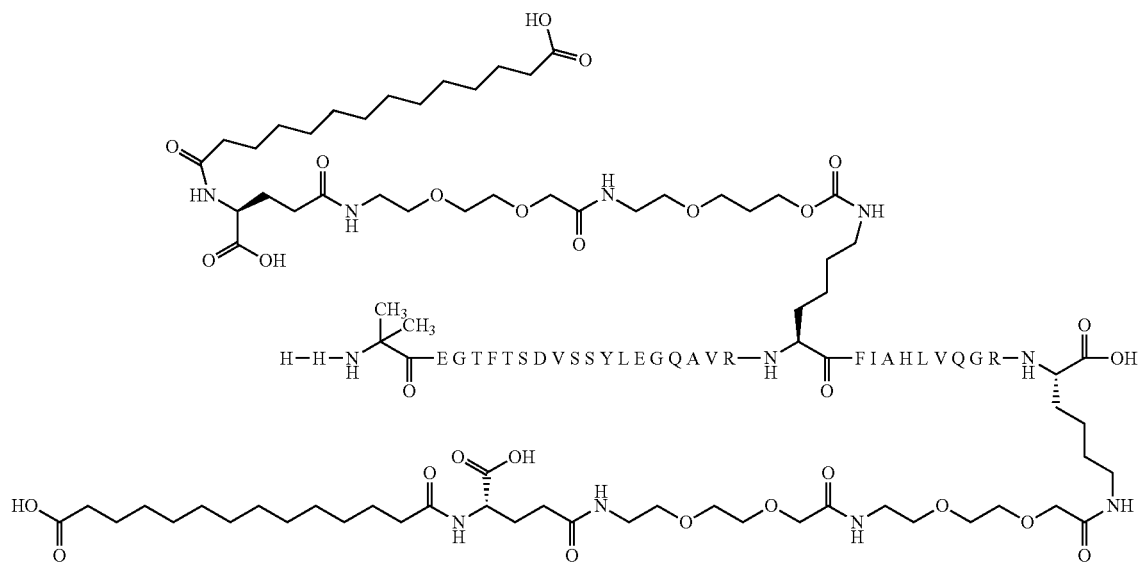

Preparation method: SPPS method B
UPLC (Method 08_B4_1): Rt=8.3 min
UPLC (Method 05_B9_1): Rt=7.1 min
LCMS4: Rt=2.1 min, m/z=1589 (m/3), 1192 (m/4), 954 (m/5)

Example 16

N$^{\varepsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], N$^{\varepsilon 37}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Val$^{25}$, Arg$^{26}$,Lys$^{27}$,His$^{31}$,Gln$^{34}$,Lys$^{37}$]-GLP-1-(7-37)-peptide (SEQ ID NO: 19)

Chem. 65

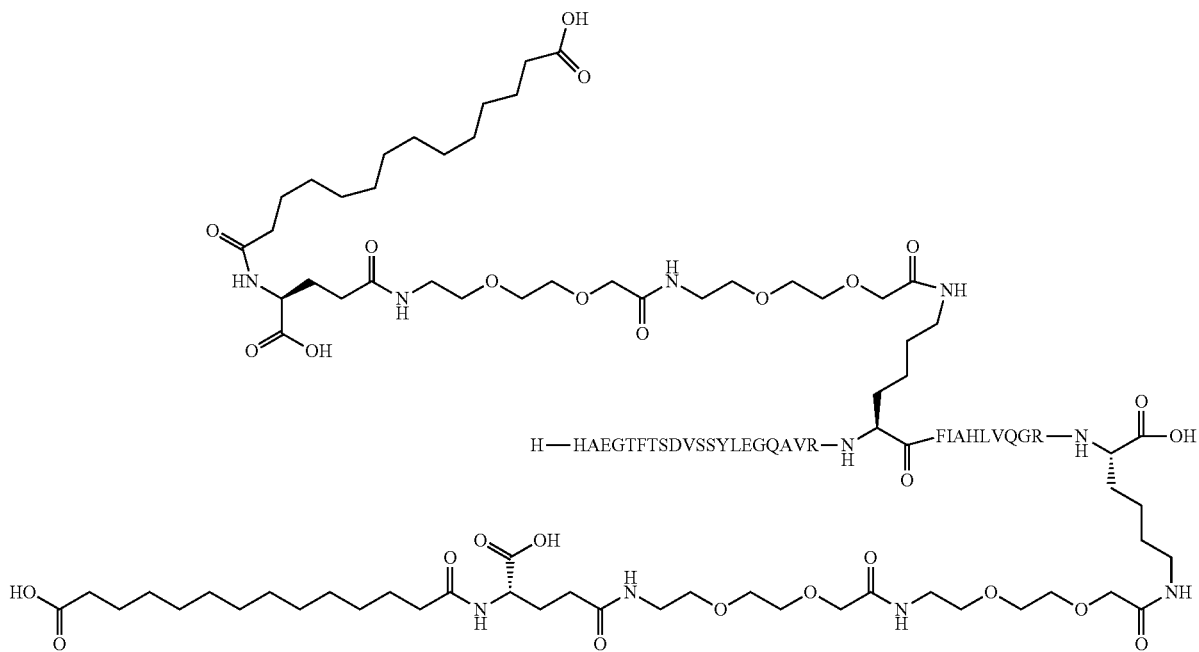

Preparation method: SPPS method B
UPLC (Method 08_B4_1): Rt=8.1 min
LCMS4: Rt=2.1 min, m/z=1585 (m/3), 1189 (m/4), 951 (m/5)

Example 17

$N^{\epsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 37}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Glu$^{22}$,Glu$^{23}$,Val$^{25}$,Arg$^{26}$,Lys$^{27}$,His$^{31}$,Gln$^{34}$,Lys$^{37}$]-GLP-1-(7-37)-peptide (SEQ ID NO: 20)

Chem. 66

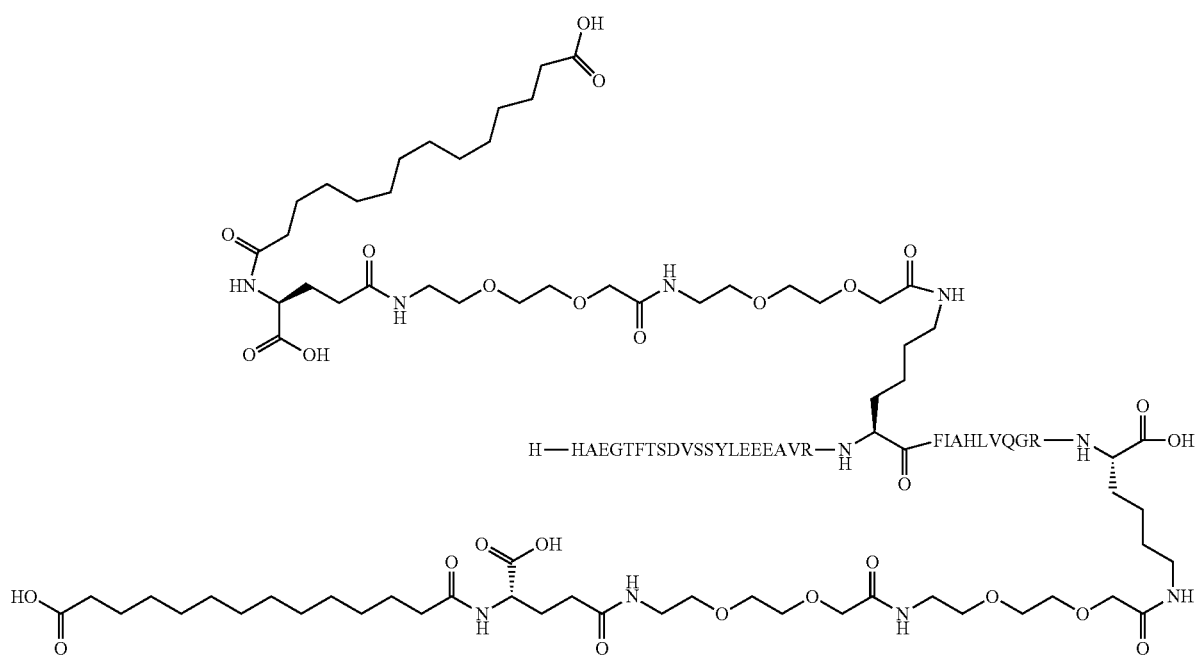

Preparation method: SPPS method B
UPLC (Method 08_B4_1): Rt=8.0 min
UPLC (Method 05_B9_1): Rt=6.6 min
LCMS4: Rt=2.1 min, m/z=1609 (m/3), 1206 (m/4), 966 (m/5)

Example 18

N$^{\varepsilon 12}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], N$^{\varepsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$,Lys$^{12}$,Glu$^{22}$,Arg$^{26}$,Lys$^{27}$,His$^{31}$,Gln$^{34}$]-GLP-1-(7-37)-peptide (SEQ ID NO: 21)

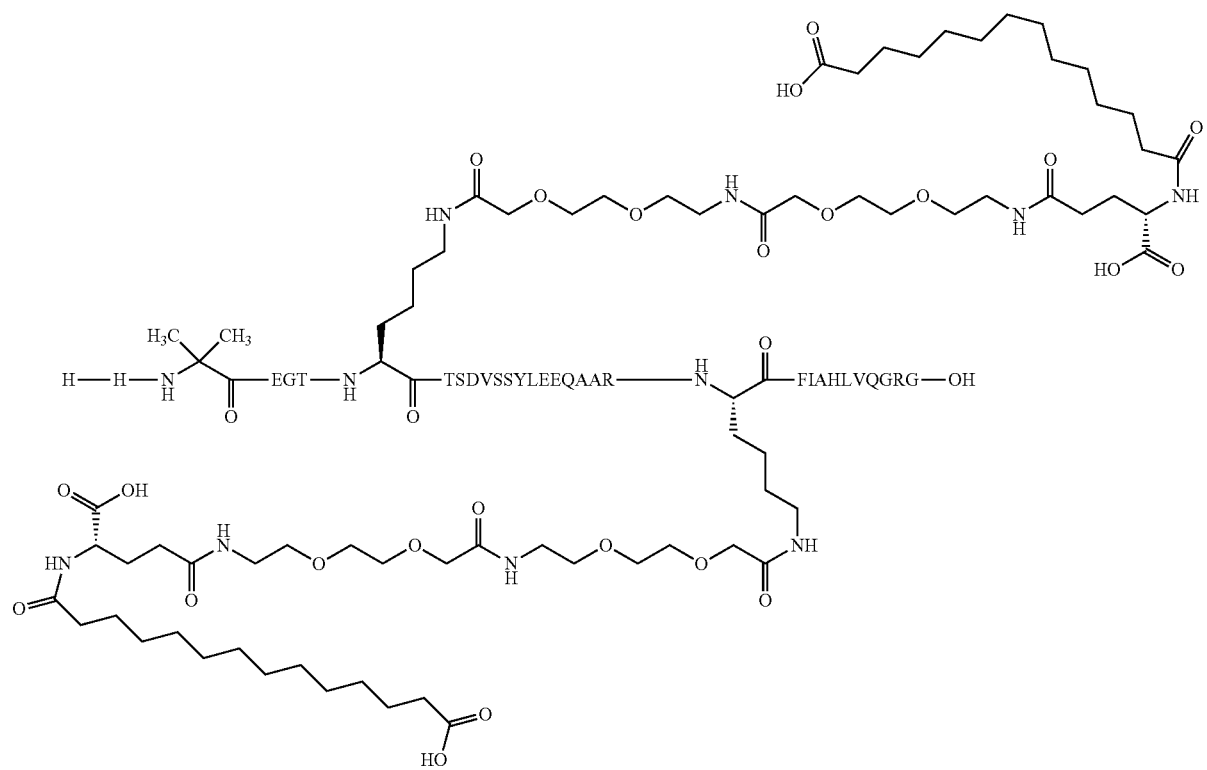

Chem. 67

Preparation method: SPPS method B
UPLC (Method 09_B4_1): Rt=7.66 min
UPLC (Method 04_A6_1): Rt=4.09 min
LCMS4: Rt=1.83 min, m/z=1181(m/4), 945 (m/5)

Example 19

$N^{\varepsilon 22}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\varepsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib$^8$, Lys$^{22}$,Arg$^{26}$,Lys$^{27}$,His$^{31}$,Gly$^{34}$]-GLP-1-(7-34)-peptide (SEQ ID NO: 22)

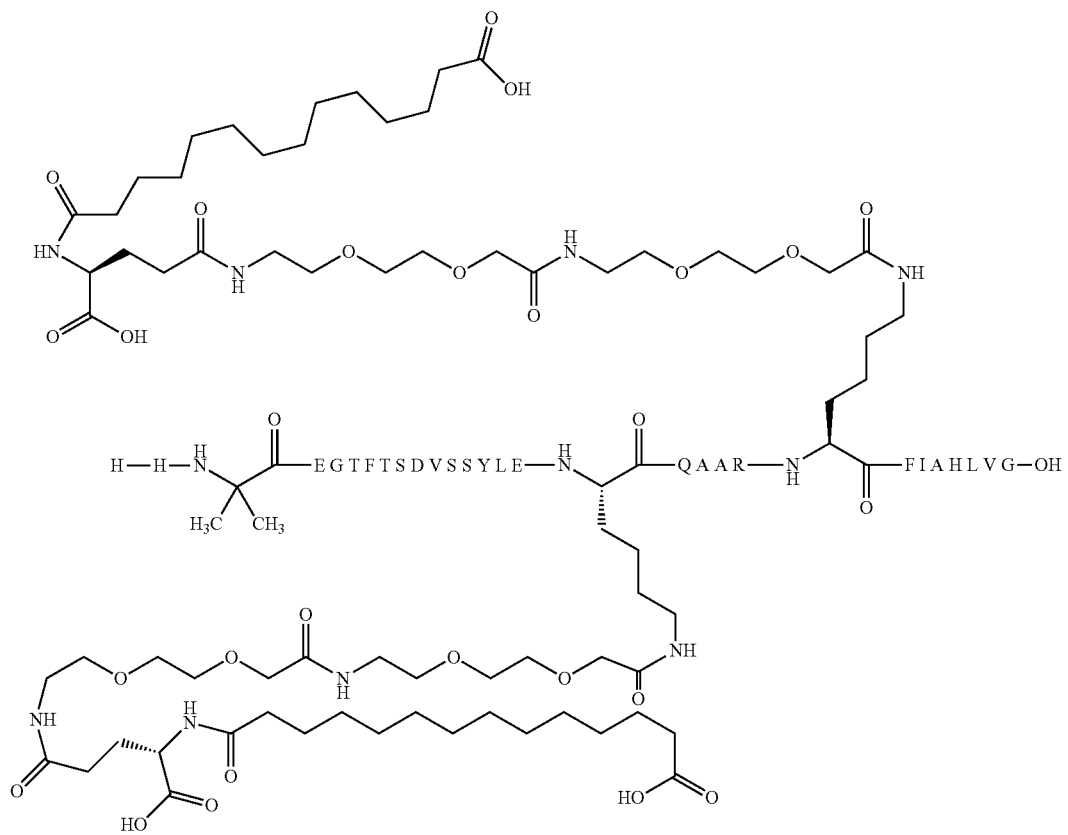

Chem. 68

Preparation method: SPPS method B
UPLC (Method 09_B4_1): Rt=8.37 min
UPLC (Method 04_A6_1): Rt=4.41 min
LCMS4: Rt=2.00 min, m/z=1466 (m/3), 1100 (m/4)

Example 20

$N^{\epsilon 22}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl], $N^{\epsilon 27}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl]-[Lys$^{22}$,Val$^{25}$,Arg$^{26}$,Lys$^{27}$,Glu$^{30}$,Gln$^{34}$]-GLP-1-(7-37)-peptide (SEQ ID NO: 23)

Chem. 69

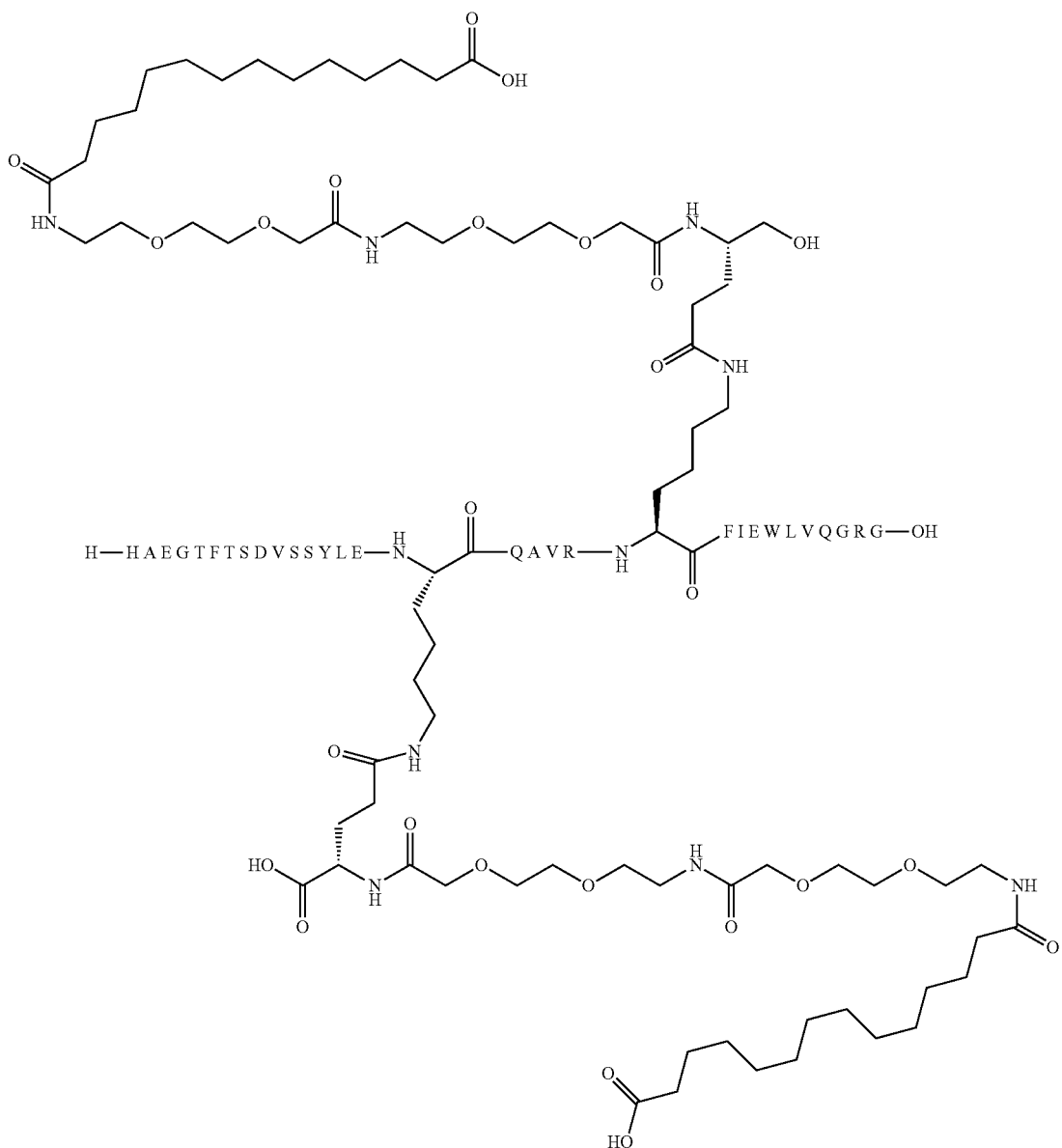

Preparation method: SPPS Method E
UPLC (Method 09_B4_1): Rt=9.00 min
UPLC (Method 04_A6_1): Rt=6.50 min
LCMS4: Rt=2.23 min, m/z=1215(m/4), 972(m/5)

Example 21

$N^{\epsilon 27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 36}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Glu$^{22}$, His$^{26}$,Lys$^{27}$,Glu$^{30}$,Arg$^{34}$,Lys$^{36}$]-GLP-1-(7-37)-peptidyl-Glu (SEQ ID NO: 24)

Chem. 70

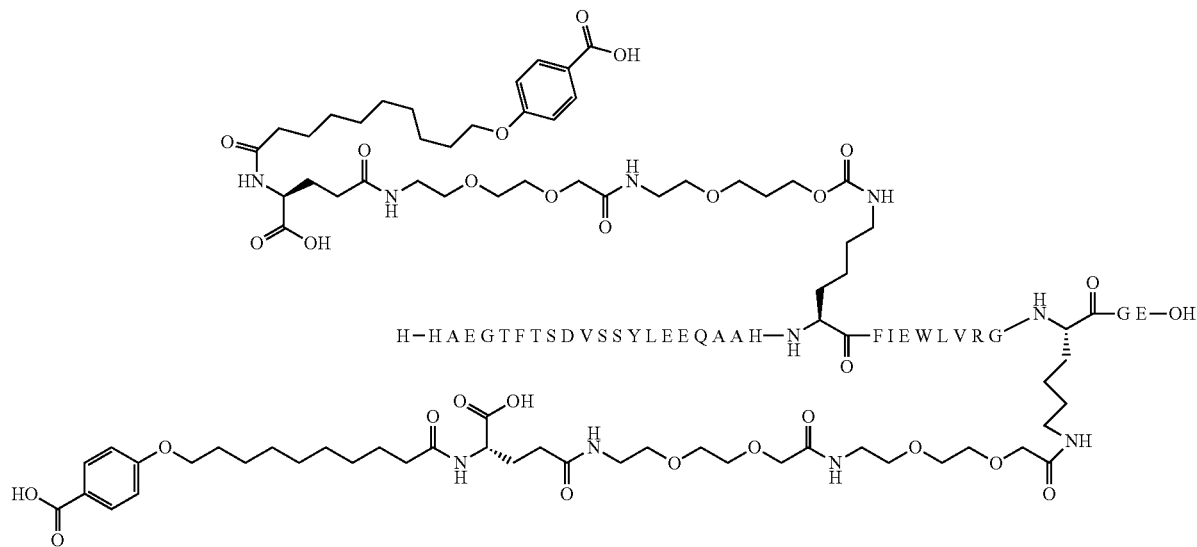

Preparation method: SPPS method B
UPLC (Method 09_B4_1): Rt=8.4 min
UPLC (Method 04_A6_1): Rt=9.3 min
LCMS4: Rt=2.2 min, m/z=1681 (m/3), 1261 (m/4), 1009 (m/5)

Example 22

N^ε24^-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl], N^ε27^-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl]-[Glu²², Lys²⁴,Arg²⁶,Lys²⁷, His³¹,Gly³⁴]-GLP-1-(7-34)-peptide (SEQ ID NO: 25)

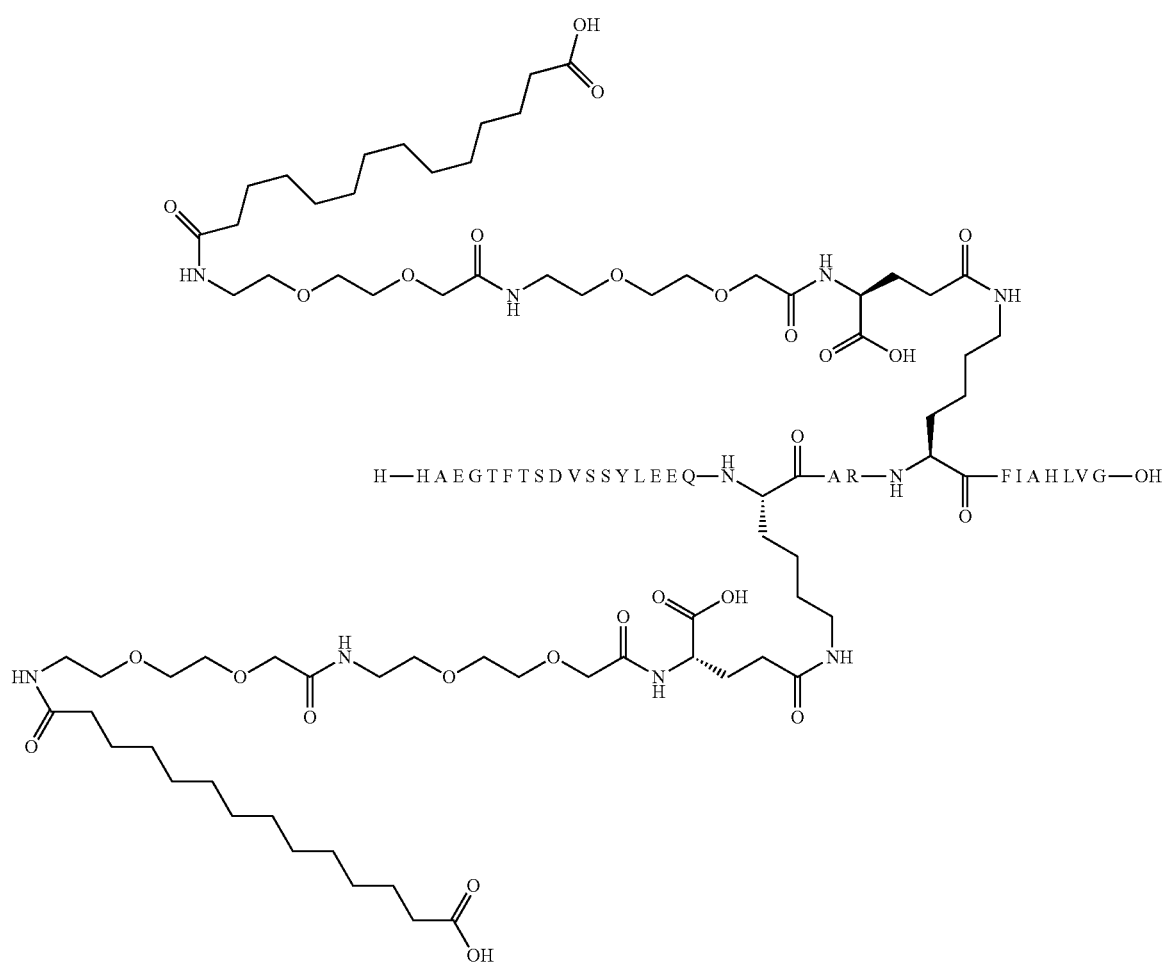

Chem. 71

Preparation method: SPPS method B
UPLC (Method 09_B4_1): Rt=8.17 min
UPLC (Method 04_A6_1): Rt=4.65 min
LCMS4: Rt=1.98 min, m/z=1481 (m/3), 1111 (m/4)

Example 23

$N^{\epsilon 27}$-[2-[2-[2-[[2-[2-[2-[[(4S)-4-carboxy-4-[[(4S)-4-carboxy-4-[10-(4-carboxyphenoxy)decanoylamino]butanoyl]amino]butanoyl]amino]ethoxy]ethoxy]acetyl]amino]ethoxy]ethoxy]acetyl], $N^{36}$-[2-[2-[2-[[2-[2-[2-[[(4S)-4-carboxy-4-[[(4S)-4-carboxy-4-[10-(4-carboxyphenoxy)decanoylamino]butanoyl]amino]butanoyl]amino]ethoxy]ethoxy]acetyl]amino]ethoxy]ethoxy]acetyl]-[Val$^{25}$,Arg$^{26}$,Lys$^{27}$,Gln$^{34}$,Lys$^{36}$]-GLP-1-(7-37)-peptide (SEQ ID NO: 26)

Chem. 72

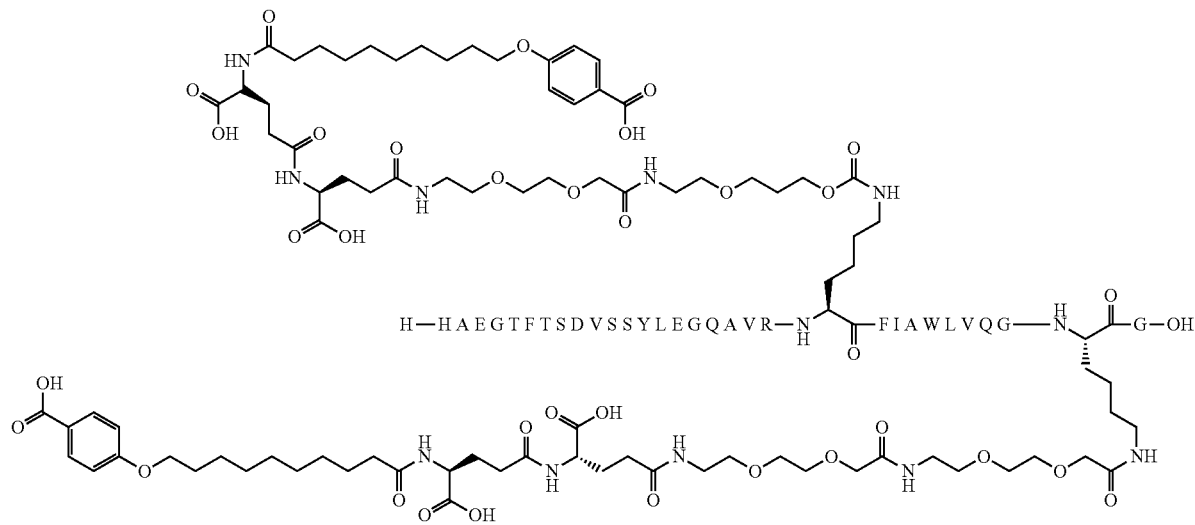

Preparation method: SPPS method B
UPLC (Method 08_B4_1): Rt=8.82 min
UPLC (Method 05_B5_1): Rt=6.10 min
LCMS4: Rt=2.37 min, m/z=1687 (m/3), 1266 (m/4), 1013 (m/5)

Example 24

N$^{\epsilon 24}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], N$^{\epsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Glu$^{22}$, Lys$^{24}$,Val$^{25}$,Arg$^{26}$,Lys$^{27}$, His$^{31}$,Arg$^{34}$]-GLP-1-(7-37)-peptide (SEQ ID NO: 27)

Chem. 73

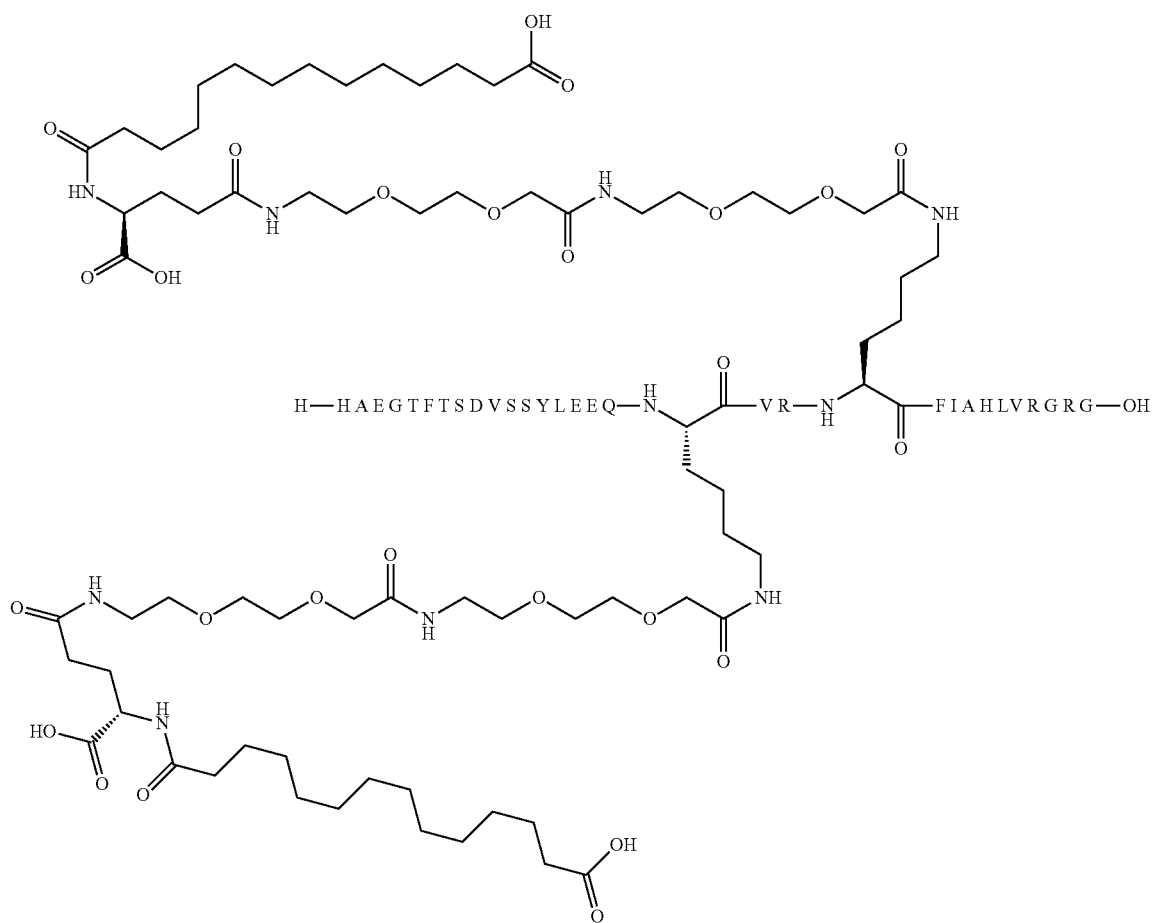

Preparation method: SPPS method B
UPLC (Method 08_B4_1): Rt=7.52 min
UPLC (Method 04_A9_1): Rt=10.35 min
LCMS4: Rt=1.92 min, m/z=1613 (m/3), 1210 (m/4), 968 (m/5), 807 (m/6)

Example 25

N$^{\varepsilon 24}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], N$^{\varepsilon 27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Glu$^{22}$,Lys$^{24}$,Arg$^{26}$,Lys$^{27}$,His$^{31}$,Gly$^{34}$]-GLP-1-(7-34)-peptide (SEQ ID NO: 28)

Chem. 74

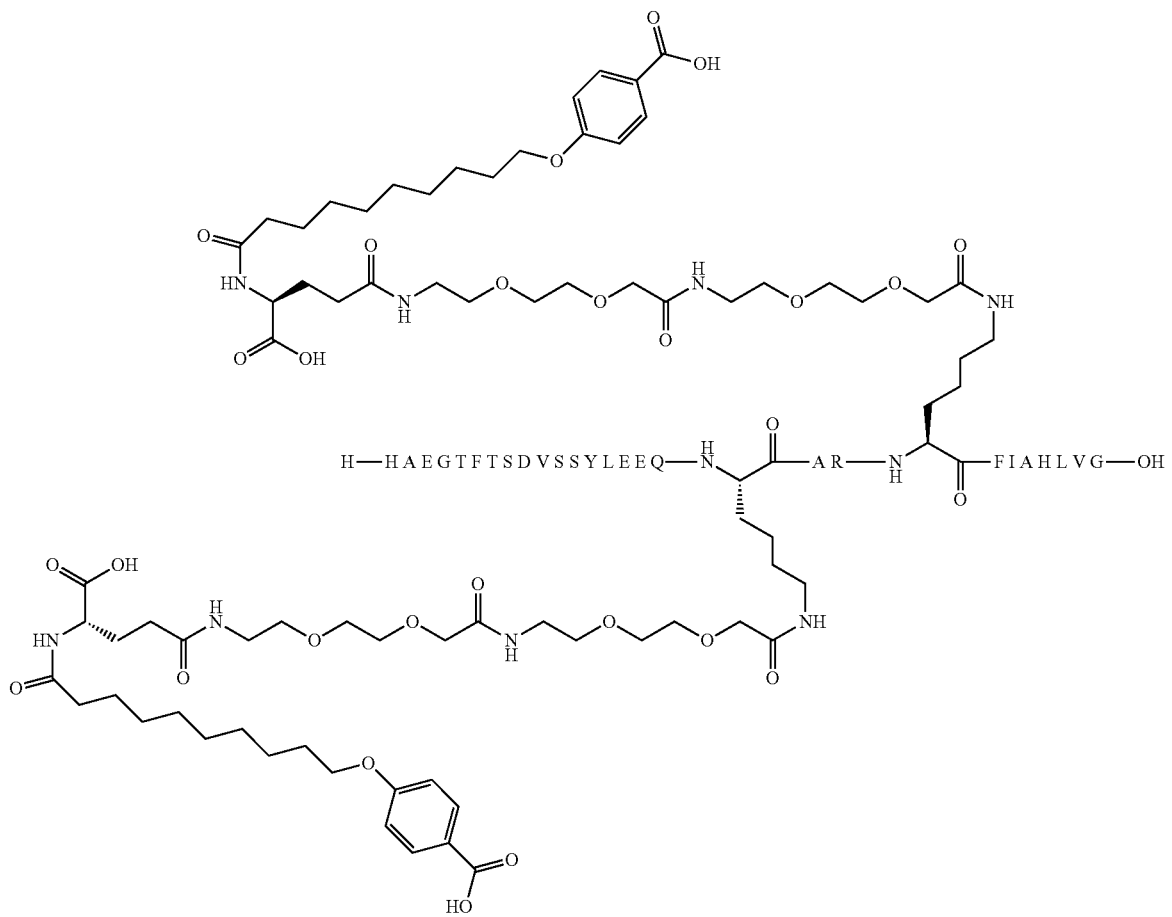

Preparation method: SPPS method B
UPLC (Method 08_B4_1): Rt=8.01 min
UPLC (Method 04_A9_1): Rt=8.00 min
LCMS4: Rt=2.08 min, m/z=1513 (m/3), 1135 (m/4), 908 (m/5)

Example 26

$N^{\epsilon 27}$-[(4S)-4-carboxy-4-[[2-[2-[2-[[2-[2-[2-[[(4R)-4-carboxy-4-[10-(4-carboxyphenoxy)decanoylamino]butanoyl]amino]ethoxy]ethoxy]acetyl]amino]ethoxy]ethoxy]acetyl]amino]butanoyl], $N^{\epsilon 36}$-[(4S)-4-carboxy-4-[[2-[2-[2-[[2-[2-[2-[[(4R)-4-carboxy-4-[10-(4-carboxyphenoxy)decanoylamino]butanoyl]amino]ethoxy]ethoxy]acetyl]amino]ethoxy]ethoxy]acetyl]amino]butanoyl]-[Val$^{25}$,Arg$^{26}$,Lys$^{27}$,Gln$^{34}$, Lys$^{36}$]-GLP-1-(7-37)-peptide (SEQ ID NO: 29)

Chem. 75

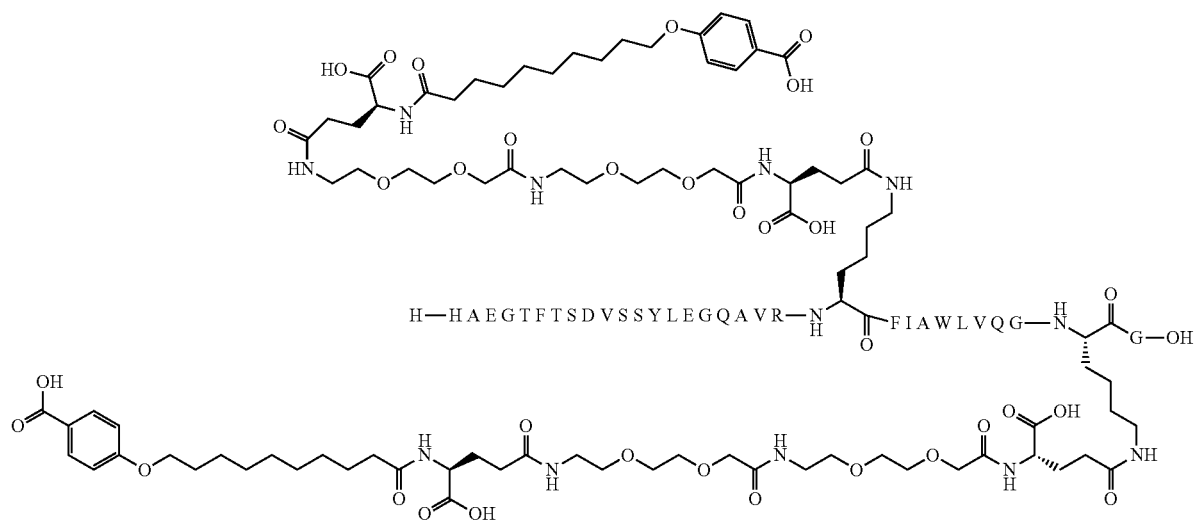

Preparation method: SPPS method B
UPLC (Method 09_B4_1): Rt=8.96 min
UPLC (Method 05_B5_1): Rt=6.54 min
UPLC (Method 04_A6_1): Rt=5.69 min
LCMS4: m/z: Rt=3.07 min, m/z=1687 (m/3), 1266 (m/4), 1013 (m/5)

Example 27

$N^{\epsilon 24}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], $N^{\epsilon 27}$-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Glu$^{22}$,Lys$^{24}$,Val$^{25}$,Arg$^{26}$,Lys$^{27}$,Gly$^{34}$]-GLP-1-(7-34)-peptide (SEQ ID NO: 30)

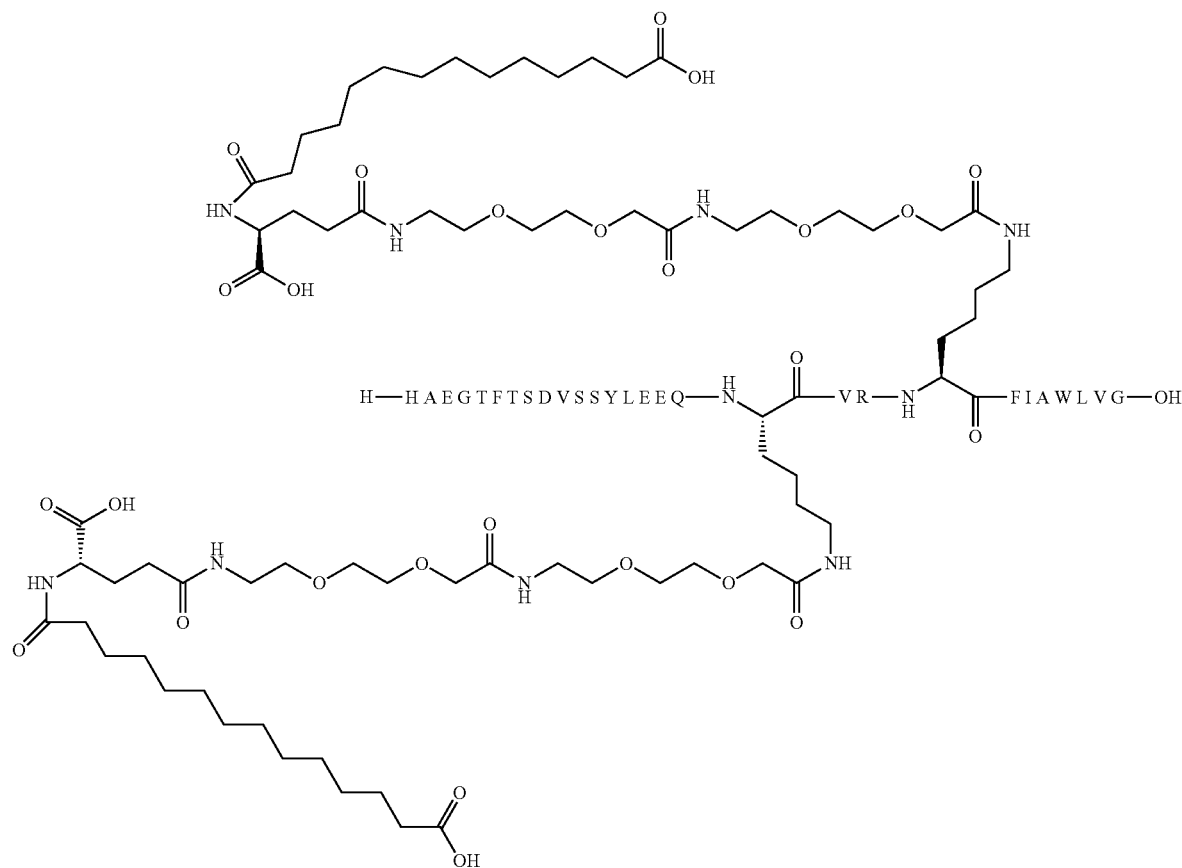

Chem. 76

Preparation method: SPPS method B
UPLC (Method 09_B4_1): Rt=9.25 min
UPLC (Method 04_A6_1): Rt=6.01 min
LCMS4: Rt=3.31 min, m/z=1506 (m/3), 1130 (m/4), 4520 (m/5)

Example 28

N^ε24-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], N^ε27-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Glu22,Lys24,Val25,Arg26,Lys27,Arg34]-GLP-1-(7-37)-peptide (SEQ ID NO: 31)

Chem. 77

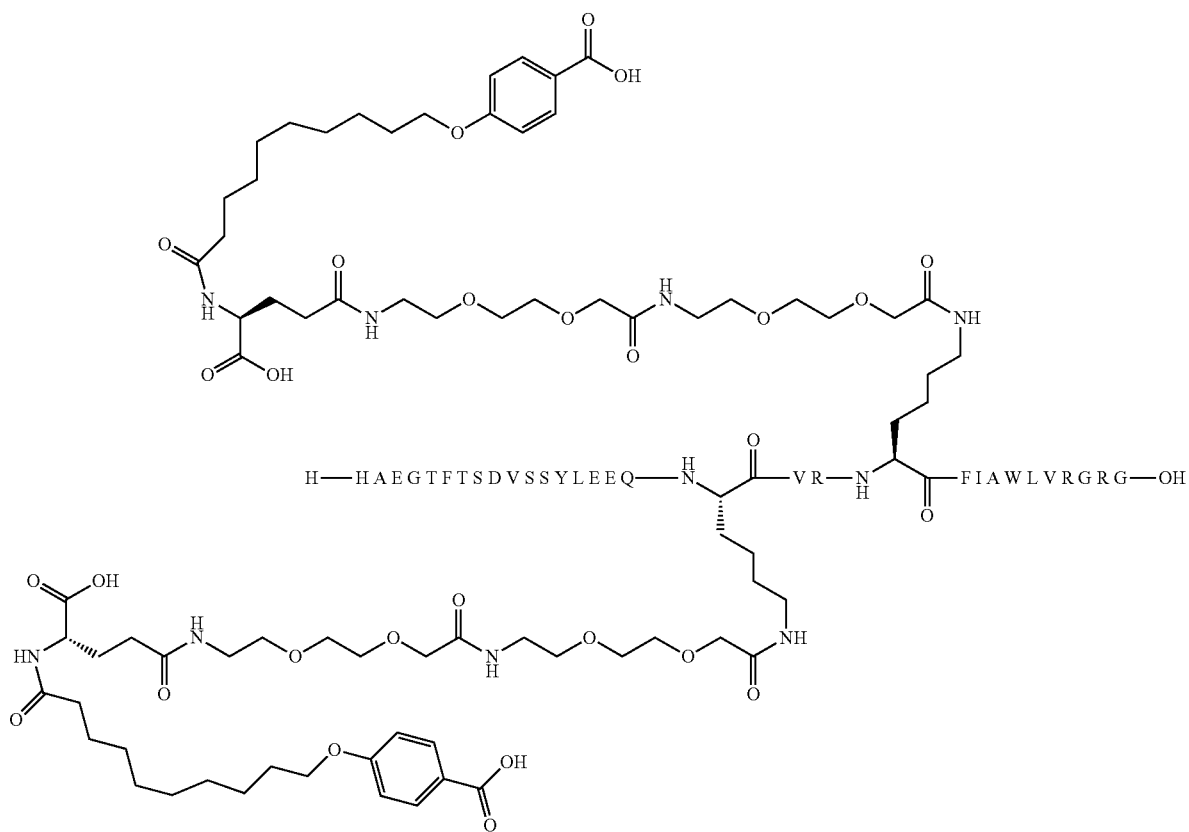

Preparation method: SPPS method B
UPLC (Method 08_B4_1): Rt=8.19 min
UPLC (Method 04_A6_1): Rt=5.24 min
LCMS4: Rt=3.22 min, m/z=1663 (m/3), 1247 (m/4), 998 (m/5), 832 (m/6)

Example 29

N^ε24-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl], N^ε27-[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]-[Aib⁸,Glu²²,Lys²⁴,Val²⁵,Arg²⁶,Lys²⁷,His³¹,Gln³⁴]-GLP-1-(7-37)-peptide (SEQ ID NO: 36)

Chem. 78

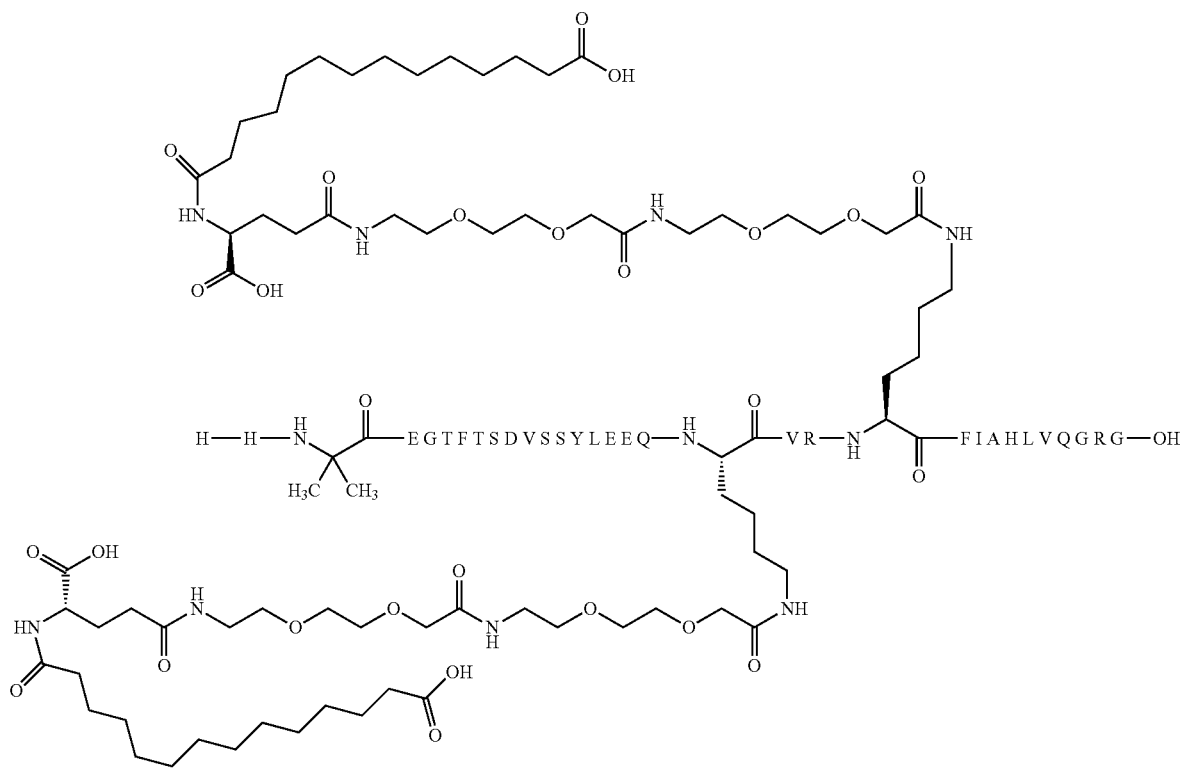

Preparation method: SPPS method B
UPLC (Method 08_B4_1): Rt=7.79 min
UPLC (Method 04_A6_1): Rt=4.87 min

Example 30

N$^{\epsilon 24}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl], N$^{\epsilon 27}$-[(4S)-4-carboxy-4-[[2-[2-[2-[[2-[2-[2-(13-carboxytridecanoylamino)ethoxy]ethoxy]acetyl]amino]ethoxy]ethoxy]acetyl]amino]butanoyl]-[Glu$^{22}$, Lys$^{24}$,Val$^{25}$,Arg$^{26}$,Lys$^{27}$,Gly$^{34}$]-GLP-1-(7-34)-peptide (SEQ ID NO: 33)

Chem. 79

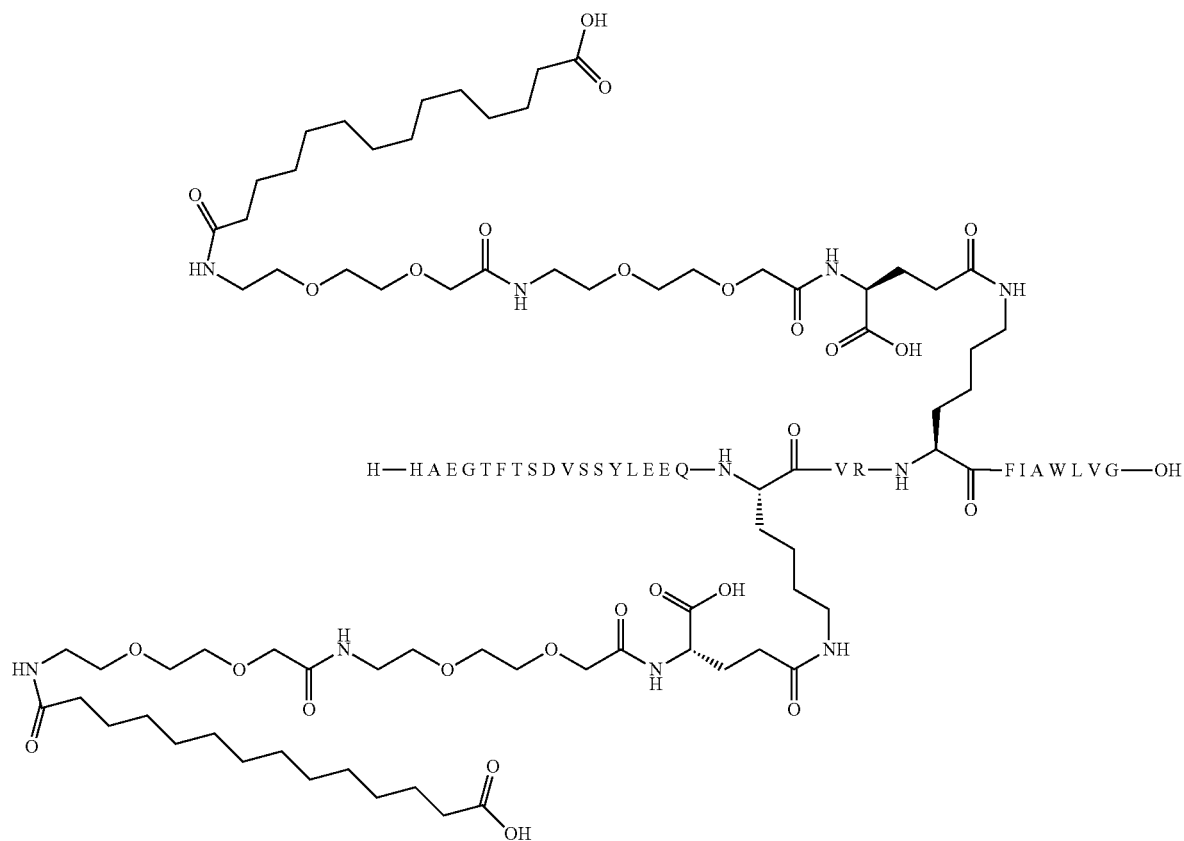

Preparation method: SPPS method B
UPLC (Method 08_B4_1): Rt=9.33 min
UPLC (Method 04_A6_1): Rt=6.13 min
LCMS4: Rt=2.98 min, m/z=1506 (m/3), 1130 (m/4), 904 (m/5)

Example 31

N^ε27-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], N^ε36-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib$^8$,Glu$^{22}$,Arg$^{26}$, Lys$^{27}$,Glu$^{30}$,Arg$^{34}$, Lys$^{36}$]-GLP-1-(7-37)-peptidyl-Glu-Gly (SEQ ID NO: 34)

Chem. 80

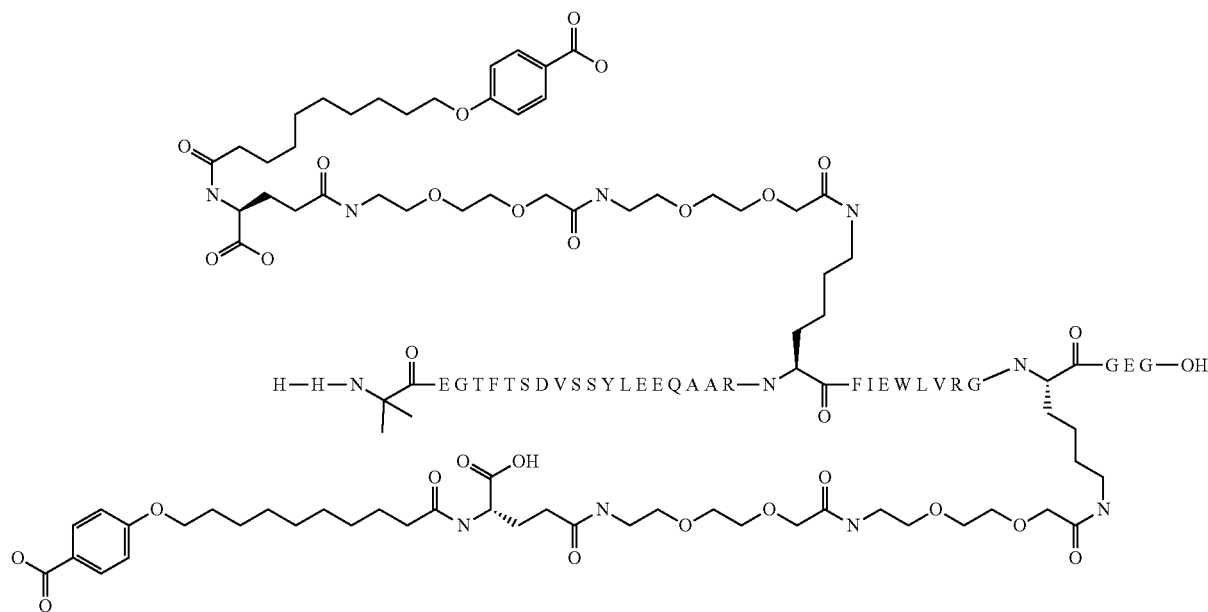

Preparation method: SPPS method B
UPLC (Method 09_B4_1):_Rt=8.58 min
UPLC (Method 10_B29_1): Rt=10.6 min
UPLC (Method 04_A6_1): Rt=4.43 min
LCMS4: Rt=3.72 min; m/3: 1712; m/4: 1284; m/5: 1028

Example 32

N^ε27-[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl], N^ε36-[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]-[Glu$^{22}$,Arg$^{26}$,Lys$^{27}$,Glu$^{30}$,Arg$^{34}$,Lys$^{36}$]-GLP-1-(7-37)-peptidyl-Glu-Gly (SEQ ID NO: 35)

Chem. 81

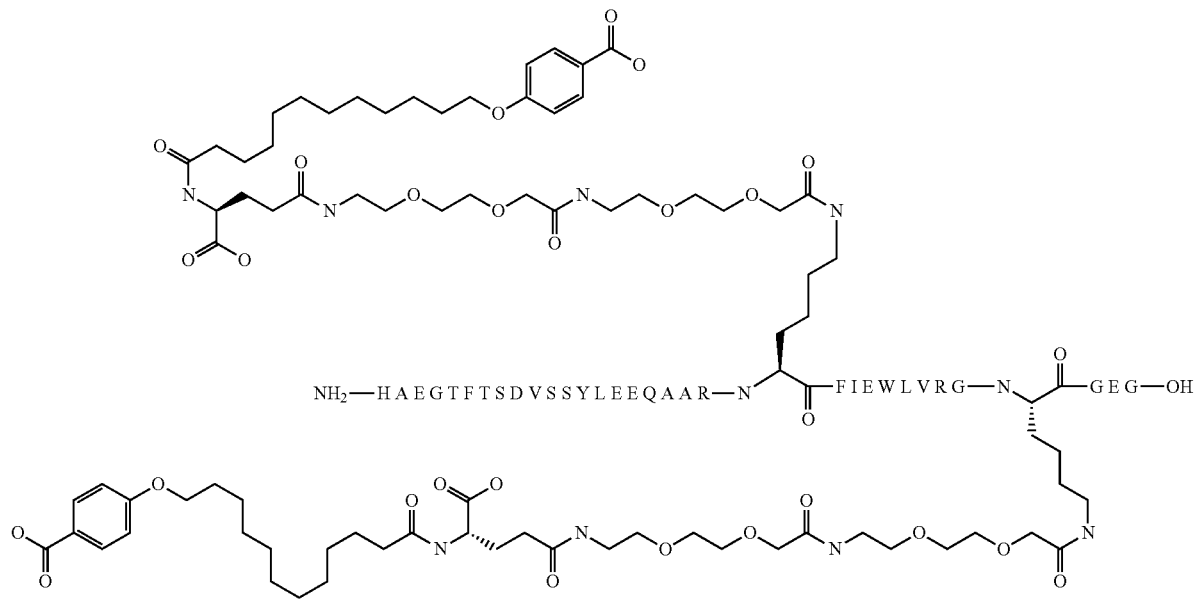

Preparation method: SPPS method B
UPLC (Method 09_B4_1): Rt=9.19 min
UPLC (Method 10_B29_1): Rt=13.73 min
UPLC (Method 04_A6_1): Rt=5.40 min
LCMS4: Rt=2.44 min; m/3: 1726; m/4: 1294; m/5:1036

Pharmacological Methods

Example 33: In Vitro Potency

The purpose of this example is to test the activity, or potency, of the GLP-1 derivatives in vitro.

The potencies of the GLP-1 derivatives of Examples 1-32 were determined as described below, i.e. as the stimulation of the formation of cyclic AMP (cAMP) in a medium containing membranes expressing the human GLP-1 receptor.

Principle

Purified plasma membranes from a stable transfected cell line, BHK467-12A (tk-ts13), expressing the human GLP-1 receptor were stimulated with the GLP-1 analogue or derivative in question, and the potency of cAMP production was measured using the AlphaScreen™ cAMP Assay Kit from Perkin Elmer Life Sciences. The basic principle of the AlphaScreen Assay is a competition between endogenous cAMP and exogenously added biotin-cAMP. The capture of cAMP is achieved by using a specific antibody conjugated to acceptor beads.

Cell Culture and Preparation of Membranes

A stable transfected cell line and a high expressing clone were selected for screening.

The cells were grown at 5% $CO_2$ in DMEM, 5% FCS, 1% Pen/Strep (Penicillin/Streptomycin) and 0.5 mg/ml of the selection marker G418.

Cells at approximately 80% confluence were washed 2× with PBS and harvested with Versene (aqueous solution of the tetrasodium salt of ethylenediaminetetraacetic acid), centrifuged 5 min at 1000 rpm and the supernatant removed. The additional steps were all performed on ice. The cell pellet was homogenised by the Ultrathurax for 20-30 s in 10 ml of Buffer 1 (20 mM N$^α$-HEPES, 10 mM EDTA, pH=7.4), centrifuged 15 min at 20,000 rpm and the pellet resuspended in 10 ml of Buffer 2 (20 mM N$^α$-HEPES, 0.1 mM EDTA, pH=7.4). The suspension was homogenised for 20-30 s and centrifuged 15 min at 20,000 rpm. Suspension in Buffer 2, homogenisation and centrifugation was repeated once and the membranes were resuspended in Buffer 2. The protein concentration was determined and the membranes stored at −80° C. until use.

The assay was performed in flat-bottom 96-well plates (Costar cat. no:3693). The final volume per well was 50 µl.

Solutions and Reagents

AlphaScreen cAMP Assay Kit from Perkin Elmer Life Sciences (cat. No: 6760625M); containing Anti-cAMP Acceptor beads (10 U/µl), Streptavidin Donor beads (10 U/µl) and Biotinylated-cAMP (133 U/µl).

AlphaScreen Buffer, pH=7.4: 50 mM TRIS-HCl (Sigma, cat. no: T3253); 5 mM HEPES (Sigma, cat. no: H3375); 10 mM $MgCl_2$, $6H_2O$ (Merck, cat. no: 5833); 150 mM NaCl (Sigma, cat. no: S9625); 0.01% Tween (Merck, cat. no: 822184). The following was added to the AlphaScreen Buffer prior to use (final concentrations indicated): BSA (Sigma, cat. no. A7906): 0.1%; IBMX (Sigma, cat. no. I5879): 0.5 mM; ATP (Sigma, cat. no. A7699): 1 mM; GTP (Sigma, cat. no. G8877): 1 uM.

cAMP standard (dilution factor in assay=5): cAMP Solution: 5 µL of a 5 mM cAMP-stock+495 µL AlphaScreen Buffer.

Suitable dilution series in AlphaScreen Buffer were prepared of the cAMP standard as well as the GLP-1 analogue or derivative to be tested, e.g. the following eight concentrations of the GLP-1 compound: $10^{-7}$, $10^{-8}$, $10^{-9}$, $10^{-10}$, $10^{-11}$, $10^{-12}$, $10^{-13}$ and $10^{-14}$M, and a series from, e.g., $10^{-6}$ to $3\times10^{-11}$ of cAMP.

Membrane/Acceptor Beads

Membranes were prepared from hGLP-1/BHK 467-12A cells with a concentration of 6 g/well corresponding to 0.6 mg/ml (the amount of membranes used pr. well may vary)

"No membranes": Acceptor Beads (15 µg/ml final) in AlphaScreen buffer

"6 µg/well membranes": membranes+Acceptor Beads (15 g/ml final) in AlphaScreen buffer An aliquot (10 µl) of "No membranes" was added to the cAMP standard (per well in duplicate wells) and the positive and negative controls An aliquot (10 µl) of "6 µg/well membranes" was added to GLP-1 and analogues (per well in duplicate or triplicate wells)

Pos. Control: 10 µl "no membranes"+10 µl AlphaScreen Buffer

Neg. Control: 10 µl "no membranes"+10 µl cAMP Stock Solution (50 µM)

As the beads are sensitive to direct light, any handling was in the dark (as dark as possible), or in green light. All dilutions were made on ice.

Procedure

1. Make the AlphaScreen Buffer.
2. Dissolve and dilute the GLP-1/Analogues/cAMP standard in AlphaScreen Buffer.
3. Make the Donor Beads Solution by mixing streptavidin donor beads (2 units/well) and biotinylated cAMP (1.2 units/well) and incubate 20-30 min in the dark at room temperature.
4. Add the cAMP/GLP-1/Analogues to the plate: 10 µl per well.
5. Prepare membrane/Acceptor Beads solution and add this to the plates: 10 µl per well.
6. Add the Donor Beads: 30 µl per well.
7. Wrap the plate in aluminum foil and incubate on the shaker for 3 hours (very slowly) at RT.
8. Count on AlphaScreen—each plate pre incubates in the AlphaScreen for 3 minutes before counting.

Results

The $EC_{50}$ [pM] values were calculated using the GraphPad Prism software (version 5) and are shown in Table 1 below. The potency of all derivatives in vitro was confirmed.

TABLE 1

| In vitro potency | |
|---|---|
| Compound of Example no. | $EC_{50}$/pM |
| 1 | 26 |
| 2 | 43 |
| 3 | 62 |
| 4 | 143 |
| 5 | 468 |
| 6 | 96 |
| 7 | 9 |
| 8 | 159 |
| 9 | 242 |
| 10 | 214 |
| 11 | 81 |
| 12 | 41 |
| 13 | 79 |
| 14 | 42 |
| 15 | 5 |
| 16 | 21 |
| 17 | 17 |
| 18 | 3025 |
| 19 | 52 |
| 20 | 67 |
| 21 | 52 |
| 22 | 1178 |
| 23 | 140 |
| 24 | 70 |
| 25 | 380 |
| 26 | 200 |
| 27 | 835 |
| 28 | 68 |
| 29 | 40 |
| 30 | 3000 |
| 31 | 37 |
| 32 | 76 |

The average in vitro potency for the tested compounds ($EC_{50}$ average) was 340 pM. Most derivatives had a good in vitro potency corresponding to an $EC_{50}$ of below 1200 pM.

For comparison, compound no. 13 in Table 1 of Journal of Medicinal Chemistry (2000), vol. 43, no. 9, p. 1664-669 (GLP-1(7-37) acylated at $K^{26,34}$ with bis-C12-diacid) had an in vitro potency corresponding to an $EC_{50}$ of 1200 pM.

Example 34: GLP-1 Receptor Binding

The purpose of this experiment is to investigate the binding to the GLP-1 receptor of the GLP-1 derivatives, and how the binding is potentially influenced by the presence of albumin.

This is done in an in vitro experiment as described below.

The binding affinity of the GLP-1 derivatives of Examples 1-32 to the human GLP-1 receptor was measured by way of their ability to displace of $^{125}$I-GLP-1 from the receptor. In order to test the binding of the derivatives to albumin, the assay was performed with a low concentration of albumin (0.001%–corresponding to the residual amount thereof in the tracer), as well as with a high concentration of albumin (2.0% added). A shift in the binding affinity, $IC_{50}$, is an indication that the peptide in question binds to albumin, and thereby a prediction of a potential protracted pharmacokinetic profile of the peptide in question in animal models.

Conditions

Species (in vitro): Hamster

Biological End Point: Receptor Binding

Assay Method: SPA

Receptor: GLP-1 receptor
Cell Line: BHK tk-ts13
Cell Culture and Membrane Purification A stable transfected cell line and a high expressing clone were selected for screening.

The cells were grown at 5% $CO_2$ in DMEM, 10% FCS, 1% Pen/Strep (Penicillin/Streptomycin) and 1.0 mg/ml of the selection marker G418.

The cells (approx. 80% confluence) were washed twice in PBS and harvested with Versene (aqueous solution of the tetrasodium salt of ethylenediaminetetraacetic acid), following which they were separated by centrifugation at 1000 rpm for 5 min. The cells/cell pellet must be kept on ice to the extent possible in the subsequent steps. The cell pellet was homogenised with Ultrathurrax for 20-30 seconds in a suitable amount of Buffer 1 (depending on the amount of cells, but e.g. 10 ml). The homogenate was centrifuged at 20000 rpm for 15 minutes. The pellet was resuspended (homogenised) in 10 ml Buffer 2 and re-centrifuged. This step was repeated once more. The resulting pellet was resuspended in Buffer 2, and the protein concentration was determined. The membranes were stored at minus 80° C.

Buffer 1: 20 mM Na-HEPES+10 mM EDTA, pH 7.4
Buffer 2: 20 mM NaHEPES+0.1 mM EDTA, pH 7.4

Binding Assay:
SPA:

Test compounds, membranes, SPA-particles and [$^{125}$I]-GLP-1(7-36)$NH_2$ were diluted in assay buffer. 50 ul (micro liter) HSA ("high albumin" experiment containing 2% HSA), or buffer ("low albumin" experiment containing 0.001% HSA), was added to Optiplate, and 25 ul of test compounds were added. 5-10 ug membrane protein/sample was added (50 ul) corresponding to 0.1-0.2 mg protein/ml (to be preferably optimised for each membrane preparation). SPA-particles (Wheatgerm agglutinin SPA beads, Perkin Elmer, #RPNQ0001) were added in an amount of 0.5 mg/well (50 ul). The incubation was started with [$^{125}$I]-GLP-1]-(7-36)$NH_2$ (final concentration 0.06 nM corresponding to 49.880 DPM, 25 ul). The plates were sealed with PlateSealer and incubated for 120 minutes at 30° C. while shaking. The plates were centrifuged (1500 rpm, 10 min) and counted in Topcounter.

Assay Buffer:
50 mM HEPES
5 mM EGTA
5 mM $MgCl_2$
0.005% Tween 20
pH 7.4
HSA was SIGMA A1653

Calculations

The $IC_{50}$ value was read from the curve as the concentration which displaces 50% of $^{125}$I-GLP-1 from the receptor, and the ratio of [($IC_{50}$/nM) high HSA]/[($IC_{50}$/nM) low HSA] was determined.

Generally, the binding to the GLP-1 receptor at low albumin concentration should be as good as possible, corresponding to a low $IC_{50}$ value.

The $IC_{50}$ value at high albumin concentration is a measure of the influence of albumin on the binding of the derivative to the GLP-1 receptor. As is known, the GLP-1 derivatives also bind to albumin. This is a generally desirable effect, which extends their lifetime in plasma. Therefore, the $IC_{50}$ value at high albumin will generally be higher than the $IC_{50}$ value at low albumin, corresponding to a reduced binding to the GLP-1 receptor, caused by albumin binding competing with the binding to the GLP-1 receptor.

A high ratio ($IC_{50}$ value (high albumin)/$I_{50}$ value (low albumin)) may therefore be taken as an indication that the derivative in question binds well to albumin (may have a long half-life), and also per se binds well to the GLP-1 receptor (the $IC_{50}$ value (high albumin) is high, and the $IC_{50}$ value (low albumin) is low).

Results

The following results were obtained, where "ratio" refers to [($IC_{50}$/nM) high HSA]/[($IC_{50}$/nM) low HSA]):

TABLE 2

| Receptor binding affinity | | | |
|---|---|---|---|
| Compound of Example no. | $IC_{50}$/nM (low HSA) | $IC_{50}$/nM (high HSA) | Ratio |
| 1 | 0.19 | 42 | 219 |
| 2 | 0.39 | 320 | 821 |
| 3 | 0.29 | 29 | 101 |
| 4 | 0.15 | 33 | 217 |
| 5 | 5.68 | 446 | 79 |
| 6 | 0.50 | 123 | 246 |
| 7 | 0.12 | 21 | 174 |
| 8 | 1.41 | 80 | 57 |
| 9 | 0.38 | 60 | 157 |
| 10 | 6.49 | 452 | 70 |
| 11 | 0.23 | 213 | 926 |
| 12 | 0.16 | 72 | 453 |
| 13 | 0.25 | 201 | 804 |
| 14 | 1.45 | 443 | 306 |
| 15 | 0.19 | 29 | 155 |
| 16 | 0.20 | 25 | 127 |
| 17 | 0.45 | 174 | 387 |
| 18 | 373 | 789 | 2.1 |
| 19 | 2.38 | 143 | 60 |
| 20 | 0.19 | 333 | 1752 |
| 21 | 1.57 | 256 | 163 |
| 22 | 9.31 | 812 | 87 |
| 23 | 0.85 | 40 | 47 |
| 24 | 2.74 | 50 | 18 |
| 25 | 10.9 | 39 | 3.5 |
| 26 | 0.38 | 54 | 143 |
| 27 | 10.3 | >1000 | 97 |
| 28 | 0.20 | 29 | 144 |
| 29 | 3.95 | 363 | 92 |
| 30 | 7.44 | >1000 | 134 |
| 31 | 0.35 | 220 | 629 |
| 32 | 0.18 | 369 | 2050 |

The average ratio was very good (about 300). Most derivatives had a ratio above 50.

Furthermore as regards $IC_{50}$ (low albumin) the average $IC_{50}$ of the compounds tested was 14 nM, and most derivatives were below 15.0 nM.

Finally as regards $IC_{50}$ (high albumin) most derivatives had an $IC_{50}$ (high albumin) below 900 nM.

For comparison, compound no. 13 in Table 1 of Journal of Medicinal Chemistry (2000), vol. 43, no. 9, p. 1664-669 (GLP-1(7-37) acylated at $K^{26,34}$ with bis-C12-diacid) had a ratio of 51.3, an $IC_{50}$ (low albumin) of 17.7 nM, and an $IC_{50}$ (high albumin) of 908 nM.

Example 35: Estimate of Oral Bioavailability—Gut Injection in Rat (Caprate)

The purpose of this experiment is to estimate the oral bioavailability of the GLP-1 derivatives.

To this end, the exposure in plasma after direct injection into the intestinal lumen of the GLP-1 derivatives of Examples 2-17 and 19-22 was studied in vivo in rats, as described in the following.

The GLP-1 derivatives were tested in a concentration of 1000 uM in a solution of 55 mg/ml sodium caprate.

Male Sprague Dawley rats with a body weight upon arrival of approximately 240 g were obtained from Taconic (Denmark) and assigned to the different treatments by simple randomisation, 4 rats per group. The rats were fasted for approximately 18 hours before the experiment and taken into general anaesthesia (Hypnorm/Dormicum).

The GLP-1 derivatives were administered in the jejunum either in the proximal part (10 cm distal for the duodenum) or in the mid-intestine (50 cm proximal for the cecum). A PE50-catheter, 10 cm long was inserted into the jejunum, forwarded at least 1.5 cm into the jejunum, and secured before dosing by ligature around the gut and the catheter with 3/0 suture distal to tip to prevent leak or catheter displacement. Catheter was placed without syringe and needle and 2 ml saline was administered into abdomen before closing the incision with wound clips.

100 µl of the respective GLP-1 derivative was injected into the jejunal lumen through the catheter with a 1 ml syringe. Subsequently, 200 µl of air was pushed into the jejunal lumen with another syringe to "flush" the catheter. This syringe was leaved connected to the catheter to prevent flow back into the catheter.

Blood samples (200 ul) were collected at desired intervals (usually at times 0, 10, 30, 60, 120 and 240 min) into EDTA tubes from the tail vein and centrifuged 5 minutes, 10000 G, at 4° C. within 20 minutes. Plasma (75 ul) was separated to Micronic tubes, immediately frozen, and kept at −20° C. until analyzed for plasma concentration of the respective GLP-1 derivative with LOCI (Luminescent Oxygen Channeling Immunoassay), generally as described for the determination of insulin by Poulsen and Jensen in Journal of Biomolecular Screening 2007, vol. 12, p. 240-247. The donor beads were coated with streptavidin, while acceptor beads were conjugated with a monoclonal antibody recognising a mid-/C-terminal epitope of the peptide. Another monoclonal antibody, specific for the N-terminus, was biotinylated. The three reactants were combined with the analyte and formed a two-sited immuno-complex. Illumination of the complex released singlet oxygen atoms from the donor beads, which were channeled into the acceptor beads and triggered chemiluminescence which was measured in an Envision plate reader. The amount of light was proportional to the concentration of the compound.

After the blood sampling the rats were sacrificed under anaesthesia and the abdomen was opened to verify correct catheter placement.

The mean (n=4) plasma concentrations (pmol/I) were determined as a function of time. The ratio of plasma concentration (pmol/I) divided by the concentration of the dosing solution (µmol/I) was calculated for each treatment, and the results for t=30 min (30 minutes after the injection of the compound in the jejunum) were assessed (dose-corrected exposure at 30 min) as a surrogate measure of intestinal bioavailability. The dose-corrected exposure has been shown to correlate significantly with the actual bioavailability.

The following results were obtained, where dose-corrected exposure at 30 min refers to (the plasma concentration 30 minutes after injection of the compound in the jejunum (pM)), divided by (the concentration of the compound in the dosing solution (µM)):

TABLE 3

| Compound of Example no. | Dose-corrected exposure at 30 min |
|---|---|
| 2 | 98 |
| 3 | 67 |
| 4 | 39 |
| 5 | 124 |
| 6 | 93 |
| 7 | 99 |
| 8 | 86 |
| 9 | 65 |
| 10 | 187 |
| 11 | 66 |
| 12 | 68 |
| 13 | 126 |
| 14 | 121 |
| 15 | 98 |
| 16 | 115 |
| 17 | 168 |
| 19 | 61 |
| 20 | 123 |
| 21 | 140 |
| 22 | 275 |

All derivatives had a dose-corrected exposure at 30 min of above 38.

For comparison, compound no. 13 in Table 1 of Journal of Medicinal Chemistry (2000), vol. 43, no. 9, p. 1664-669 (GLP-1(7-37) acylated at $K^{26,34}$ with bis-C12-diacid) had a dose-corrected exposure at 30 min of 38.

Example 36: Effect on Blood Glucose and Body Weight

The purpose of the study is to verify the effect of the GLP-1 derivatives on blood glucose (BG) and body weight (BVW) in a diabetic setting.

The GLP-1 derivatives are tested in a dose-response study in an obese, diabetic mouse model (db/db mice) as described in the following.

db/db mice (Taconic, Denmark), fed from birth with the diet NIH31 (NIH 31M Rodent Diet, commercially available from Taconic Farms, Inc., US, see www.taconic.com), are enrolled for the study at the age of 7-9 weeks. The mice are given free access to standard chow (e.g. Altromin 1324, Brogaarden, Gentofte, Denmark) and tap water and kept at 24° C. After 1-2 weeks of acclimatisation, the basal blood glucose is assessed twice on two consecutive days (i.e. at 9 am). The mice with the lowest blood glucose values are excluded from the experiments. Based on the mean blood glucose values, the remaining mice are selected for further experimentation and allocated to 7 groups (n=6) with matching blood glucose levels. The mice are used in experiments with a duration of 48 hours, and for up to 4 times. After the last experiment the mice are euthanised.

The seven groups receive treatment as follows:
1: Vehicle, s.c.
2: GLP-1 derivative, 0.3 nmol/kg, s.c.
3: GLP-1 derivative, 1.0 nmol/kg, s.c.
4: GLP-1 derivative, 3.0 nmol/kg, s.c.
5: GLP-1 derivative, 10 nmol/kg, s.c.
6: GLP-1 derivative, 30 nmol/kg, s.c.
7: GLP-1 derivative, 100 nmol/kg, s.c.
Vehicle: 50 mM sodium phosphate, 145 mM sodium chloride, 0.05% tween 80, pH 7.4.

The GLP-1 derivative is dissolved in the vehicle, to concentrations of 0.05, 0.17, 0.5, 1.7, 5.0 and 17.0 nmol/ml. Animals are dosed s.c. with a dose-volume of 6 ml/kg (i.e. 300 µl per 50 g mouse).

On the day of dosing, blood glucose is assessed at time −½ h (8.30 am), where after the mice are weighed. The GLP-1 derivative is dosed at approximately 9 am (time 0). On the day of dosing, blood glucose is assessed at times 1, 2, 4 and 8 h (10 am, 11 am, 1 pm and 5 pm). Following the 8 h blood sampling, the mice are weighed.

On the following days, the blood glucose is assessed at time 24 and 48 after dosing (i.e. at 9 am on day 2 and 3). On each day, the mice are weighed following blood glucose sampling.

The mice are weighed individually on a digital weight.

Samples for the measurement of blood glucose are obtained from the tail tip capillary of conscious mice. Blood, 10 µl, is collected into heparinised capillaries and transferred to 500 µl glucose buffer (EKF system solution, Eppendorf, Germany). The glucose concentration is measured using the glucose oxidase method (glucose analyser Biosen 5040, EKF Diagnostic, GmbH, Barleben, Germany). The samples are kept at room temperature for up to 1 h until analysis. If analysis has to be postponed, samples are kept at 4° C. for a maximum of 24 h.

$ED_{50}$ is the dose giving rise to half-maximal effect in nmol/kg. This value is calculated on the basis of the ability of the derivatives to lower body weight as well as the ability to lower blood glucose, as explained below.

$ED_{50}$ for body weight is calculated as the dose giving rise to half-maximum effect on delta BW 8 hours following the subcutaneous administration of the derivative. For example, if the maximum decrease in body weight after 8 hours is 2.0 g, then $ED_{50}$ bodyweight would be that dose in nmol/kg which gives rise to a decrease in body weight after 8 hours of 1.0 g. This dose ($ED_{50}$ body weight) may be read from the dose-response curve.

$ED_{50}$ for blood glucose is calculated as the dose giving rise to half-maximum effect on AUC delta BG 8 hours and/or 24 hours following the subcutaneous administration of the analogue.

The $ED_{50}$ value may only be calculated if a proper sigmoidal dose-response relationship exists with a clear definition of the maximum response. Thus, if this would not be the case the derivative in question may be re-tested in a different range of doses to see if a sigmoidal dose-response relationship is obtained.

Example 37: Half-Life in Minipigs

The purpose of this study is to determine the protraction in vivo of the GLP-1 derivatives after i.v. administration to minipigs, i.e. the prolongation of their time of action. This is done in a pharmacokinetic (PK) study, where the terminal half-life of the derivative in question is determined. By terminal half-life is generally meant the period of time it takes to halve a certain plasma concentration, measured after the initial distribution phase.

Male Göttingen minipigs were obtained from Ellegaard Göttingen Minipigs (Dalmose, Denmark) approximately 7-14 months of age and weighing from approximately 16-35 kg were used in the studies. The minipigs were housed individually and fed restrictedly once or twice daily with SDS minipig diet (Special Diets Services, Essex, UK). After at least 2 weeks of acclimatisation two permanent central venous catheters were implanted in vena cava caudalis or cranialis in each animal. The animals were allowed 1 week recovery after the surgery, and were then used for repeated pharmacokinetic studies with a suitable wash-out period between successive GLP-1 derivative dosings.

The animals were fasted for approximately 18 h before dosing and from 0 to 4 h after dosing, but had ad libitum access to water during the whole period.

The GLP-1 derivatives were dissolved in 50 mM sodium phosphate, 145 mM sodium chloride, 0.05% tween 80, pH 7.4 to a concentration of usually from 20-60 nmol/ml. Intravenous injections (the volume corresponding to usually 1-2 nmol/kg, for example 0.033 ml/kg) of the compounds were given through one catheter, and blood was sampled at predefined time points for up till 13 days post dosing (preferably through the other catheter). Blood samples (for example 0.8 ml) were collected in EDTA buffer (8 mM) and then centrifuged at 4° C. and 1942 G for 10 minutes. Plasma was pippetted into Micronic tubes on dry ice, and kept at −20° C. until analyzed for plasma concentration of the respective GLP-1 compound using ELISA or a similar antibody based assay or LC-MS. Individual plasma concentration-time profiles were analyzed by a non-compartmental model in Phoenix WinNonLin ver. 6.2. (Pharsight Inc., Mountain View, Calif., USA), and the resulting terminal half-lives (harmonic mean) determined.

Results

The derivative of Example 2 was tested and it had a half-life of 87 hours.

For comparison, compound no. 13 in Table 1 of Journal of Medicinal Chemistry (2000), vol. 43, no. 9, p. 1664-669 (GLP-1(7-37) acylated at $K^{26,34}$ with bis-C12-diacid) had a half-life of 5 hours.

Example 38: Effect on Food Intake

The purpose of this experiment was to investigate the effect of GLP-1 derivatives on food intake in pigs. This was done in a pharmacodynamic (PD) study as described below, in which food intake was measured from 1 to 4 days after administration of a single dose of the GLP-1 derivative, as compared to a vehicle-treated control group.

Female Landrace Yorkshire Duroc (LYD) pigs, approximately 3 months of age, weighing approximately 30-35 kg were used (n=3-4 per group). The animals were housed in a group for approximately 1 week during acclimatisation to the animal facilities. During the experimental period the animals were placed in individual pens at least 2 days before dosing and during the entire experiment for measurement of individual food intake. The animals were fed ad libitum with pig fodder (Svinefoder Danish Top) at all times both during the acclimatisation and the experimental period. Food intake was monitored on line by logging the weight of fodder every 15 minutes. The system used was Mpigwin (Ellegaard Systems, Faaborg, Denmark).

The GLP-1 derivatives are dissolved in a phosphate buffer (50 mM sodium phosphate, 145 mM sodium chloride, 0.05% tween 80, pH 7.4) at concentrations of 12, 40, 120, 400 or 1200 nmol/ml corresponding to doses of 0.3, 1, 3, 10 or 30 nmol/kg. The phosphate buffer serves as vehicle. Animals are dosed with a single subcutaneous dose of the GLP-1 derivative or vehicle (dose volume 0.025 ml/kg) on the morning of day 1, and food intake is measured for 1-4 days after dosing. On the last day of each study, 1-4 days after dosing, a blood sample for measurement of plasma exposure of the GLP-1 derivative is taken from the heart in anaesthetised animals. The animals are thereafter euthanised with an intra-cardial overdose of pentobarbitone. Plasma content of the GLP-1 derivatives is analysed using ELISA or a similar antibody based assay, or LC-MS.

Food intake is calculated as mean±SEM 24 h food intake on each of the experimental days. Statistical comparisons of the 24 hour food intake in the vehicle vs. GLP-1 derivative group are done using two-way-ANOVA repeated measures, followed by Bonferroni post-test.

The compound of Example 10 was tested in a dose of 3 nmol/kg, and in this dose no effect was seen on food intake. The compound of Example 2 was tested in a dose of 3 nmol/kg and showed a significant reduction of food intake on both days of the experiment (23% on day 1, and 35% on day 2).

Example 39: Pharmacokinetics in Rat

The purpose of this Example is to investigate half-life in vivo in rat.

In vivo pharmacokinetic studies in rats were performed with the GLP-1 derivatives of Examples 2, 10, 17-18, and 31, as described in the following. Semaglutide was included for comparison.

Male Sprague Dawley rats of same age with a body weight of approximately 400 g were obtained from Taconic (Denmark) and assigned to the treatments by simple randomisation on body weight, approximately 4 rats per group, so that all animals in each group were of similar body weight.

The GLP-1 derivatives (approximately 6 nmol/ml) were dissolved in 50 mM sodium phosphate, 145 mM sodium chloride, 0.05% tween 80, pH 7.4. Intravenous injections (1.0 ml/kg) of the compounds were given through a catheter implanted in the right jugular vein. Blood was sampled from vena sublingualis for 5 days post dosing. Blood samples (200 μl) were collected in EDTA buffer (8 mM) and then centrifuged at 4° C. and 10000 G for 5 minutes. Plasma samples were kept at −20° C. until analyzed for plasma concentration of the respective GLP-1 compound.

The plasma concentrations of the GLP-1 compounds were determined using a Luminescence Oxygen Channeling Immunoasssay (LOCI), generally as described for the determination of insulin by Poulsen and Jensen in Journal of Biomolecular Screening 2007, vol. 12, p. 240-247. The donor beads were coated with streptavidin, while acceptor beads were conjugated with a monoclonal antibody recognising a mid-/C-terminal epitope of the peptide. Another monoclonal antibody, specific for the N-terminus, was biotinylated. The three reactants were combined with the analyte and formed a two-sited immuno-complex. Illumination of the complex released singlet oxygen atoms from the donor beads, which were channeled into the acceptor beads and triggered chemiluminescence which was measured in an Envision plate reader. The amount of light was proportional to the concentration of the compound.

Plasma concentration-time profiles were analyzed using Phoenix WinNonLin ver. 6.2, Pharsight Inc., Mountain View, Calif., USA), and the half-life ($T_{1/2}$) calculated using individual plasma concentration-time profiles from each animal.

Results

The half-life of semaglutide tested in the same set-up (but with n=8) was 11 hours.

TABLE 4

| Half-life in rat | |
|---|---|
| Compound of Example no. | t½/h |
| 2 | 26 |
| 10 | 23 |

TABLE 4-continued

| Half-life in rat | |
|---|---|
| Compound of Example no. | t½/h |
| 17 | 10 |
| 18 | 10 |
| 31 | 19 |

The tested derivatives of the invention had a half-life that was similar or better to that of semaglutide.

Example 40: Estimate of Oral Bioavailability—Gut Injection and Oral Gavage in Rat (SNAC)

The purpose of this experiment is to estimate the oral bioavailability of the GLP-1 derivatives in a rat model. In brief, a liquid solution of the GLP-1 derivative in sodium N-[8-(2-hydroxybenzoyl)amino]caprylate (SNAC) is administered by gut injection (to the intestines), or by oral gavage (to the stomach), and the subsequent exposure in plasma of the GLP-1 derivative is measured.

A 250 mg/ml stock solution of SNAC is prepared by dissolving SNAC (12.5 g) in highly pure laboratory water (MilliQ) (50.0 ml). The pH is adjusted to about 8.5 with 1 N NaOH (aq).

Solutions with about 1000 uM (800-1200 uM) of the GLP-1 derivatives in 250 mg/ml SNAC are prepared by dissolving the desired amount of the respective GLP-1 derivative in the SNAC stock solution. The concentration of the GLP-1 derivative is determined prior to administration by a state-of-the-art method, such as CLND-HPLC (chemiluminescent nitrogen detection for HPLC).

32 male Sprague Dawley rats with a body weight upon arrival of approximately 240 g are obtained from Taconic (Denmark) and assigned to the different treatments by simple randomisation, 8 rats per group. All rats are fasted on grids for approximately 18 hours before the experiment.

For gut injection, on the day of experiment, rats are taken into general anaesthesia (Hypnorm/Dormicum) and remained anaesthetized during the entire experiment. The GLP-1 derivatives of Examples 5-7 are administered in the proximal part of the jejunum (10 cm distal for the duodenum). A PE50-catheter, 10 cm long, is inserted into the jejunum, forwarded at least 1.5 cm into the jejunum, and secured before dosing by ligature around the gut. Furthermore, the catheter is provided with a 3/0 suture distal to tip to prevent leak or catheter displacement. The catheter is placed without syringe and needle and 2 ml saline is administered into abdomen before closing the incision with wound clips.

100 μl SNAC solution of the respective GLP-1 derivative is injected into the jejunal lumen through the catheter with a 1 ml syringe. Subsequently, 200 μl of air is pushed into the jejunal lumen with another syringe to "flush" the catheter. This syringe is left connected to the catheter to prevent flow back into the catheter.

Blood samples (200 ul) are collected at desired intervals (usually at times 0, 30, 60, 120 and 180 min) into EDTA tubes from the tail vein.

For oral gavage, the animals are conscious during the entire experiment.

100 μl SNAC solution of the GLP-1 derivatives is administered by oral gavage directly to the stomach.

Blood samples (200 ul) are collected at desired intervals (usually at times 0, 30, 60, 120 and 180 min) into EDTA tubes from the sublingual plexus.

All obtained blood samples are kept on ice and centrifuged for 5 minutes, 10000 G, at 4° C. within 20 minutes. Plasma (75 ul) is separated to Micronic tubes, immediately frozen, and kept at −20° C. until analyzed for plasma concentration of the respective GLP-1 derivative with LOCI (Luminescent Oxygen Channeling Immunoassay), generally as described for the determination of insulin by Poulsen and Jensen in Journal of Biomolecular Screening 2007, vol. 12, p. 240-247. The donor beads are coated with streptavidin, while acceptor beads are conjugated with a monoclonal antibody recognising a mid-/C-terminal epitope of the peptide. Another monoclonal antibody, specific for the N-terminus, is biotinylated. The three reactants are combined with the analyte and formed a two-sited immuno-complex. Illumination of the complex released singlet oxygen atoms from the donor beads, which are channeled into the acceptor beads and triggered chemiluminescence which is measured in an Envision plate reader. The amount of light is proportional to the concentration of the compound.

After the blood sampling all rats are sacrificed under anaesthesia and the abdomen of the gut injection rats is opened to verify correct catheter placement.

The mean (n=8) plasma concentrations (pmol/I) are determined as a function of time. The AUC of the plasma exposure (pmol/I) vs time curve, from time 30 to 180 (min), is dose-corrected, i.e., divided by the amount (dose) of the derivative in the dosed solution (pmol). The thus dose-corrected AUC of plasma exposure from time 30-180 min (having the unit of min×pM/pmol=min/L) is used as a surrogate measure of bioavailability—a measure to rank the derivatives with regards to their absorption in the rat model.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A derivative of a GLP-1 analogue, which analogue comprises a first K residue at a position corresponding to position 27 of GLP-1(7-37) (SEQ ID NO: 1); a second K residue at a position corresponding to position 24 of GLP-1(7-37); and a maximum of ten amino acid changes as compared to GLP-1(7-37); wherein the first K residue is designated $K^{27}$, and the second K residue is designated $K^{24}$; wherein the analogue comprises no K residues other than the first and the second K residue; which derivative comprises two protracting moieties attached to $K^{27}$ and $K^{24}$, respectively, via a linker, wherein the protracting moiety is selected from the group consisting of Chem. 2 and Chem. 1:

HOOC—$C_6H_4$—O—$(CH_2)_y$—CO—*    Chem. 2:

HOOC—$(CH_2)_x$—CO—*,    Chem. 1:

in which x is an integer in the range of 6-16, and y is an integer in the range of 3-17; and
the linker comprises Chem. 5, wherein Chem. 5 is included m times, wherein m is an integer in the range of 1-10:

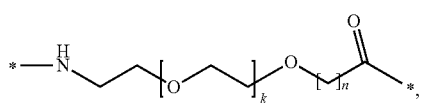

Chem. 5 wherein k is an integer in the range of 1-5, and n is an integer in the range of 1-5;
or a pharmaceutically acceptable salt, amide, or ester thereof.

2. The derivative of claim 1, wherein the linker further comprises a Glu di-radical selected from the group consisting of

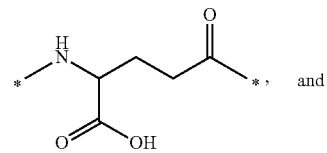

Chem. 6

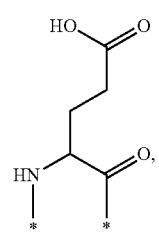

Chem. 7 wherein the Glu di-radical is included p times, wherein p is an integer in the range of 1-2.

3. The derivative of claim 2, wherein the protracting moiety is Chem. 1.

4. The derivative of claim 3, wherein k is 1.

5. The derivative of claim 4, wherein n is 1.

6. The derivative of claim 5, wherein m is an integer in the range of 1-2.

7. The derivative of claim 6, wherein x is an integer in the range of 12-16.

8. The derivative of claim 7, wherein the linker further comprises a Glu di-radical that is Chem. 6.

9. The derivative of claim 1, wherein the derivative is a derivative of a GLP-1 analogue of Formula I (SEQ ID NO:3):

Xaa$_7$-Xaa$_8$-Glu-Gly-Thr-Xaa$_{12}$-Thr-Ser-Asp-Xaa$_{16}$-Ser-Xaa$_{18}$-Xaa$_{19}$-Xaa$_{20}$-Glu-Xaa$_{22}$-Xaa$_{23}$-Xaa$_{24}$-Xaa$_{25}$-Xaa$_{26}$-Lys-Phe-Ile-Xaa$_{30}$-Xaa$_{31}$-Leu-Val-Xaa$_{34}$-Xaa$_{35}$-Xaa$_{36}$-Xaa$_{37}$-Xaa$_{38}$-Xaa$_{39}$,  Formula I:

(1) wherein

Xaa$_7$ is selected from the group consisting of L-histidine, imidazopropionyl, α-hydroxy-histidine, D-histidine, desamino-histidine, 2-amino-histidine, β-hydroxy-histidine, homohistidine, N$^α$-acetyl-histidine, N$^α$-formyl-histidine, α-fluoromethyl-histidine, α-methyl-histidine, 3-pyridylalanine, 2-pyridylalanine, and 4-pyridylalanine;

Xaa$_8$ is selected from the group consisting of Ala, Gly, Val, Leu, Ile, Thr, Ser, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, and (1-aminocyclooctyl) carboxylic acid;

Xaa$_{12}$ is Phe;

Xaa$_{16}$ is selected from the group consisting of Val and Leu;

Xaa$_{18}$ is selected from the group consisting of Ser, Arg, Asn, Gln, and Glu;

Xaa$_{19}$ is selected from the group consisting of Tyr and Gln;

Xaa$_{20}$ is selected from the group consisting of Leu and Met;

Xaa$_{22}$ is selected from the group consisting of Gly, Glu and Aib;

Xaa$_{23}$ is selected from the group consisting of Gln, Glu, and Arg;

Xaa$_{24}$ is Lys;

Xaa$_{25}$ is selected from the group consisting of Ala and Val;

Xaa$_{26}$ is selected from the group consisting of Val, His, and Arg;

Xaa$_{30}$ is selected from the group consisting of Ala, Glu, and Arg;

Xaa$_{31}$ is selected from the group consisting of Trp and His;

Xaa$_{34}$ is selected from the group consisting of Glu, Asn, Gly, Gln, and Arg;

Xaa$_{35}$ is selected from the group consisting of Gly, Aib, and absent;

Xaa$_{36}$ is selected from the group consisting of Arg, Gly and absent;

Xaa$_{37}$ is selected from the group consisting of Gly, Ala, Glu, Pro and absent;

Xaa$_{38}$ is selected from the group consisting of Ser, Gly, Ala, Glu, Gln, Pro, Arg, and absent; and Xaa$_{39}$ is selected from the group consisting of Gly and absent.

10. The derivative of claim 9, wherein the linker further comprises a Glu di-radical selected from the group consisting of Chem. 6

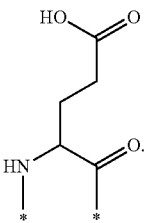

and

Chem. 7

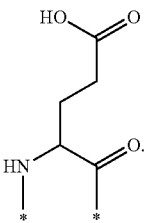

11. The derivative of claim 9, wherein

Xaa$_7$ is selected from the group consisting of L-histidine, imidazopropionyl, α-hydroxy-histidine, D-histidine, desamino-histidine, 2-amino-histidine, β-hydroxy-histidine, homohistidine, N$^α$-acetyl-histidine, N$^α$-formyl-histidine, α-fluoromethyl-histidine, α-methyl-histidine, 3-pyridylalanine, 2-pyridylalanine, and 4-pyridylalanine;

Xaa$_8$ is selected from the group consisting of Ala, Gly, Val, Leu, Ile, Thr, Ser, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, and (1-aminocyclooctyl) carboxylic acid;

Xaa$_{12}$ is Phe;

Xaa$_{16}$ is Val;

Xaa$_{18}$ is Ser;

Xaa$_{19}$ is Tyr;

Xaa$_{20}$ is Leu;

Xaa$_{22}$ is selected from the group consisting of Gly, Glu and Aib;

Xaa$_{23}$ is Gln;

Xaa$_{24}$ is Lys;

Xaa$_{25}$ is selected from the group consisting of Ala and Val;

Xaa$_{26}$ is selected from the group consisting of Val, His, and Arg;

Xaa$_{30}$ is selected from the group consisting of Ala, Glu, and Arg;

Xaa$_{31}$ is selected from the group consisting of Trp and His;

Xaa$_{34}$ is selected from the group consisting of Glu, Asn, Gly, Gln, and Arg;

Xaa$_{35}$ is selected from the group consisting of Gly and absent;

Xaa$_{36}$ is selected from the group consisting of Arg and absent;

Xaa$_{37}$ is selected from the group consisting of Gly and absent;

Xaa$_{38}$ is selected from the group consisting of Ser and absent; and

Xaa$_{39}$ is selected from the group consisting of Gly and absent.

12. The derivative of claim 11, wherein Xaa$_{38}$ and Xaa$_{39}$ are absent.

13. The derivative of claim 12, wherein Xaa$_{26}$ is Arg.

14. The derivative of claim 13, wherein Xaa$_{34}$ is selected from the group consisting of Gly, Gln, and Arg.

15. The derivative of claim 14, wherein Xaa$_{34}$ is selected from the group consisting of Gly and Gln.

16. The derivative of claim 15, wherein Xaa$_{30}$ is Glu.

17. The derivative of claim 16, wherein Xaa$_{25}$ is Val.

18. The derivative of claim 15, wherein Xaa$_{31}$ is His.

19. The derivative of claim 18, wherein Xaa$_{35}$, Xaa$_{36}$ and Xaa$_{37}$ are absent.

20. The derivative of claim 13, wherein Xaa$_{34}$ is Arg.

21. The derivative of claim 20, wherein Xaa$_{31}$ is His.

22. The derivative of claim 21, wherein Xaa$_{25}$ is Val.

23. The derivative of claim 22, wherein Xaa$_{36}$ and Xaa$_{37}$ are absent.

24. The derivative of claim 14, wherein the protracting moiety is Chem. 1.

25. The derivative of claim 24, further comprising a Glu di-radical that is Chem. 6:

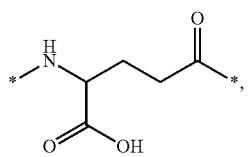

wherein the Glu di-radical is included p times, wherein p is an integer in the range of 1-2.

26. The derivative of claim 25, wherein n is 1 and k is 1.

27. The derivative of claim 26, wherein m is an integer in the range of 1-3.

28. The derivative of claim 27, wherein x is an integer in the range of 12-16.

29. The derivative of claim 28, wherein p is 1.

30. A derivative according to claim 1, wherein the derivative is selected from the following:

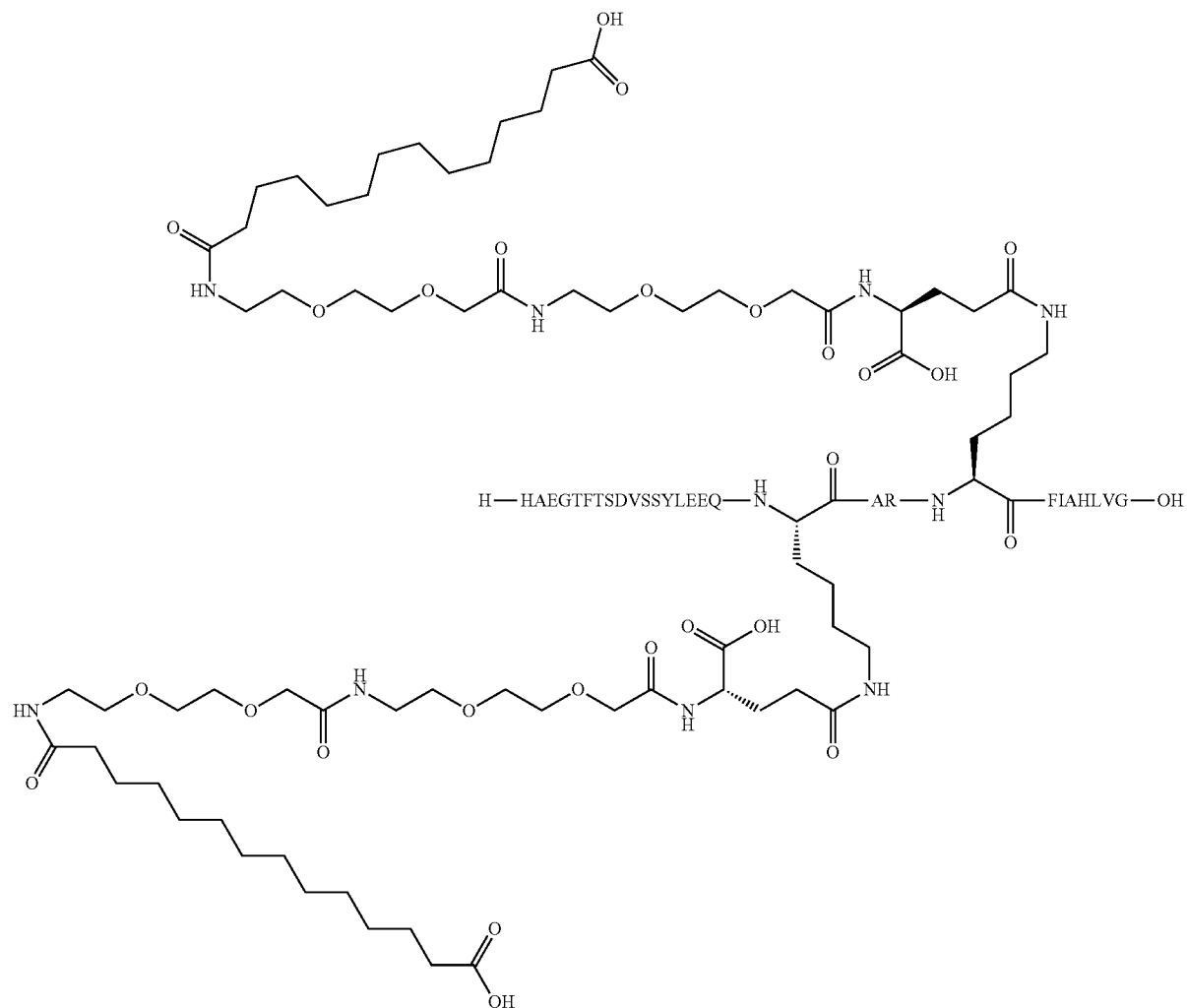

Chem. 71 where the amino acid sequence is that of SEQ ID NO:25,
Chem. 73
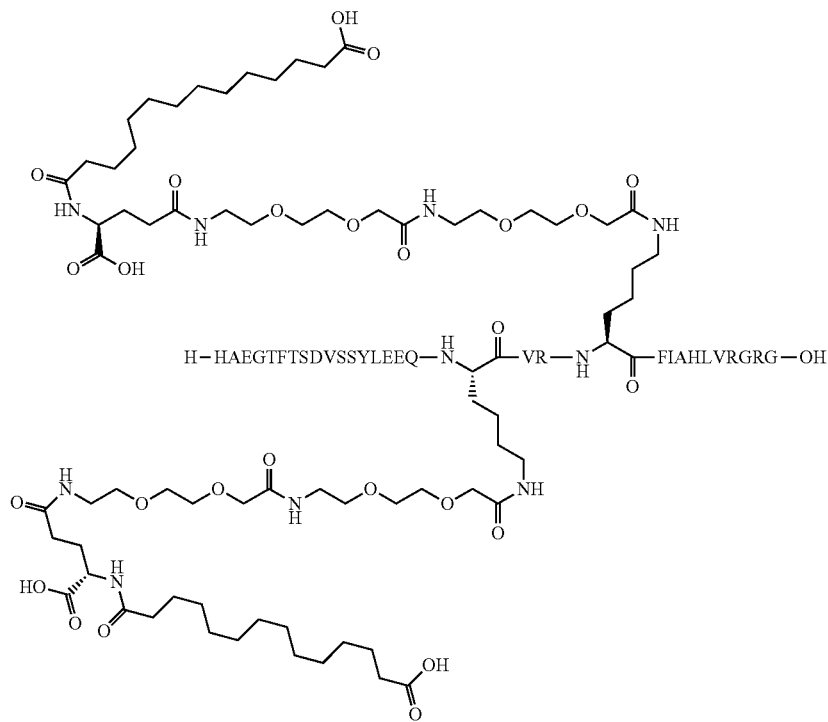
where the amino acid sequence is that of SEQ ID NO:27,
Chem. 74
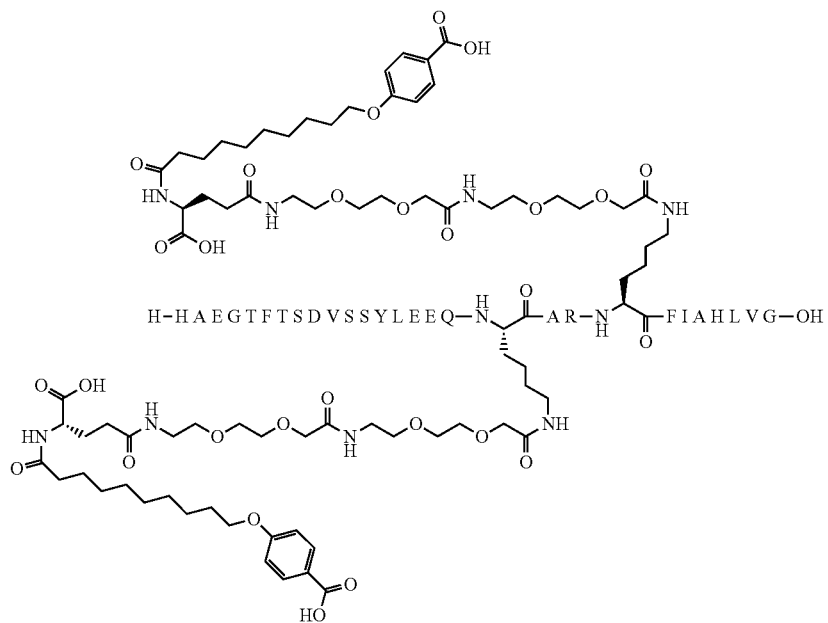

where the amino acid sequence is that of SEQ ID NO:28,
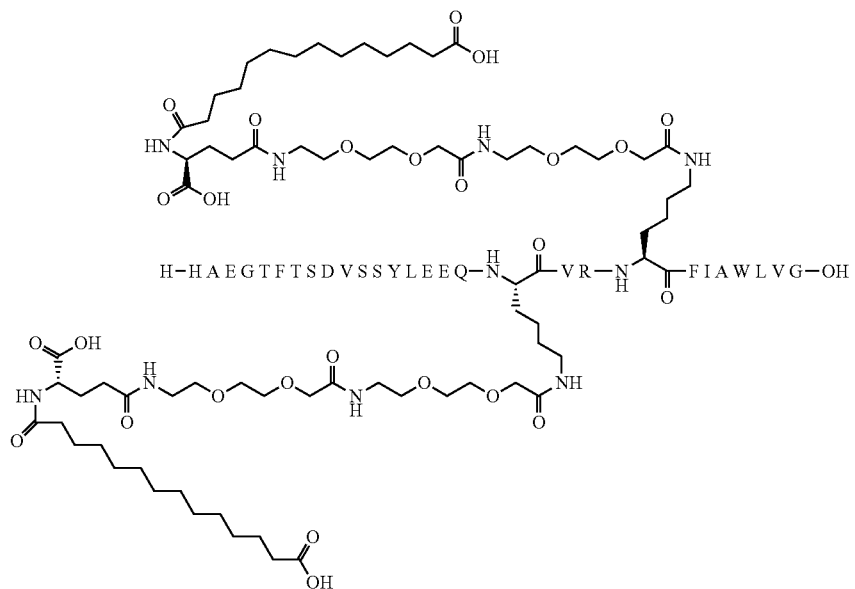
Chem. 76
where the amino acid sequence is that of SEQ ID NO:30,
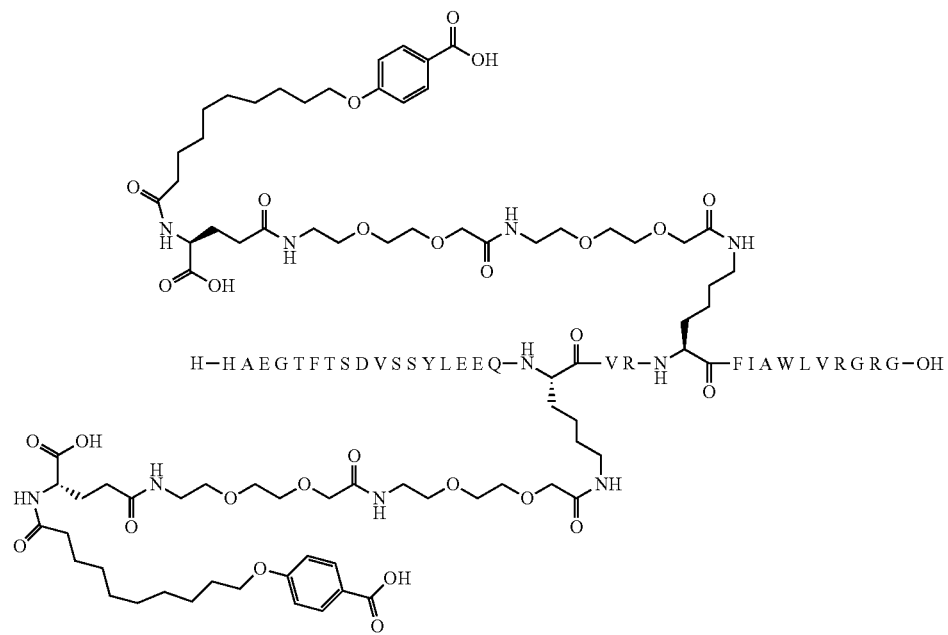
Chem. 77 where the amino acid sequence is that of SEQ ID NO:31,

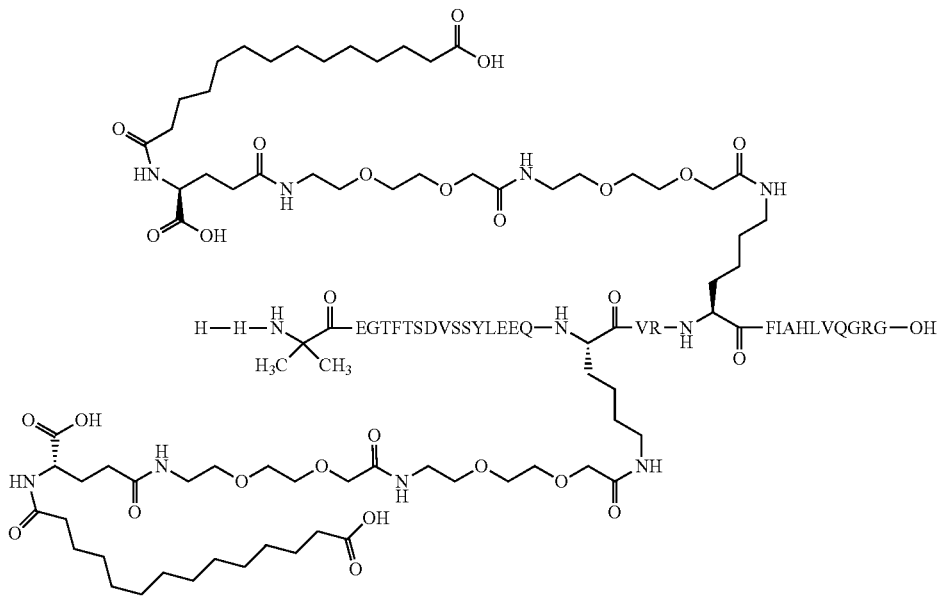

Chem. 78 where the amino acid sequence is that of SEQ ID NO:36
SEQ ID NO:32, and

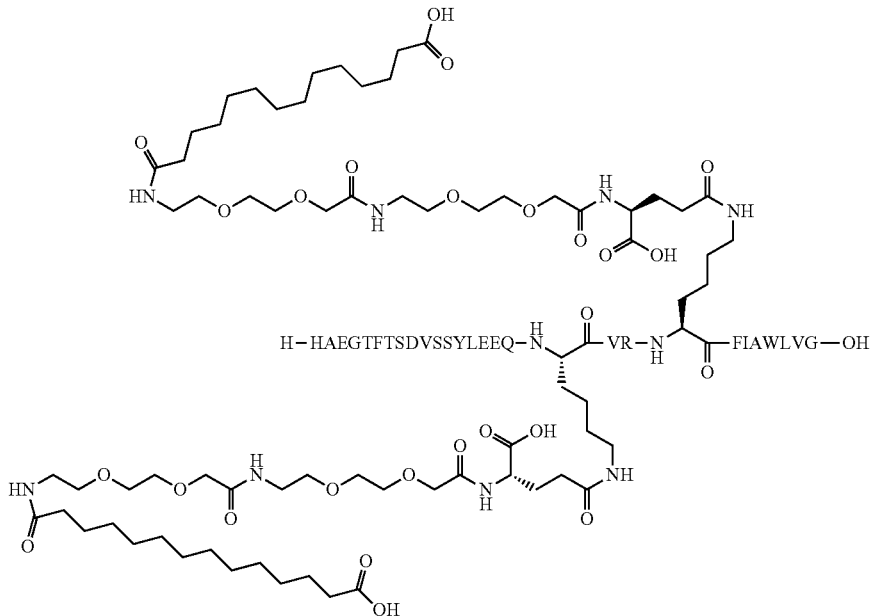

Chem. 79 where the amino acid sequence is that of SEQ ID NO:33; or a pharmaceutically acceptable salt, amide, or ester thereof.

31. A pharmaceutical composition comprising a derivative according to claim 1 and a pharmaceutically acceptable excipient.

32. A method for treating diabetes in a subject, said method comprising administering to a subject in need thereof a therapeutically effective amount of a pharmaceutical composition according to claim 31.

33. A method for treating obesity in a subject, said method comprising administering to a subject in need thereof a therapeutically effective amount of a pharmaceutical composition according to claim 31.

34. A pharmaceutical composition comprising a derivative according to claim 9 and a pharmaceutically acceptable excipient.

35. A method for treating diabetes in a subject, said method comprising administering to a subject in need thereof a therapeutically effective amount of a pharmaceutical composition according to claim 34.

36. A method for treating obesity in a subject, said method comprising administering to a subject in need thereof a therapeutically effective amount of a pharmaceutical composition according to claim 34.

37. A pharmaceutical composition comprising a derivative according to claim 30 and a pharmaceutically acceptable excipient.

38. A method for treating diabetes in a subject, said method comprising administering to a subject in need thereof a therapeutically effective amount of a pharmaceutical composition according to claim 37.

39. A method for treating obesity in a subject, said method comprising administering to a subject in need thereof a therapeutically effective amount of a pharmaceutical composition according to claim 37.

40. The derivative of claim 1, wherein the amino acid sequence of the analogue is SEQ ID NO:32.

* * * * *

UNITED STATES PATENT AND TRADEMARK OFFICE
CERTIFICATE OF CORRECTION

PATENT NO. : 11,034,746 B2
APPLICATION NO. : 15/968950
DATED : June 15, 2021
INVENTOR(S) : Birgit Wieczorek et al.

Page 1 of 1

It is certified that error appears in the above-identified patent and that said Letters Patent is hereby corrected as shown below:

In the Claims

At Column 161, Claim number 9, Line number 50, should read: "Glu, Pro, Arg and absent;"
At Column 162, Claim number 11, Line number 40, please replace "Xaa$_3$o" with "Xaa$_{30}$"
At Column 162, Claim number 11, Line number 52, please replace "Xaa$_3$s" with "Xaa$_{38}$"
At Column 169, Claim number 30, Chem. 79, please remove "SEQ ID NO:32"

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*